US010703738B2

(12) United States Patent
Altman et al.

(10) Patent No.: US 10,703,738 B2
(45) Date of Patent: Jul. 7, 2020

(54) BENZO[B]THIOPHENE COMPOUNDS AS STING AGONISTS

(71) Applicant: MERCK SHARP & DOHME CORP., Rahway, NJ (US)

(72) Inventors: Michael D. Altman, Needham, MA (US); Brandon D. Cash, Stoughton, MA (US); Wonsuk Chang, Princeton, NJ (US); Jared N. Cumming, Winchester, MA (US); Andrew M. Haidle, Somerville, MA (US); Timothy J. Henderson, Natick, MA (US); James P. Jewell, Newton, MA (US); Matthew A. Larsen, Dedham, MA (US); Rui Liang, New Brunswick, NJ (US); Jongwon Lim, Lexington, MA (US); Min Lu, Brookline, MA (US); Ryan D. Otte, Natick, MA (US); Tony Siu, Brookline, MA (US); Benjamin Wesley Trotter, Medfield, MA (US); Sriram Tyagarajan, Edison, NJ (US)

(73) Assignee: Merck Sharp & Dohme Corp., Rahway, NY (US)

( * ) Notice: Subject to any disclaimer, the term of this patent is extended or adjusted under 35 U.S.C. 154(b) by 0 days.

(21) Appl. No.: 16/513,409

(22) Filed: Jul. 16, 2019

(65) Prior Publication Data

US 2019/0337917 A1    Nov. 7, 2019

Related U.S. Application Data

(62) Division of application No. 15/722,093, filed on Oct. 2, 2017, now Pat. No. 10,414,747.

(60) Provisional application No. 62/404,062, filed on Oct. 4, 2016.

(51) Int. Cl.
*C07D 333/60* (2006.01)
*C07D 333/62* (2006.01)
*C07D 409/12* (2006.01)
*C07D 498/04* (2006.01)

(52) U.S. Cl.
CPC ......... *C07D 333/60* (2013.01); *C07D 333/62* (2013.01); *C07D 409/12* (2013.01); *C07D 498/04* (2013.01)

(58) Field of Classification Search
CPC .. C07D 333/60; C07D 333/62; C07D 409/12; C07D 498/04
USPC .................................................... 424/184.1
See application file for complete search history.

(56) References Cited

U.S. PATENT DOCUMENTS

| 4,299,769 | A  | 11/1981 | McEvoy et al. |
|---|---|---|---|
| 4,342,689 | A  | 8/1982  | McEvoy et al. |
| 4,342,690 | A  | 8/1982  | McEvoy et al. |
| 4,342,691 | A  | 8/1982  | McEvoy et al. |
| 4,952,571 | A  | 8/1990  | Redpath et al. |
| 6,262,055 | B1 | 7/2001  | Young et al. |
| 7,288,567 | B2 | 10/2007 | Delorme et al. |
| 7,488,802 | B2 | 2/2009  | Collins et al. |
| 7,521,051 | B2 | 4/2009  | Collins et al. |
| 7,595,048 | B2 | 9/2009  | Honjo et al. |
| 8,008,449 | B2 | 8/2011  | Korman et al. |
| 8,168,757 | B2 | 5/2012  | Finnefroch et al. |
| 8,354,509 | B2 | 1/2013  | Carven et al. |
| 8,383,796 | B2 | 2/2013  | Korman et al. |
| 8,664,255 | B2 | 3/2014  | Freundlich et al. |
| 9,724,408 | B2 | 8/2017  | Dubensky, Jr. et al. |
| 2002/0115826 | A1 | 8/2002 | Delorme et al. |
| 2006/0040887 | A1 | 2/2006 | Karaolis |
| 2008/0025979 | A1 | 1/2008 | Honjo et al. |
| 2008/0286296 | A1 | 11/2008 | Ebensen et al. |
| 2009/0181971 | A1 | 7/2009 | Delorme et al. |
| 2010/0113477 | A1 | 5/2010 | Freundlich et al. |
| 2011/0271358 | A1 | 11/2011 | Gordon et al. |
| 2014/0017444 | A1 | 1/2014 | Shimizu et al. |
| 2014/0206640 | A1 | 7/2014 | Girijavallabhan et al. |
| 2014/0329889 | A1 | 11/2014 | Vance et al. |
| 2014/0341976 | A1 | 11/2014 | Dubensky, Jr. et al. |
| 2015/0056224 | A1 | 2/2015 | Dubensky, Jr. et al. |
| 2015/0158886 | A1 | 6/2015 | Jones et al. |
| 2016/0287698 | A1 | 10/2016 | Yan et al. |
| 2016/0362441 | A1 | 12/2016 | Vernejoul et al. |

(Continued)

FOREIGN PATENT DOCUMENTS

| EP | 0146243       | 6/1985 |
|---|---|---|
| EP | 0350990 A1    | 1/1990 |
| EP | 0350990 B1    | 9/1995 |

(Continued)

OTHER PUBLICATIONS

U.S. Appl. No. 15/722,093, filed Oct. 2, 2017.

(Continued)

*Primary Examiner* — Kahsay Habte

(74) *Attorney, Agent, or Firm* — Julie M. Lake; Catherine D. Fitch

(57) ABSTRACT

Compounds of general formula (Ia), compounds of general formula (Ia'), compounds of general formula (Ib), compounds of general formula (Ib'), compounds of general formula (I), compounds of general formula (I'), and their pharmaceutically acceptable salts, wherein $R^1$, $R^2$, $R^3$, $R^4$, $R^5$, $R^6$, $R^8$, $R^9$, $X^1$, $X^2$, and $X^3$ are defined herein, that may be useful as inductors of type I interferon production, specifically as STING active agents, are provided. Also provided are processes for the synthesis and use of compounds of the disclosure.

6 Claims, No Drawings

Specification includes a Sequence Listing.

(56) References Cited

U.S. PATENT DOCUMENTS

| | | |
|---|---|---|
| 2017/0050967 A1 | 2/2017 | Burai et al. |
| 2017/0158724 A1 | 6/2017 | Adams et al. |

FOREIGN PATENT DOCUMENTS

| | | |
|---|---|---|
| EP | 3135290 A1 | 1/2018 |
| GB | 532822 | 1/1941 |
| WO | 1994008962 | 4/1994 |
| WO | 199962897 | 12/1999 |
| WO | 2001002369 A2 | 1/2001 |
| WO | 2001002369 A3 | 1/2001 |
| WO | 2001070675 | 9/2001 |
| WO | 2002010192 | 2/2002 |
| WO | 2002068470 | 9/2002 |
| WO | 2004004771 A1 | 2/2004 |
| WO | 2004056875 | 7/2004 |
| WO | 2004072286 | 8/2004 |
| WO | 2005020917 | 3/2005 |
| WO | 2010027827 A3 | 3/2010 |
| WO | 2010047774 | 4/2010 |
| WO | 2010077634 A1 | 7/2010 |
| WO | 2011066342 A3 | 6/2011 |
| WO | 2012068702 | 5/2012 |
| WO | 2013019906 A1 | 2/2013 |
| WO | 2013185052 A1 | 12/2013 |
| WO | 2014093936 | 6/2014 |
| WO | 2014099824 | 6/2014 |
| WO | 2014099941 | 6/2014 |
| WO | 2014139388 A1 | 9/2014 |
| WO | 201479335 A1 | 11/2014 |
| WO | 2014179760 | 11/2014 |
| WO | 2014189805 A1 | 11/2014 |
| WO | 2014189806 | 11/2014 |
| WO | 2015017652 | 2/2015 |
| WO | 2015074145 A1 | 5/2015 |
| WO | 2015077354 A1 | 5/2015 |
| WO | 2015148746 A1 | 10/2015 |
| WO | 2015161137 | 10/2015 |
| WO | 2015185565 | 12/2015 |
| WO | 2015189117 | 12/2015 |
| WO | 2016096174 | 6/2016 |
| WO | 2016096577 | 6/2016 |
| WO | 2016100261 | 6/2016 |
| WO | 2016120305 | 8/2016 |
| WO | 2016145102 | 9/2016 |
| WO | 2017011622 | 1/2017 |
| WO | 2017011920 | 1/2017 |
| WO | 2017027645 | 2/2017 |
| WO | 2017027646 | 2/2017 |
| WO | 2017075477 A1 | 5/2017 |
| WO | 2017093933 A1 | 6/2017 |
| WO | 2017100305 | 6/2017 |
| WO | 2017123657 | 7/2017 |
| WO | 2017123669 | 7/2017 |
| WO | 2017161349 A1 | 9/2017 |
| WO | 2017175147 | 10/2017 |
| WO | 2017175156 | 10/2017 |
| WO | 2017216726 | 12/2017 |
| WO | 2018009466 | 1/2018 |

OTHER PUBLICATIONS

Ablasser et al., Cell intrinsic immunity spreads to bystander cells via the intercellular transfer of cGAMP, Nature, Nov. 28, 2013, 530-546, 503.

Ablasser et al., cGAS produces a 2'-5'-linked cyclic dinucleotide second messenger that activates STING, Nature, Jun. 20, 2013, 380-385, 498.

Ausmees et al., Genetic Data Indicate that Proteins Containing the GGDEF Domain Possess Diguanylate Cyclase Activity, FEMS Microbiology, 2001, 163-167, Letters 204.

Berge, S.M., et al.,, "Pharmaceutical Salts", J. Pharm. Sci, 1977, pp. 1-19, vol. 66, No. 1.

Bhattacharjee et al, Synthesis of heterocyclic steroids-III: An unsuccessful attempt at the Synthesis of B-Nor-6-thiaequilenin through 3-cyano-7-methoxy-4-oxo-1,2,3,4-Tetrahydrodibenzothiophene, Tetrahedron, 1960, 215-222, 10.

Bookser et al., High-Throughput Five Minute Microwave Accelerated Glycosylation Approach to the Synthesis of Nucleoside Libraries, JOC Article, 2007, 173-179, 72.

Bruno et al., N-Substituted 2-aminobiphenylpalladium Methanesulfonate Precatalysts and Their Use in C-C and C-N Cross Couplings, The Journal of Organic Chamistry, 2014, 4161-4166, 79.

Burtner, et al., Synthetic Choleretics. I. Naphthol Derivatives, Journal of the American Chemical Society, 1951, 897-900, vol. 73.

Cagniant, et al., Condensed sulfur heterocycles. III. 1,2,3,4-Tetrahydrodibenzothiophene and, Bulletin de la Societe Chimique de France, 1952, 336-343.

Cagniant, et al., Condensed sulfur heterocycles. IV. Condensation of thianaphthene with glutaric anhydride and the, Bulletin de la Societe Chimique de France, 1952, 629-633.

Cagniant, et al., Condensed sulfur heterocycles. XIX. Synthesis of some ω-thionaphthenylalkanoic acids, Bulletin de la Societe Chimique de France, 1962, 576-581.

Child, et al., A New Non-steroidal Anti-Inflammatory Analgesic: y-Oxo.(1,1'-biphenyl)-4-butanoic Acid (Fenbufen), Arzneimittel-Forschung, 1980, 695-702, vol. 30; Issue 4A.

Dande et al., Improving RNA Interference in Mammalian Cells by 4'-Thio-Modified Small Interfering RNA (siRNA): Effect on siRNA Activity and Nuclease Stability When Used in Combination with 2'-O-Alkyl Modifications, Journal of Medicinal Chemistry, 2006, 1624-1634, 49(5).

Diner et al., The Innate Immune DNA Sensor cGAS Produces a Noncanonical Cyclic Dinucleotide that Activates Human STING, 3 Cell Reports, Cell Reports, 2013, 1355-1361, 3.

Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, Plos One, 2014, 1-14, 9-6-e99988.

Ertem et al., Synthesis of RNA oligomers on heterogeneous templates, Nature, 1996, 238-240, 379-18.

Fagundes et al., Building unique bonds to tight misplaced DNA, Cell Research, 2013, 1065-1066, 2-9.

Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.

Gao et al., Cyclic [G(2',5')pA(3',5")p] Is the Metazoan Second Messenger Produced by DNA-Activated Cyclic GMP-AMP Synthase, Cell, 2013, 1094-1107, 153.

Gao et al., Structure-Function Ananlysis of STING Activation by c[G(2',5')pA(3',5')p] and Targeting by Antiviral DMXAA, Cell, 2013, 748-762, 154.

Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.

Gopinath et al., As many as six tandem reactions in one step! Unprecendented formation of highly functionalized benzothiophenes, Chemical Communication, Jul. 17, 2009, 7131-7133, vol. 46.

Sopinath, et al., Highly chemoselective Esterification Reactions and Boc/THP/TBDMS Discriminating Deprotections Under Samarium(III) Catalysis, Organic Letters, 2011, 1932-1935, vol. 13, Issue No. 8.

Gosselin et al., Systematic Synthesis and Biological Evaluation of α- and β-D-lyxofuranosyl Nucleosides of the Five Naturally Occurring Nucleic Acid Bases, J. Med. Chem, 1987, 982-991, 30.

Gould, Salt Selections for Basic Drugs, Intl. J. Pharmaceutics, 1986, pp. 201-217, vol. 33.

Guanghui Yi et al., Single Nucleotide Polymorphisms of Human STING Can Affect Innate Immune Response to Cyclic Dinucleotides, Plos One, 2013, 1-16, 8-10-e77846.

Hornfeldt, et al., Unsaturted y-thiolactones II*. The Structures of 3-and 4-Methyl-2-thienols, Acta chem. Scand., 1962, 789-791, vol. 16; Issue No. 2.

(56) References Cited

OTHER PUBLICATIONS

Ikeuchi et al., Practical synthesis of natural plant-growth regulator 2-azahypoxanthine, its derivatives, and biotin-labeled probes, Organic & Biomolecular Chemistry, 2014, 3813, 12(23).
Joshi et al., Selectivity of montmorillonite catalyzed prebiotic reactions of D, L-nucleotides, Orig Life Evol Biosph, 2007, 3-26, 37-3.
Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.
Kobayashi et al., Bacterial c-di-GMP Affects Hematopoietic Stem/ Progenitors and their Niches through STING, Cell Reports, 2015, 71-84, 11.
Kranzusch et al., Structure-Guided Reporgramming of Human cGAS Dinucleotide Linkage Specificity, Cell Inc., Elsevier Inc., 2014, 1011-1021, 158.
Kudo, et al., Synthesis of Monoamino and Monohydroxydibenzothiophenes, J. Heterocyclic Chem., 1985, 215218, vol. 22.
Li et al., Cyclic GMP-AMP Synthase is Activated by Double-Stranded DNA-Induced Oligomerization, Immunity, 2013, 1019-1031, 39.
Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs: ERRATUM, Nature Chemical Biology, 2014, 1043, 10.
Liu et al., Activated STING in a Vascular and Pulmonary Syndrome, The New England Journal of Medicine, 2015, 507, 371-6.
Liu et al., Hepatitis B Virus Polymerase Disrupts K63-Linked Ubiquitination of STING to Block Inate Cytosolic DNA-Sensing Pathways, Journal of Virology, 2015, 2287, 89-4.
Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.
Mikhailov et al., Conformational Peculiarities of 5'-C-methylnucleosides, Bioorganicheskaya Khimiya, 1989, 969-975, 15(7).
Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or -carbonitrile, Tetrahedron, 1993, 557-570, 49(3).
Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).
Mlochowski, et al., A Simple Route to Benzo[b]thiophenes: Sulfanylation-acylation of C-H Acids With 2-(Chlorosulfanyl)benzoyl Chloride, Phosphorus, Sulfur, and Silicon, 2009, 1115-1123, vol. 184; Issue 5.
D'Neill et al., Sensing the Dark Side of DNA, Sceince, 2013, 763, 339.
Ora et al., Hydrolytic reactions of cyclic bis(3'-5') diadenylic acid (c-di-AMP), J. Phys. Org. Chem, 2013, 218-225, 26.
Panne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).

Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sali, et al., Characterization of a Novel Human-Specific STING Agonist that Elicits Antiviral Activity Against Emerging Alphaviruses, Plos Pathogens, 2015, 1-30.
Simm et al., Phenotypic Convergence Mediated by GGDEF-Domain-Containing Proteins, Journal of Bacteriology, 2005, 6816-6823, 187(19).
Stahl et al., Aminoquinazoline Compounds as A2A Antagonist, Handbook of Pharmaceutical Salts Properties, Selection, and Use, 2002, 330-331.
Sun et al., Cyclic GMP-AMP Synthase Is a Cytosolic DNA Sensor That Activates the Type I Interferon Pathway, Science, 2013, 786, 339.
Tang et al., Single Amino Acid change in STING Leads to Constitutive Active Signaling, Plos One, 2015, 1-10, (10)3.
Tosolini et al., Human Monocyte Recognition of Adenosine-Based Cyclic Dinucleotides Unveils the A2a G∞ s Protein-Coupled Receptor Tonic Inhibition of Mitochondrially Induced Cell Death, Molecular and Cellular Biology, 2015, 479-495, 35-2.
Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.
Wang et al., Synthesis and Biological Activity of 5-Fluorotubercidin, Nucleosides, Nucleotides and Nucleic Acids, 2004, 161-170, 23(1).
Wu et al., Cyclic GMP-AMP Is an Endogenous Second Messenger in Innate Immune Signaling by Cytosolic DNA, Science 826, 2013, 826-830, 339.
Zeng et al., MAVS, cGAS, and Endogenous Retroviruses in T-Independent B Cell Responses, Science, 2014, 1486-1492, 346-6216.
Zhang et al., Cyclic GMP-AMP Containing Mixed Phosphodiester Linkages Is an Endogenous High-Affinity Ligand for STING, Molecular Cell, 2013, 226-235, 51.
Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.
Burdette, Dana L., STING is a direct innate immune sensor of cyclic di-GMP, Nature, Oct. 27, 2011, 515-519, 478.
Burdette, Dara L., STING and the innate immune response to nucleic acids in the cytosol, Nature Immunology, Jan. 2013, 19-26, 14(1).
English language translation of Markert, Jurgen et al., Darstellung von 1,2-Benzisothiazolen und einige Folgereaktionen, Liebigs Ann. Chem., 1980, 768-778, 5.
Fu, Juan, et al., STING agonist formulated cancer vaccines can cure established tumors resistant to PD-1 blockade, Science Translational Medicine, 2015, 1-13, 7.
Heping Shi, et al., Molecular basis for the specific recognition of the metazoan cyclic GMP-AMP by the innate immune adaptor protein STING, PNAS, 2015, 8947-8952, vol. 112/No. 29.
Markert, Jurgen et al., Darstellung von 1,2-Benzisothiazolen und einige Folgereaktionen, Liebigs Ann. Chem., 1980, 768-778, 5.
Sheridan, Cormac, Drug Developers Switch Gears to Inhibit STING, Nature Biotechnology, Mar. 4, 2019, 199-208, 37.

BENZO[B]THIOPHENE COMPOUNDS AS STING AGONISTS

CROSS-REFERENCE TO RELATED APPLICATIONS

This application is a divisional of U.S. Nonprovisional patent application Ser. No. 15/722,093, filed Oct. 2, 2017, which claims priority to U.S. Provisional Patent Application No. 62/404,062, filed Oct. 4, 2016.

FIELD OF THE INVENTION

The present disclosure relates to compounds and derivatives thereof that may be useful as STING (Stimulator of Interferon Genes) agonists that activate the STING pathway. The present disclosure also relates to processes for the synthesis and to uses of such compounds.

REFERENCE TO SEQUENCE LISTING SUBMITTED ELECTRONICALLY

The sequence listing of the present application is submitted electronically via EFS-Web as an ASCII-formatted sequence listing, with a file name of "24170USDIV-SE-QLIST-JUL2019", a creation date of Jul. 8, 2019 and a size of 25 KB. This sequence listing submitted via EFS-Web is part of the specification and is herein incorporated by reference in its entirety.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize as foreign those antigens not naturally expressed in the host and to mount an anti-antigen response through the coordinated actions of many leukocyte subsets. The hallmark of adaptive immune responses is their ability to provide "memory" or long-lasting immunity against the encountered antigen. While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'3'-cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T-cell activation by enhancing the ability of dendritic cells and macrophages to uptake, process, present and cross-present antigens to T-cells. The T-cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents. Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in today's anti-tumor therapy landscape.

SUMMARY OF THE INVENTION

The present disclosure relates to novel compounds of general formula (Ia). In particular, the present disclosure relates to compounds having the general structural formula (Ia):

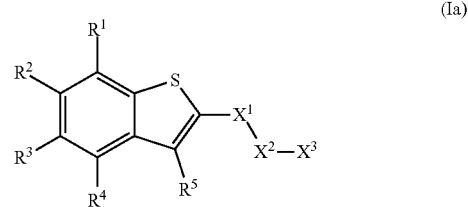

or pharmaceutically acceptable salts thereof, as described herein. Embodiments of the disclosure include compounds of general formula (Ia), and pharmaceutically acceptable salts thereof, as well as synthesis and isolation of compounds of general formula (Ia), and pharmaceutically acceptable salts thereof. Uses of compounds of general formula (Ia) are also disclosed.

The present disclosure also relates to novel compounds of general formula (Ia'). In particular, the present disclosure relates to compounds having the general structural formula (Ia'):

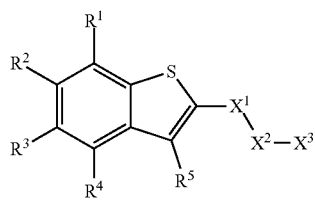

(Ia')

or pharmaceutically acceptable salts thereof, as described herein. Embodiments of the disclosure include compounds of general formula (Ia'), and pharmaceutically acceptable salts thereof, as well as synthesis and isolation of compounds of general formula (Ia'), and pharmaceutically acceptable salts thereof. Uses of compounds of general formula (Ia') are also disclosed.

The present disclosure also relates to novel compounds of general formula (Ib). In particular, the present disclosure relates to compounds having the general structural formula (Ib):

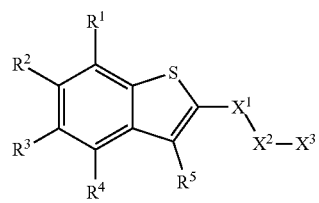

(Ib)

or pharmaceutically acceptable salts thereof, as described herein. Embodiments of the disclosure include compounds of general formula (Ib), and pharmaceutically acceptable salts thereof, as well as synthesis and isolation of compounds of general formula (Ib), and pharmaceutically acceptable salts thereof. Uses of compounds of general formula (Ib) are also disclosed.

The present disclosure also relates to novel compounds of general formula (Ib'). In particular, the present disclosure relates to compounds having the general structural formula (Ib'):

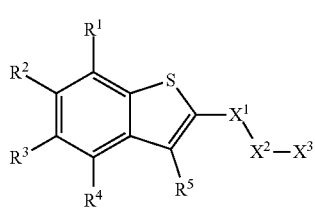

(Ib')

or pharmaceutically acceptable salts thereof, as described herein. Embodiments of the disclosure include compounds of general formula (Ib'), and pharmaceutically acceptable salts thereof, as well as synthesis and isolation of compounds of general formula (Ib'), and pharmaceutically acceptable salts thereof. Uses of compounds of general formula (Ib') are also disclosed.

In addition, this disclosure relates to uses of compounds of general formula (I):

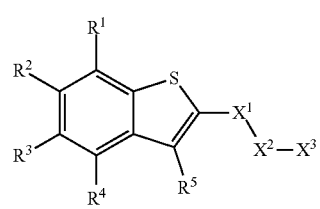

(I)

or pharmaceutically acceptable salts thereof, as described herein.

In addition, this disclosure relates to uses of compounds of general formula (I'):

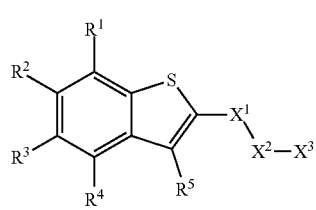

(I')

or pharmaceutically acceptable salts thereof, as described herein.

Other embodiments, aspects and features of the present disclosure are either further described in or will be apparent from the ensuing description, examples and appended claims.

BRIEF DESCRIPTION OF THE DRAWINGS

Not Applicable.

DETAILED DESCRIPTION OF THE INVENTION

The present disclosure includes compounds of general formula (Ia), and pharmaceutically acceptable salts thereof. These compounds and their pharmaceutically acceptable salts may be useful as agents to induce immune responses, to induce STING-dependent type I interferon production, and/or to treat a cell proliferation disorder.

The present disclosure includes compounds of general formula (Ia'), and pharmaceutically acceptable salts thereof. These compounds and their pharmaceutically acceptable salts may be useful as agents to induce immune responses, to induce STING-dependent type I interferon production, and/or to treat a cell proliferation disorder.

The present disclosure also includes compounds of general formula (Ib), and pharmaceutically acceptable salts thereof. These compounds and their pharmaceutically acceptable salts may be useful as agents to induce immune responses, to induce STING-dependent type I interferon production, and/or to treat a cell proliferation disorder.

The present disclosure also includes compounds of general formula (Ib'), and pharmaceutically acceptable salts thereof. These compounds and their pharmaceutically acceptable salts may be useful as agents to induce immune responses, to induce STING-dependent type I interferon production, and/or to treat a cell proliferation disorder.

In addition, the present disclosure includes uses of compounds of general formula (I), and pharmaceutically acceptable salts thereof. The compounds of general formula (I) may be useful as agents to induce immune responses, to induce STING-dependent type I interferon production, and/or to treat a cell proliferation disorder.

In addition, the present disclosure includes uses of compounds of general formula (I'), and pharmaceutically acceptable salts thereof. The compounds of general formula (I') may be useful as agents to induce immune responses, to induce STING-dependent type I interferon production, and/or to treat a cell proliferation disorder.

A first embodiment relates to compounds of general formula (Ia):

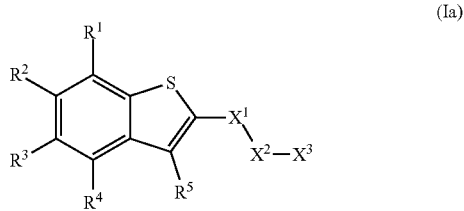

(Ia)

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is C(O); $X^2$ is $(C(R^8)_2)_{(1-3)}$; each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein when $X^1$—$X^2$—$X^3$ is $X^1$—$CHR^8$—$X^3$ or $X^1$—$CHR^8CH_2$—$X^3$, at least one of $R^2$ and $R^3$ is not selected from the group consisting of halogen, $OR^6$, $C_1$-$C_6$ alkyl, and $C_1$-$C_6$ haloalkyl.

In a first aspect of the first embodiment, $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, $R^1$ is selected from the group consisting of H, F, Cl, $C_1$-$C_3$ alkyl, and $C_1$-$C_3$ haloalkyl. In particular instances of this aspect, $R^1$ is selected from the group consisting of H and F. In this aspect, all other groups are as provided in the general formula (Ia) of the first embodiment above.

In a second aspect of the first embodiment, $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^2$ is selected from the group consisting of Br, Cl, $CH_3$, $CH_2CH_3$, $CH=CH_2$, $OCH_3$, and $N(R^6)_2$. In this aspect, all other groups are as provided in the general formula (Ia) of the first embodiment above or the first aspect described above.

In a third aspect of the first embodiment, $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^3$ is selected from the group consisting of Br, Cl, $CH_3$, $CH_2CH_3$, $CH=CH_2$, $OCH_3$, and $N(R^6)_2$. In this aspect, all other groups are as provided in the general formula (Ia) of the first embodiment above or the first through second aspects described above.

In a fourth aspect of the first embodiment, $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, $R^4$ is selected from the group consisting of H, F, Cl, $C_1$-$C_3$ alkyl, and $C_1$-$C_3$ haloalkyl. In particular instances of this aspect, $R^4$ is selected from the group consisting of H and F. In this aspect, all other groups are as provided in the general formula (Ia) of the first embodiment above or the first through third aspects described above.

In a fifth aspect of the first embodiment, $R^5$ is selected from the group consisting of H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$. In instances of this aspect, $R^5$ is selected from the group consisting of H, F, Cl, $C_1$-$C_3$ alkyl, and $C_1$-$C_3$ haloalkyl. In particular instances of this aspect, $R^5$ is H. In this aspect, all other groups are as provided in the general formula (Ia) of the first embodiment above or the first through fourth aspects described above.

In a sixth aspect of the first embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H and $CH_3$. In this aspect, all other groups are as provided in the general formula (Ia) of the first embodiment above or the first through fifth aspects described above.

In a seventh aspect of the first embodiment, $X^3$ is selected from the group consisting of $COOR^6$, $C(O)SR^6$, $C(S)OR^6$, $SO_2R^6$, and $C(O)N(R^9)_2$. In instances of this aspect, $X^3$ is selected from the group consisting of $COOR^6$, $SO_2R^6$, and $C(O)N(R^9)_2$. In particular instances of this aspect, $X^3$ is $COOR^6$. In even more particular instances of this aspect, $X^3$ is COOH. In this aspect, all other groups are as provided in the general formula (Ia) of the first embodiment above or the first through sixth aspects described above.

In an eighth aspect of the first embodiment, each $R^9$ is independently selected from the group consisting of H, $COOR^6$, and $SO_2R^6$. In instances of this aspect, each $R^9$ is independently H. In this aspect, all other groups are as provided in the general formula (Ia) of the first embodiment above or the first through seventh aspects described above.

In a ninth aspect of the first embodiment, $X^2$ is $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle. In a first instance of this aspect, $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, $X^2$ is $CHR^8CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally 2 $R^8$ are taken together, along with the atoms to which they are attached, to form a 3- to 6-membered fused ring. In particular occurrences of this second instance, $X^2$ is $CHR^8CHR^8$, where $R^8$ is selected from the group consisting of H and $C_1$-$C_3$ alkyl, and optionally 2 $R^8$ are taken together, along with the atoms to which they are attached, to form a 3- to 6-membered fused ring. In a third instance of this aspect, $X^2$ is $CH_2C(R^8)_2$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally 2 $R^8$ are taken together, along with the atoms to which they are attached, to form a 3- to 6-membered spirocycle. In particular occurrences of this third instance, $X^2$ is $CH_2C(R^8)_2$, where $R^8$ is selected from the group consisting of H and $C_1$-$C_3$ alkyl, and optionally 2 $R^8$ are taken together, along with the atoms to which they are attached, to form a 3- to 6-membered spirocycle. In this aspect, all other groups are as provided in the general formula (Ia) of the first embodiment above or the first through eighth aspects described above.

In a tenth aspect of the first embodiment, $R^1$ is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^2$ is $CH_2CHR^8$; each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl; and $X^3$ is selected from the group consisting of $COOR^6$, $SO_2R^6$, and $C(O)N(R^9)_2$; wherein $X^1$—$X^2$—$X^3$ is selected from the group consisting of $C(O)$—$CH_2CHR^8$—$COOR^6$, $C(O)$—$CH_2CHR^8$—$SO_2R^6$, and $C(O)$—$CH_2CHR^8$—$C(O)N(R^9)_2$. In instances of this aspect, $R^1$ is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^2$ is $CH_2CHR^8$; $R^8$ is selected from the group consisting of H, $CH_3$, $CH_2CH_3$, $CH_2CH_2CH_3$, $CH(CH_3)_2$, $CH_2OCH_3$, and cyclopropyl; and $X^3$ is COOH; wherein $X^1$—$X^2$—$X^3$ is $C(O)$—$CH_2CHR^8$—COOH. In this aspect, all other groups are as provided in the general formula (Ia) of the first embodiment above.

In an eleventh aspect of the first embodiment, $R^1$ is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^2$ is $CHR^8CHR^8$; each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and where optionally 2 $R^8$ are taken together, along with the atoms to which they are attached, to form a 3- to 6-membered fused ring; and $X^3$ is selected from the group consisting of $COOR^6$, $SO_2R^6$, and $C(O)N(R^9)_2$; wherein $X^1$—$X^2$—$X^3$ is selected from the group consisting of $C(O)$—$CHR^8CHR^8$—$COOR^6$, $C(O)$—$CHR^8CHR^8$—$SO_2R^6$, and $C(O)$—$CHR^8CHR^8$—$C(O)N(R^9)_2$. In instances of this aspect, $R^1$ is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^2$ is $CHR^8CHR^8$; each $R^8$ is selected from the group consisting of H and $C_1$-$C_3$ alkyl, and where optionally 2 $R^8$ are taken together, along with the atoms to which they are attached, to form a 3- to 6-membered fused ring; and $X^3$ is COOH; wherein $X^1$—$X^2$—$X^3$ is C(O)—CHR$^8$CHR$^8$—COOH. In this aspect, all other groups are as provided in the general formula (Ia) of the first embodiment above.

In a twelfth aspect of the first embodiment, $R^1$ is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^2$ is $CH_2C(R^8)_2$; each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and where optionally 2 $R^8$ are taken together, along with the atoms to which they are attached, to form a 3- to 6-membered spirocycle; and $X^3$ is selected from the group consisting of $COOR^6$, $SO_2R^6$, and $C(O)N(R^9)_2$; wherein $X^1$—$X^2$—$X^3$ is selected from the group consisting of C(O)—$CH_2C(R^8)_2$—$COOR^6$, C(O)—$CH_2C(R^8)_2$—$SO_2R^6$, and C(O)—$CH_2C(R^8)_2$—$C(O)N(R^9)_2$. In instances of this aspect, $R^1$ is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^2$ is $CH_2C(R^8)_2$; each $R^8$ is selected from the group consisting of H and $C_1$-$C_3$ alkyl, and where optionally 2 $R^8$ are taken together, along with the atoms to which they are attached, to form a 3- to 6-membered spirocycle; and $X^3$ is COOH; wherein $X^1$—$X^2$—$X^3$ is C(O)—$CH_2C(R^8)_2$—COOH. In this aspect, all other groups are as provided in the general formula (Ia) of the first embodiment above.

A thirteenth aspect of the first embodiment relates to a pharmaceutical composition, said pharmaceutical composition comprising (a) a compound according to general formula (Ia) of the first embodiment above or the first through twelfth aspects described above or a pharmaceutically acceptable salt thereof; and (b) a pharmaceutically acceptable carrier.

A fourteenth aspect of the first embodiment relates to methods of inducing an immune response in a subject, comprising administering a therapeutically effective amount of a compound according to general formula (Ia) of the first embodiment above or the first through twelfth aspects described above or a pharmaceutically acceptable salt thereof to the subject.

A fifteenth aspect of the first embodiment relates to methods of inducing an immune response in a subject, comprising administering a therapeutically effective amount of a composition according to the thirteenth aspect described above to the subject.

A sixteenth aspect of the first embodiment relates to methods of inducing a STING-dependent type I interferon production in a subject, comprising administering a therapeutically effective amount of a compound according to general formula (Ia) of the first embodiment above or the first through twelfth aspects described above or a pharmaceutically acceptable salt thereof to the subject.

A seventeenth aspect of the first embodiment relates to methods of inducing STING-dependent type I interferon production in a subject, comprising administering a therapeutically effective amount of a composition according to the thirteenth aspect described above to the subject.

An eighteenth aspect of the first embodiment relates to methods of inducing STING-dependent cytokine production in a subject, comprising administering a therapeutically effective amount of a compound according to general formula (Ia) of the first embodiment above or the first through twelfth aspects described above or a pharmaceutically acceptable salt thereof to the subject.

A nineteenth aspect relates to methods of inducing a STING-dependent cytokine production in a subject, comprising administering a therapeutically effective amount of a composition according to the thirteenth aspect described above to the subject.

In each aspect of the first embodiment described herein, variables $R^1$, $R^2$, $R^3$, $R^4$, $R^5$, $R^6$, $R^8$, $R^9$, $X^1$, $X^2$, and $X^3$ of general formula (Ia), and the various aspects and instances thereof, are each selected independently from each other, with the proviso that at least one of $R^1$, $R^2$, $R^3$, $R^4$, $R^5$, $R^6$, $R^8$, and $R^9$ is not H.

A second embodiment relates to compounds of general formula (Ia'):

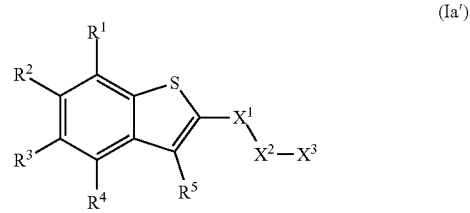

(Ia')

or a pharmaceutically acceptable salt thereof, wherein $R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; $R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; optionally $R^3$ and $R^4$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl; $R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), and $O(C_1$-$C_3$ haloalkyl); $X^1$ is C(O); $X^2$ is $(C(R^8)_2)_{(1-3)}$; each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; optionally 2 $R^8$ on different carbon atoms may be taken together, along with the atoms to which they are attached, to form a 3- to 6-membered fused ring; optionally 2 $R^8$ on a single carbon atom may be taken together, along with the atoms to which they are attached, to form a 3- to 6-membered spirocycle; $X^3$ is selected from the group consisting of $COOR^6$,

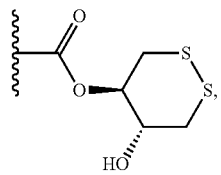 [SMILES: *C(=O)O[C@H]1CSSC[C@@H]1O]

$C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein when $X^1$—$X^2$—$X^3$ is $X^1$—$CHR^8$—$X^3$ or $X^1$—$CHR^8CH_2$—$X^3$, at least one of $R^2$ and $R^3$ is not selected from the group consisting of halogen, $OR^6$, $C_1$-$C_6$ alkyl, and $C_1$-$C_6$ haloalkyl.

In a first aspect of the second embodiment, $R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$. In instances of this aspect, $R^1$ is selected from the group consisting of H, F, $C_1$-$C_3$ alkyl, and $C_1$-$C_3$ haloalkyl. In particular instances of this aspect, $R^1$ is selected from the group consisting of H and F. In this aspect, all other groups are as provided in the general formula (Ia') of the second embodiment above.

In a second aspect of the second embodiment, $R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl. In instances of this aspect, $R^2$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl)$_2$, $NH(C_1$-$C_3$ alkyl), and $SC_1$-$C_3$ alkyl. In particular instances of this aspect, $R^2$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$. In this aspect, all other groups are as provided in the general formula (Ia') of the second embodiment above or the first aspect described above.

In a third aspect of the second embodiment, $R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl. In instances of this aspect, $R^3$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl)$_2$, $NH(C_1$-$C_3$ alkyl), and $SC_1$-$C_3$ alkyl. In particular instances of this aspect, $R^3$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$. In this aspect, all other groups are as provided in the general formula (Ia') of the second embodiment above or the first through second aspects described above.

In a fourth aspect of the second embodiment, $R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$. In instances of this aspect, $R^4$ is selected from the group consisting of H, F, $C_1$-$C_3$ alkyl, and $C_1$-$C_3$ haloalkyl. In particular instances of this aspect, $R^4$ is selected from the group consisting of H and F. In this aspect, all other groups are as provided in the general formula (Ia') of the second embodiment above or the first through third aspects described above.

In some instances of the third and fourth aspects of the second embodiment, $R^3$ and $R^4$ are taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl. In a first such instance, $R^3$ and $R^4$ are taken together with the atoms to which they are attached form a fused 5-membered heterocyclic ring including 1 to 2 ring members selected from the group consisting of O, S, and N, and that heterocyclic ring is optionally substituted optionally substituted with or more $C_1$-$C_3$ alkyl. In a second such instance, $R^3$ and $R^4$ are taken together with the atoms to which they are attached form a fused 5-membered heterocyclic ring including 1 to 2 ring members selected from the group consisting of O and N, and that heterocyclic ring is optionally substituted optionally substituted with $CH_3$. In such instances, all other groups are as provided in the general formula (Ia') of the second embodiment above.

In a fifth aspect of the second embodiment, $R^5$ is selected from the group consisting of H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$. In instances of this aspect, $R^5$ is selected from the group consisting of H, F, Cl, $C_1$-$C_3$ alkyl, and $C_1$-$C_3$ haloalkyl. In particular instances of this aspect, $R^5$ is selected from the group consisting of H and Cl. In this aspect, all other groups are as provided in the general formula (Ia') of the second embodiment above or the first through fourth aspects described above.

In a sixth aspect of the second embodiment, each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), $O(C_1$-$C_3$ haloalkyl). In instances of this aspect, each $R^6$ is independently selected from the group consisting of H, $C_1$-$C_4$ alkyl, and $C_1$-$C_4$ haloalkyl. In this aspect, all other groups are as provided in the general formula (Ia') of the second embodiment above or the first through fifth aspects described above.

In a seventh aspect of the second embodiment, $X^3$ is selected from the group consisting of $COOR^6$,

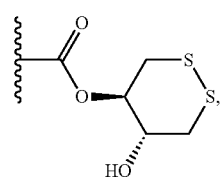 [SMILES: *C(=O)O[C@H]1CSSC[C@@H]1O]

$C(O)SR^6$, $C(S)OR^6$, $SO_2R^6$, and $C(O)N(R^9)_2$. In instances of this aspect, $X^3$ is selected from the group consisting of $COOR^6$,

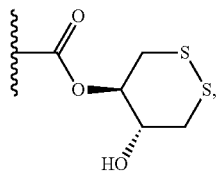 [SMILES: *C(=O)O[C@H]1CSSC[C@@H]1O]

$SO_2R^6$, and $C(O)N(R^9)_2$. In particular instances of this aspect, $X^3$ is selected from the group consisting of $COOR^6$ and

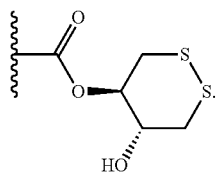 [SMILES: *C(=O)O[C@H]1CSSC[C@@H]1O]

In even more particular instances of this aspect, $X^3$ is selected from the group consisting of COOH, $COOC(CH_3)_3$, and

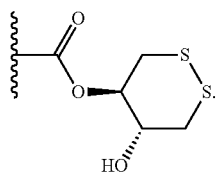 [SMILES: *C(=O)O[C@H]1CSSC[C@@H]1O]

In this aspect, all other groups are as provided in the general formula (Ia') of the second embodiment above or the first through sixth aspects described above.

In an eighth aspect of the second embodiment, each $R^9$ is independently selected from the group consisting of H, $COOR^6$, and $SO_2R^6$. In instances of this aspect, each $R^9$ is independently H. In this aspect, all other groups are as provided in the general formula (Ia') of the second embodiment above or the first through seventh aspects described above.

In a ninth aspect of the second embodiment, $X^2$ is $(C(R^8)_2)_{(1-3)}$, wherein each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl. In a first instance of this aspect, $X^2$ is $CH_2CHR^8$, where $R^8$ is selected from the group consisting of H, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl. In particular occurrences of this first instance, $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, $X^2$ is $CHR^8CHR^8$, where $R^8$ is selected from the group consisting of H, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl, and optionally 2 $R^8$ are taken together, along with the atoms to which they are attached, to form a 3- to 6-membered fused ring. In particular occurrences of this second instance, $X^2$ is $CHR^8CHR^8$, where $R^8$ is selected from the group consisting of H and $C_1$-$C_4$ alkyl, and optionally 2 $R^8$ are taken together, along with the atoms to which they are attached, to form a 3- to 6-membered fused ring. In specific occurrences of this second instance, $X^2$ is $CHR^8CHR^8$, where the 2 $R^8$ are taken together, along with the atoms to which they are attached, to form a 3-membered fused ring. In a third instance of this aspect, $X^2$ is $CH_2C(R^8)_2$, where $R^8$ is selected from the group consisting of H, OH, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl, and optionally 2 $R^8$ are taken together, along with the atoms to which they are attached, to form a 3- to 6-membered spirocycle. In particular occurrences of this third instance, $X^2$ is $CH_2C(R^8)_2$, where $R^8$ is selected from the group consisting of H, OH, and $CH_3$. In additional occurrences of this third instance, $X^2$ is $CH_2C(R^8)_2$, where the 2 $R^8$ are taken together, along with the atoms to which they are attached, to form a 3- to 6-membered spirocycle. In this aspect, all other groups are as provided in the general formula (Ia') of the second embodiment above or the first through eighth aspects described above.

In a tenth aspect of the second embodiment, $R^1$ is selected from the group consisting of H, F, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl; $R^3$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl; $R^4$ is selected from the group consisting of H, F, $C_1$-$C_3$ alkyl, and $C_1$-$C_3$ haloalkyl; $R^5$ is selected from the group consisting of H, F, Cl, $C_1$-$C_3$ alkyl, and $C_1$-$C_3$ haloalkyl; each $R^6$ is independently selected from the group consisting of H, $C_1$-$C_4$ alkyl, and $C_1$-$C_4$ haloalkyl; $X^1$ is C(O); $X^2$ is $CH_2CHR^8$; $X^3$ is selected from the group consisting of $COOR^6$,

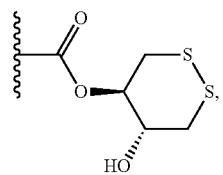 [SMILES: *C(=O)O[C@H]1CSSC[C@@H]1O]

$SO_2R^6$, and $C(O)N(R^9)_2$, where each $R^9$ is independently selected from the group consisting of H, $COOR^6$, and $SO_2R^6$; and $R^8$ is selected from the group consisting of H, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl. In instances of this aspect, $R^1$ is selected from the group consisting of H and F; $R^2$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$; $R^3$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$; $R^4$ is selected from the group consisting of H and F; $R^5$ is selected from the group consisting of H and Cl; each $R^6$ is independently selected from the group consisting of H, $C_1$-$C_4$ alkyl, and $C_1$-$C_4$ haloalkyl; $X^1$ is C(O); $X^2$ is $CH_2CHR^8$; $X^3$ is selected from the group consisting of COOH, $COOC(CH_3)_3$, and

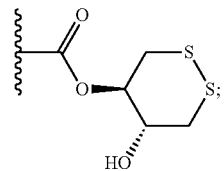 [SMILES: *C(=O)O[C@H]1CSSC[C@@H]1O]

and $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In this aspect, all other groups are as provided in the general formula (Ia') of the second embodiment above.

In an eleventh aspect of the second embodiment, $R^1$ is selected from the group consisting of H, F, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl; $R^3$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl; $R^4$ is selected from the group consisting of H, F, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_4$ alkyl, and $C_1$-$C_4$ haloalkyl; $X^1$ is C(O); $X^2$ is $CHR^8CHR^8$; $X^3$ is selected from the group consisting of $COOR^6$,

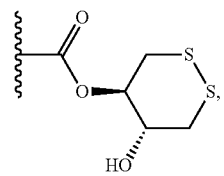 [SMILES: *C(=O)O[C@H]1CSSC[C@@H]1O]

$SO_2R^6$, and $C(O)N(R^9)_2$, where each $R^9$ is independently selected from the group consisting of H, $COOR^6$, and $SO_2R^6$; and each $R^8$ is selected from the group consisting of H, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl, and where optionally 2 $R^8$ are taken together, along with the atoms to which they are attached, to form a 3- to 6-membered fused ring. In instances of this aspect, $R^1$ is selected from the group consisting of H and F; $R^2$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$; $R^3$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$; $R^4$ is selected from the group consisting of H and F; $R^5$ is selected from the group consisting of H and Cl; each $R^6$ is independently selected from the group consisting of H, $C_1$-$C_4$ alkyl, and $C_1$-$C_4$ haloalkyl; $X^1$ is C(O); $X^2$ is $CHR^8CHR^8$; $X^3$ is selected from the group consisting of COOH, $COOC(CH_3)_3$, and

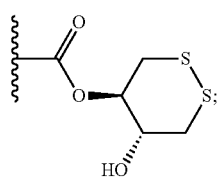 [SMILES: *C(=O)O[C@H]1CSSC[C@@H]1O]

and each $R^8$ is selected from the group consisting of H and $C_1$-$C_4$ alkyl. In additional instances of this aspect, $R^1$ is selected from the group consisting of H and F; $R^2$ is selected from the group consisting of Br, Cl, F, $CH_3$, $CH_2CH_3$, $CH_2CH_2CH_3$, $CH_2CH_2F$, $CH=CH_2$, $C≡CH$, OH, $OCH_3$, $OCH_2CH_3$, $OCHF_2$, $SCH_3$, and $NHCH_3$; $R^3$ is selected from the group consisting of Br, Cl, F, $CH_3$, $CH_2CH_3$, $CH_2CH_2CH_3$, $CH_2CH_2F$, $CH=CH_2$, $C≡CH$, OH, $OCH_3$, $OCH_2CH_3$, $OCHF_2$, $SCH_3$, and $NHCH_3$, $R^4$ is selected from the group consisting of H and F; $R^5$ is selected from the group consisting of H and Cl; each $R^6$ is independently selected from the group consisting of H, $C_1$-$C_4$ alkyl, and $C_1$-$C_4$ haloalkyl; $X^1$ is C(O); $X^2$ is $CHR^8CHR^8$; $X^3$ is selected from the group consisting of COOH, $COOC(CH_3)_3$, and

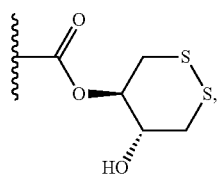 [SMILES: *C(=O)O[C@H]1CSSC[C@@H]1O]

and the 2 $R^8$ are taken together, along with the atoms to which they are attached, to form a 3- to 6-membered fused ring. In this aspect, all other groups are as provided in the general formula (Ia') of the second embodiment above.

In a twelfth aspect of the second embodiment, $R^1$ is selected from the group consisting of H, F, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl; $R^3$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl; $R^4$ is selected from the group consisting of H, F, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_4$ alkyl, and $C_1$-$C_4$ haloalkyl; $X^1$ is C(O); $X^2$ is $CH_2C(R^8)_2$; $X^3$ is selected from the group consisting of $COOR^6$,

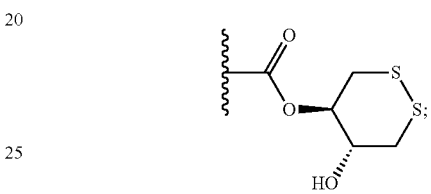

$SO_2R^6$, and $C(O)N(R^9)_2$, where each $R^9$ is independently selected from the group consisting of H, $COOR^6$, and $SO_2R^6$; and each $R^8$ is selected from the group consisting of H, OH, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl, and where optionally 2 $R^8$ are taken together, along with the atoms to which they are attached, to form a 3- to 6-membered spirocycle. In instances of this aspect, $R^1$ is selected from the group consisting of H and F; $R^2$ is selected from the group consisting of Br, Cl, F, $CH_3$, $CH_2CH_3$, $CH_2CH_2CH_3$, $CH_2CH_2F$, $CH=CH_2$, $C≡CH$, OH, $OCH_3$, $OCH_2CH_3$, $OCHF_2$, $SCH_3$, and $NHCH_3$; $R^3$ is selected from the group consisting of Br, Cl, F, $CH_3$, $CH_2CH_3$, $CH_2CH_2CH_3$, $CH_2CH_2F$, $CH=CH_2$, $C≡CH$, OH, $OCH_3$, $OCH_2CH_3$, $OCHF_2$, $SCH_3$, and $NHCH_3$; $R^4$ is selected from the group consisting of H and F; $R^5$ is selected from the group consisting of H and Cl; each $R^6$ is independently selected from the group consisting of H, $C_1$-$C_4$ alkyl, and $C_1$-$C_4$ haloalkyl; $X^1$ is C(O); $X^2$ is $CH_2C(R^8)_2$; $X^3$ is selected from the group consisting of COOH, $COOC(CH_3)_3$, and

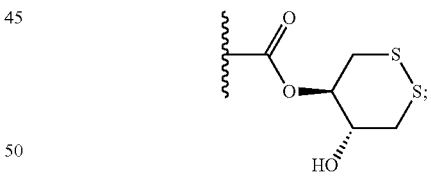

and each $R^8$ is selected from the group consisting of H, OH, and $CH_3$. In additional instances of this aspect, $R^1$ is selected from the group consisting of H and F; $R^2$ is selected from the group consisting of Br, Cl, F, $CH_3$, $CH_2CH_3$, $CH_2CH_2CH_3$, $CH_2CH_2F$, $CH=CH_2$, $C≡CH$, OH, $OCH_3$, $OCH_2CH_3$, $OCHF_2$, $SCH_3$, and $NHCH_3$; $R^3$ is selected from the group consisting of Br, Cl, F, $CH_3$, $CH_2CH_3$, $CH_2CH_2CH_3$, $CH_2CH_2F$, $CH=CH_2$, $C≡CH$, OH, $OCH_3$, $OCH_2CH_3$, $OCHF_2$, $SCH_3$, and $NHCH_3$; $R^4$ is selected from the group consisting of H and F; $R^5$ is selected from the group consisting of H and Cl; each $R^6$ is independently selected from the group consisting of H, $C_1$-$C_4$ alkyl, and $C_1$-$C_4$ haloalkyl; $X^1$ is C(O); $X^2$ is $CH_2C(R^8)_2$; $X^3$ is selected from the group consisting of COOH, $COOC(CH_3)_3$, and and the 2 $R^8$ are taken together, along with the atoms to which they are attached, to form a 3- to 6-membered spirocycle. In this aspect, all other groups are as provided in the general formula (Ia') of the second embodiment above.

A thirteenth aspect of the second embodiment relates to a pharmaceutical composition, said pharmaceutical composition comprising (a) a compound according to general formula (Ia') of the second embodiment above or the first through twelfth aspects described above or a pharmaceutically acceptable salt thereof; and (b) a pharmaceutically acceptable carrier.

A fourteenth aspect of the second embodiment relates to methods of inducing an immune response in a subject, comprising administering a therapeutically effective amount of a compound according to general formula (Ia') of the second embodiment above or the first through twelfth aspects described above or a pharmaceutically acceptable salt thereof to the subject.

A fifteenth aspect of the second embodiment relates to methods of inducing an immune response in a subject, comprising administering a therapeutically effective amount of a composition according to the thirteenth aspect described above to the subject.

A sixteenth aspect of the second embodiment relates to methods of inducing a STING-dependent type I interferon production in a subject, comprising administering a therapeutically effective amount of a compound according to general formula (Ia') of the first embodiment above or the first through twelfth aspects described above or a pharmaceutically acceptable salt thereof to the subject.

A seventeenth aspect of the second embodiment relates to methods of inducing STING-dependent type I interferon production in a subject, comprising administering a therapeutically effective amount of a composition according to the thirteenth aspect described above to the subject.

An eighteenth aspect of the second embodiment relates to methods of inducing STING-dependent cytokine production in a subject, comprising administering a therapeutically effective amount of a compound according to general formula (Iaa) of the second embodiment above or the first through twelfth aspects described above or a pharmaceutically acceptable salt thereof to the subject.

A nineteenth aspect of the second embodiment relates to methods of inducing a STING-dependent cytokine production in a subject, comprising administering a therapeutically effective amount of a composition according to the thirteenth aspect described above to the subject.

In each aspect of the second embodiment described herein, variables $R^1$, $R^2$, $R^3$, $R^4$, $R^5$, $R^6$, $R^8$, $R^9$, $X^1$, $X^2$, and $X^3$ of general formula (Ia'), and the various aspects and instances thereof, are each selected independently from each other, with the proviso that at least one of $R^1$, $R^2$, $R^3$, $R^4$, $R^5$, $R^6$, $R^8$, and $R^9$ is not H.

A third embodiment relates to compounds of general formula (Ib):

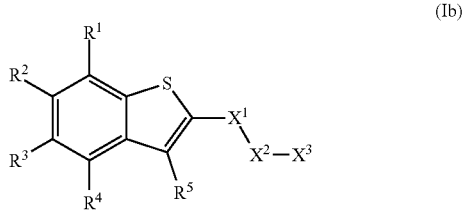

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is C(O); $X^2$ is $CH_2CHR^8$; each $R^8$ is independently selected from the group consisting of halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein $X^1$—$X^2$—$X^3$ is $X^1$—$CH_2CHR^8$—$X^3$.

In a first aspect of the third embodiment, $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, $R^1$ is selected from the group consisting of H, F, Cl, $C_1$-$C_3$ alkyl, and $C_1$-$C_3$ haloalkyl. In particular instances of this aspect, $R^1$ is selected from the group consisting of H and F. In this aspect, all other groups are as provided in the general formula (Ib) of the third embodiment above.

In a second aspect of the third embodiment, $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^2$ is selected from the group consisting of Br, Cl, $CH_3$, $CH_2CH_3$, $CH$=$CH_2$, $OCH_3$, and $N(R^6)_2$. In this aspect, all other groups are as provided in the general formula (Ib) of the third embodiment above or the first aspect described above.

In a third aspect of the third embodiment, $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^3$ is selected from the group consisting of Br, Cl, $CH_3$, $CH_2CH_3$, $CH$=$CH_2$, $OCH_3$, and $N(R^6)_2$. In this aspect, all other groups are as provided in the general formula (Ib) of the third embodiment above or the first through second aspects described above.

In a fourth aspect of the third embodiment, $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)

$N(R^6)_2$. In instances of this aspect, $R^4$ is selected from the group consisting of H, F, Cl, $C_1$-$C_3$ alkyl, and $C_1$-$C_3$ haloalkyl. In particular instances of this aspect, $R^4$ is selected from the group consisting of H and F. In this aspect, all other groups are as provided in the general formula (Ib) of the third embodiment above or the first through third aspects described above.

In a fifth aspect of the third embodiment, $R^5$ is selected from the group consisting of H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$. In instances of this aspect, $R^5$ is selected from the group consisting of H, F, Cl, $C_1$-$C_3$ alkyl, and $C_1$-$C_3$ haloalkyl. In particular instances of this aspect, $R^5$ is H. In this aspect, all other groups are as provided in the general formula (Ib) of the third embodiment above or the first through fourth aspects described above.

In a sixth aspect of the third embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H and $CH_3$. In this aspect, all other groups are as provided in the general formula (Ib) of the third embodiment above or the first through fifth aspects described above.

In a seventh aspect of the third embodiment, $X^3$ is selected from the group consisting of $COOR^6$, $C(O)SR^6$, $C(S)OR^6$, $SO_2R^6$, and $C(O)N(R^9)_2$. In instances of this aspect, $X^3$ is selected from the group consisting of $COOR^6$, $SO_2R^6$, and $C(O)N(R^9)_2$. In particular instances of this aspect, $X^3$ is $COOR^6$. In even more particular instances of this aspect, $X^3$ is COOH. In this aspect, all other groups are as provided in the general formula (Ib) of the third embodiment above or the first through sixth aspects described above.

In an eighth aspect of the third embodiment, each $R^9$ is independently selected from the group consisting of H, $COOR^6$, and $SO_2R^6$. In instances of this aspect, each $R^9$ is independently H. In this aspect, all other groups are as provided in the general formula (Ib) of the third embodiment above or the first through seventh aspects described above.

In a ninth aspect of the third embodiment, $X^2$ is $CH_2CHR^8$, wherein each $R^8$ is independently selected from the group consisting of halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$. In instances of this aspect, $R^8$ is selected from the group consisting of $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular instances, $R^8$ is selected from the group consisting of $CH_3$, $CH_2CH_3$, $CH_2CH_2CH_3$, $CH(CH_3)_2$, $CH_2OCH_3$, and cyclopropyl. In this aspect, all other groups are as provided in the general formula (Ib) of the third embodiment above or the first through eighth aspects described above.

In a tenth aspect of the third embodiment, $R^1$ is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $R^8$ is selected from the group consisting of $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl; and $X^3$ is selected from the group consisting of $COOR^6$, $SO_2R^6$, and $C(O)N(R^9)_2$; wherein $X^1$—$X^2$—$X^3$ is selected from the group consisting of $C(O)$—$CH_2CHR^8$—$COOR^6$, $C(O)$—$CH_2CHR^8$—$SO_2R^6$, and $C(O)$—$CH_2CHR^8$—$C(O)N(R^9)_2$. In instances of this aspect, $R^1$ is selected from the group consisting of H and F; $R^2$ is selected from the group consisting of Br, Cl, $CH_3$, $CH_2CH_3$, $CH=CH_2$, $OCH_3$, and $N(R^6)_2$; $R^3$ is selected from the group consisting of Br, Cl, $CH_3$, $CH_2CH_3$, $CH=CH_2$, $OCH_3$, and $N(R^6)_2$; $R^4$ is selected from the group consisting of H and F; $R^5$ is H; each $R^6$ is independently selected from the group consisting of H and $CH_3$; $R^8$ is selected from the group consisting of $CH_3$, $CH_2CH_3$, $CH_2CH_2CH_3$, $CH(CH_3)_2$, $CH_2OCH_3$, and cyclopropyl; and $X^3$ is COOH; wherein $X^1$—$X^2$—$X^3$ is $C(O)$—$CH_2CHR^8$—COOH. In this aspect, all other groups are as provided in the general formula (Ib) of the third embodiment above.

An eleventh aspect of the third embodiment relates to a pharmaceutical composition, said pharmaceutical composition comprising (a) a compound according to general formula (Ib) of the third embodiment above or the first through eleventh aspects described above or a pharmaceutically acceptable salt thereof; and (b) a pharmaceutically acceptable carrier.

A twelfth aspect of the third embodiment relates to methods of inducing an immune response in a subject, comprising administering a therapeutically effective amount of a compound according to general formula (Ib) of the third embodiment above or the first through tenth aspects described above or a pharmaceutically acceptable salt thereof to the subject.

A thirteenth aspect of the third embodiment relates to methods of inducing an immune response in a subject, comprising administering a therapeutically effective amount of a composition according to the eleventh aspect described above to the subject.

A fourteenth aspect of the third embodiment relates to methods of inducing a STING-dependent type I interferon production in a subject, comprising administering a therapeutically effective amount of a compound according to general formula (Ib) of the third embodiment above or the first through tenth aspects described above or a pharmaceutically acceptable salt thereof to the subject.

A fifteenth aspect of the third embodiment relates to methods of inducing a STING-dependent type I interferon production in a subject, comprising administering a therapeutically effective amount of a composition according to the eleventh aspect described above to the subject.

A sixteenth aspect of the third embodiment relates to methods of inducing STING-dependent cytokine production in a subject, comprising administering a therapeutically effective amount of a compound according to general formula (Ib) of the third embodiment above or the first through tenth aspects described above or a pharmaceutically acceptable salt thereof to the subject.

A seventeenth aspect of the third embodiment relates to methods of inducing STING-dependent cytokine production in a subject, comprising administering a therapeutically effective amount of a composition according to the eleventh aspect described above to the subject.

In each aspect of the third embodiment described herein, variables $R^1$, $R^2$, $R^3$, $R^4$, $R^5$, $R^6$, $R^8$, $R^9$, $X^1$, $X^2$, and $X^3$ of general formula (Ib), and the various aspects and instances thereof, are each selected independently from each other, with the proviso that at least one of $R^1$, $R^2$, $R^3$, $R^4$, $R^5$, $R^6$, $R^8$, and $R^9$ is not H.

A fourth embodiment relates to compounds of general formula (Ib'):

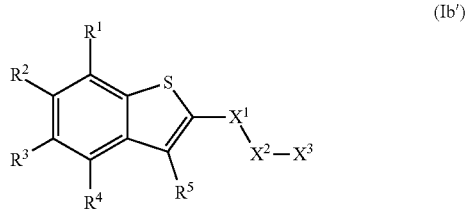

(Ib')

or a pharmaceutically acceptable salt thereof, wherein $R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; $R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; optionally $R^3$ and $R^4$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl; $R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), and $O(C_1$-$C_3$ haloalkyl); $X^1$ is C(O); $X^2$ is $CH_2CHR^8$; each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $X^3$ is selected from the group consisting of $COOR^6$,

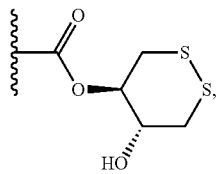

$C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein $X^1$—$X^2$—$X^3$ is C(O)—$CH_2CHR^8$—$X^3$.

In a first aspect of the fourth embodiment, $R^1$ is selected from the group consisting of $R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$. In instances of this aspect, $R^1$ is selected from the group consisting of H, F, $C_1$-$C_3$ alkyl, and $C_1$-$C_3$ haloalkyl. In particular instances of this aspect, $R^1$ is selected from the group consisting of H and F. In this aspect, all other groups are as provided in the general formula (Ib') of the fourth embodiment above.

In a second aspect of the fourth embodiment, $R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl. In instances of this aspect, $R^2$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl. In particular instances of this aspect, $R^2$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$. In this aspect, all other groups are as provided in the general formula (Ib') of the fourth embodiment above or the first aspect described above.

In a third aspect of the fourth embodiment, $R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl. In instances of this aspect, $R^3$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl$)_2$, $NH(C_1$-$C_3$ alkyl), and $SC_1$-$C_3$ alkyl. In particular instances of this aspect, $R^3$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$. In this aspect, all other groups are as provided in the general formula (Ib') of the fourth embodiment above or the first through second aspects described above.

In a fourth aspect of the fourth embodiment, $R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$. In instances of this aspect, $R^4$ is selected from the group consisting of H, F, $C_1$-$C_3$ alkyl, and $C_1$-$C_3$ haloalkyl. In particular instances of this aspect, $R^4$ is selected from the group consisting of H and F. In this aspect, all other groups are as provided in the general formula (Ib') of the fourth embodiment above or the first through third aspects described above.

In some instances of the third and fourth aspects of the fourth embodiment, $R^3$ and $R^4$ are taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl. In a first such instance, $R^3$ and $R^4$ are taken together with the atoms to which they are attached form a fused 5-membered heterocyclic ring including 1 to 2 ring members selected from the group consisting of O, S, and N, and that heterocyclic ring is optionally substituted optionally substituted with or more $C_1$-$C_3$ alkyl. In a second such instance, $R^3$ and $R^4$ are taken together with the atoms to which they are attached form a fused 5-membered heterocyclic ring including 1 to 2 ring members selected from the group consisting of O and N, and that heterocyclic ring is optionally substituted optionally substituted with $CH_3$. In such instances, all other groups are as provided in the general formula (Ib') of the fourth embodiment above.

In a fifth aspect of the fourth embodiment, $R^5$ is selected from the group consisting of H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$. In instances of this aspect, $R^5$ is selected from the group consisting of H, F, Cl, $C_1$-$C_3$ alkyl, and $C_1$-$C_3$ haloalkyl. In particular instances of this aspect, $R^5$ is selected from the group consisting of H and Cl. In this aspect, all other groups are as provided in the general formula (Ib') of the fourth embodiment above or the first through fourth aspects described above.

In a sixth aspect of the fourth embodiment, each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), and $O(C_1$-$C_3$ haloalkyl). In instances of this aspect, each $R^6$ is independently selected from the group consisting of H, $C_1$-$C_4$ alkyl, and $C_1$-$C_4$ haloalkyl. In this aspect, all other groups are as provided in the general formula (Ib') of the fourth embodiment above or the first through fifth aspects described above.

In a seventh aspect of the fourth embodiment, $X^3$ is selected from the group consisting of $COOR^6$,

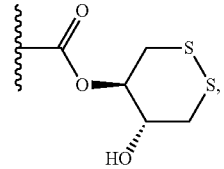 [SMILES: *C(=O)O[C@H]1CSSC[C@@H]1O]

$C(O)SR^6$, $C(S)OR^6$, $SO_2R^6$, and $C(O)N(R^9)_2$. In instances of this aspect, $X^3$ is selected from the group consisting of $COOR^6$,

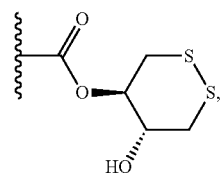 [SMILES: *C(=O)O[C@H]1CSSC[C@@H]1O]

$SO_2R^6$, and $C(O)N(R^9)_2$. In particular instances of this aspect, $X^3$ is selected from the group consisting of $COOR^6$ and

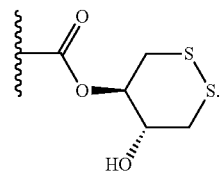 [SMILES: *C(=O)O[C@H]1CSSC[C@@H]1O]

In even more particular instances of this aspect, $X^3$ is selected from the group consisting of COOH, $COOC(CH_3)_3$, and

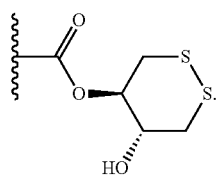 [SMILES: *C(=O)O[C@H]1CSSC[C@@H]1O]

In this aspect, all other groups are as provided in the general formula (Ib') of the fourth embodiment above or the first through sixth aspects described above.

In an eighth aspect of the fourth embodiment, each $R^9$ is independently selected from the group consisting of H, $COOR^6$, and $SO_2R^6$. In instances of this aspect, each $R^9$ is independently H. In this aspect, all other groups are as provided in the general formula (Ib') of the fourth embodiment above or the first through seventh aspects described above.

In a ninth aspect of the fourth embodiment, $X^2$ is $CH_2CHR^8$, wherein each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl. In instances of this aspect, $R^8$ is selected from the group consisting of H, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl. In particular instances, $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In this aspect, all other groups are as provided in the general formula (Ib') of the fourth embodiment above or the first through eighth aspects described above.

In a tenth aspect of the fourth embodiment, $R^1$ is selected from the group consisting of H, F, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl)$_2$, $NH(C_1$-$C_3$ alkyl), and $SC_1$-$C_3$ alkyl; $R^3$ is selected from the group consisting of halogen, $C_1$-$C_3$ alkyl, $C_1$-$C_3$ haloalkyl, $OC_1$-$C_3$ alkyl, $OC_1$-$C_3$ haloalkyl, OH, $C_2$-$C_3$ alkenyl, $C_2$-$C_3$ alkynyl, $N(C_1$-$C_3$ alkyl)$_2$, $NH(C_1$-$C_3$ alkyl), and $SC_1$-$C_3$ alkyl; $R^4$ is selected from the group consisting of H, F, $C_1$-$C_3$ alkyl, and $C_1$-$C_3$ haloalkyl; $R^5$ is selected from the group consisting of H, F, Cl, $C_1$-$C_3$ alkyl, and $C_1$-$C_3$ haloalkyl; each $R^6$ is independently selected from the group consisting of H, $C_1$-$C_4$ alkyl, and $C_1$-$C_4$ haloalkyl; $X^1$ is C(O); $X^2$ is $CH_2CHR^8$; $X^3$ is selected from the group consisting of $COOR^6$,

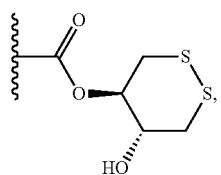 [SMILES: *C(=O)O[C@H]1CSSC[C@@H]1O]

$SO_2R^6$, and $C(O)N(R^9)_2$, where each $R^9$ is independently selected from the group consisting of H, $COOR^6$, and $SO_2R^6$; and $R^8$ is selected from the group consisting of H, $C_1$-$C_4$ alkyl, $C_1$-$C_4$ alkyl substituted by OH, $C_1$-$C_4$ alkyl substituted by $OC_1$-$C_4$ alkyl, and $C_3$-$C_6$ cycloalkyl. In instances of this aspect, $R^1$ is selected from the group consisting of H and F; $R^2$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$; $R^3$ is selected from the group consisting of Br, Cl, F, $CH_3$, $CH_2CH_3$, $CH_2CH_2CH_3$, $CH_2CH_2F$, $CH=CH_2$, $C\equiv CH$, OH, $OCH_3$, $OCH_2CH_3$, $OCHF_2$, $SCH_3$, and $NHCH_3$; $R^4$ is selected from the group consisting of H and F; $R^5$ is selected from the group consisting of H and Cl; each $R^6$ is independently selected from the group consisting of H, $C_1$-$C_4$ alkyl, and $C_1$-$C_4$ haloalkyl; $X^1$ is C(O); $X^2$ is $CH_2CHR^8$; $X^3$ is selected from the group consisting of COOH, $COOC(CH_3)_3$, and

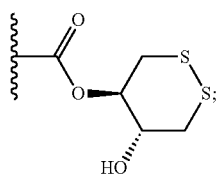 [SMILES: *C(=O)O[C@H]1CSSC[C@@H]1O]

and $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In this aspect, all other groups are as provided in the general formula (Ib') of the fourth embodiment above.

An eleventh aspect of the fourth embodiment relates to a pharmaceutical composition, said pharmaceutical composition comprising (a) a compound according to general formula (Ib') of the fourth embodiment above or the first through eleventh aspects described above or a pharmaceutically acceptable salt thereof; and (b) a pharmaceutically acceptable carrier.

A twelfth aspect of the fourth embodiment relates to methods of inducing an immune response in a subject, comprising administering a therapeutically effective amount of a compound according to general formula (Ib') of the fourth embodiment above or the first through tenth aspects described above or a pharmaceutically acceptable salt thereof to the subject.

A thirteenth aspect of the fourth embodiment relates to methods of inducing an immune response in a subject, comprising administering a therapeutically effective amount of a composition according to the eleventh aspect described above to the subject.

A fourteenth aspect of the fourth embodiment relates to methods of inducing a STING-dependent type I interferon production in a subject, comprising administering a therapeutically effective amount of a compound according to general formula (Ib') of the fourth embodiment above or the first through tenth aspects described above or a pharmaceutically acceptable salt thereof to the subject.

A fifteenth aspect of the fourth embodiment relates to methods of inducing a STING-dependent type I interferon production in a subject, comprising administering a therapeutically effective amount of a composition according to the eleventh aspect described above to the subject.

A sixteenth aspect of the fourth embodiment relates to methods of inducing STING-dependent cytokine production in a subject, comprising administering a therapeutically effective amount of a compound according to general formula (Ib') of the fourth embodiment above or the first through tenth aspects described above or a pharmaceutically acceptable salt thereof to the subject.

A seventeenth aspect of the fourth embodiment relates to methods of inducing STING-dependent cytokine production in a subject, comprising administering a therapeutically effective amount of a composition according to the eleventh aspect described above to the subject.

In each aspect of the fourth embodiment described herein, variables $R^1$, $R^2$, $R^3$, $R^4$, $R^5$, $R^6$, $R^8$, $R^9$, $X^1$, $X^2$, and $X^3$ of general formula (Ib'), and the various aspects and instances thereof, are each selected independently from each other, with the proviso that at least one of $R^1$, $R^2$, $R^3$, $R^4$, $R^5$, $R^6$, $R^8$, and $R^9$ is not H.

Aspects of a fifth embodiment of this disclosure relate to uses of compounds of general formula (I), and pharmaceutically acceptable salts thereof. The compounds of general formula (I) may be useful as agents to induce immune responses, to induce STING-dependent type I interferon production, and/or to treat a cell proliferation disorder. In these aspects of the fifth, the compound of formula (I) is

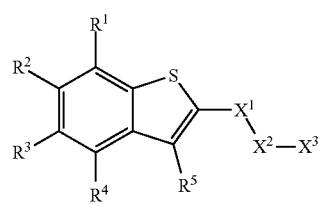

(I)

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ is selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is C(O); $X^2$ is $(C(R^8)_2)_{(1-3)}$; each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$.

A first aspect of the fifth embodiment relates to methods of inducing an immune response in a subject, comprising administering a therapeutically effective amount of a compound of general formula (I) above or a pharmaceutically acceptable salt thereof to the subject.

A second aspect of the fifth embodiment relates to methods of inducing an immune response in a subject, comprising administering a therapeutically effective amount of a composition comprising a compound of general formula (I) above or a pharmaceutically acceptable salt thereof to the subject.

A third aspect of the fifth embodiment relates to methods of inducing STING-dependent type I interferon production in a subject, comprising administering a therapeutically effective amount of a compound of general formula (I) or a pharmaceutically acceptable salt thereof to the subject.

A fourth aspect of the fifth embodiment relates to methods of inducing STING-dependent type I interferon production in a subject, comprising administering a therapeutically effective amount of a composition comprising a compound of general formula (I) above or a pharmaceutically acceptable salt thereof to the subject.

A fifth aspect of the fifth embodiment relates to methods of inducing STING-dependent cytokine production in a subject, comprising administering a therapeutically effective amount of a compound of general formula (I) above or a pharmaceutically acceptable salt thereof to the subject.

A sixth aspect of the fifth embodiment relates to methods of inducing STING-dependent cytokine production in a subject, comprising administering a therapeutically effective amount of a composition comprising a compound of general formula (I) above or a pharmaceutically acceptable salt thereof to the subject.

In each aspect of the fifth embodiment described herein, variables $R^1$, $R^2$, $R^3$, $R^4$, $R^5$, $R^6$, $R^8$, $R^9$, $X^1$, $X^2$, and $X^3$ of general formula (I), and the various aspects and instances thereof, are each selected independently from each other, with the proviso that at least one of $R^1$, $R^2$, $R^3$, $R^4$, $R^5$, $R^6$, $R^8$, and $R^9$ is not H.

Aspects of a sixth embodiment of this disclosure relate to uses of compounds of general formula (I'), and pharmaceutically acceptable salts thereof. The compounds of general formula (I') may be useful as agents to induce immune responses, to induce STING-dependent type I interferon production, and/or to treat a cell proliferation disorder. In these aspects of the fifth, the compound of formula (I') is

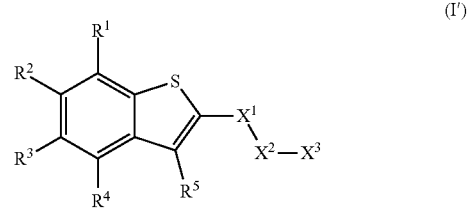

(I')

or a pharmaceutically acceptable salt thereof, wherein $R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; $R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; optionally $R^3$ and $R^4$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl; $R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), and $O(C_1$-$C_3$ haloalkyl); $X^1$ is C(O); $X^2$ is $(C(R^8)_2)_{(1-3)}$; each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; optionally 2 $R^8$ on different carbon atoms may be taken together, along with the atoms to which they are attached, to form a 3- to 6-membered fused ring; optionally 2 $R^8$ on a single carbon atom may be taken together, along with the atoms to which they are attached, to form a 3- to 6-membered spirocycle; $X^3$ is selected from the group consisting of $COOR^6$,

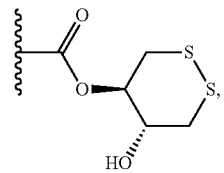 [SMILES: *C(=O)O[C@H]1CSSC[C@@H]1O]

$C(O)SR^6$, $C(S)OR^6$, $SO_2R^6$, and $C(O)N(R^9)_2$; and each $R^9$ is independently selected from the group consisting of H, $COOR^6$, and $SO_2R^6$.

A first aspect of the sixth embodiment relates to methods of inducing an immune response in a subject, comprising administering a therapeutically effective amount of a compound of general formula (I') above or a pharmaceutically acceptable salt thereof to the subject.

A second aspect of the sixth embodiment relates to methods of inducing an immune response in a subject, comprising administering a therapeutically effective amount of a composition comprising a compound of general formula (I') above or a pharmaceutically acceptable salt thereof to the subject.

A third aspect of the sixth embodiment relates to methods of inducing STING-dependent type I interferon production in a subject, comprising administering a therapeutically effective amount of a compound of general formula (I') or a pharmaceutically acceptable salt thereof to the subject.

A fourth aspect of the sixth embodiment relates to methods of inducing STING-dependent type I interferon production in a subject, comprising administering a therapeutically effective amount of a composition comprising a compound of general formula (I') above or a pharmaceutically acceptable salt thereof to the subject.

A fifth aspect of the sixth embodiment relates to methods of inducing STING-dependent cytokine production in a subject, comprising administering a therapeutically effective amount of a compound of general formula (I') above or a pharmaceutically acceptable salt thereof to the subject.

A sixth aspect of the sixth embodiment relates to methods of inducing STING-dependent cytokine production in a subject, comprising administering a therapeutically effective amount of a composition comprising a compound of general formula (I') above or a pharmaceutically acceptable salt thereof to the subject.

In each aspect of the sixth embodiment described herein, variables $R^1$, $R^2$, $R^3$, $R^4$, $R^5$, $R^6$, $R^8$, $R^9$, $X^1$, $X^2$, and $X^3$ of general formula (I'), and the various aspects and instances thereof, are each selected independently from each other, with the proviso that at least one of $R^1$, $R^2$, $R^3$, $R^4$, $R^5$, $R^6$, $R^8$, and $R^9$ is not H.

A seventh embodiment relates to a compound selected from the group consisting of 33
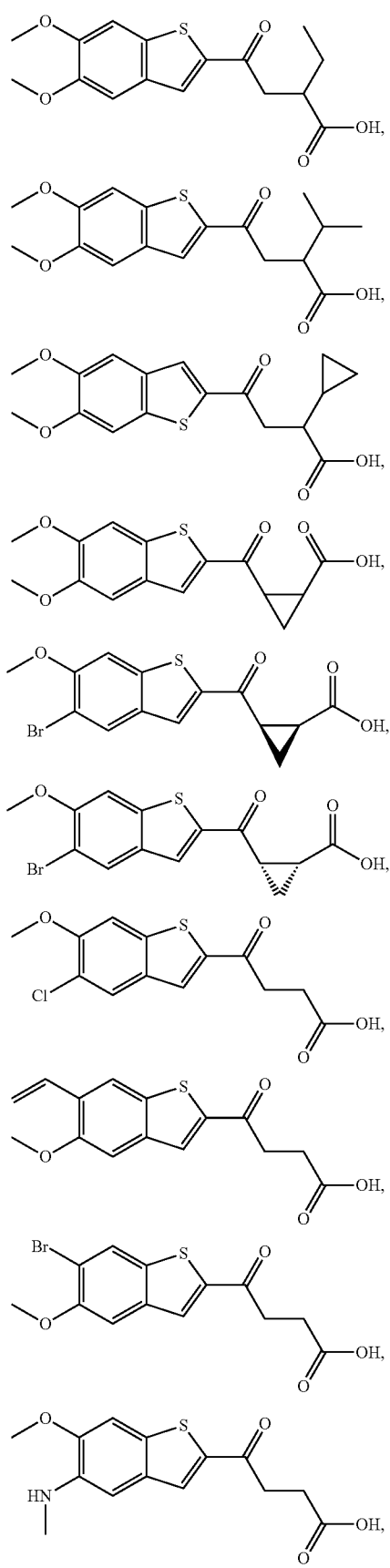
34
-continued
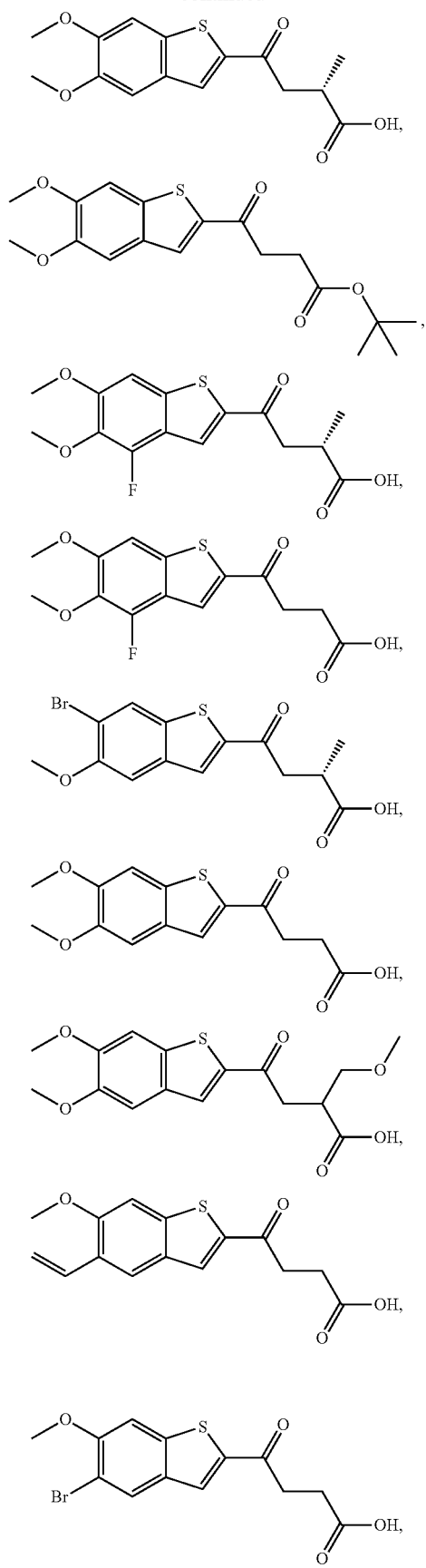

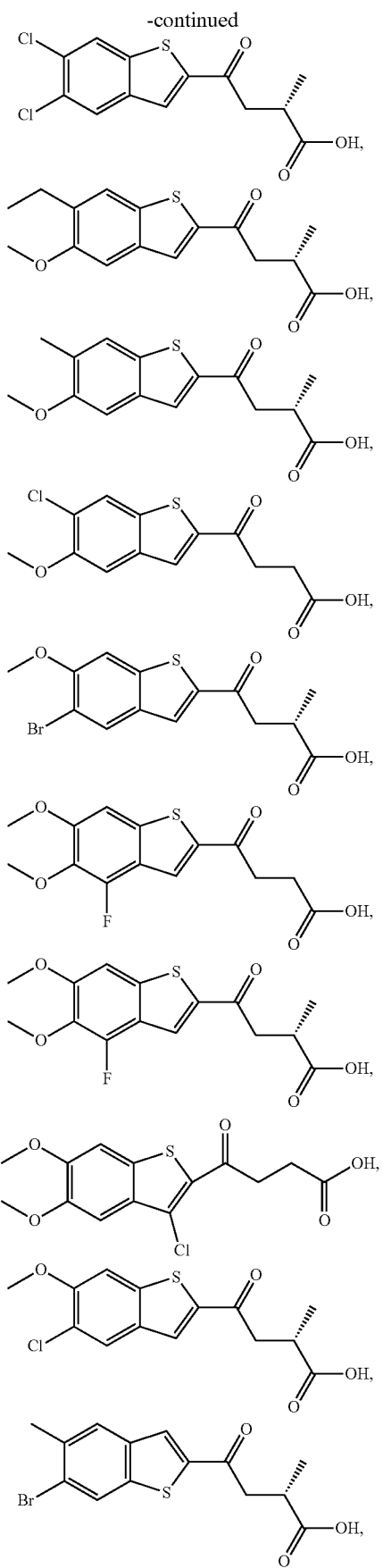
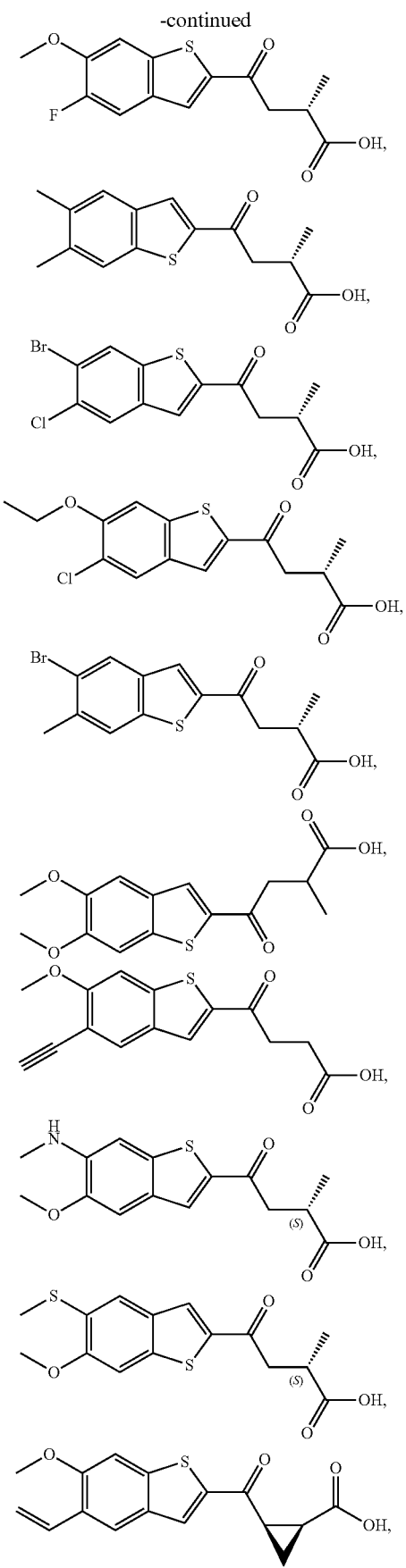

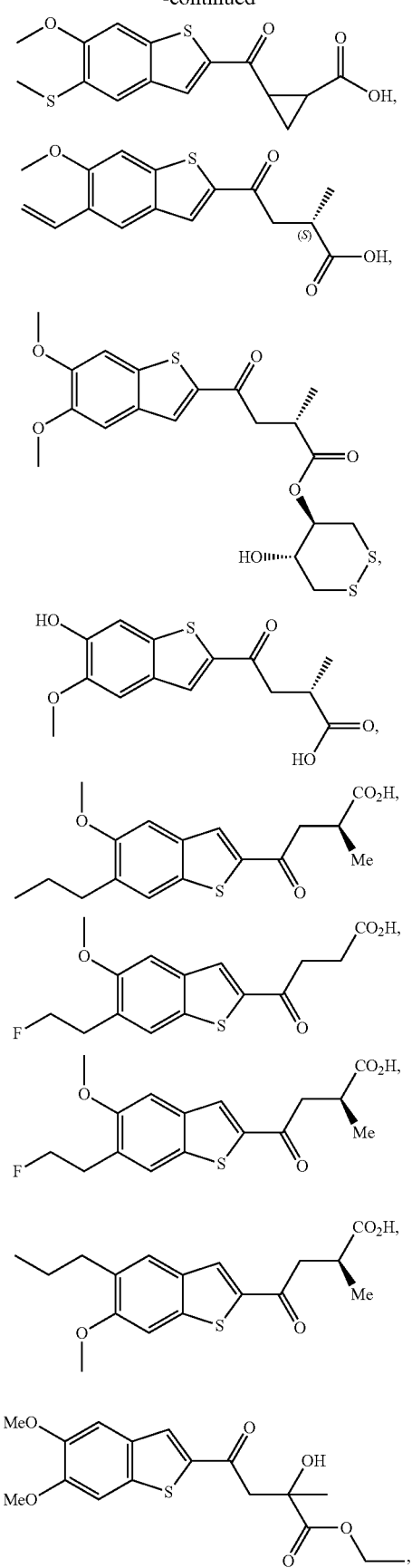
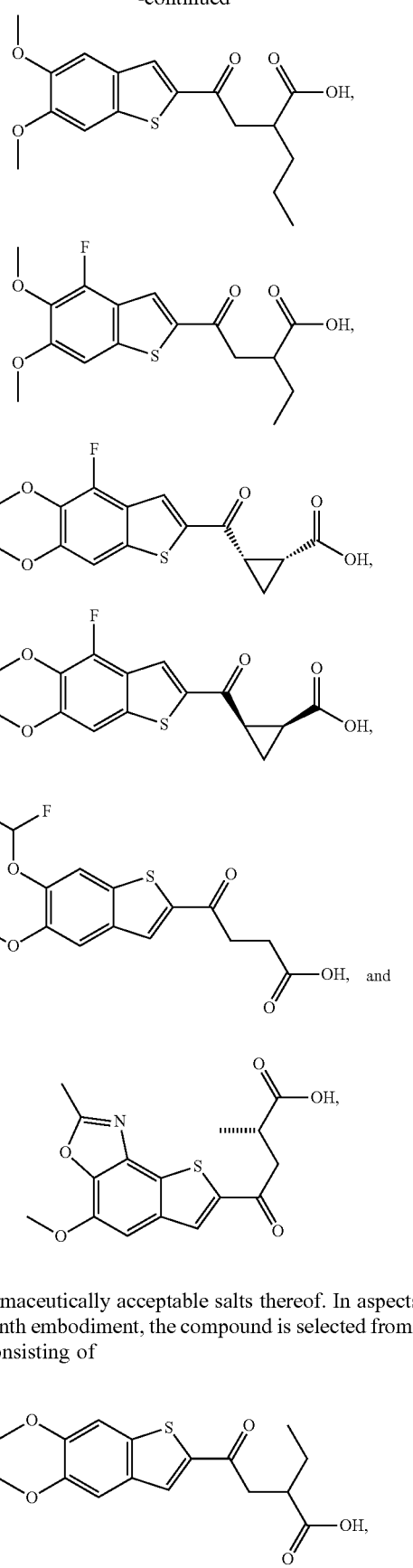
and pharmaceutically acceptable salts thereof. In aspects of this seventh embodiment, the compound is selected from the group consisting of

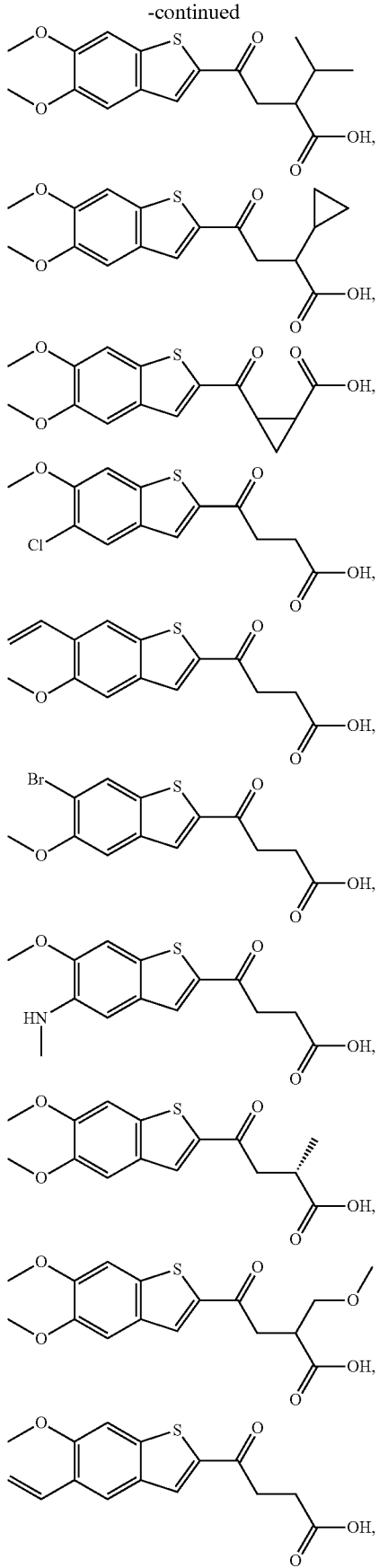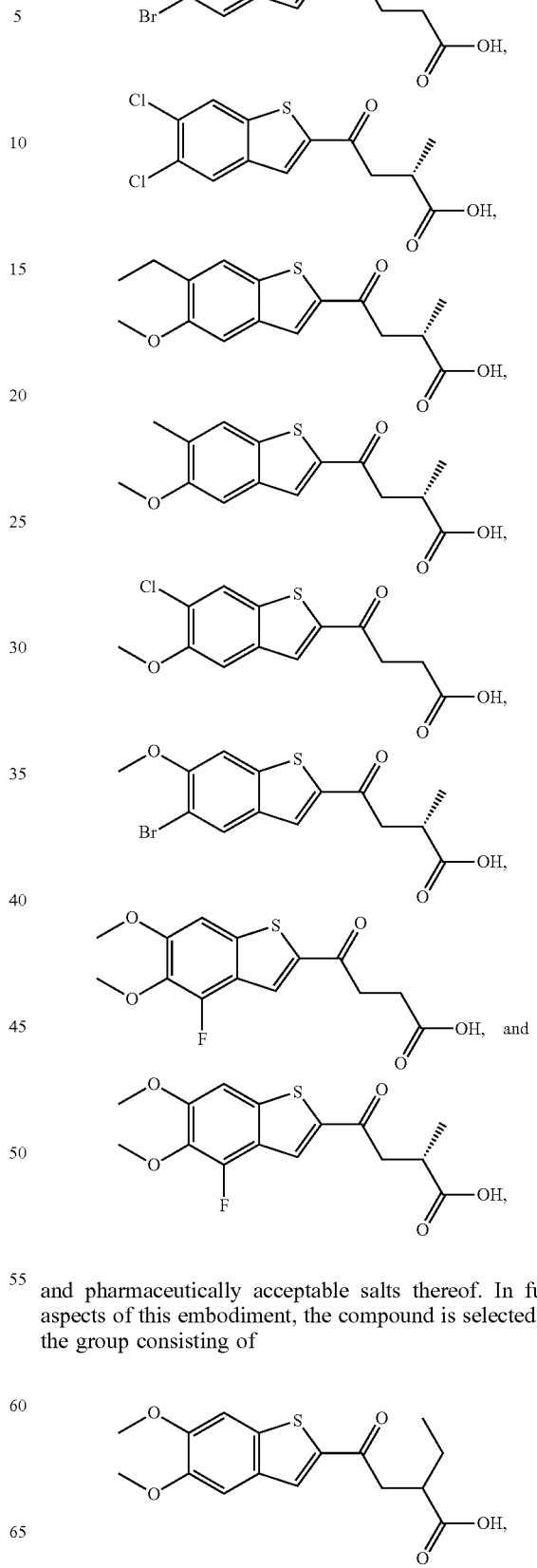
and pharmaceutically acceptable salts thereof. In further aspects of this embodiment, the compound is selected from the group consisting of

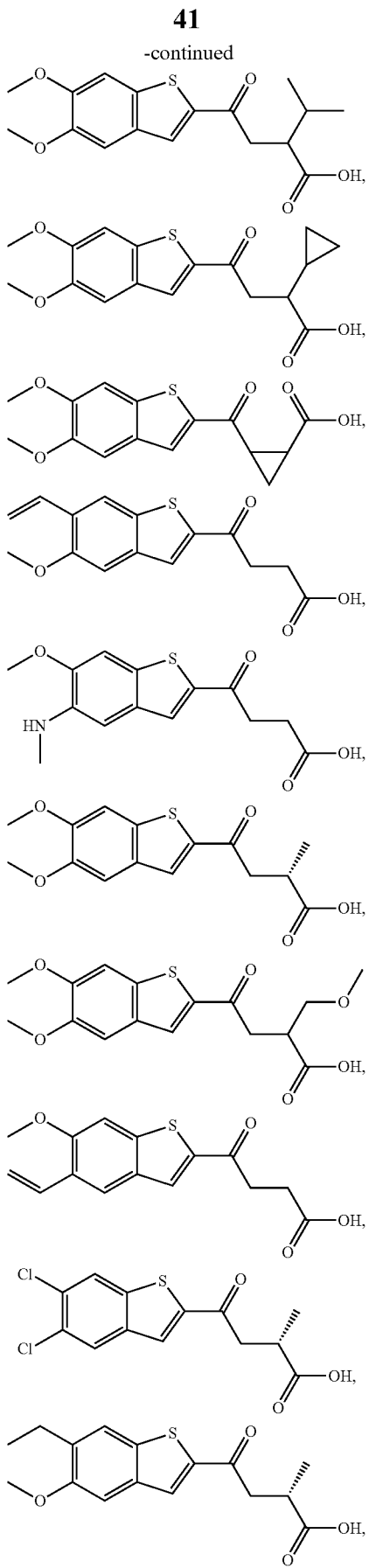

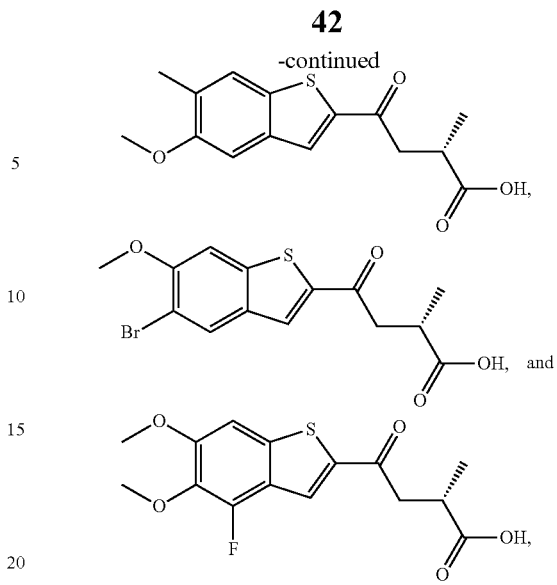

and pharmaceutically acceptable salts thereof.

A first aspect of the seventh embodiment relates to methods of inducing an immune response in a subject, comprising administering a therapeutically effective amount of a compound according to the seventh embodiment above or a pharmaceutically acceptable salt thereof to the subject.

A second aspect of the seventh embodiment relates to methods of inducing an immune response in a subject, comprising administering a therapeutically effective amount of a composition comprising a compound according to the seventh embodiment above or a pharmaceutically acceptable salt thereof to the subject.

A third aspect of the seventh embodiment relates to methods of inducing STING-dependent type I interferon production in a subject, comprising administering a therapeutically effective amount of a compound according to the seventh embodiment above or a pharmaceutically acceptable salt thereof to the subject.

A fourth aspect of the seventh embodiment relates to methods of inducing STING-dependent type I interferon production in a subject, comprising administering a therapeutically effective amount of a composition comprising a compound according to the seventh embodiment above or a pharmaceutically acceptable salt thereof to the subject.

A fifth aspect of the seventh embodiment relates to methods of inducing STING-dependent cytokine production in a subject, comprising administering a therapeutically effective amount of a compound according to the seventh embodiment above or a pharmaceutically acceptable salt thereof to the subject.

A sixth aspect of the seventh embodiment relates to methods of inducing a STING-dependent cytokine production in a subject, comprising administering a therapeutically effective amount of a composition comprising a compound according to the seventh embodiment above or a pharmaceutically acceptable salt thereof to the subject.

An eighth embodiment relates to a compound selected from the exemplary species depicted in Examples 1 through 54 shown below.

A first aspect of the eighth embodiment relates to methods of inducing an immune response in a subject, comprising administering a therapeutically effective amount of a compound according to the eighth embodiment above or a pharmaceutically acceptable salt thereof to the subject.

A second aspect of the eighth embodiment relates to methods of inducing an immune response in a subject, comprising administering a therapeutically effective amount of a composition comprising a compound according to the eighth embodiment above or a pharmaceutically acceptable salt thereof to the subject.

A third aspect of the eighth embodiment relates to methods of inducing STING-dependent type I interferon production in a subject, comprising administering a therapeutically effective amount of a compound according to the eighth embodiment above or a pharmaceutically acceptable salt thereof to the subject.

A fourth aspect of the eighth embodiment relates to methods of inducing STING-dependent type I interferon production in a subject, comprising administering a therapeutically effective amount of a composition comprising a compound according to the eighth embodiment above or a pharmaceutically acceptable salt thereof to the subject.

A fifth aspect of the eighth embodiment relates to methods of inducing STING-dependent cytokine production in a subject, comprising administering a therapeutically effective amount of a compound according to the eighth embodiment above or a pharmaceutically acceptable salt thereof to the subject.

A sixth aspect of the eighth embodiment relates to methods of inducing STING-dependent cytokine production in a subject, comprising administering a therapeutically effective amount of a composition comprising a compound according to the eighth embodiment above or a pharmaceutically acceptable salt thereof to the subject.

Other embodiments of the present disclosure include the following:

(a) A pharmaceutical composition comprising an effective amount of a compound of general formula (Ia), or a pharmaceutically acceptable salt thereof, and a pharmaceutically acceptable carrier.

(b) A pharmaceutical composition comprising an effective amount of a compound of general formula (Ia'), or a pharmaceutically acceptable salt thereof, and a pharmaceutically acceptable carrier.

(c) A pharmaceutical composition comprising an effective amount of a compound of general formula (Ib), or a pharmaceutically acceptable salt thereof, and a pharmaceutically acceptable carrier.

(d) A pharmaceutical composition comprising an effective amount of a compound of general formula (Ib'), or a pharmaceutically acceptable salt thereof, and a pharmaceutically acceptable carrier.

(e) The pharmaceutical composition of (a), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(f) The pharmaceutical composition of (b), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(g) The pharmaceutical composition of (c), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(h) The pharmaceutical composition of (d), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(i) A pharmaceutical combination that is (i) a compound of general formula (Ia), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (Ia), or pharmaceutically acceptable salt thereof, and the active agent are each employed in an amount that renders the combination effective for inducing an immune response in a patient.

(j) A pharmaceutical combination that is (i) a compound of general formula (Ia'), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (Ia), or pharmaceutically acceptable salt thereof, and the active agent are each employed in an amount that renders the combination effective for inducing an immune response in a patient.

(k) A pharmaceutical combination that is (i) a compound of general formula (Ib), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (Ib), or pharmaceutically acceptable salt thereof, and the active agent are each employed in an amount that renders the combination effective for inducing an immune response in a patient.

(l) A pharmaceutical combination that is (i) a compound of general formula (Ib'), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (Ib), or pharmaceutically acceptable salt thereof, and the active agent are each employed in an amount that renders the combination effective for inducing an immune response in a patient.

(m) A method of inducing an immune response in a patient, which comprises administering to the subject a therapeutically effective amount of a compound of general formula (Ia), or a pharmaceutically acceptable salt thereof.

(n) A method of inducing an immune response in a patient, which comprises administering to the subject a therapeutically effective amount of a compound of general formula (Ia'), or a pharmaceutically acceptable salt thereof.

(o) A method of inducing an immune response in a patient, which comprises administering to the subject a therapeutically effective amount of a compound of general formula (Ib), or a pharmaceutically acceptable salt thereof.

(p) A method of inducing an immune response in a patient, which comprises administering to the subject a therapeutically effective amount of a compound of general formula (Ib'), or a pharmaceutically acceptable salt thereof.

(q) A method of inducing an immune response in a patient, which comprises administering to the subject a therapeutically effective amount of a compound of general formula (I), or a pharmaceutically acceptable salt thereof.

(r) A method of inducing an immune response in a patient, which comprises administering to the subject a therapeutically effective amount of a compound of general formula (I'), or a pharmaceutically acceptable salt thereof.

(s) A method of inducing an immune response in a patient, which comprises administering to the subject a therapeutically effective amount of a composition of (a), a composition of (e), or a combination of (i).

(t) A method of inducing an immune response in a patient, which comprises administering to the subject a therapeutically effective amount of a composition of (b), a composition of (f), or a combination of (j).

(u) A method of inducing an immune response in a patient, which comprises administering to the subject a therapeutically effective amount of a composition of (c), a composition of (g), or a combination of (k).

(v) A method of inducing an immune response in a patient, which comprises administering to the subject a therapeutically effective amount of a composition of (d), a composition of (h), or a combination of (l).

(w) A method of inducing STING-dependent type I interferon production in a patient, which comprises administering to the subject a therapeutically effective amount of a compound of general formula (Ia), or a pharmaceutically acceptable salt thereof.

(x) A method of inducing STING-dependent type I interferon production in a patient, which comprises administering to the subject a therapeutically effective amount of a compound of general formula (Ia'), or a pharmaceutically acceptable salt thereof.

(y) A method of inducing STING-dependent type I interferon production in a patient, which comprises administering to the subject a therapeutically effective amount of a compound of general formula (Ib), or a pharmaceutically acceptable salt thereof.

(z) A method of inducing STING-dependent type I interferon production in a patient, which comprises administering to the subject a therapeutically effective amount of a compound of general formula (Ib'), or a pharmaceutically acceptable salt thereof.

(a1) A method of inducing STING-dependent type I interferon production in a patient, which comprises administering to the subject a therapeutically effective amount of a compound of general formula (I), or a pharmaceutically acceptable salt thereof.

(b1) A method of inducing STING-dependent type I interferon production in a patient, which comprises administering to the subject a therapeutically effective amount of a compound of general formula (I'), or a pharmaceutically acceptable salt thereof.

(c1) A method of inducing STING-dependent type I interferon production in a patient, which comprises administering to the subject a therapeutically effective amount of a composition of (a), a composition of (e), or a combination of (i).

(d1) A method of inducing STING-dependent type I interferon production in a patient, which comprises administering to the subject a therapeutically effective amount of a composition of (b), a composition of (f), or a combination of (j).

(e1) A method of inducing STING-dependent type I interferon production in a patient, which comprises administering to the subject a therapeutically effective amount of a composition of (c), a composition of (g), or a combination of (k).

(f1) A method of inducing STING-dependent type I interferon production in a patient, which comprises administering to the subject a therapeutically effective amount of a composition of (d), a composition of (h), or a combination of (l).

(g1) A method of inducing STING-dependent cytokine production in a patient, which comprises administering to the subject a therapeutically effective amount of a compound of general formula (Ia), or a pharmaceutically acceptable salt thereof.

(h1) A method of inducing STING-dependent cytokine production in a patient, which comprises administering to the subject a therapeutically effective amount of a compound of general formula (Ia'), or a pharmaceutically acceptable salt thereof.

(i1) A method of inducing STING-dependent cytokine production in a patient, which comprises administering to the subject a therapeutically effective amount of a compound of general formula (Ib), or a pharmaceutically acceptable salt thereof.

(j1) A method of inducing STING-dependent cytokine production in a patient, which comprises administering to the subject a therapeutically effective amount of a compound of general formula (Ib'), or a pharmaceutically acceptable salt thereof.

(k1) A method of inducing STING-dependent cytokine production in a patient, which comprises administering to the subject a therapeutically effective amount of a compound of general formula (I), or a pharmaceutically acceptable salt thereof.

(l1) A method of inducing STING-dependent cytokine production in a patient, which comprises administering to the subject a therapeutically effective amount of a compound of general formula (I'), or a pharmaceutically acceptable salt thereof.

(m1) A method of inducing STING-dependent cytokine production in a patient, which comprises administering to the subject a therapeutically effective amount of a composition of (a), a composition of (e), or a combination of (i).

(n1) A method of inducing STING-dependent cytokine production in a patient, which comprises administering to the subject a therapeutically effective amount of a composition of (b), a composition of (f), or a combination of (j).

(o1) A method of inducing STING-dependent cytokine production in a patient, which comprises administering to the subject a therapeutically effective amount of a composition of (c), a composition of (g), or a combination of (k).

(p1) A method of inducing STING-dependent cytokine production in a patient, which comprises administering to the subject a therapeutically effective amount of a composition of (d), a composition of (h), or a combination of (l).

(q1) A method of treating a cell proliferation disorder in a subject, said method comprising administering a therapeutically effective amount of a compound of general formula (Ia), or a pharmaceutically acceptable salt thereof to the subject;

(r1) The method of (q1), wherein the cell proliferation disorder is cancer.

(s1) A method of treating a cell proliferation disorder in a subject, said method comprising administering a therapeutically effective amount of a compound of general formula (Ia'), or a pharmaceutically acceptable salt thereof to the subject;

(t1) The method of (s1), wherein the cell proliferation disorder is cancer.

(u1) A method of treating a cell proliferation disorder in a subject, said method comprising administering a therapeutically effective amount of a compound of general formula (Ib), or a pharmaceutically acceptable salt thereof to the subject;

(v1) The method of (u1), wherein the cell proliferation disorder is cancer.

(w1) A method of treating a cell proliferation disorder in a subject, said method comprising administering a therapeutically effective amount of a compound of general formula (Ib'), or a pharmaceutically acceptable salt thereof to the subject;

(x1) The method of (w1), wherein the cell proliferation disorder is cancer.

(y1) A method of treating a cell proliferation disorder in a subject, said method comprising administering a therapeutically effective amount of a compound of general formula (I), or a pharmaceutically acceptable salt thereof to the subject;

(z1) The method of (y1), wherein the cell proliferation disorder is cancer.

(a2) A method of treating a cell proliferation disorder in a subject, said method comprising administering a therapeutically effective amount of a compound of general formula (I'), or a pharmaceutically acceptable salt thereof to the subject;

(b2) The method of (a2), wherein the cell proliferation disorder is cancer.

(c2) A method of treating a cell proliferation disorder in a subject, said method comprising administering a therapeutically effective amount of a composition of (a), a composition of (e), or a combination of (i) to the subject.

(d2) The method of (c2), wherein the cell proliferation disorder is cancer.

(e2) A method of treating a cell proliferation disorder in a subject, said method comprising administering a therapeutically effective amount of a composition of (b), a composition of (f), or a combination of (j) to the subject.

(f2) The method of (e2), wherein the cell proliferation disorder is cancer.

(g2) A method of treating a cell proliferation disorder in a subject, said method comprising administering a therapeutically effective amount of a composition of (c), a composition of (g), or a combination of (k) to the subject.

(h2) The method of (g2), wherein the cell proliferation disorder is cancer.

(i2) A method of treating a cell proliferation disorder in a subject, said method comprising administering a therapeutically effective amount of a composition of (d), a composition of (h), or a combination of (l) to the subject.

(j2) The method of (i2), wherein the cell proliferation disorder is cancer.

The present disclosure also includes a compound of the present disclosure for use (i) in, (ii) as a medicament for, or (iii) in the preparation of a medicament for: (a) inducing an immune response in a patient, or (b) inducing STING-dependent cytokine production in a patient. In these uses, the compounds of the present disclosure can optionally be employed in combination with one or more active agents selected from STING agonist compounds, anti-viral compounds, antigens, adjuvants, CTLA-4 and PD-1 pathway antagonists and other immunomodulatory agents, lipids, liposomes, peptides, anti-cancer agents, and chemotherapeutic agents.

Additional embodiments of the disclosure include the pharmaceutical compositions, combinations and methods set forth in (a) through (j2) above and the uses set forth in the preceding paragraph, wherein the compound of the present disclosure employed therein is a compound of one of the embodiments, aspects, instances, occurrences, or features of the compounds described above. In all of these embodiments, the compound may optionally be used in the form of a pharmaceutically acceptable salt, as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (j2) above are understood to include all embodiments of the compounds, including such embodiments as result from combinations of embodiments.

The term "subject" (alternatively "patient") as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), Procyon lotor (e.g., raccoons). In particular embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, is administered in conjunction with one or more additional therapeutic agents including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc. In certain embodiments, a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, is administered in conjunction with one or more additional compositions including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc.

Compounds

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bonds.

As used herein, the term "alkenylene" refers to a bivalent straight chain, unsaturated aliphatic hydrocarbon radical having a number of carbon atoms in the specified range and including one or more double bonds.

As used herein, the term "alkynyl" refers to a monovalent straight or branched chain, unsaturated aliphatic hydrocarbon radical having a number of carbon atoms in the specified range and including one or more triple bonds.

As used herein, the term "alkynylene" refers to a bivalent straight chain, unsaturated aliphatic hydrocarbon radical having a number of carbon atoms in the specified range and including one or more triple bonds.

The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, the term "cycloalkyl" refers to a saturated hydrocarbon containing one ring having a specified number of carbon atoms. Examples of cycloalkyl include cyclopropyl, cyclobutyl, cyclopentyl, and cyclohexyl.

As used herein, the term "heterocycle", "heterocyclyl", or "heterocyclic", as used herein, represents a stable 3- to 6-membered monocyclic that is either saturated or unsaturated, and that consists of carbon atoms and from one to two heteroatoms selected from the group consisting of N, O, and S. The heterocyclic ring may be attached at any heteroatom or carbon atom which results in the creation of a stable structure. The term includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

As used herein, the term "fused ring" refers to a cyclic group formed by substituents on separate atoms in a straight or branched alkane, or to a cyclic group formed by substituents on separate atoms in another ring.

As used herein, the term "spirocycle" or "spirocyclic ring" refers to a pendant cyclic group formed by substituents on a single atom.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents.

As used herein, the term "one or more" item includes a single item selected from the list as well as mixtures of two or more items selected from the list.

In the compounds of general formula (Ia), the compounds of general formula (Ia'), the compounds of general formula (Ib), the compounds of general formula (Ib'), the compounds of general formula (I), the compounds of general formula (I'), and pharmaceutically acceptable salts of the foregoing, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the the compounds of general formula (Ia), the compounds of general formula (Ia'), the compounds of general formula (Ib), the compounds of general formula (Ib'), the compounds of general formula (I), the compounds of general formula (I'), and pharmaceutically acceptable salts of the foregoing. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched the compounds of general formula (Ia), the compounds of general formula (Ia'), the compounds of general formula (Ib), the compounds of general formula (Ib'), the compounds of general formula (I), the compounds of general formula (I'), and pharmaceutically acceptable salts of the foregoing, can be prepared without undue experimentation by conventional techniques well known to those skilled in the art or by processes analogous to those described in the Schemes and Examples herein using appropriate isotopically-enriched reagents and/or intermediates.

In particular embodiments of the the compounds of general formula (Ia), the compounds of general formula (Ia'), the compounds of general formula (Ib), the compounds of general formula (Ib'), the compounds of general formula (I), the compounds of general formula (I'), and pharmaceutically acceptable salts of the foregoing, the compounds are isotopically enriched with deuterium. In aspects of these embodiments, one or more of $R^1$, $R^2$, $R^3$, $R^4$, $R^5$, $R^6$, $R^8$, and $R^9$ may include deuterium.

As shown in the general structural formulas and the structures of specific compounds as provided herein, a straight line at a chiral center includes both (R) and (S) stereoisomers and mixtures thereof. Also, unless otherwise specified (e.g., 100% purified compound), reference to a particular stereochemistry at a position provides a compound having the indicated stereochemistry but does not exclude the presence of stereoisomers having different stereochemistry at the indicated position.

Recitation or depiction of a specific compound in the claims (i.e., a species) without a specific stereoconfiguration designation, or with such a designation for less than all chiral centers, is intended to encompass, for such undesignated chiral centers, the racemate, racemic mixtures, each individual enantiomer, a diastereoisomeric mixture and each individual diastereomer of the compound where such forms are possible due to the presence of one or more asymmetric centers. The separation of a mixture of stereoisomers can be carried out at an intermediate step during the synthesis of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, or it can be done on a final racemic product. Absolute stereochemistry may be determined by X-ray crystallography of crystalline products or crystalline intermediates, which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (including hydrates), and solvated salts of such racemates, enantiomers, diastereomers, tautomers, and mixtures thereof.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form, as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, or it can be done on a final racemic product. Absolute stereochemistry may be determined by X-ray crystallography of crystalline products or crystalline intermediates that are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates), and solvated salts of such racemates, enantiomers, diastereomers, and mixtures thereof.

The term "compound" refers to the compound and, in certain embodiments, to the extent they are stable, any hydrate or solvate thereof. A hydrate is the compound complexed with water, and a solvate is the compound complexed with a solvent, which may be an organic solvent or an inorganic solvent.

A "stable" compound is a compound that can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by general formula (Ia), general formula (Ia'), general formula (Ib), general formula (Ib'), general formula (I), and general formula (I'), or pharmaceutically acceptable salts thereof.

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only. Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Methods of Preparing Compounds

Several methods for preparing the compounds of general formula (Ia), the compounds of general formula (Ia'), the compounds of general formula (Ib), the compounds of general formula (Ib'), the compounds of general formula (I), the compounds of general formula (I'), and pharmaceutically acceptable salts of the foregoing, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

In the following Methods and Schemes, LG represents a leaving group, which may be a halide or triflate group. The variables $R^1$, $R^2$, $R^3$, $R^4$, $R^6$, $R^8$, and $X^2$, have the same meaning as provided above.

Method 1

Benzo[b]thiophene 2-carboxylic acids b, and pharmaceutically acceptable salts thereof, are typically prepared from ortho-halo benzaldehydes. The sequence starts with treatment with an alpha-thio acetic acid ester under basic conditions. The ester in the resulting compound was cleaved to the carboxylic acid under basic conditions to provide the desired substituted benzo[b]thiophene 2-carboxylic acid 1C.

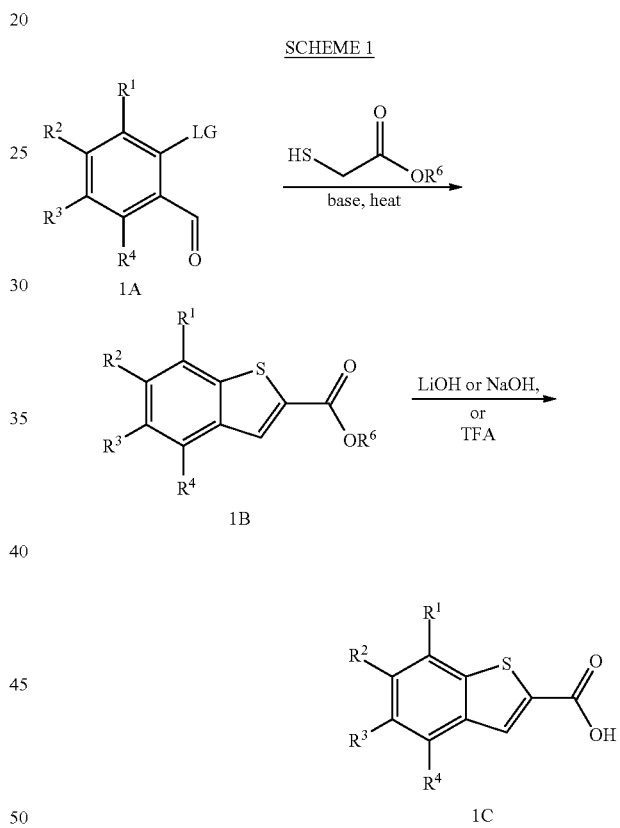

Method 2

Another method for the preparation of benzo[b]thiophene 2-carboxylic acids, and pharmaceutically acceptable salts thereof, is detailed in Scheme 2. The sequence starts with a benzo[b]thiophene substituted at the 2-position with an appropriate 1,3-dicarbonyl group, such as a beta-keto ester. It was reacted with an alpha-halo ester under basic conditions to afford substitution at the 2 position of the alkyl chain. Then, both esters were hydrolyzed using either acidic or basic conditions; upon further exposure to basic conditions, the carboxylic acid corresponding to the ester in the starting material underwent decarboxylation to give the desired benzo[b]thiophene keto acid 2C.

SCHEME 2

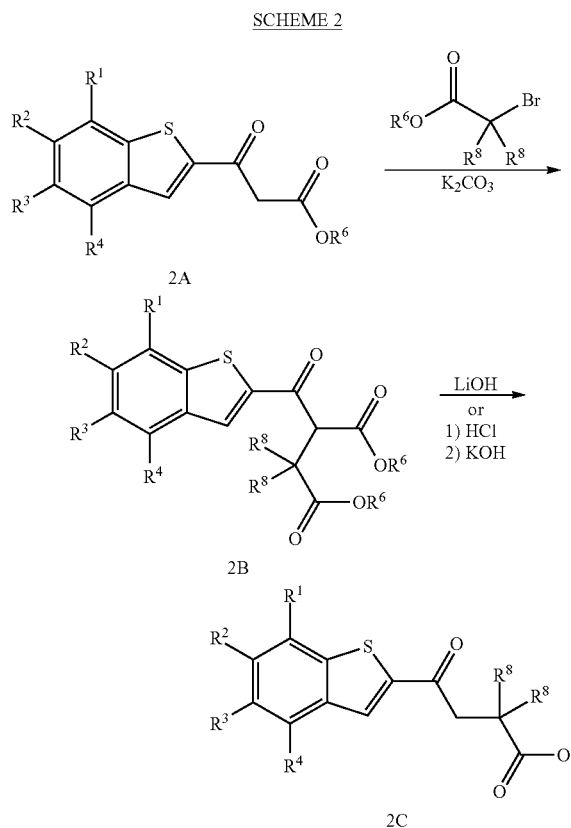

thereof, is detailed in Scheme 4. The sequence starts with a benzo[b]thiophene substituted with a carboxylic acid at the 2 position. It was treated with oxalyl chloride/dichloromethane. The resulting acid chloride was reacted with an alkyl zinc reagent, typically containing an ester, using a transition metal such as copper or palladium to mediate the coupling. Then, the ester was cleaved under basic or acidic conditions to provide the desired benzo[b]thiophene gamma-keto acid 4D.

SCHEME 4

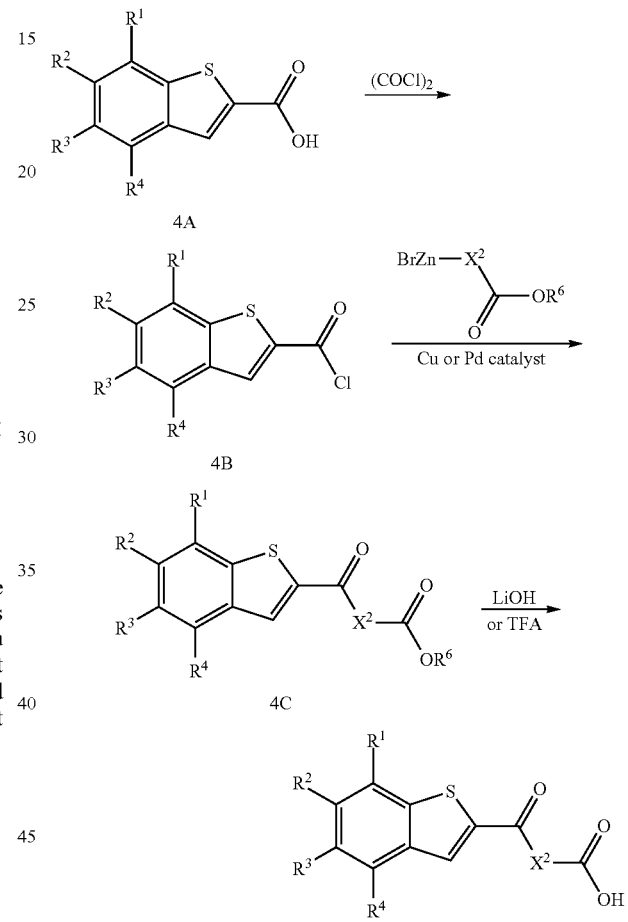

Method 3

Another method for the preparation of benzo[b]thiophene 2-carboxylic acids, and pharmaceutically acceptable salts thereof, is detailed in Scheme 3. The sequence starts with a benzo[b]thiophene without substitution at the 2 position. It was treated with tert-butyllithium followed by a cyclic acid anhydride to give the desired 4-keto carboxylic acid product 3B.

SCHEME 3

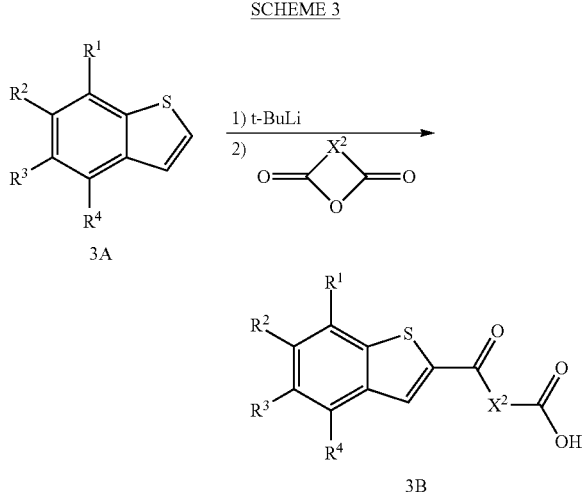

Method 4

Another method for the preparation of benzo[b]thiophene 2-carboxylic acids, and pharmaceutically acceptable salts Method 5

Another method for the preparation of benzo[b]thiophene 2-carboxylic acids, and pharmaceutically acceptable salts thereof, is detailed in Scheme 5. The sequence starts with a benzo[b]thiophene substituted at the 2 position with a gamma-keto ester and with a halide or triflate on the benzo[b]thiophene. It was treated with a boronic ester, acid, or trifluoroborate salt and a palladium catalyst under aqueous basic conditions. Then the ester in the resulting compound was cleaved to the carboxylic acid under basic conditions to provide the desired substituted benzo[b]thiophene 5C. The following scheme depicts introduction of the $R^2$ substituent, but this same general method couple bring in certain $R^3$ substituents as well when employing a related substrate with an appropriately placed LG.

SCHEME 5

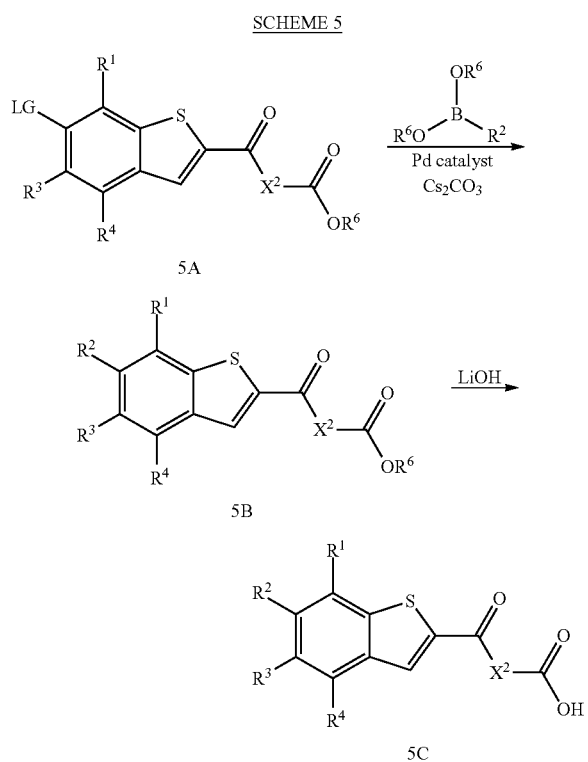

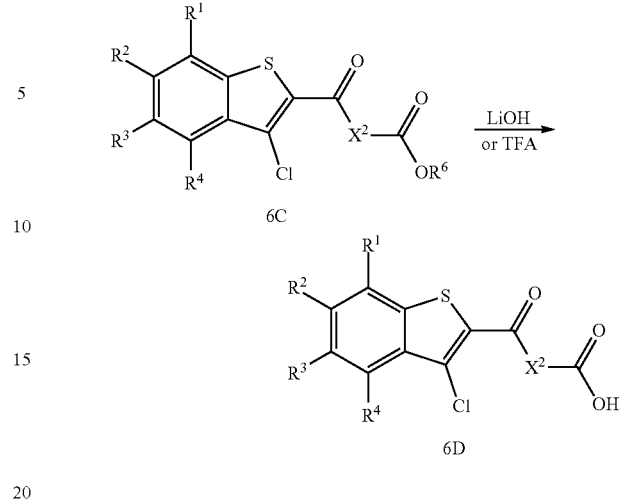

Method 6

Another method for the preparation of benzo[b]thiophene 2-carboxylic acids, and pharmaceutically acceptable salts thereof, involves the cyclization of a cinnamic acid in the presence of thionyl chloride. The resulting acid chloride was reacted with an alkyl zinc reagent, typically containing an ester, using a transition metal such as copper or palladium to mediate the coupling. Then, the ester was cleaved under basic or acidic conditions to provide the desired benzo[b]thiophene gamma-keto acid 6D.

SCHEME 6

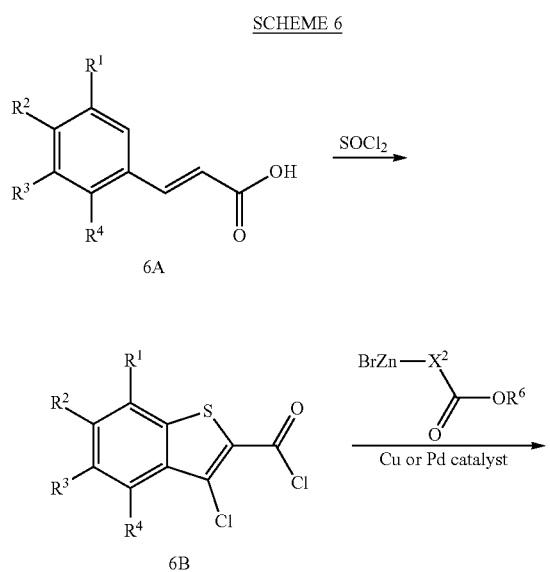

Method 7

Another method for the preparation of benzo[b]thiophene 2-carboxylic acids, and pharmaceutically acceptable salts thereof, is detailed in Scheme 7. The sequence starts with a Grignard reaction with the Weinreb amide 7A to provide the methyl ketone 7B. Deprotonation of the ketone with LDA followed by the addition of ethyl pyruvate gives 7C.

SCHEME 7

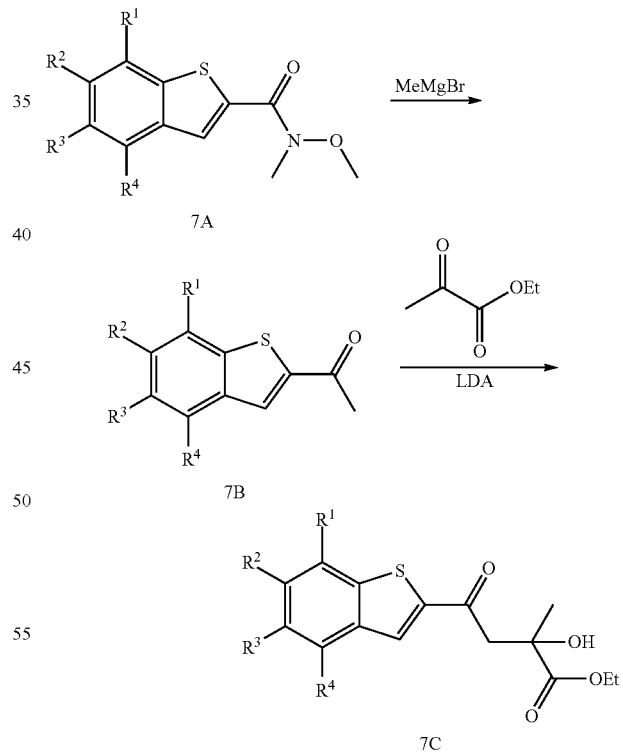

Methods of Use

Compounds described herein having therapeutic applications, such as the compounds of general formula (Ia), the compounds of general formula (Ia'), the compounds of general formula (Ib), the compounds of general formula (Ib'), the compounds of general formula (I), the compounds of general formula (I'), the compounds of the Examples 1 through 54, and pharmaceutically acceptable salts of the foregoing, may be administered to a patient for the purpose of inducing an immune response, inducing STING-dependent cytokine production and/or inducing anti-tumor activity. The term "administration" and variants thereof (e.g., "administering" a compound) means providing the compound to the individual in need of treatment. When a compound is provided in combination with one or more additional active agents (e.g., antiviral agents useful for treating HCV infection or anti-tumor agents for treating cancers), "administration" and its variants are each understood to include concurrent and sequential provision of the compound or salt and other agents.

The compounds disclosed herein may be STING agonists. These compounds are potentially useful in treating diseases or disorders including, but not limited to, cell proliferation disorders. Cell-proliferation disorders include, but are not limited to, cancers, benign papillomatosis, gestational trophoblastic diseases, and benign neoplastic diseases, such as skin papilloma (warts) and genital papilloma.

In specific embodiments, the disease or disorder to be treated is a cell proliferation disorder. In certain embodiments, the cell proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sP-NET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt thereof, and compositions of the foregoing to a subject.

The amount of a compound administered to a subject is an amount sufficient to induce an immune response and/or to induce STING-dependent type I interferon production in the subject. In an embodiment, the amount of a compound can be an "effective amount" or "therapeutically effective amount," such that the subject compound is administered in an amount that will elicit, respectively, a biological or medical (i.e., intended to treat) response of a tissue, system, animal, or human that is being sought by a researcher, veterinarian, medical doctor, or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen where a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life, that can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen.

One embodiment of the present disclosure provides for a method of treating a cell proliferation disorder comprising administration of a therapeutically effective amount of a compound of general formula (Ia), a compound of general formula (Ia'), a compound of general formula (Ib), a compound of general formula (Ib'), a compound of general formula (I), a compound of general formula (I'), and pharmaceutically acceptable salts of the foregoing, to a subject in need of treatment thereof. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

In one embodiment, disclosed herein is the use of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, in a therapy. The compound may be useful in a method of inducing an immune response and/or inducing STING-dependent type I interferon production in a subject, such as a mammal in need of such inhibition, comprising administering an effective amount of the compound to the subject.

In one embodiment, disclosed herein is a pharmaceutical composition comprising at least one compound of general formula (Ia), at least one compound of general formula (Ia'), at least one compound of general formula (Ib), at least one compound of general formula (Ib'), at least one compound of general formula (I), at least one compound of general formula (I'), or at least one pharmaceutically acceptable salt of the foregoing, for use in potential treatment to induce an immune response and/or to induce STING-dependent type I interferon production.

One embodiment disclosed herein is the use of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, in the manufacture of a medicament to induce an immune response and/or to induce STING-dependent type I interferon production. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

Compositions

The term "composition" as used herein is intended to encompass a dosage form comprising a specified compound in a specified amount, as well as any dosage form that results, directly or indirectly, from combination of a specified compound in a specified amount. Such term is intended to encompass a dosage form comprising a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing STING-dependent type I interferon production, the compounds of general formula (Ia), the compounds of general formula (Ia'), the compounds of general formula (Ib), the compounds of general formula (Ib'), the compounds of general formula (I), the compounds of general formula (I'), or pharmaceutically acceptable salts of the foregoing, can be administered by means that produces contact of the active agent with the agent's site of action. The compounds can be administered by conventional means available for use in conjunction with pharmaceuticals, either as individual therapeutic agents or in a combination of therapeutic agents. The compounds can be administered alone, but typically are administered with a pharmaceutical carrier selected on the basis of the chosen route of administration and standard pharmaceutical practice.

In one embodiment, disclosed herein is a composition comprising a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, and one or more pharmaceutically acceptable carriers or excipients. The composition may be prepared and packaged in bulk form in which a therapeutically effective amount of a compound of the disclosure can be extracted and then given to a subject, such as with powders or syrups. Alternatively, the composition may be prepared and packaged in unit dosage form in which each physically discrete unit contains a therapeutically effective amount of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the compositions of the disclosure. In addition, there are a number of resources available to the skilled artisan, which describe pharmaceutically acceptable carriers and excipients and may be useful in selecting suitable pharmaceutically acceptable carriers and excipients. Examples include REMINGTON'S PHARMACEUTICAL SCIENCES (Mack Publishing Company), THE HANDBOOK OF PHARMACEUTICAL ADDITIVES (Gower Publishing Limited), and THE HANDBOOK OF PHARMACEUTICAL EXCIPIENTS (the American Pharmaceutical Association and the Pharmaceutical Press).

The compositions of the disclosure are prepared using techniques and methods known to those skilled in the art. Some methods commonly used in the art are described in REMINGTON'S PHARMACEUTICAL SCIENCES (Mack Publishing Company).

In one embodiment, the disclosure is directed to a solid oral dosage form such as a tablet or capsule comprising a therapeutically effective amount of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The solid oral dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The solid oral dosage form may further comprise a disintegrant. Suitable disintegrants include crospovidone, sodium starch glycolate, croscarmelose, alginic acid, and sodium carboxymethyl cellulose. The solid oral dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolyly-sine substituted with palmitoyl residues. Furthermore, the compounds of the disclosure may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanacrylates, and cross-linked or amphipathic block copolymers of hydrogels.

In one embodiment, the disclosure is directed to a liquid oral dosage form. Oral liquids such as solutions, syrups, and elixirs can be prepared in dosage unit form so that a given quantity contains a predetermined amount of a compound or a pharmaceutically acceptable salt thereof disclosed herein. Syrups can be prepared by dissolving the compound of the disclosure in a suitably flavored aqueous solution; elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil, or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions that may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze-dried (lyophilized) condition, requiring only the addition of the sterile liquid carrier, for example water for injections, immediately prior to use. Extemporaneous injection solutions and suspensions may be prepared from sterile powders, granules, and tablets.

Combinations

The compounds of general formula (Ia), the compounds of general formula (Ia'), the compounds of general formula (Ib), the compounds of general formula (Ib'), the compounds of general formula (I), the compounds of general formula (I'), and/or pharmaceutically acceptable salts of the foregoing, may be administered in combination with one or more additional active agents. In embodiments, one or more compounds of general formula (Ia), one or more compounds of general formula (Ia'), one or more compounds of general formula (Ib), one or more compounds of general formula (Ib'), one or more compounds of general formula (I), one or more compounds of general formula (I'), or one or more pharmaceutically acceptable salts of the foregoing, and the one or more additional active agents may be co-administered. The additional active agent(s) may be administered in a single dosage form with the compound of general formula (Ia), the compound of general formula (Ia'), the compound of general formula (Ib), the compound of general formula (Ib'), the compound of general formula (I), the compound of general formula (I'), or pharmaceutically acceptable salt of the foregoing, or the additional active agent(s) may be administered in separate dosage form(s) from the dosage form containing the compound of general formula (Ia), the compound of general formula (Ia'), the compound of general formula (Ib), the compound of general formula (Ib'), the compound of general formula (I), the compound of general formula (I'), or pharmaceutically acceptable salt of the foregoing.

The additional active agent(s) may be provided as a pharmaceutically acceptable salt, where appropriate.

The additional active agent(s) may be one or more agents selected from the group consisting of STING agonist compounds, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood that such additional active agent(s) may be provided as a pharmaceutically acceptable salt. It will be understood the descriptions of the above additional active agents may be overlapping. It will also be understood that the treatment combinations are subject to optimization, and it is understood that the best combination to use of the compounds of general formula (Ia), the compounds of general formula (Ia'), the compounds of general formula (Ib), the compounds of general formula (Ib'), the compounds of general formula (I), the compounds of general formula (I'), or pharmaceutically acceptable salts of the foregoing, and one or more additional active agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other active agent(s). A compound disclosed herein may be administered separately, by the same or different route of administration, or together in the same pharmaceutical composition as the other agent(s).

Products provided as combinations may include a composition comprising a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, and one or more other active agent(s) together in the same pharmaceutical composition, or may include a composition comprising a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, and a composition comprising one or more other active agent(s) in separate form, e.g. in the form of a kit or in any form designed to enable separate administration either concurrently or on separate dosing schedules.

The weight ratio of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, to a second active agent may be varied and will depend upon the therapeutically effective dose of each agent. Generally, a therapeutically effective dose of each will be used. Combinations of a compound disclosed herein and other active agents will generally also be within the aforementioned range, but in each case, a therapeutically effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, and at least one other active agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, for treating a cell proliferation disorder, where the medicament is prepared for administration with another active agent. The disclosure also provides the use of another active agent for treating a cell proliferation disorder, where the medicament is administered with a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing.

The disclosure also provides the use of a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing, for treating a cell proliferation disorder, where the patient has previously (e.g., within 24 hours) been treated with another active agent. The disclosure also provides the use of another active agent for treating a cell proliferation disorder, where the patient has previously (e.g., within 24 hours) been treated with a compound of general formula (Ia), a compound of general formula (Ia'), a compound of general formula (Ib), a compound of general formula (Ib'), a compound of general formula (I), a compound of general formula (I'), or a pharmaceutically acceptable salt of the foregoing. The second agent may be administered a week, several weeks, a month, or several months after the administration of a compound disclosed herein.

STING agonist compounds that may be used in combination with the compounds of general formula (Ia), the compounds of general formula (Ia'), the compounds of general formula (Ib), the compounds of general formula (Ib'), the compounds of general formula (I), the compounds of general formula (I'), or pharmaceutically acceptable salts of the foregoing, disclosed herein include but are not limited to cyclic di-nucleotide compounds.

Anti-viral compounds that may be used in combination with the compounds of general formula (Ia), the compounds of general formula (Ia'), the compounds of general formula (Ib), the compounds of general formula (Ib'), the compounds of general formula (I), the compounds of general formula (I'), or pharmaceutically acceptable salts of the foregoing, disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors. Such anti-viral compounds may be provided as a pharmaceutically acceptable salt, where appropriate. Antigens and adjuvants that may be used in combination with the compounds of general formula (Ia), the compounds of general formula (Ia'), the compounds of general formula (Ib), the compounds of general formula (Ib'), the compounds of general formula (I), the compounds of general formula (I'), or the pharmaceutically acceptable salts of the foregoing, include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants. Such antigens and anjuvants may be provided as a pharmaceutically acceptable salt, where appropriate.

CLTA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (Ia), the compounds of general formula (Ia'), the compounds of general formula (Ib), the compounds of general formula (Ib'), the compounds of general formula (I), the compounds of general formula (I'), or the pharmaceutically acceptable salts of the foregoing, disclosed herein, include ipilimumab, tremelimumab, nivolumab, pembrolizumab, CT-011, AMP-224, and MDX-1106. "PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488,802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Examples of cytotoxic agents that may be used in combination with the compounds of general formula (Ia), the compounds of general formula (Ia'), the compounds of general formula (Ib), the compounds of general formula (Ib'), the compounds of general formula (I), the compounds of general formula (I'), or pharmaceutically acceptable salts of the foregoing, include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the compounds of general formula (Ia), the compounds of general formula (Ia'), the compounds of general formula (Ib), the compounds of general formula (Ib'), the compounds of general formula (I), the compounds of general formula (I'), or pharmaceutically acceptable salts of the foregoing, disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl) benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine. Such chemotherapeutic agents may be provided as a pharmaceutically acceptable salt, where appropriate.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR). Such inhibitors may be provided as a pharmaceutically acceptable salt, where appropriate.

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON). Such inhibitors may be provided as a pharmaceutically acceptable salt, where appropriate.

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®. Such alkylating agents may be provided as a pharmaceutically acceptable salt, where appropriate.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®). Such anti-tumor antibiotics may be provided as a pharmaceutically acceptable salt, where appropriate.

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™) fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®). Such anti-metabolites may be provided as a pharmaceutically acceptable salt, where appropriate.

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®). Such compounds may be provided as a pharmaceutically acceptable salt, where appropriate.

Activity: STING Biochemical [3H]cGAMP Competition Assay

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and (ii) demonstrating interferon production with a 6% or greater induction of IFN-β secretion at 30 uM in the THP1 cell assay (where induction caused by cGAMP at 30 uM was set at 100%).

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

EXAMPLES

| ABBREVIATIONS | |
|---|---|
| (COCl)$_2$ | Oxalyl chloride |
| $^{19}$F NMR | $^{19}$F nuclear magnetic resonance spectroscopy |
| $^1$H NMR | $^1$H (Proton) nuclear magnetic resonance spectroscopy |
| 2',3'cGAMP, cGAMP | 2',3'-cyclic guanosine monophosphate-adenosine monophosphate |
| ACN, MeCN, CH$_3$CN | Acetonitrile |
| AcOH, HOAc | Acetic acid |
| AlCl$_3$ | Aluminum trichloride |
| AMP | Adenosine monophosphate |
| aq | Aqueous |
| Ar | Argon |
| ATP | Adenosine 5'-triphosphate |
| BIIC | Baculovirus Infected Insect Cell |
| br | Broad |
| Br$_2$ | Bromine |
| cat | Catalog number |
| CD$_3$OD | Deuterium-enriched methyl alcohol, deuterium-enriched methanol |
| CDCl$_3$ | Deuterated trichloromethane |
| cGAMP | Cyclic GMP-AMP synthase |
| CH$_2$I$_2$ | Diiodomethane |
| CH$_3$Cl | Chloromethane, methyl chloride |
| CHCl$_3$ | Trichloromethane |
| Ci | Curie, a non-standard unit of radioactivity; 1Ci = 3.7 × 10$^{10}$Bq, where Bq is Becquerel, the SI unit of radioactivity, equivalent to 1 disintegration per second (dps) |
| CO$_2$ | Carbon dioxide |
| CPhos Pd G4 | 2-Aminobiphenylpalladium methanesulfonate palladium CPhos precatalyst (4$^{th}$ generation precatalyst) |
| Cs$_2$CO$_3$ | Cesium carbonate |
| Cu—Cl | Copper(I) chloride |
| Cu—I | Copper(I) iodide |
| Cy | Cyclohexyl |
| d | Doublet |
| DCE | 1,2-Dichloroethane |
| DCM, CH$_2$Cl$_2$ | Dichloromethane |
| ddd | Doublet of doublet of doublet |
| ddt | Doublet of doublet of triplet |
| DMAP | 4-dimethylaminopyridine |
| DMEA | N,N-dimethyl ethyl amine |
| DMF | N,N-dimethylformamide |
| DMSO | Dimethyl sulfoxide |
| DMTr | 4,4'-dimethoxytrityl |
| DMTrCl | 4,4'-dimethoxytrityl chloride |
| dq | Doublet of quartet |
| EC$_{50}$ | half maximal effective concentration; concentration of a drug, antibody, or toxicant that induces a response halfway between the baseline and maximum after a specified exposure time |
| EDC | Ethylene dichloride |
| eq | Equivalents |
| ES | Electron spray |
| Et | Ethyl |
| Et$_2$O | Diethyl ether |

-continued

| ABBREVIATIONS | |
|---|---|
| $Et_2Z$ | Diethyl zinc |
| EtOAc | Ethyl acetate |
| EtOH | Ethyl alcohol, ethanol |
| g | Gram |
| GMP | Guanosine 5'-monophosphate |
| GTP | Guanosine 5'-triphosphate |
| h | Hour |
| $H_2$ | Hydrogen (gas) |
| $H_2SO_4$ | Sulfuric acid |
| HAQ STING | Common STING variant containing the three mutations R71H-G230A-R293Q (DNA construct used herein: STING(1-379)R71H, G230A, H232R, R293Q-GG-AviTag-GS-HRV3C-HIS8/pBAC1) |
| HCl | Hydrochloric acid |
| HEPES | 2-[4-(2-hydroxyethyl)piperazin-1-yl]ethanesulfonic acid, a zwitterionic organic chemical buffering agent |
| hept | Heptet |
| Hex | Hexanes |
| $HNO_3$ | Nitric acid |
| HPLC | High performance liquid chromatography |
| Hz | Hertz |
| $IC_{50}$ | half maximal inhibitory concentration; concentration of a drug, antibody, or toxicant required for 50% inhibition of response or binding |
| Inh | Inhibition |
| J | NMR Coupling constant |
| $K_2CO_3$ | Potassium carbonate |
| KCl | Potassium chloride |
| KOH | Potassium hydroxide |
| LCMS | Liquid chromatography - mass spectroscopy |
| LDA | Lithium di-isopropyl amide |
| LiOH | Lithium hydroxide |
| $LiOH \cdot H_2O$ | Lithium hydroxide monohydrate |
| m | Multiplet |
| M | Molar, moles per liter |
| m/z | Mass-to-charge ratio |
| M + H | Protonated mass, mass measurement produced by mass spectrometry |
| mCi | Millicurie |
| Me | Methyl |
| $MeB(OH)_2$ | Methyl boronic acid |
| MeMgBr | Methyl magnesium bromide |
| MeOH, $CH_3OH$ | Methanol |
| mg | Milligram |
| $MgCl_2$ | Magnesium chloride |
| $MgSO_4$ | Magnesium sulfate |
| MHz | Megahertz |
| min | Minute(s) |
| mL, ml | Milliliter |
| mM | Millimole per liter |
| mmol | Millimole |
| MOI | Multiplicity of infection |
| $N_2$ | Nitrogen (gas) |
| $Na_2CO_3$ | Sodium carbonate |
| $Na_2SO_4$ | Sodium sulfate |
| NaCl | Sodium chloride |
| $NaHCO_3$ | Sodium bicarbonate |
| $NaHSO_3$ | Sodium bisulfite |
| $NaHSO_4$ | Sodium bisulfate, sodium hydrogen sulfate |
| NaOH | Sodium hydroxide |
| ng | Nanogram(s) |
| $NH_3$ | Ammonia |
| $NH_4Cl$ | Ammonium chloride |
| $NH_4OH$ | Ammonium hydroxide |
| nL | Nanoliter |
| nm | Nanometer |
| nM | Nanomolar |
| NMP | N-methyl-2-pyrrolidone |
| $Pd(Ph_3P)_4$ | Tetrakis(triphenyl phosphine) palladium(0) |
| Pd/C | Palladium on carbon |
| $Pd_2(dba)_3$ | Tris(dibenzylidene acetone) dipalladium(0) |
| PE | Petroleum ether |
| pfu | Plaque-forming unit |
| prep-HPLC | Preparative high performance liquid chromatography |
| prep-TLC | Preparative thin layer liquid chromatography |
| PSI | Pounds per square inch |
| Py, py | Pyridine |
| q | Quartet |
| RPM, rpm | Revolutions per minute |
| RT, rt | Room temperature, approximately 25° C. |

ABBREVIATIONS

| | |
|---|---|
| s | Singlet |
| sat | Saturated |
| SFC | Supercritical fluid chromatography |
| $SiO_2$ | Silica, silicon dioxide |
| $SO_2Cl_2$ | Sulfuryl chloride |
| $SOCl_2$ | Thionyl chloride |
| t | Triplet |
| t-BuLi | t-Butyl lithium, tert-butyl lithium |
| TFA | Trifluoroacetic acid |
| THF | Tetrahydrofuran |
| TLC | Thin layer chromatography |
| TMSCl | Trimethylsilyl chloride |
| $T_R$ | Retention time |
| TrisCl | Tris(hydroxymethyl)aminomethane hydrochloride |
| v/v | Volume/volume |
| WT STING | The wild type (most abundant) variant of STING in humans (DNA construct used herein: STING(1-379)H232R-gg-AviTag-gs-HRV3C-HIS8/pBAC1) |
| X-Phos | 2-Dicyclohexylphosphino-2',4',6'-triisopropylbiphenyl |
| $\lambda_{em}$ | Emission wavelength |
| $\lambda_{ex}$ | Excitation wavelength |
| µg, ug | Microgram |
| µL, uL, µl, ul | Microliter |
| µM, uM | Micromolar |
| µm, um | Micrometer |

Preparation 1: CPhos Pd G4

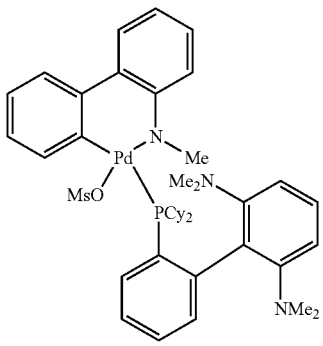

Step 1: CPhos Pd G4

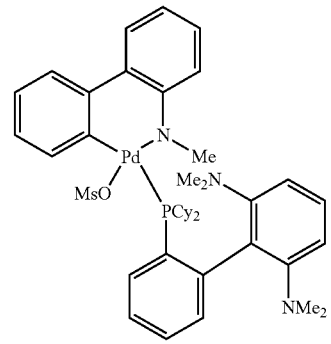

A mixture of (2'-methylamino-1,1'-biphenyl-2-yl)methanesulfonatopalladium (II) dimer (439 mg, 0.573 mmol) and 2'-(dicyclohexylphosphino)-N2,N2,N6,N6-tetramethyl-[1,1'-biphenyl]-2,6-diamine (500 mg, 1.15 mmol) in DCM (6 mL) was stirred at rt for 2 h. The solution was then diluted with $Et_2O$ (30 mL). The solution was filtered and concentrated under reduced pressure. The residue was then slurried in pentanes and again concentrated under reduced pressure to afford CPhos Pd G4. See Bruno, N. C.; Niljianskul, N.; Buchwald, S. L. *J. Org. Chem.* 2014, 79, 4161.

Preparation 2: Methyl-5,6-dimethoxybenzo[b]thiophene-2-carboxylate

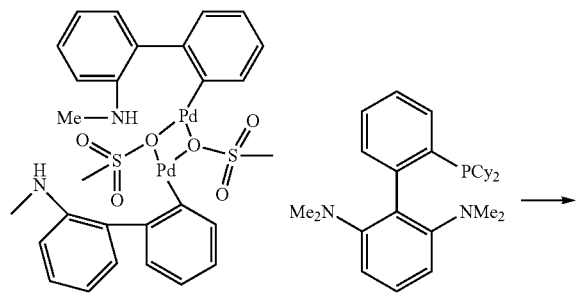

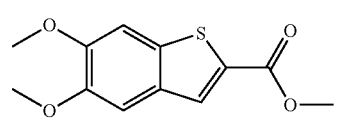

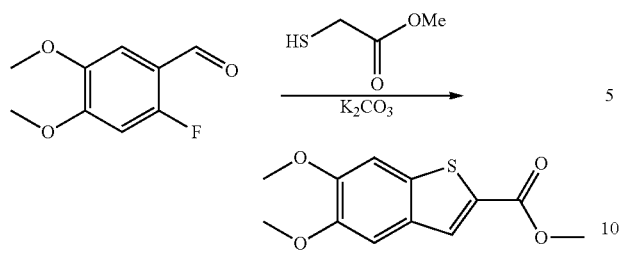
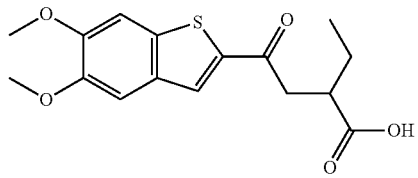

Example 1: 4-(5,6-Dimethoxybenzo[b]thiophen-2-yl)-2-ethyl-4-oxobutanoic acid

To a stirred solution of 2-fluoro-4,5-dimethoxybenzaldehyde (18.7 g, 102 mmol) in DMF (600 mL) was added methyl 2-mercaptoacetate (11.9 g, 112 mmol) and $K_2CO_3$ (42.1 g, 305 mmol). The resulting mixture was then heated at 60° C. for 15 h. After cooling to rt, the reaction mixture was concentrated under reduced pressure. The resulting residue was diluted with $H_2O$ (500 mL) and extracted with DCM (600 mL). The organic phase was dried over $Na_2SO_4$, filtered, and concentrated under reduced pressure to afford methyl 5,6-dimethoxybenzo[b]thiophene-2-carboxylate. LCMS ($C_{12}H_{13}O_4S$) (ES, m/z): 253 [M+H]$^+$. $^1$H NMR (400 MHz, DMSO-$d_6$): δ 8.03 (s, 1H), 7.60 (s, 1H), 7.49 (s, 1H), 3.85 (s, 6H), 3.82 (s, 3H).

Preparation 3: 5,6-Dimethoxybenzo[b]thiophene-2-carboxylic acid

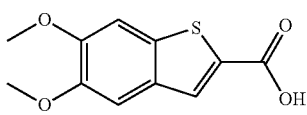 [SMILES: COc1cc2cc(C(=O)O)sc2cc1OC]

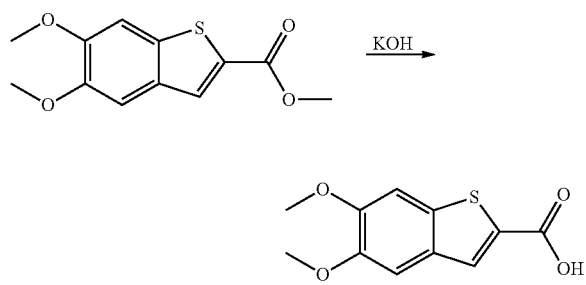

To a suspension of methyl 5,6-dimethoxybenzo[b]thiophene-2-carboxylate from Preparation 2 (23 g, 91 mmol) in MeOH (200 mL), THF (200 mL) and $H_2O$ (200 mL) was added KOH (51 g, 910 mmol). The resulting suspension was heated to 60° C. for 30 min. After cooling to rt, the reaction mixture was concentrated under reduced pressure. $H_2O$ (600 mL) was added to the resulting residue, and then citric acid was added to the solution to adjust to pH 6. The precipitated material was collected via filtration to afford 5,6-dimethoxybenzo[b]thiophene-2-carboxylic acid. $^1$H NMR (400 MHz, DMSO-$d_6$): δ 7.94 (s, 1H), 7.58 (s, 1H), 7.48 (s, 1H), 3.85 (s, 3H), 3.82 (s, 3H).

Step 1: 1-Ethyl 4-methyl 2-(5,6-dimethoxybenzo[b]thiophene-2-carbonyl)-3-ethylsuccinate

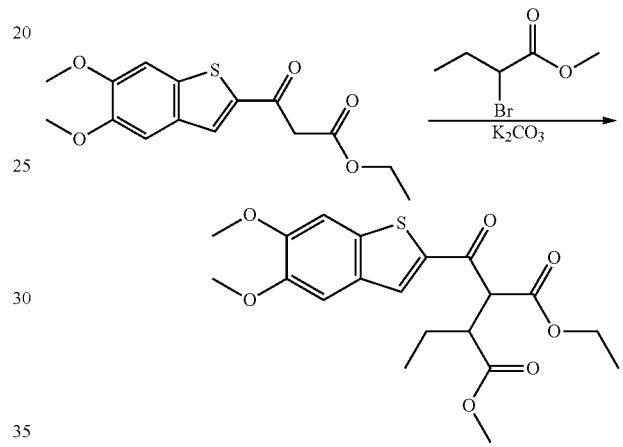

To a stirring solution of 3-(5,6-dimethoxybenzo[b]thiophen-2-yl)-3-oxopropanoate (commercially available from SPECS, 0.10 g, 0.32 mmol) in DMF (1.6 mL) was added methyl 2-bromobutyrate (37 uL, 0.32 mmol) and $K_2CO_3$ (54 mg, 0.39 mmol) at rt. The reaction mixture was stirred overnight at rt and then diluted with $H_2O$ (3 mL) and DCM (6 ml). The phases were separated, and the aq layer was washed with additional DCM (3×6 mL). The combined organic layers were concentrated under reduced pressure and dried overnight under high vacuum. The resulting residue was purified by silica gel column chromatography (EtOAc in Hex) to give 1-ethyl 4-methyl 2-(5,6-dimethoxybenzo[b]thiophene-2-carbonyl)-3-ethylsuccinate, which was used without further purification. LCMS ($C_{20}H_{25}O_7S$) (ES, m/z): 409 [M+H]$^+$.

Step 2: 4-(5,6-Dimethoxybenzo[b]thiophen-2-yl)-2-ethyl-4-oxobutanoic acid

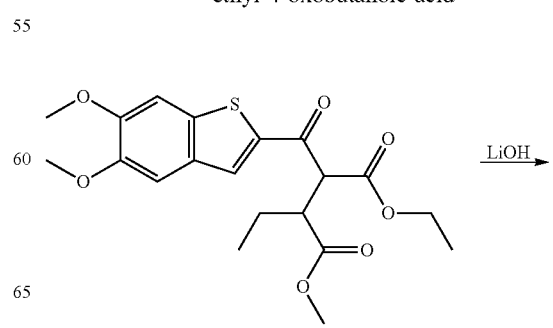

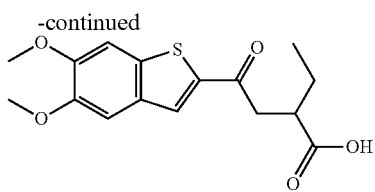

To a mixture of 1-ethyl 4-methyl 2-(5,6-dimethoxybenzo[b]thiophene-2-carbonyl)-3-ethylsuccinate (83 mg, 0.20 mmol) in THF (1.8 mL) and H$_2$O (0.18 mL) was added LiOH (39 mg, 1.6 mmol). The reaction mixture was stirred overnight at rt before the mixture was quenched with aq 2M HCl (0.30 mL, 0.59 mmol) and then diluted with EtOAc and H$_2$O. The organic layer was separated, dried over MgSO$_4$, filtered, and concentrated under reduced pressure. The resulting residue was purified by prep-HPLC (ACN/H$_2$O with 0.1% TFA) to afford 4-(5,6-dimethoxybenzo[b] thiophen-2-yl)-2-ethyl-4-oxobutanoic acid. The racemic mixture was resolved by CHIRAL-SFC (CHIRACEL OJ-H (250 mm*21 mm), 25% MeOH (+0.25% DMEA) in CO$_2$), affording two compounds with retention times of 3.65 min and 5.26 min. Concentration of the first eluting peak afforded the product. LCMS (C$_{16}$H$_{19}$O$_5$S) (ES, m/z): 323 [M+H]$^+$. $^1$H NMR (500 MHz, DMSO-d$_6$): δ 8.15 (s, 1H), 7.52 (s, 1H), 7.40 (s, 1H), 3.79 (s, 3H), 3.77 (s, 3H), 3.35-3.27 (m, 1H), 3.00-2.94 (m, 1H), 2.73-2.67 (m, 1H), 1.58-1.50 (m, 2H), 0.85 (t, J=7.3 Hz, 3H).

Example 2: 4-(5,6-Dimethoxybenzo[b]thiophen-2-yl)-2-isopropyl-4-oxobutanoic acid

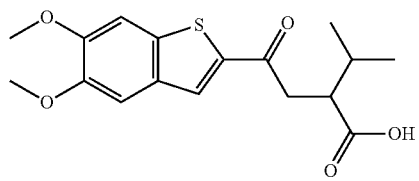 [SMILES: COc1cc2cc(C(=O)CC(C(=O)O)C(C)C)sc2cc1OC]

Step 1: 1-Ethyl 4-methyl 2-(5,6-dimethozybenzo[b]thiophene-2-carbonyl)-3-isopropylsuccinate

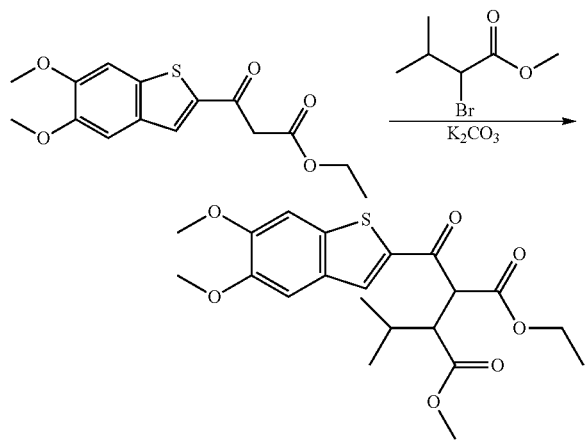

To a stirring mixture of ethyl 3-(5,6-dimethoxybenzo[b]thiophen-2-yl)-3-oxopropanoate (SPECS, 0.15 g, 0.49 mmol) in DMF (2.4 mL) was added methyl 2-bromoisovalerate (73 uL, 0.49 mmol) and K$_2$CO$_3$ (81 mg, 0.58 mmol) at rt. The reaction mixture was stirred overnight at rt and then diluted with H$_2$O (3.0 mL) and DCM (6.0 ml). The phases were separated, and the aq layer was washed with additional DCM (3×6.0 mL). The combined organic layers were concentrated under reduced pressure and dried overnight under high vacuum. The resulting residue was purified by silica gel column chromatography (EtOAc in hexanes) to afford 1-ethyl 4-methyl 2-(5,6-dimethoxybenzo[b]thiophene-2-carbonyl)-3-isopropylsuccinate, which was used in the next reaction without further purification. LCMS (C$_{21}$H$_{27}$O$_7$S) (ES, m/z): 423 [M+H]$^+$.

Step 2: 4-(5,6-Dimethoxybenzo[b]thiophen-2-yl)-2-isopropyl-4-oxobutanoic acid

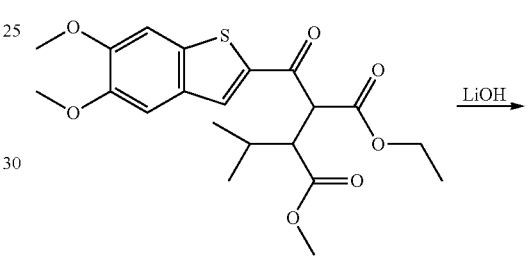

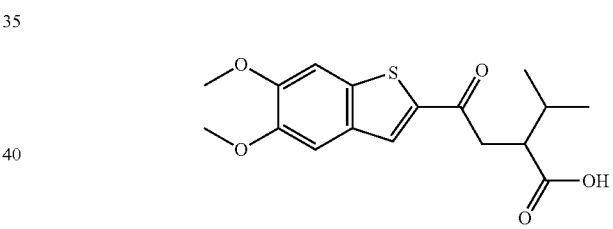

To a mixture of 1-ethyl 4-methyl 2-(5,6-dimethoxybenzo[b]thiophene-2-carbonyl)-3-isopropylsuccinate (68 mg, 0.16 mmol) in THF (0.80 mL), MeOH (0.40 mL), and H$_2$O (0.18 mL) was added LiOH (19 mg, 0.80 mmol). The reaction mixture was stirred for 2 h at rt before the mixture was quenched with aq 2M HCl (0.40 mL, 0.80 mmol) and then diluted with EtOAc and H$_2$O. The organic layer was separated, dried over MgSO$_4$, filtered, and concentrated under reduced pressure. The resulting residue was purified by silica gel column chromatography (EtOAc in Hex) to afford 4-(5,6-dimethoxybenzo[b]thiophen-2-yl)-2-isopropyl-4-oxobutanoic acid. The racemic mixture was resolved by CHIRAL-SFC (CHIRALPAK IC (250 mm*21 mm), 40% MeOH (+0.25% DMEA) in CO$_2$), affording two compounds with retention times of 5.70 min and 7.05 min. Concentration of the second eluting peak afforded the product. LCMS (C$_{17}$H$_{21}$O$_5$S) (ES, m/z): 337 [M+H]$^+$. $^1$H NMR (500 MHz, DMSO-d$_6$): δ 8.17 (1H, s), 7.49 (s, 1H), 7.37 (s, 1H), 3.76 (s, 3H), 3.74 (s, 3H), 3.35-3.25 (m, 1H), 3.05-2.85 (m, 1H), 2.67-2.61 (m, 1H), 1.95-1.87 (m, 1H), 0.88-0.82 (m, 6H).

Example 3: 2-Cyclopropyl-4-(5,6-dimethoxybenzo[b]thiophen-2-yl)-4-oxobutanoic acid

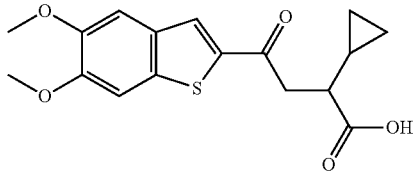 [SMILES: COc1cc2cc(C(=O)CC(C(=O)O)C3CC3)sc2cc1OC]

Step 1: Diethyl 2-cyclopropyl-3-(5,6-dimethoxy-benzo[b]thiophen-2-carbonyl)succinate

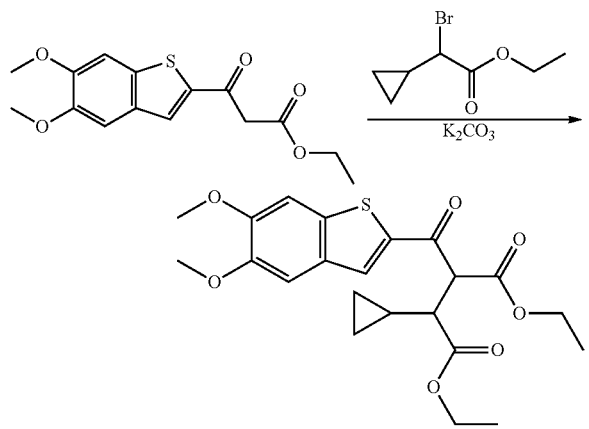

To a stirring mixture of ethyl 3-(5,6-dimethoxybenzo[b]thiophen-2-yl)-3-oxopropanoate (Specs, 0.30 g, 0.97 mmol) in DMF (4.9 mL) was added ethyl 2-bromo-2-cyclopropylacetate (0.20 g, 0.97 mmol) and then $K_2CO_3$ (0.16 g, 1.2 mmol) at rt. The mixture was allowed to stir overnight and then diluted with $H_2O$ (3.0 mL) and DCM (6.0 mL). The phases were separated, and the aq layer was washed with DCM (3×6 mL). The combined organics were concentrated under reduced pressure and dried overnight under high vacuum. The resulting residue was purified by silica gel column chromatography (EtOAc in Hex) to afford diethyl 2-cyclopropyl-3-(5,6-dimethoxybenzo[b]thiophen-2-carbonyl)succinate. LCMS ($C_{22}H_{27}O_7S$) (ES, m/z): 435 [M+H]$^+$.

Step 2: 2-Cyclopropyl-4-(5,6-dimethoxybenzo[b]thiophen-2-yl)-4-oxobutanoic acid

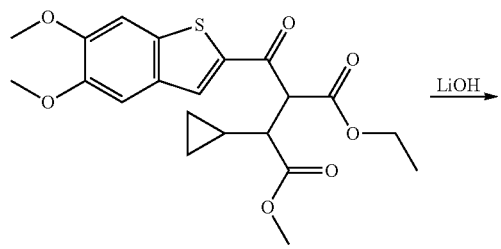

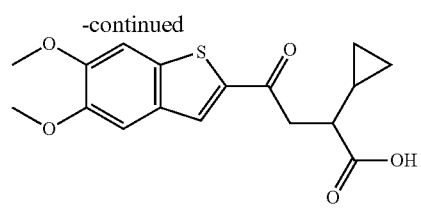

To a mixture of diethyl 2-cyclopropyl-3-(5,6-dimethoxy-benzo[b]thiophen-2-carbonyl)succinate (90 mg, 0.21 mmol) in THF (1.0 mL), MeOH (0.50 mL) and $H_2O$ (0.50 mL) was added LiOH (25 mg, 1.0 mmol), and the mixture was allowed to stir for 2 h at rt. After 2 h, the mixture was acidified with 1N HCl (0.50 mL, 1.0 mmol) and then diluted with EtOAc and $H_2O$. The organic layer was separated, dried over $MgSO_4$, filtered and concentrated under reduced pressure. The resulting residue was purified by silica gel column chromatography (EtOAc in hexanes) to afford 2-cyclopropyl-4-(5,6-dimethoxybenzo[b]thiophen-2-yl)-4-oxobutanoic acid as a racemic mixture. The racemic mixture was resolved by Chiral-SFC (OJ-H column, 25% MeOH (+0.25% DMEA) in $CO_2$), affording two compounds with retention times of 5.3 min and 6.9 min. Concentration of the first eluting peak afforded the product. LCMS ($C_{17}H_{19}O_5S$) (ES, m/z): 335 [M+H]$^+$. $^1$H NMR (500 MHz, DMSO-$d_6$) δ 8.23 (s, 1H), 7.58 (s, 1H), 7.46 (s, 1H), 3.85 (s, 3H), 3.83 (s, 3H), 3.51-3.43 (m, 2H), 2.13-2.08 (m, 1H), 0.99-0.87 (m, 1H), 0.54-0.34 (m, 4H).

Example 4: 2-(5,6-Dimethoxybenzo[b]thiophene-2-carbonyl)cyclopropane carboxylic acid

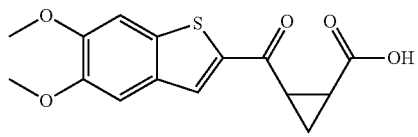 [SMILES: COc1cc2cc(C(=O)C3CC3C(=O)O)sc2cc1OC]

Step 1: 5,6-Dimethoxybenzo[b]thiophene

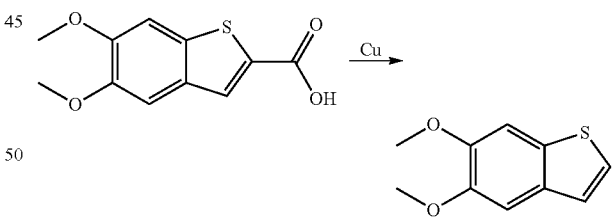

To a stirring solution of 5,6-dimethoxybenzo[b]thiophene-2-carboxylic acid (Preparation 3, 2.00 g, 8.39 mmol) in quinoline (20 mL) was added copper (0.907 g, 14.3 mmol) and then the mixture was heated at 190° C. for 2 h. Upon cooling to rt, the mixture was diluted with EtOAc and then successively washed with aq HCl (2M), $H_2O$, sat aq $NaHCO_3$, and brine. The organic layer was dried over $MgSO_4$, filtered, and concentrated under reduced pressure. The residue was purified by silica gel column chromatography (EtOAc in Hex) to give 5,6-dimethoxybenzo[b]thiophene. LCMS ($C_{10}H_{11}O_2S$) (ES, m/z): 195 [M+H]$^+$. $^1$H NMR (500 MHz, DMSO-$d_6$): δ 7.54 (s, 1H), 7.51 (d, J=5.3 Hz, 1H), 7.38 (s, 1H), 7.29 (d, J=5.3 Hz, 1H), 3.81 (s, 3H), 3.80 (s, 3H).

Step 2: 2-(5,6-Dimethoxybenzo[b]thiophene-2-carbonyl)cyclopropane carboxylic acid

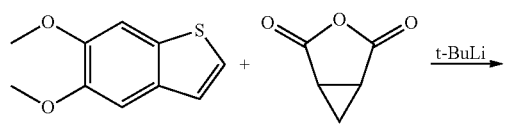

6.74 (s, 1H), 6.67 (s, 1H), 3.01 (s, 3H), 3.00 (s, 3H), 2.20 (m, 1H), 1.46-1.38 (m, 1H), 0.72-0.63 (m, 1H), 0.51-0.43 (m, 1H).

Examples 5 and 6, as shown in Table 1 below, were or may be prepared according to procedures analogous to those outlined in Example 4 above using the appropriate starting materials, decribed as Preparations or as obtained from commercial sources.

TABLE 1

| Ex. | Structure | Name | Mass [M + H]$^+$ |
|---|---|---|---|
| 5 | 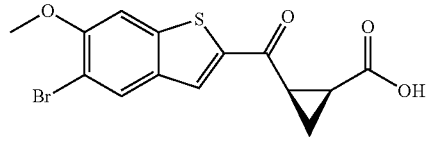 [SMILES: COc1cc2sc(C(=O)[C@@H]3C[C@@H]3C(=O)O)cc2cc1Br] | 2-(5-bromo-6-methoxybenzo[b]thiophene-2-carbonyl)cyclopropane-1-carboxylic acid (Single Enantiomer) | 355, 357 |
| 6 | 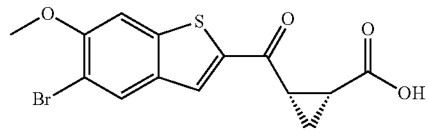 [SMILES: COc1cc2sc(C(=O)[C@H]3C[C@H]3C(=O)O)cc2cc1Br] | 2-(5-bromo-6-methoxybenzo[b]thiophene-2-carbonyl)cyclopropane-1-carboxylic acid (Single Enantiomer) | 355, 357 |

-continued-

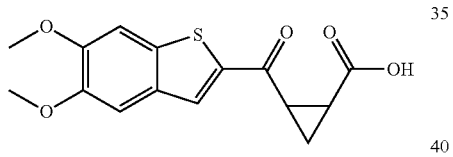

To a stirring solution of 5,6-dimethoxybenzo[b]thiophene (500 mg, 2.57 mmol) in THF (12 mL) was added t-BuLi (3.0 mL, 3.9 mmol) (1.3M in n-pentane) dropwise over 5 min at −78° C. under N$_2$ atmosphere. The mixture was stirred at −78° C. for 1 h, and then 3-oxabicyclo[3.1.0]hexane-2,4-dione (577 mg, 5.15 mmol) in THF (10 mL) was added dropwise over 10 min. The mixture was allowed to warm to rt and then stirred at rt for 12 h under N$_2$ atmosphere. H$_2$O (15 mL) was added to the mixture, and the mixture was then extracted with EtOAc (10 mL). The aq layer was extracted with additional EtOAc (10 mL) and then was adjusted to pH=5-6 with aq HCl (1.0M) and further extracted with EtOAc (3×30 mL). The combined organic layers were washed with brine (20 mL), dried over MgSO$_4$, filtered, and concentrated under reduced pressure. The resulting residue was purified by prep-HPLC (ACN/H$_2$O with 0.1% TFA) to give 2-(5,6-dimethoxybenzo[b]thiophene-2-carbonyl)cyclopropane carboxylic acid. The racemic mixture was resolved by C$_{HIRAL}$-SFC (Column AD (250 mm*30 mm), 40% (1:1 H$_2$O (+0.1% NH$_3$) and EtOH) in CO$_2$), affording two compounds with retention times of 5.61 min and 6.22 min. Concentration of the first eluting peak afforded the product. LCMS (C$_{15}$H$_{15}$O$_5$S) (ES, m/z): 307 [M+H]$^+$. $^1$H NMR (400 MHz, DMSO-d$_6$): δ 11.35 (s, 1H), 7.37 (s, 1H),

Example 7: 4-(5-Chloro-6-methoxybenzo[b]thiophen-2-yl)-4-oxobutanoic acid

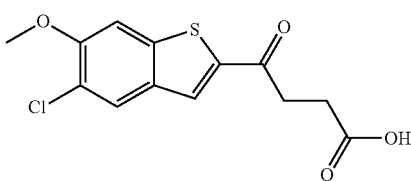 [SMILES: COc1cc2sc(C(=O)CCC(=O)O)cc2cc1Cl]

Step 1: 5-Chloro-2-fluoro-4-methoxybenzaldehyde

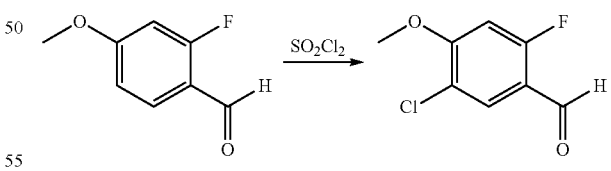

To a stirring solution of 2-fluoro-4-methoxybenzaldehyde (1.00 g, 6.49 mmol) in AcOH (2 mL) was added SO$_2$Cl$_2$ (1.05 mL, 13.0 mmol). After stirring at rt for 12 h, the reaction was complete. The reaction mixture was poured into ice water (50 mL). The resulting precipitate was collected by vacuum filtration, washed with H$_2$O (3×20 mL), and air dried to afford 5-chloro-2-fluoro-4-methoxybenzaldehyde. LCMS (C$_8$H$_7$ClFO$_2$) (ES, m/z): 189 [M+H]$^+$. $^1$H NMR (400 MHz, CDCl$_3$): δ 10.18 (s, 1H), 7.88 (d, J=7.28 Hz, 1H), 6.72 (d, J=11.69 Hz, 1H), 3.99 (s, 3H). $^{19}$F NMR (376 MHz, CDCl$_3$): δ −119.91 (dd, J=7.15, 11.32 Hz).

Step 2: Methyl 5-chloro-6-methoxybenzo[b]thiophene-2-carboxylate

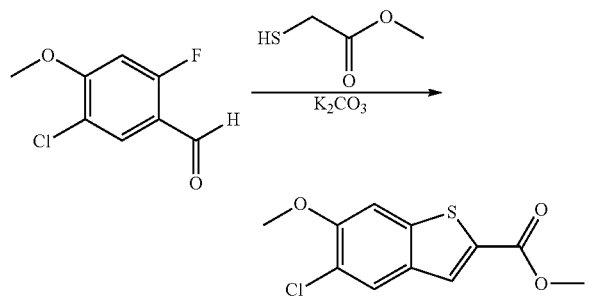

A mixture of 5-chloro-2-fluoro-4-methoxybenzaldehyde (1.04 g, 5.51 mmol), methyl 2-mercaptoacetate (0.740 mL, 8.27 mmol), K$_2$CO$_3$ (2.29 g, 16.5 mmol) and DMF (50 mL) was stirred for 12 h at 80° C. The reaction mixture was cooled to rt and poured into 500 mL of ice water. Aq HCl (1M) was added to adjust the mixture to pH 5. The precipitate was collected by filtration, washed with H$_2$O (3×100 mL), and dried under reduced pressure to give methyl 5-chloro-6-methoxybenzo[b] thiophene-2-carboxylate, which was used directly in the next step. LCMS (C$_{11}$H$_{10}$ClO$_3$S) (ES, m/z): 257 [M+H]$^+$.

Step 3: 5-Chloro-6-methoxybenzo[b]thiophene-2-carboxylic acid

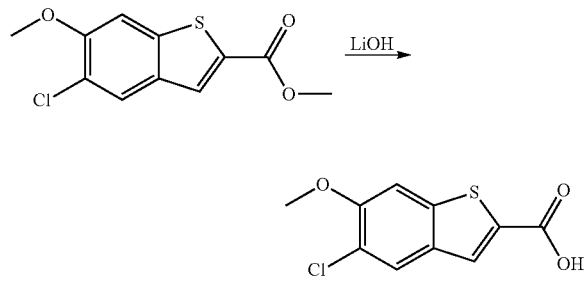

To a stirring suspension of methyl 5-chloro-6-methoxybenzo[b]thiophene-2-carboxylate (1.15 g, 4.46 mmol) in H$_2$O (10 mL), THF (10 mL), and MeOH (10 mL) was added LiOH.H$_2$O (0.562 g, 13.4 mmol). The resulting mixture was heated to 50° C. for 3 h. The reaction mixture was then cooled to rt, and the organic solvents were removed by distillation under reduced pressure. The residue was diluted with H$_2$O (20 mL) and washed with DCM (3×10 mL). The aq layer was acidified with aq 1M HCl to pH 5, and the resulting precipitate was washed with H$_2$O (3×10 mL). The remaining solid was dried under reduced pressure to give 5-chloro-6-methoxybenzo[b]thiophene-2-carboxylic acid. LCMS (C$_{10}$H$_8$ClO$_3$S) (ES, m/z): 243 [M+H]$^+$. $^1$H NMR (400 MHz, DMSO-d$_6$): δ 13.43 (br, 1H), 8.10 (s, 1H), 7.99 (s, 1H), 7.83 (s, 1H), 3.94 (s, 3H).

Step 4: 5-Chloro-6-methoxybenzo[b]thiophene-2-carbonyl chloride

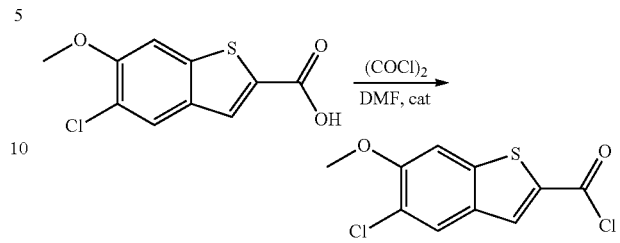

To a mixture of 5-chloro-6-methoxybenzo[b]thiophene-2-carboxylic acid (215 mg, 0.886 mmol) and THF (10 mL) was added (COCl)$_2$ (0.4 mL, 4.73 mmol) and DMF (4 uL, 0.055 mmol) at 0° C. The resulting mixture was stirred at 80° C. for 16 h and then cooled to rt. The mixture was diluted with toluene (20 mL) and concentrated under reduced pressure. The concentrated reaction mixture was then twice redissolved in toluene (20 mL) and concentrated under reduced pressure. The resulting concentrated reaction mixture was dried in vacuo at 50° C.-80° C. for 1 h and then backfilled with Ar gas for storage. The resultant 5-chloro-6-methoxybenzo[b] thiophene-2-carbonyl chloride was used in the next step directly.

Step 5: Ethyl 4-(5-chloro-6-methoxybenzo[b]thiophen-2-yl)-4-oxobutanoate

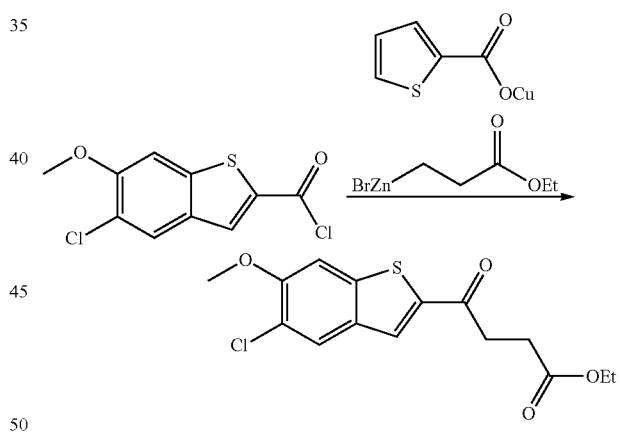

An oven-dried Schlenk flask was charged with stir bar and ((thiophene-2-carbonyl)oxy)copper (500 mg, 2.62 mmol) under an Ar balloon. The flask was dried while attached to a high vacuum source by heating with a heat gun for 3 min. After cooling to 0° C., (3-ethoxy-3-oxopropyl)zinc(II) bromide (5.0 mL, 0.5M in THF, 2.5 mmol) was added to the flask via syringe to form a mixture. After stirring at 0° C. for 40 min, a solution of 5-chloro-6-methoxybenzo[b]thiophene-2-carbonyl chloride (272 mg, 0.885 mmol) in THF (5 mL) was added to the mixture. The resulting mixture was gradually warmed to rt and stirred for 16 h. The reaction mixture was quenched with sat aq NH$_4$Cl solution (20 mL) and extracted with EtOAc (3×30 mL). The combined organic layers were washed with sat aq Na$_2$CO$_3$ solution (2×15 mL) and brine (10 mL), dried over anhydrous Na$_2$SO$_4$, filtered, and concentrated under reduced pressure.

The residue was purified by prep-HPLC (ACN/H₂O with 0.1% TFA) to give ethyl 4-(5-chloro-6-methoxybenzo[b]thiophen-2-yl)-4-oxobutanoate. LCMS (C₁₅H₁₆ClO₄S) (ES, m/z): 327 [M+H]⁺. ¹H NMR (400 MHz, CDCl₃): δ 7.87 (s, 1H), 7.86 (s, 1H), 7.32 (s, 1H), 4.16 (q, J=7.0 Hz, 2H), 3.99 (s, 3H), 3.32 (t, J=6.8 Hz, 2H), 2.78 (t, J=6.8 Hz, 2H), 1.27 (t, J=7.0 Hz, 5H).

Step 6: 4-(5-Chloro-6-methoxybenzo[b]thiophen-2-yl)-4-oxobutanoic acid

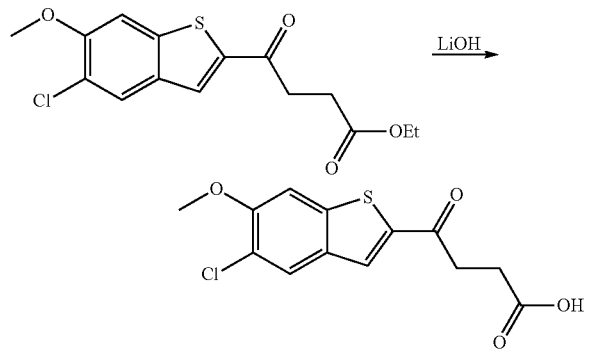

To a stirred solution of ethyl 4-(5-chloro-6-methoxybenzo[b]thiophen-2-yl)-4-oxobutanoate (62 mg, 0.19 mmol) in MeOH (6 mL) and H₂O (3 mL) was added LiOH.H₂O (0.12 g, 5.0 mmol). The mixture was stirred at 45° C. for 2 h, and the solvent was removed under reduced pressure. The residue was dissolved in H₂O (15 mL) and washed with DCM (2×15 mL). The aq layer was acidified with concentrated aq HCl to pH~2 and then extracted with DCM (5×10 mL). The combined organic phases were dried over anhydrous Na₂SO₄, filtered, and concentrated under reduced pressure. The residue was purified by prep-HPLC (ACN/H₂O with 0.1% TFA) to give 4-(5-chloro-6-methoxybenzo[b] thiophen-2-yl)-4-oxobutanoic acid. LCMS (C₁₃H₁₂ClO₄S) (ES, m/z): 299 [M+H]⁺. ¹H NMR (400 MHz, MeOH-d₄): δ 8.10 (s, 1H), 7.98 (s, 1H), 7.60 (s, 1H), 3.98 (s, 3H), 3.37-3.33 (m, 2H), 2.73 (t, J=6.5 Hz, 2H).

Example 8: 4-(5-Methoxy-6-vinylbenzo[b]thiophen-2-yl)-4-oxobutanoic acid

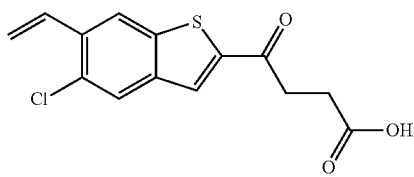 [SMILES: C=Cc1cc2sc(C(=O)CCC(=O)O)cc2cc1Cl]

Step 1: Methyl 6-bromo-5-methoxybenzo[b]thiophene-2-carboxylate

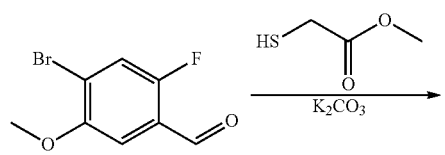

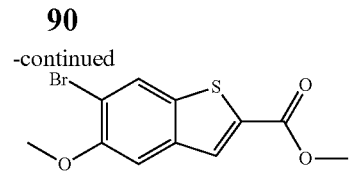

To a stirred solution of 4-bromo-2-fluoro-5-methoxybenzaldehyde (5.00 g, 21.5 mmol) in DMF (100 mL) was added methyl 2-mercaptoacetate (2.51 g, 23.6 mmol) and K₂CO₃ (8.90 g, 64.4 mmol). The reaction mixture was degassed with N₂ 3 times. The resulting mixture was then stirred at rt for 15 h. EtOAc (500 mL) and H₂O (1200 mL) were added to the reaction mixture. The organic layer was separated and washed with brine (2×200 mL), dried over anhydrous Na₂SO₄, filtered, and concentrated under reduced pressure. The residue was purified by silica gel column chromatography (EtOAc in PE) to give methyl 6-bromo-5-methoxybenzo [b]thiophene-2-carboxylate. LCMS (C₁₁H₁₀BrO₃S) (ES, m/z): 301, 303 [M+H]⁺. ¹H NMR (400 MHz, CDCl₃): δ=8.01 (s, 1H), 7.93 (s, 1H), 7.26 (s, 1H), 3.96 (s, 3H), 3.94 (s, 3H).

Step 2: 6-Bromo-5-methoxybenzo[b]thiophene-2-carboxylic acid

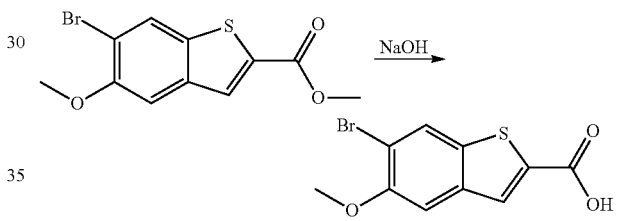

To a suspension of methyl 6-bromo-5-methoxybenzo[b]thiophene-2-carboxylate (1.45 g, 4.81 mmol) in MeOH (20 mL), THF (20 mL), and H₂O (20 mL) was added NaOH (1.93 g, 48.1 mmol). The resulting suspension was heated to 50° C. for 0.5 h. The reaction mixture was concentrated under reduced pressure to remove the solvent. H₂O (200 mL) was added to the residue, and citric acid was added to adjust the solution to pH=6. The remaining aq suspension was extracted with EtOAc (3×50 mL). The combined organic layers were washed with brine (100 mL), dried over Na₂SO₄, filtered, and concentrated under reduced pressure to give 6-bromo-5-methoxybenzo[b]thiophene-2-carboxylic acid, which was used directly for the next step without further purification. ¹H NMR (400 MHz, DMSO-d₆): δ=13.52 (br s, 1H), 8.35 (s, 1H), 8.01 (s, 1H), 7.65 (s, 1H), 3.90 (s, 3H).

Step 3: 6-Bromo-5-methoxybenzo[b]thiophene-2-carbonyl chloride

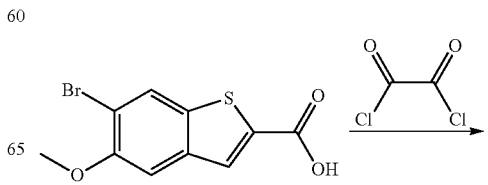

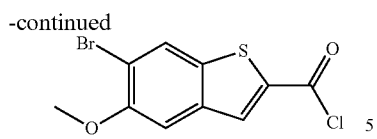

To a stirred solution of 6-bromo-5-methoxybenzo[b]thiophene-2-carboxylic acid (800 mg, 2.79 mmol) in anhydrous THF (6 mL) was added (COCl)$_2$ (1.06 g, 8.36 mmol) dropwise at 0° C. The mixture was then heated at 75° C. for 15 h and then cooled to rt. The solvent was removed under reduced pressure to give the crude 6-bromo-5-methoxybenzo[b]thiophene-2-carbonyl chloride, which was used directly in the next step without further purification.

Step 4: Ethyl 4-(6-bromo-5-methoxybenzo[b]thiophen-2-yl)-4-oxobutanoate

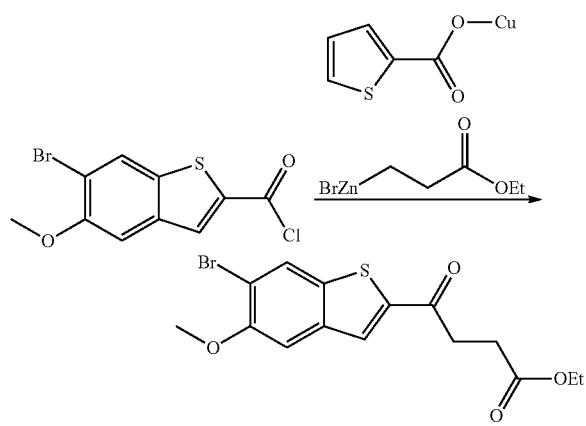

A solution of (3-ethoxy-3-oxopropyl)zinc(II) bromide (19.6 mL, 0.5M in THF, 9.82 mmol) was added to an oven-dried flask containing ((thiophene-2-carbonyl)oxy)copper (1.87 g, 9.82 mmol) under Ar atmosphere at 0° C. The reaction mixture was stirred for 20 min at 0° C. under Ar atmosphere. An Ar-degassed solution of 6-bromo-5-methoxybenzo[b]thiophene-2-carbonyl chloride (1.00 g, 3.27 mmol) in THF (20 mL) was then added to the reaction mixture at 0° C. The resulting suspension was allowed to warm to rt and was stirred for an additional 3 h. The reaction mixture was then cooled to 0° C. and quenched with sat aq NH$_4$Cl solution (50 mL). The mixture was allowed to warm to rt and stirred for 10 min. The mixture was then filtered to remove any precipitated solid, and the filtrate was diluted with EtOAc (50 mL) and brine (20 mL). The organic layer was separated, washed with additional brine (50 mL), dried over MgSO$_4$, filtered, and concentrated under reduced pressure to afford the crude product residue. The residue was purified by silica gel column chromatography (DCM in PE) to give ethyl 4-(6-bromo-5-methoxybenzo[b]thiophen-2-yl)-4-oxobutanoate. LCMS (C$_{15}$H$_{16}$BrO$_4$S) (ES, m/z): 371, 373 [M+H]$^+$. $^1$H NMR (400 MHz, CDCl$_3$): δ=8.05 (s, 1H), 7.92 (s, 1H), 7.30 (s, 1H), 4.18 (q, J=7.2 Hz, 2H), 3.98 (s, 3H), 3.34 (t, J=6.7 Hz, 2H), 2.80 (t, J=6.7 Hz, 2H), 1.28 (t, J=7.1 Hz, 3H).

Step 5: Ethyl 4-(5-methoxy-6-vinylbenzo[b]thiophen-2-yl)-4-oxobutanoate

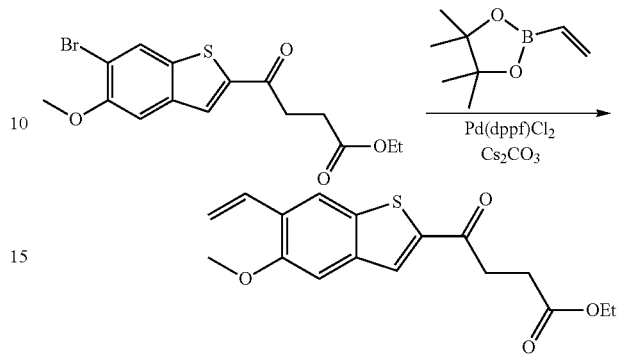

To a stirring mixture of ethyl 4-(6-bromo-5-methoxybenzo[b]thiophen-2-yl)-4-oxobutanoate (40.0 mg, 0.108 mmol), 4,4,5,5-tetramethyl-2-vinyl-1,3,2-dioxaborolane (33.2 mg, 0.215 mmol), and Cs$_2$CO$_3$ (105 mg, 0.323 mmol) in 1,4-dioxane (1.0 mL) and H$_2$O (0.2 mL) was added 1,1'-bis(diphenylphosphino)ferrocene dichloride (12 mg, 0.022 mmol). The reaction mixture was degassed by placing under reduced pressure and backfilling with N$_2$ 3 times. The reaction mixture was stirred at 90° C. under N$_2$ atmosphere for 2 h, cooled to rt, and filtered remove any solids. The filtrate was diluted with EtOAc (5 mL) and brine (5 mL). The organic layer was separated, washed with additional brine (5 mL), dried over anhydrous Na$_2$SO$_4$, filtered, and concentrated under reduced pressure to give ethyl 4-(5-methoxy-6-vinylbenzo[b]thiophen-2-yl)-4-oxobutanoate, which was used for next step without further purification. LCMS (C$_{17}$H$_{19}$O$_4$S) (ES, m/z): 319 [M+H]$^+$.

Step 6: 4-(5-Methoxy-6-vinylbenzo[b]thiophen-2-yl)-4-oxobutanoic acid

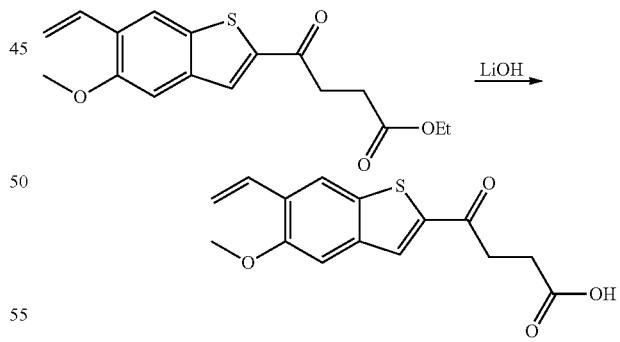

To a stirred suspension of ethyl 4-(5-methoxy-6-vinylbenzo[b]thiophen-2-yl)-4-oxobutanoate (25 mg, 0.079 mmol) in MeOH (0.5 mL), THF (0.5 mL), and H$_2$O (0.5 mL) was added LiOH (18.8 mg, 0.785 mmol). The resulting suspension was heated to 50° C. for 2 h and then cooled to rt. The reaction mixture was concentrated under reduced pressure to remove the solvent, and the residue was purified by prep-HPLC (ACN/H$_2$O with 0.1% TFA) to give 4-(5-methoxy-6-vinylbenzo[b]thiophen-2-yl)-4-oxobutanoic acid. LCMS (C$_{15}$H$_{15}$O$_4$S) (ES, m/z): 291 [M+H]$^+$. $^1$H NMR (400 MHz, MeOH-d₄): δ=8.10 (s, 1H), 7.98 (s, 1H), 7.44 (s, 1H), 7.09 (dd, J=11.3, 17.8 Hz, 1H), 5.87 (br d, J=17.4 Hz, 1H), 5.32 (br d, J=11.2 Hz, 1H), 3.91 (s, 3H), 3.37-3.32 (m, 2H), 2.71 (br t, J=6.5 Hz, 2H).

Example 9: 4-(6-Bromo-5-methoxybenzo[b]thiophen-2-yl)-4-oxobutanoic acid

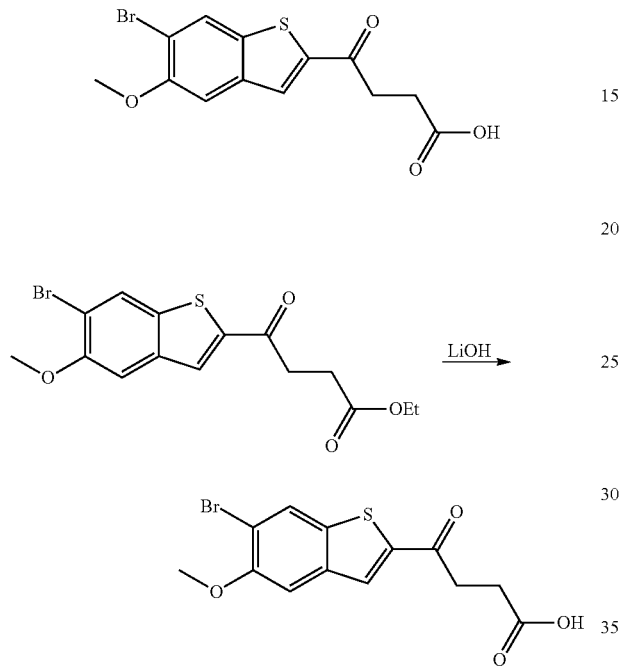

To a suspension of ethyl 4-(6-bromo-5-methoxybenzo[b]thiophen-2-yl)-4-oxobutanoate from Example 8, step 4 (20 mg, 0.054 mmol) in MeOH (0.5 mL), THF (0.5 mL), and H₂O (0.5 mL) was added LiOH (1.3 mg, 0.054 mmol). The resulting suspension was heated to 50° C. for 2 h and then cooled to rt. The reaction mixture was concentrated under reduced pressure to remove the solvent, and the residue was purified by prep-HPLC (ACN/H₂O with 0.1% TFA) to give 4-(6-bromo-5-methoxybenzo[b]thiophen-2-yl)-4-oxobutanoic acid. LCMS (C₁₃H₁₂BrO₄S) (ES, m/z): 343, 345 [M+H]⁺. ¹H NMR (400 MHz, MeOH-d₄): δ=8.12 (s, 1H), 8.11 (s, 1H), 7.53 (s, 1H), 3.95 (s, 3H), 3.36 (t, J=6.4 Hz, 2H), 2.74 (t, J=6.4 Hz, 2H).

Example 10: 4-(6-Methoxy-5-(methylamino)benzo[b]thiophen-2-yl)-4-oxobutanoic acid

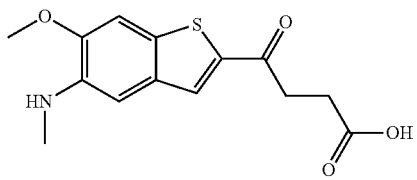 [SMILES: CNc1cc2cc(C(=O)CCC(=O)O)sc2cc1OC]

Step 1: 2-Fluoro-4-methoxy-5-nitrobenzaldehyde

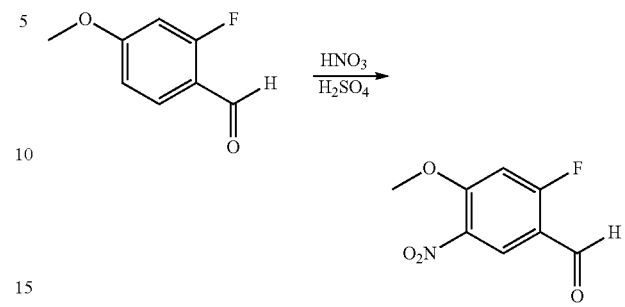

To a stirred solution of 2-fluoro-4-methoxybenzaldehyde (1.00 g, 6.49 mmol) in concentrated H₂SO₄ (5.88 mL, 110 mmol) at −15° C. was added concentrated HNO₃ (0.414 mL, 6.49 mmol) in concentrated H₂SO₄ (0.795 mL, 14.9 mmol) dropwise over 5 min. After 1 h of stirring at below −10° C., the reaction mixture was poured into 50 mL of ice water. The precipitate was collected by filtration. The filter cake was washed with H₂O (3×100 mL) and dried under reduced pressure to give 2-fluoro-4-methoxy-5-nitrobenzaldehyde, which was used directly in the next step. LCMS (C₈H₇FNO₄) (ES, m/z): 200 [M+H]⁺. ¹H NMR (400 MHz, CDCl₃): δ 10.22 (s, 1H), 8.47 (d, J=7.24 Hz, 1H), 6.88 (d, J=11.54 Hz, 1H), 4.07 (s, 3H).

Step 2: Methyl 6-methoxy-5-nitrobenzo[b]thiophene-2-carboxylate

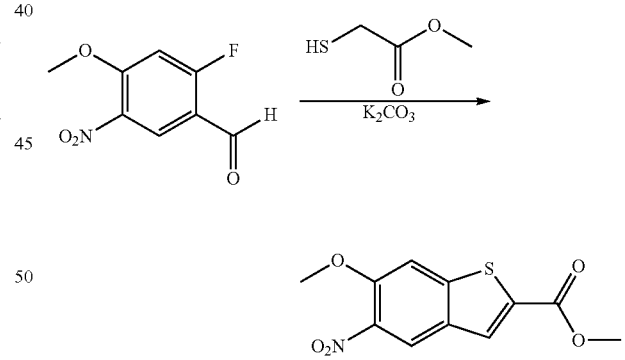

A mixture of 2-fluoro-4-methoxy-5-nitrobenzaldehyde (1.14 g, 5.72 mmol), methyl 2-mercaptoacetate (0.77 mL, 8.6 mmol), and K₂CO₃ (2.37 g, 17.2 mmol) in DMF (50 mL) was stirred for 12 h at 60° C. The reaction mixture was cooled to rt and then poured into 500 mL of ice water. Aq HCl (1M) was added to adjust to pH 5. The precipitate was collected by filtration, washed with H₂O (3×100 mL), and dried under reduced pressure to give methyl 6-methoxy-5-nitrobenzo[b]thiophene-2-carboxylate, which was used directly in the next step. LCMS (C₁₁H₁₀NO₅S) (ES, m/z): 268 [M+H]⁺.

Step 3: 6-Methoxy-5-nitrobenzo[b]thiophene-2-carboxylic acid

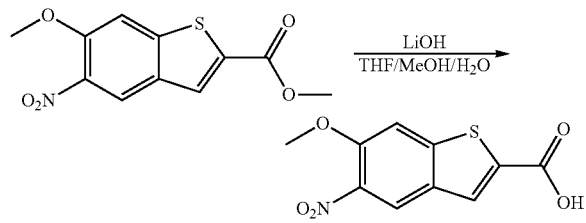

To a suspension of methyl 6-methoxy-5-nitrobenzo[b]thiophene-2-carboxylate (1.50 g, 5.61 mmol) in H$_2$O (10 mL), THF (10 mL), and MeOH (10 mL) was added LiOH.H$_2$O (0.707 g, 16.8 mmol). The resulting mixture was heated to 50° C. for 5 h and then cooled to rt. The organic solvent was removed under reduced pressure, the residue was diluted with 20 mL H$_2$O, and the mixture was extracted with DCM (3×10 mL). The aq layer was acidified with aq HCl solution (1M) to pH 5. The precipitate was collected by filtration and then washed with H$_2$O (3×10 mL). The resulting solid was dried under reduced pressure to give 6-methoxy-5-nitrobenzo[b]thiophene-2-carboxylic, which was used directly in the next step. LCMS (C$_{10}$H$_8$NO$_5$S) (ES, m/z): 254 [M+H]$^+$. $^1$H NMR (400 MHz, DMSO-d$_6$): δ 13.93-13.26 (s, 1H), 8.58 (s, 1H), 8.12 (s, 1H), 8.05 (s, 1H), 3.98 (s, 3H).

Step 4: 6-Methoxy-5-nitrobenzo[b]thiophene-2-carbonyl chloride

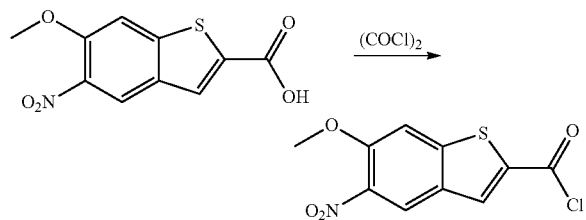

To a stirred solution of 6-methoxy-5-nitrobenzo[b]thiophene-2-carboxylic acid (400 mg, 1.58 mmol) in anhydrous THF (15 mL) was added (COCl)$_2$ (1.20 g, 9.48 mmol) dropwise at 0° C. The mixture was heated at 75° C. for 15 h and then cooled to rt. The solvent was removed under reduced pressure to give the crude 6-methoxy-5-nitrobenzo[b]thiophene-2-carbonyl chloride, which was without further purification in the next step.

Step 5: Ethyl 4-(6-methoxy-5-nitrobenzo[b]thiophen-2-yl)-4-oxobutanoate

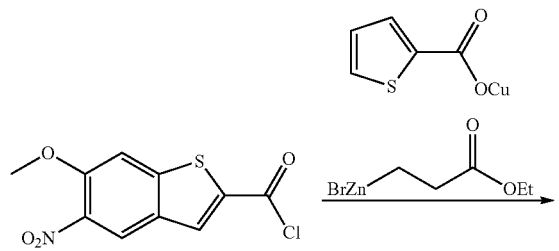

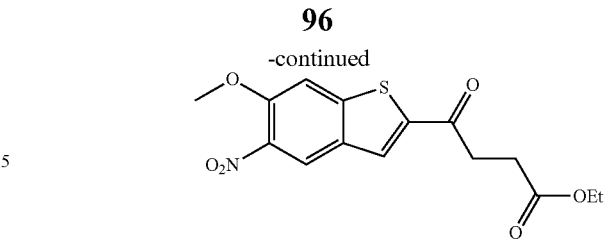

A solution of (3-ethoxy-3-oxopropyl)zinc(II) bromide (17.7 mL, 0.5M in THF, 8.83 mmol) was added to an oven-dried flask containing ((thiophene-2-carbonyl)oxy)copper (1.69 g, 8.83 mmol) under Ar atmosphere at 0° C. The reaction mixture was stirred for 20 min at 0° C. under Ar atmosphere. An Ar-degassed solution of 6-methoxy-5-nitrobenzo[b]thiophene-2-carbonyl chloride (800 mg, 2.94 mmol) in THF (10 mL) was then added to the reaction mixture at 0° C.; the resulting suspension was allowed to warm to rt and was stirred for an additional 8 h. The reaction mixture was then cooled to 0° C. and quenched with sat aq NH$_4$Cl solution (30 mL). The mixture was allowed to warm to rt and stirred for 10 min. The mixture was filtered, and the filtrate was diluted with EtOAc (50 mL) and brine (30 mL). The organic layer was separated, washed with additional brine (50 mL), dried over MgSO$_4$, filtered, and concentrated under reduced pressure to afford the crude product residue. The residue was purified by prep-TLC (SiO$_2$, DCM in PE) to give ethyl 4-(6-methoxy-5-nitrobenzo[b]thiophen-2-yl)-4-oxobutanoate. LCMS (C$_{15}$H$_{16}$NO$_6$S) (ES, m/z): 338 [M+H]$^+$. $^1$H NMR (400 MHz, CDCl$_3$): δ=8.36 (s, 1H), 7.99 (s, 1H), 7.47 (s, 1H), 4.24-4.16 (m, 2H), 4.05 (s, 3H), 3.34 (t, J=6.6 Hz, 2H), 2.81 (t, J=6.5 Hz, 2H), 1.33-1.27 (m, 3H).

Step 6: Ethyl 4-(5-amino-6-methoxybenzo[b]thiophen-2-yl)-4-oxobutanoate

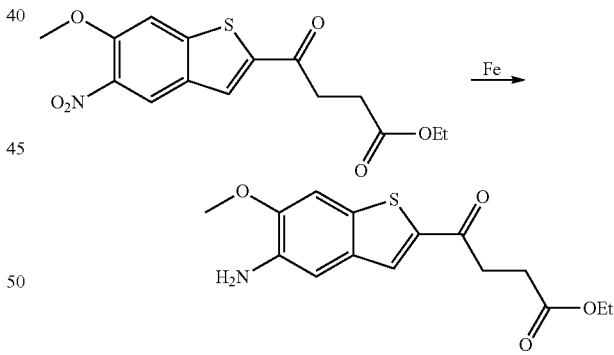

To a solution of ethyl 4-(6-methoxy-5-nitrobenzo[b]thiophen-2-yl)-4-oxobutanoate (140 mg, 0.415 mmol) in EtOH (2 mL), THF (2 mL), and H$_2$O (2 mL) was added Fe (116 mg, 2.08 mmol) and NH$_4$Cl (222 mg, 4.15 mmol). The mixture was heated to 80° C. for 1 h, cooled to rt, and filtered. H$_2$O (10 mL) was added to the filtrate, and the aq layer was extracted with EtOAc (3×5 mL). The combined organic layers were washed with brine (5 mL), dried over MgSO$_4$, and filtered. The filtrate was concentrated under the reduced pressure to give ethyl 4-(5-amino-6-methoxybenzo[b]thiophen-2-yl)-4-oxobutanoate, which was used directly for the next step without purification. LCMS (C$_{15}$H$_{18}$NO$_4$S) (ES, m/z): 308 [M+H]$^+$.

Step 7: Ethyl 4-(6-methoxy-5-(methylamino)benzo[b]thiophen-2-yl)-4-oxobutanoate

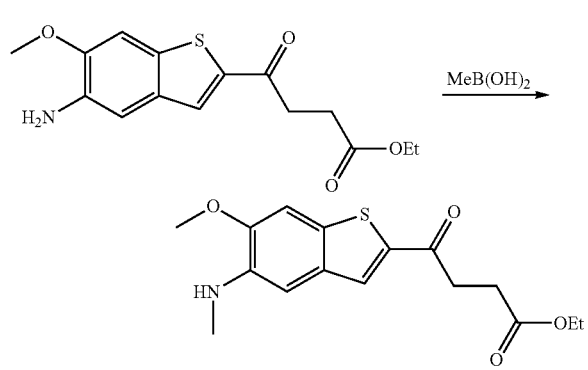

To a stirred solution of ethyl 4-(5-amino-6-methoxybenzo[b]thiophen-2-yl)-4-oxobutanoate (55 mg, 0.18 mmol), MeB(OH)$_2$ (16.1 mg, 0.268 mmol), and py (56.6 mg, 0.716 mmol) in 1,4-dioxane (2.0 mL) was added diacetoxycopper (48.8 mg, 0.268 mmol). The reaction mixture was stirred at 120° C. for 2 h and then cooled to rt. The mixture was filtered, and the filtrate was diluted with EtOAc (5.0 mL) and brine (5.0 mL). The organic layer was separated, washed with additional brine (5 mL), dried over anhydrous Na$_2$SO$_4$, and concentrated under reduced pressure to give ethyl 4-(6-methoxy-5-(methylamino)benzo[b]thiophen-2-yl)-4-oxobutanoate, which was used directly for the next step without purification. LCMS (C$_{16}$H$_{20}$NO$_4$S) (ES, m/z): 322 [M+H]$^+$.

Step 8: 4-(6-Methoxy-5-(methylamino)benzo[b]thiophen-2-yl)-4-oxobutanoic acid

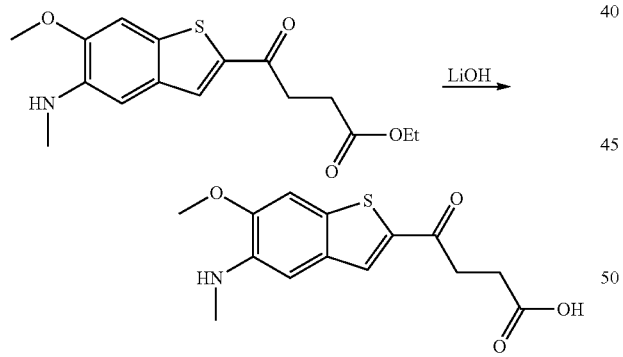

To a suspension of ethyl 4-(6-methoxy-5-(methylamino)benzo[b]thiophen-2-yl)-4-oxobutanoate (30 mg, 0.093 mmol) in MeOH (0.5 mL), THF (0.5 mL), and H$_2$O (0.5 mL) was added LiOH (44.7 mg, 1.87 mmol). The resulting suspension was heated to 50° C. for 2 h and then cooled to rt. The reaction mixture was concentrated under reduced pressure to remove the solvent, and the residue was purified by prep-HPLC (ACN/H$_2$O with 0.1% TFA) to give 4-(6-methoxy-5-(methylamino)benzo[b]thiophen-2-yl)-4-oxobutanoic acid. LCMS (C$_{14}$H$_{16}$NO$_4$S) (ES, m/z): 294 [M+H]$^+$.
$^1$H NMR (400 MHz, MeOH-d$_4$): δ 8.07 (s, 1H), 7.44 (s, 1H), 7.27 (s, 1H), 3.99 (s, 3H), 3.36-3.33 (m, 2H), 2.94 (s, 3H), 2.73 (t, J=6.4 Hz, 2H).

Example 11: (S)-4-(5,6-Dimethoxybenzo[b]thiophen-2-yl)-2-methyl-4-oxobutanoic acid

Step 1: 5,6-Dimethoxybenzo[b]thiophene-2-carbonyl chloride

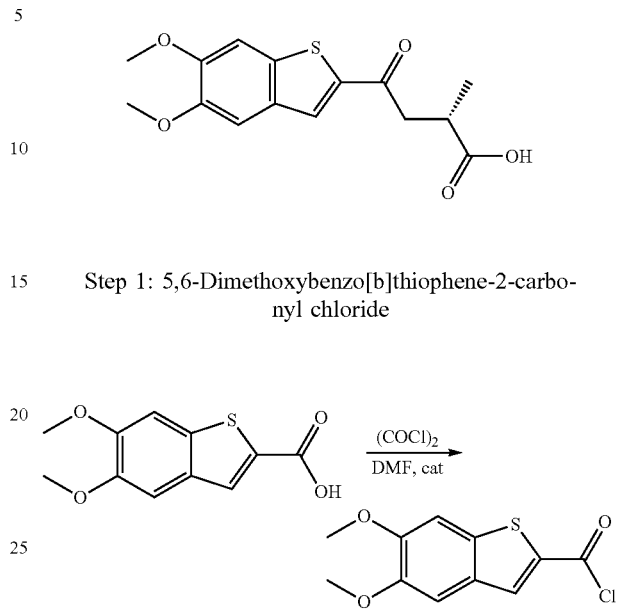

To a stirring solution of 5,6-dimethoxybenzo[b]thiophene-2-carboxylic acid from Preparation 3 (5.0 g, 21 mmol) in THF (200 mL) at 0° C. under Ar was added (COCl)$_2$ (5.5 ml, 63 mmol) followed by DMF (0.1 ml, 1.3 mmol). The reaction mixture was stirred at 0° C. for 1 h and then allowed to warm to rt and stirred overnight. The reaction mixture was concentrated under reduced pressure, and the resulting 5,6-dimethoxybenzo[b]thiophene-2-carbonyl chloride was used in the next step without purification.
$^1$H NMR (600 MHz, CH$_3$CN-d$_3$): δ 8.25 (s, 1H), 7.46 (s, 1H), 7.45 (s, 1H), 3.92 (s, 3H), 3.88 (s, 3H).

Step 2: Methyl (S)-4-(5,6-dimethoxybenzo[b]thiophen-2-yl)-2-methyl-4-oxobutanoate

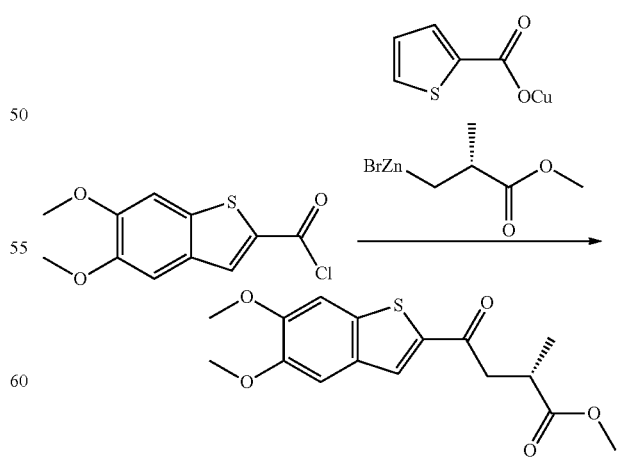

To an oven-dried, Ar-purged, round-bottomed flask containing copper (I) thiophene-2-carboxylate (797 mg, 4.2 mmol) at 0° C. was added (R)-(3-methoxy-2-methyl-3- oxopropyl)zinc(II) bromide (7.8 mL, 0.5M in THF, 3.9 mmol) dropwise. The reaction mixture was stirred at 0° C. for 20 min. A suspension of 5,6-dimethoxybenzo[b]thiophene-2-carbonyl chloride (777 mg, 3.0 mmol) in THF (15 mL) was added dropwise to the reaction mixture. The reaction mixture was allowed to warm to rt and stirred for 6 h. The reaction mixture was diluted with sat aq NH$_4$Cl solution (15 mL), followed by DCM (30 mL). Precipitates were removed by filtration prior to extraction. The layers were separated, and the aq layer was extracted with DCM (3×30 mL). The combined organic layers were concentrated under reduced pressure. The residue was purified by silica gel column chromatography ((25% EtOH in EtOAc) in Hex) to afford methyl (S)-4-(5,6-dimethoxybenzo[b]thiophen-2-yl)-2-methyl-4-oxobutanoate. LCMS ($C_{16}H_{19}O_5S$) (ES, m/z): 323 [M+H]$^+$. $^1$H NMR (500 MHz, CHCl$_3$-d): δ 7.89 (s, 1H), 7.26 (s, 2H), 4.00 (s, 3H), 3.97 (s, 3H), 3.72 (s, 3H), 3.48 (dd, J=16.9, 7.6 Hz, 1H), 3.22-3.16 (m, 1H), 3.05 (dd, J=16.9, 6.0 Hz, 1H), 1.31 (d, J=7.2 Hz, 3H).

Step 3: (S)-4-(5,6-Dimethoxybenzo[b]thiophen-2-yl)-2-methyl-4-oxobutanoic acid

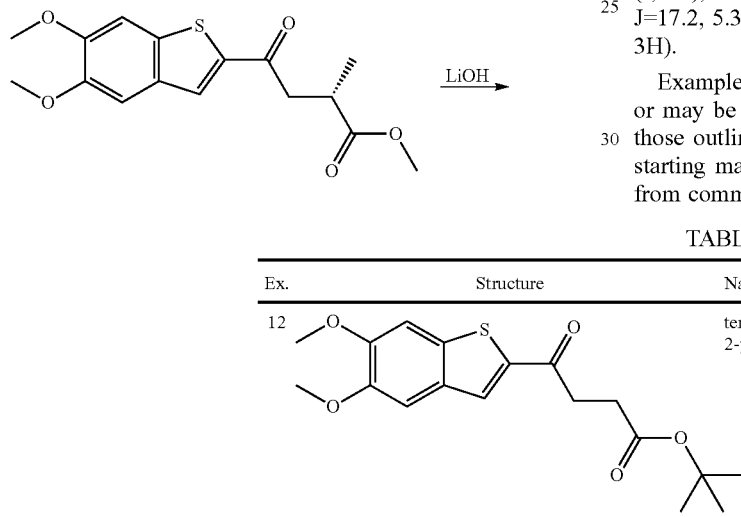

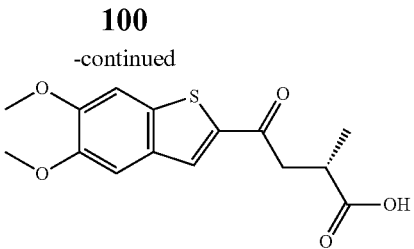

To a solution of methyl (S)-4-(5,6-dimethoxybenzo[b]thiophen-2-yl)-2-methyl-4-oxobutanoate (200 mg, 0.62 mmol) in H$_2$O (1.2 mL) and THF (5 mL) was added LiOH (59 mg, 2.5 mmol). The reaction mixture was stirred overnight at rt. The reaction mixture was adjusted to ~pH 2 using additional 1M aq HCl. DCM (15 mL) was added to the reaction mixture, and the layers were separated. The organic layer was concentrated under reduced pressure. The resulting residue was purified by silica gel column chromatography ((25% EtOH in EtOAc) in Hex) to afford (S)-4-(5,6-dimethoxybenzo[b]thiophen-2-yl)-2-methyl-4-oxobutanoic acid. LCMS ($C_{15}H_{17}O_5S$) (ES, m/z): 309 [M+H]$^+$. $^1$H NMR (600 MHz, CH$_3$OH-d$_4$,): δ 8.06 (s, 1H), 7.41 (s, 2H), 3.90 (s, 3H), 3.88 (s, 3H), 3.46 (dd, J=17.1, 8.3 Hz, 1H), 3.08 (dd, J=17.2, 5.3 Hz, 1H), 3.04-2.98 (m, 1H), 1.26 (d, J=7.1 Hz, 3H).

Examples 12 through 16, as shown in Table 2 below, were or may be prepared according to procedures analogous to those outlined in Example 11 above using the appropriate starting materials, decribed as Preparations or as obtained from commercial sources.

TABLE 2

| Ex. | Structure | Name | Mass [M + H]$^+$ |
|---|---|---|---|
| 12 | 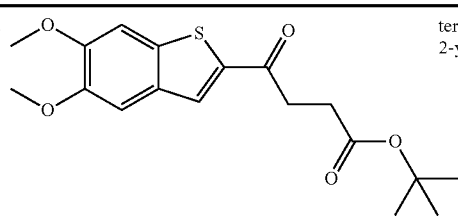 | tert-butyl 4-(5,6-dimethoxybenzo[b]thiophen-2-yl)-4-oxobutanoate | 295 [M − C$_4$H$_8$] |
| 13 | 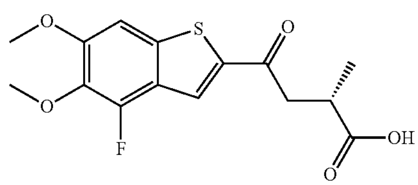 [SMILES: COc1cc2sc(C(=O)C[C@H](C)C(=O)O)cc2c(F)c1OC] | (S)-4-(4-fluoro-5,6-dimethoxybenzo[b]thiophen-2-yl)-2-methyl-4-oxobutanoic acid | 327 |
| 14 | 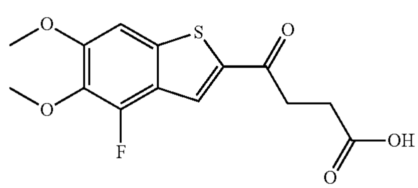 [SMILES: COc1cc2sc(C(=O)CCC(=O)O)cc2c(F)c1OC] | 4-(4-fluoro-5,6-dimethoxybenzo[b]thiophen-2-yl)-4-oxobutanoic acid | 313 |
| 15 | 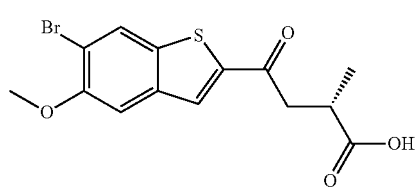 [SMILES: COc1cc2cc(C(=O)C[C@H](C)C(=O)O)sc2cc1Br] | (S)-4-(6-bromo-5-methoxybenzol[b]thiophen-2-yl)-2-methyl-4-oxobutanoic acid | 357, 359 |

TABLE 2-continued

| Ex. | Structure | Name | Mass [M + H]+ |
|---|---|---|---|
| 16 | 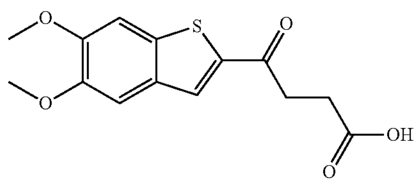 [SMILES: COc1cc2cc(C(=O)CCC(=O)O)sc2cc1OC] | 4-(5,6-dimethoxybenzo[b]thiophen-2-yl)-4-oxobutanoic acid | 295 |

Example 17: 4-(5,6-Dimethoxybenzo[b]thiophen-2-yl)-2-(methoxymethyl)-4-oxobutanoic acid Step 1: 1-Ethyl 4-methyl 2-(5,6-dimethoxybenzo[b]thiophene-2-carbonyl)-3-(methoxymethyl)succinate

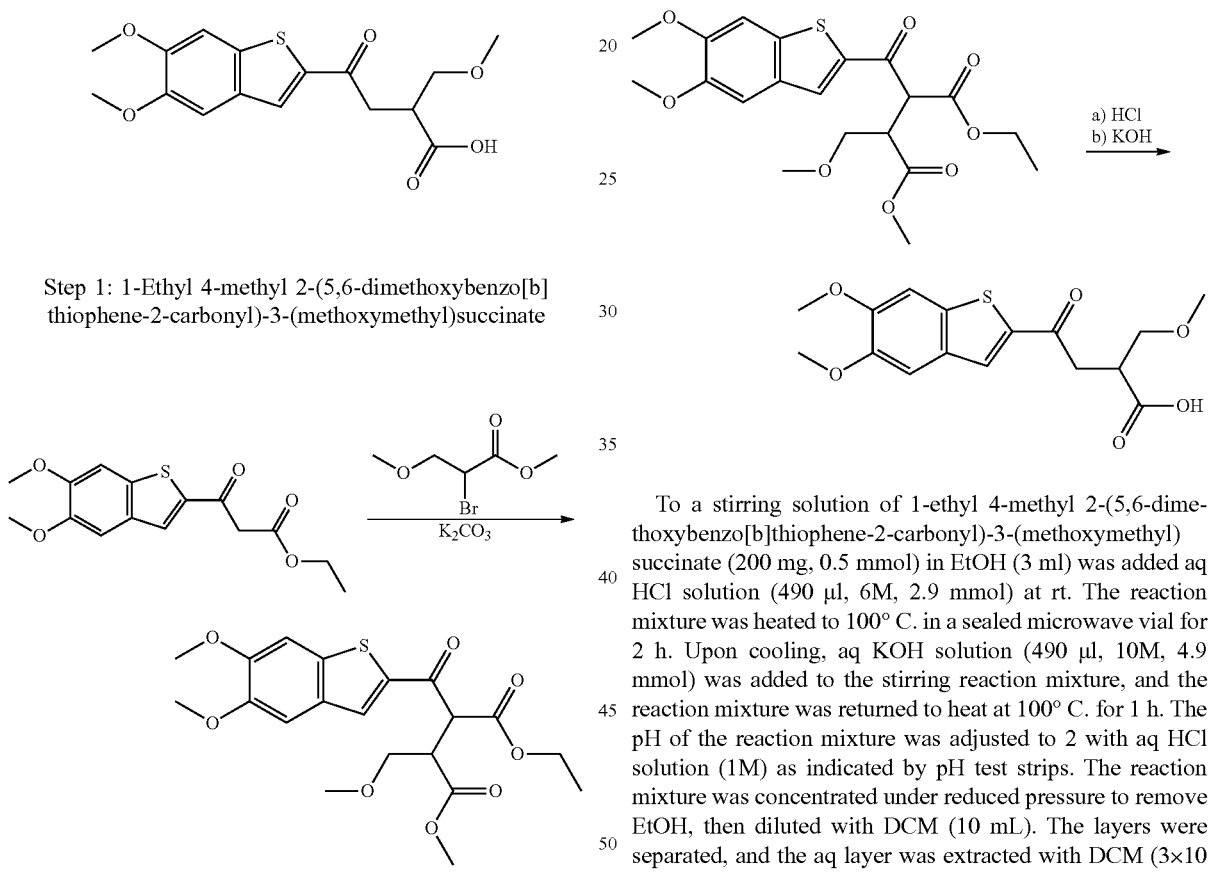

Step 2: 4-(5,6-Dimethoxybenzo[b]thiophen-2-yl)-2-(methozymethyl)-4-oxobutanoic acid To a stirring solution of ethyl 3-(5,6-dimethoxybenzo[b]thien-2-yl)-3-oxopropanoate (SPECS, 231 mg, 0.75 mmol) in DMF (2.5 mL) was added methyl 2-bromo-3-methoxypropanoate (125 μl, 0.93 mmol) at rt. The reaction mixture was stirred overnight at rt. Then, the reaction mixture was diluted with H$_2$O (3 mL) and DCM (6 ml). The phases were separated, and the aq layer was washed with DCM (3×6 mL). The combined organics were concentrated under reduced pressure and dried overnight in vacuo. The product was purified by silica gel column chromatography ((25% EtOH in EtOAc) in Hex) to give 1-ethyl 4-methyl 2-(5,6-dimethoxybenzo[b]thiophene-2-carbonyl)-3-(methoxymethyl)succinate, which was used without further purification. LCMS (C$_{20}$H$_{25}$O$_8$S) (ES, m/z): 425 [M+H]+.

To a stirring solution of 1-ethyl 4-methyl 2-(5,6-dimethoxybenzo[b]thiophene-2-carbonyl)-3-(methoxymethyl)succinate (200 mg, 0.5 mmol) in EtOH (3 ml) was added aq HCl solution (490 μl, 6M, 2.9 mmol) at rt. The reaction mixture was heated to 100° C. in a sealed microwave vial for 2 h. Upon cooling, aq KOH solution (490 μl, 10M, 4.9 mmol) was added to the stirring reaction mixture, and the reaction mixture was returned to heat at 100° C. for 1 h. The pH of the reaction mixture was adjusted to 2 with aq HCl solution (1M) as indicated by pH test strips. The reaction mixture was concentrated under reduced pressure to remove EtOH, then diluted with DCM (10 mL). The layers were separated, and the aq layer was extracted with DCM (3×10 mL). The combined organic layers were concentrated under reduced pressure, and the residue was purified by column chromatography on silica ((25% EtOH in EtOAc) in Hex). Product-containing fractions were concentrated under reduced pressure to give 4-(5,6-dimethoxybenzo[b]thiophen-2-yl)-2-(methoxymethyl)-4-oxobutanoic acid. The racemic mixture was resolved by Chiral-SFC (CHIRACEL OJ-H (250 mm*21 mm), 25% MeOH (+0.25% DMEA) in CO$_2$), affording two compounds with retention times of 3.12 min and 3.96 min. Concentration of the first eluting peak afforded the product. LCMS (C$_{16}$H$_{19}$O$_6$S) (ES, m/z): 339 [M+H]+. $^1$H NMR (600 MHz, DMSO-d$_6$): δ 12.32 (1H, br s), 8.18 (1H, s), 7.56 (1H, s), 7.44 (1H, s), 3.83 (3H, s), 3.80 (3H, s), 3.58-3.51 (2H, m), 3.46-3.40 (1H, m), 3.22 (3H, s), 3.09-3.07 (2H, m).

Example 18: 4-(6-Methoxy-5-vinylbenzo[b]thiophen-2-yl)-4-oxobutanoic acid

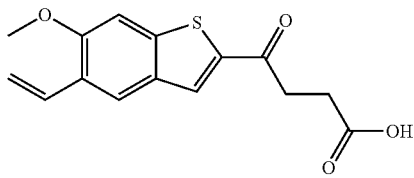 [SMILES: C=Cc1cc2cc(C(=O)CCC(=O)O)sc2cc1OC]

Step 1: 5-Bromo-2-fluoro-4-methoxybenzaldehyde

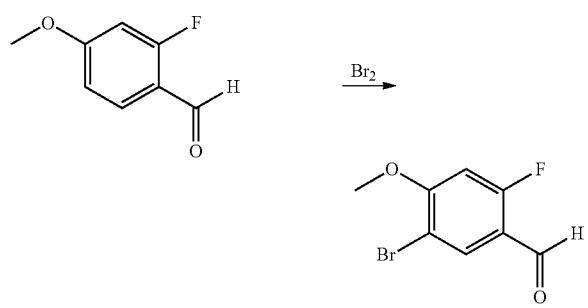

2-Fluoro-4-methoxybenzaldehyde (9.0 g, 58 mmol) was added slowly (portion-wise) to a solution of $Br_2$ (6.0 mL, 120 mmol) in MeOH (40 mL) at 0° C. The reaction mixture was stirred at 0° C. for 2 h. A solution of $NaHSO_3$ (24.3 g, 234 mmol) in $H_2O$ (300 mL) was added slowly to the reaction mixture at 0° C. The resulting suspension was then stirred for 30 min at 0° C. The reaction mixture was filtered, and the filtrate was washed with additional $H_2O$ (3×25 mL). The filtrate was then dried under reduced pressure to afford 5-bromo-2-fluoro-4-methoxybenzaldehyde. The product was used without purification. $^1$H NMR (500 MHz, DMSO-$d_6$): δ 10.02 (s, 1H), 7.98 (d, J=7.5 Hz, 1H), 7.26 (d, J=13.0 Hz, 1H), 3.97 (s, 3H).

Step 2: tert-Butyl 5-bromo-6-mehoxybenzo[b]thiophene-2-carboxylate

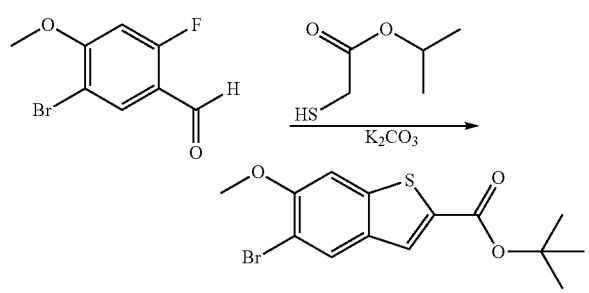

$K_2CO_3$ (19.0 g, 137 mmol) was added slowly (portion-wise) to a solution of 5-bromo-2-fluoro-4-methoxybenzaldehyde (10.7 g, 45.8 mmol) and tert-butyl 2-mercaptoacetate (6.65 mL, 45.8 mmol) in DMF (50 mL) at 20° C. under Ar atmosphere. The reaction mixture was stirred and heated to 100° C. for 16 h. The reaction mixture was then cooled to rt and diluted with $Et_2O$ (1000 mL). The mixture was then washed with $H_2O$ (500 mL, then 2×250 mL), and the combined aq layers were extracted with $Et_2O$ (2×200 mL). The organic layers were then combined and washed with brine (50 mL). The organic layer was separated, dried over $MgSO_4$, filtered, and concentrated under reduced pressure to afford tert-butyl 5-bromo-6-methoxybenzo[b]thiophene-2-carboxylate. The product was used without purification. $^1$H NMR (500 MHz, DMSO-$d_6$): δ 8.26 (s, 1H), 7.96 (s, 1H), 7.78 (s, 1H), 3.92 (s, 3H), 1.55 (s, 9H).

Step 3: 5-Bromo-6-methoxybenzo[b]thiophene-2-carboxylic acid

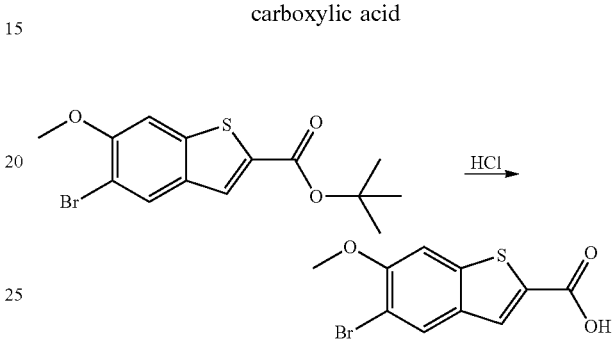

HCl (56 mL, 4.0M in 1,4-dioxane, 230 mmol) was added to a solution of tert-butyl 5-bromo-6-methoxybenzo[b]thiophene-2-carboxylate (15.5 g, 45.0 mmol) in DCM (200 mL) at 20° C. The reaction mixture was stirred at 20° C. for 3 days. The reaction mixture was then diluted by the dropwise addition of Hex (500 mL). The resulting suspension was stirred for an additional 2 h post-addition at rt. The reaction mixture was filtered, and the collected solids were washed with Hex (2×50 mL) and dried under reduced pressure to afford 5-bromo-6-methoxybenzo[b]thiophene-2-carboxylic acid, which was used without purification. $^1$H NMR (500 MHz, DMSO-$d_6$): δ 13.42 (s, 1H), 8.26 (s, 1H), 7.98 (s, 1H), 7.80 (s, 1H), 3.93 (s, 3H).

Step 4: 5-Bromo-6-methoxybenzo[b]thiophene-2-carbonyl chloride

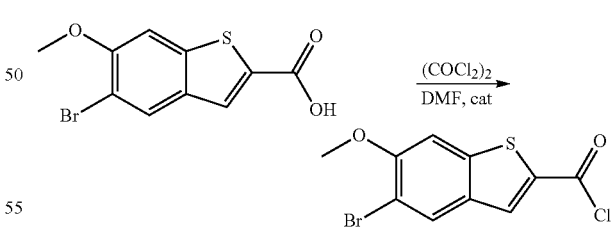

DMF (0.049 mL, 0.63 mmol) was added slowly (dropwise) to a solution of 5-bromo-6-methoxybenzo[b]thiophene-2-carboxylic acid (6.0 g, 21 mmol) and $(COCl)_2$ (5.5 mL, 63 mmol) in THF (100 mL) at 0° C. under Ar atmosphere. The reaction mixture was stirred at 0° C. for 2 h and then allowed to warm to rt. The reaction mixture was stirred for 18 h at rt. The reaction mixture was then concentrated under reduced pressure to afford 5-bromo-6-methoxybenzo[b]thiophene-2-carbonyl chloride. The product was used without purification.

Step 5: Ethyl 4-(5-bromo-6-methoxybenzo[b]thiophen-2-yl)-4-oxobutanoate

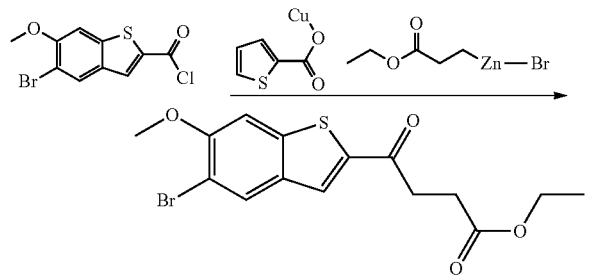

A solution of (3-ethoxy-3-oxopropyl)zinc(II) bromide (13.8 mL, 0.50M in THF, 6.9 mmol) was added to an oven-dried flask containing ((thiophene-2-carbonyl)oxy) copper (1.31 g, 6.87 mmol) under Ar atmosphere at 0° C. The reaction mixture was stirred for 20 min at 0° C. under Ar atmosphere. An Ar-degassed solution of 5-bromo-6-methoxybenzo[b]thiophene-2-carbonyl chloride (1.52 g, 4.98 mmol) in THF (25.0 mL) was then added via cannula to the reaction mixture at 0° C.; the resulting suspension was allowed to warm to rt and was stirred for an additional 3 h. The reaction mixture was cooled to 0° C. and quenched with sat aq NH$_4$Cl (50 mL). The mixture was allowed to warm to rt and stirred for an additional 10 min. The mixture was filtered, and the filtrate was diluted with EtOAc (500 mL) and brine (50 mL). The organic layer was separated, washed with additional brine (25 mL), dried over MgSO$_4$, filtered, and concentrated under reduced pressure. The residue was purified by silica gel column chromatography (EtOAc in DCM) to afford ethyl 4-(5-bromo-6-methoxybenzo[b]thiophen-2-yl)-4-oxobutanoate. LCMS (C$_{15}$H$_{16}$BrO$_4$S) (ES, m/z): 371, 373 [M+H]$^+$. $^1$H NMR (500 MHz, DMSO-d$_6$): δ 8.27 (s, 1H), 8.26 (s, 1H), 7.81 (s, 1H), 4.07-4.02 (m, 2H), 3.94 (s, 3H), 3.35-3.25 (m, 2H), 2.68-2.64 (m, 2H), 1.20-1.14 (m, 3H).

Step 6: Ethyl 4-(6-methoxy-5-vinylbenzo[b]thiophen-2-yl)-4-oxobutanoate

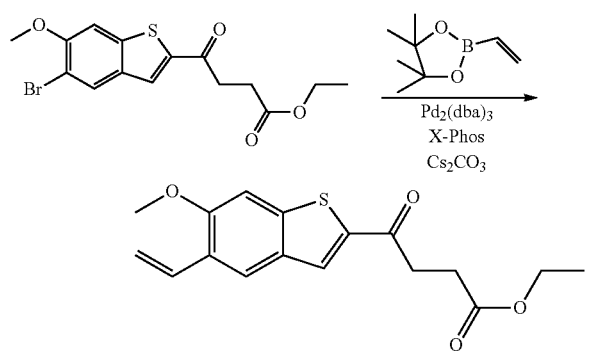

To an Ar-degassed mixture of ethyl 4-(5-bromo-6-methoxybenzo[b]thiophen-2-yl)-4-oxobutanoate (100 mg, 0.269 mmol), 4,4,5,5-tetramethyl-2-vinyl-1,3,2-dioxaborolane (50 mg, 0.32 mmol), Pd$_2$(dba)$_3$ (12 mg, 0.013 mmol), X-phos (13 mg, 0.027 mmol), and Cs$_2$CO$_3$ (263 mg, 0.808 mmol) was added 1,4-dioxane (3 mL) and H$_2$O (0.3 mL) at rt while degassing with Ar. The reaction mixture was stirred for 5 min while degassing with Ar (subsurface sparge), after which the mixture was heated to 90° C. under Ar atmosphere for 2 h. The reaction mixture was then cooled to rt and diluted with EtOAc (20 mL). The resulting suspension was filtered through a frit containing MgSO$_4$. The organic layer (filtrate) was concentrated under reduced pressure. The crude product residue was purified by silica gel column chromatography (EtOAc in DCM) to afford ethyl 4-(6-methoxy-5-vinylbenzo[b]thiophen-2-yl)-4-oxobutanoate. LCMS (C$_{17}$H$_{19}$O$_4$S) (ES, m/z): 319 [M+H]$^+$.

Step 7: 4-(6-Methoxy-5-vinylbenzo[b]thiophen-2-yl)-4-oxobutanoic acid

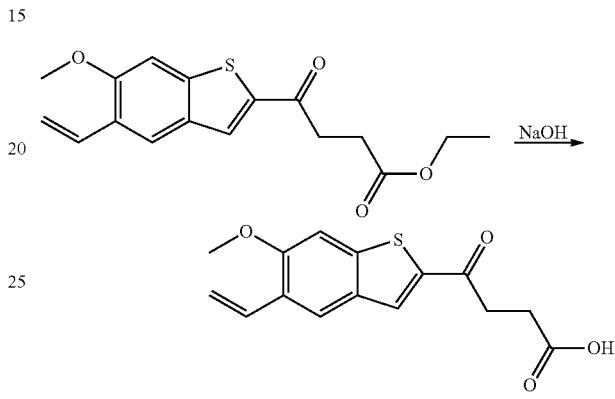

An aq NaOH solution (0.33 mL, 1.0M, 0.33 mmol) was added to a solution of ethyl 4-(6-methoxy-5-vinylbenzo[b]thiophen-2-yl)-4-oxobutanoate (21 mg, 0.066 mmol) in MeOH (4.0 mL). The reaction mixture was stirred at rt for 18 h. The reaction mixture was quenched with aq HCl solution (0.33 mL, 1.0M, 0.33 mmol) and then was concentrated under reduced pressure. The crude product residue was purified by prep-HPLC (ACN/H$_2$O with 0.1% TFA) to afford 4-(6-methoxy-5-vinylbenzo[b]thiophen-2-yl)-4-oxobutanoic acid. LCMS (C$_{15}$H$_{15}$O$_4$S) (ES, m/z): 291 [M+H]$^+$. $^1$H NMR (500 MHz, DMSO-d$_6$): δ 12.21 (s, 1H), 8.27 (s, 1H), 8.11 (s, 1H), 7.65 (s, 1H), 7.00 (dd, J=17.5, 11.5 Hz, 1H), 5.87 (d, J=17.5 Hz, 1H), 5.33 (d, J=11.5 Hz, 1H), 3.91 (s, 3H), 3.30-3.24 (m, 2H), 2.63-2.56 (m, 2H).

Example 19: 4-(5-Bromo-6-methoxybenzo[b]thiophene-2-yl)-4-oxobutanoic acid

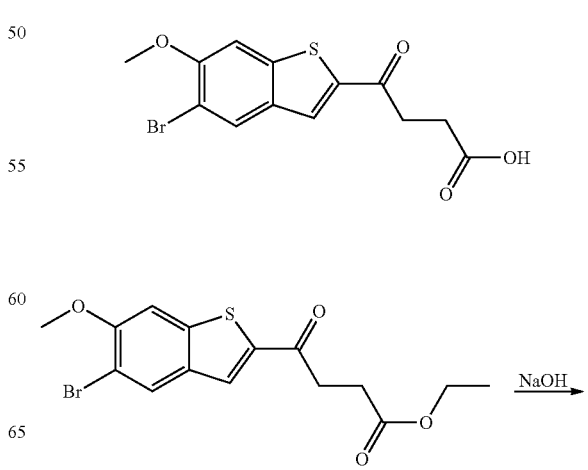

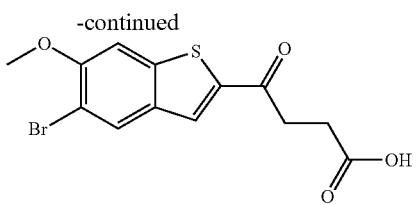

An aq NaOH solution (0.54 mL, 1.0M, 0.54 mmol) was added to a solution of ethyl 4-(5-bromo-6-methoxybenzo[b]thiophen-2-yl)-4-oxobutanoate from Example 17, step 5 (40 mg, 0.11 mmol) in MeOH (2.0 mL). The reaction mixture was stirred at 20° C. for 24 h. The reaction mixture was quenched with aq HCl solution (0.54 mL, 1.0M, 0.54 mmol). The mixture was then concentrated under reduced pressure to afford the crude product residue. The crude product residue was purified by prep-HPLC (ACN/H$_2$O with 0.1% TFA) to afford 4-(5-bromo-6-methoxybenzo[b]thiophen-2-yl)-4-oxobutanoic acid. LCMS (C$_{13}$H$_{12}$BrO$_4$S) (ES, m/z): 343, 345 [M+H]$^+$. $^1$H NMR (500 MHz, DMSO-d$_6$): δ 12.23 (s, 1H), 8.27 (s, 1H), 8.25 (s, 1H), 7.81 (s, 1H), 3.94 (s, 3H), 3.29-3.24 (m, 2H), 2.62-2.57 (m, 2H).

Example 20: 4-((S)-4-(5,6-Dichlorobenzo[b]thiophen-2-yl)-2-methyl-4-oxobutanoic acid

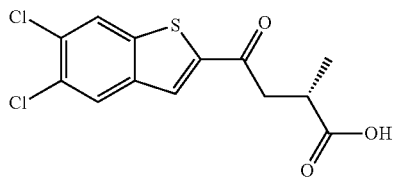 [SMILES: C[C@@H](CC(=O)c1cc2cc(Cl)c(Cl)cc2s1)C(=O)O]

Step 1: 5,6-Dichlorobenzo[b]thiophene-2-carboxylic acid

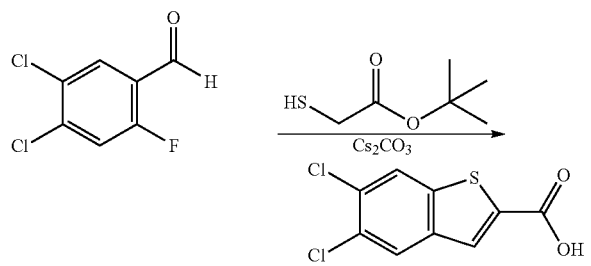

To a solution of 4,5-dichloro-2-fluorobenzaldehyde (V-Pharma, 386 mg, 2.00 mmol), tert-butyl 2-mercaptoacetate (356 mg, 2.40 mmol) and toluene (5 ml) was added Cs$_2$CO$_3$ (1.30 g, 4.00 mmol), and the reaction was heated at reflux for 2 h. The reaction mixture was then filtered, and the filtrate was washed with toluene (5 mL). TFA (10 mL) was then added to the filtrate, and the mixture was stirred for 1 h. The reaction mixture was filtered, washed with toluene and hexanes, and dried under reduced pressure to afford 5,6-dichlorobenzo[b]thiophene-2-carboxylic acid. LCMS (C$_9$H$_3$Cl$_2$O$_2$S) (ES, m/z): 245 [M−H]$^-$.

Step 2: (S)-4-(5,6-Dichlorobenzo[b]thiophen-2-yl)-2-methyl-4-oxobutanoic acid

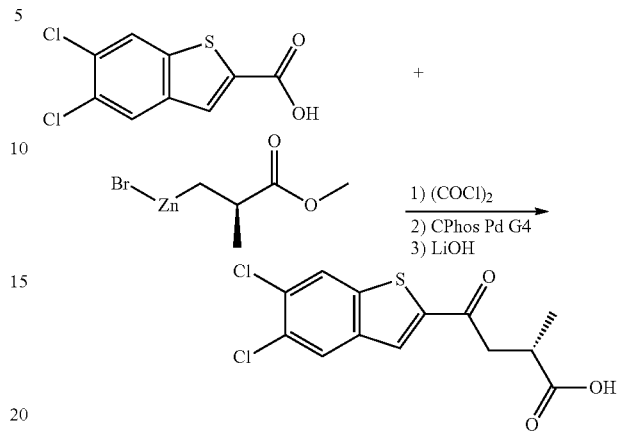

To a mixture of 5,6-dichlorobenzo[b]thiophene-2-carboxylic acid (0.049 g, 0.20 mmol) and DCM (2 ml) was added DMF (4 uL, 0.055 mmol). (COCl)$_2$ (0.175 ml, 2.00 mmol) was then added, and the reaction was stirred at rt for 1 h. The solvent was removed under reduced pressure. The residue was redissolved in THF (2.0 ml), CPhos Pd G4 from Preparation 1 (0.033 g, 0.040 mmol) was added, and the mixture was stirred while (R)-(3-methoxy-2-methyl-3-oxopropyl)zinc(II) bromide (0.40 mL, 0.5M in THF, 0.20 mmol) was added all at once. The reaction was stirred for 2 h, and then LiOH (0.048 g, 2.0 mmol), H$_2$O (1 mL), and MeOH (1 mL) were added. The reaction mixture was stirred for another 2 h, and then the solvent was removed under reduced pressure. The residue was purified via prep-HPLC (ACN/H$_2$O with 0.1% TFA) to afford (S)-4-(5,6-dichlorobenzo[b]thiophen-2-yl)-2-methyl-4-oxobutanoic acid. LCMS (C$_{13}$H$_{11}$Cl$_2$O$_3$S) (ES, m/z): 317 [M+H]$^+$. $^1$H NMR (600 MHz, DMSO-d$_6$): δ 8.45 (s, 1H), 8.31 (s, 1H), 8.28 (s, 1H), 3.38 (dd, J=17.4, 8.5 Hz, 1H), 3.10 (dd, J=17.6, 5.0 Hz, 1H), 2.90-2.84 (m, 1H), 1.16 (d, 3H).

Example 21: (S)-4-(6-Ethyl-5-methoxybenzo[b]thiophen-2-yl)-2-methyl-4-oxobutanoic acid

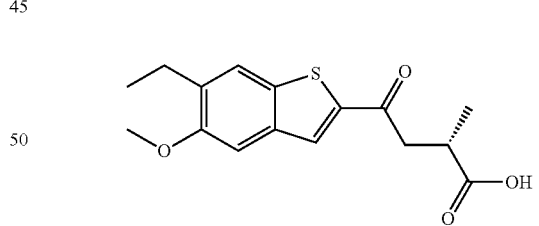

Step 1: 6-Ethyl-5-methoxybenzo[b]thiophene-2-carboxylic acid

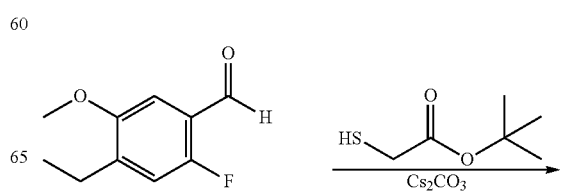

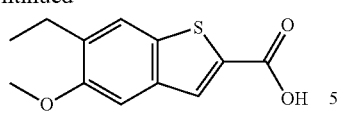

To a stirred solution of 4-ethyl-2-fluoro-5-methoxybenzaldehyde (Biogene Organics, 364 mg, 2.00 mmol), tert-butyl 2-mercaptoacetate (356 mg, 2.40 mmol), and toluene (5 ml) was added $Cs_2CO_3$ (1.30 g, 4.00 mmol), and the reaction was heated at reflux for 2 h. The reaction mixture was then filtered, and the filtrate was washed with toluene (5 mL). TFA (10 mL) was then added to the filtrate, and the mixture was stirred for 1 h. The reaction mixture was filtered, washed with toluene and Hex, and dried under reduced pressure to afford 6-ethyl-5-methoxybenzo[b]thiophene-2-carboxylic acid. LCMS ($C_{12}H_{11}O_3S$) (ES, m/z): 236 [M−H]⁻.

Step 2: (S)-4-(6-Ethyl-5-methozybenzo[b]thiophen-2-yl)-2-methyl-4-oxobutanoic acid

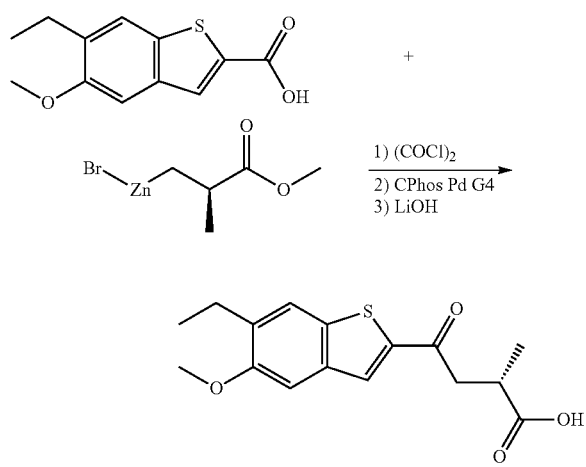

To a mixture of 6-ethyl-5-methoxybenzo[b]thiophene-2-carboxylic acid (0.047 g, 0.20 mmol), and DCM (2 ml) was added DMF (4 uL, 0.055 mmol). $(COCl)_2$ (0.175 mL, 2.00 mmol) was then added, and the reaction was stirred at rt for 1 h. The solvent was removed under reduced pressure. The residue was redissolved in THF (2.0 ml), CPhos Pd G4 from Preparation 1 (0.033 g, 0.040 mmol) was added, and the mixture was stirred while (R)-(3-methoxy-2-methyl-3-oxopropyl)zinc(II) bromide (0.40 ml, 0.5M in THF, 0.20 mmol) was added all at once. The reaction was stirred for 2 h, and then LiOH (48 mg, 2.0 mmol), $H_2O$ (1 mL), and MeOH (1 mL) were added. The reaction mixture was stirred for another 2 h, and then the solvent was removed under reduced pressure. The residue was then purified via prep-HPLC (ACN/$H_2O$ with 0.1% TFA) to afford (S)-4-(6-ethyl-5-methoxybenzo[b]thiophen-2-yl)-2-methyl-4-oxobutanoic acid. LCMS ($C_{16}H_{19}O_4S$) (ES, m/z): 307 [M+H]⁺. ¹H NMR (600 MHz, DMSO-$d_6$): δ 8.21 (s, 1H), 7.75 (s, 1H), 7.43 (s, 1H), 3.83 (s, 3H), 3.38 (dd, J=17.4, 8.5 Hz, 1H), 3.07 (dd, J=17.4, 5.1 Hz, 1H), 2.87-2.84 (m, 1H), 2.65 (q, J=7.5 Hz, 2H), 1.16-1.14 (m, 6H).

Example 22: (S)-4-(5-methoxy-6-methylbenzo[b]thiophen-2-yl)-2-methyl-4-oxobutanoic acid

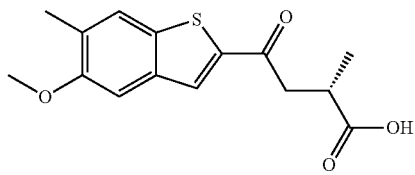 [SMILES: COc1cc2cc(C(=O)C[C@H](C)C(=O)O)sc2cc1C]

Step 1: 5-Methoxy-6-methylbenzo[b]thiophene-2-carboxylic acid

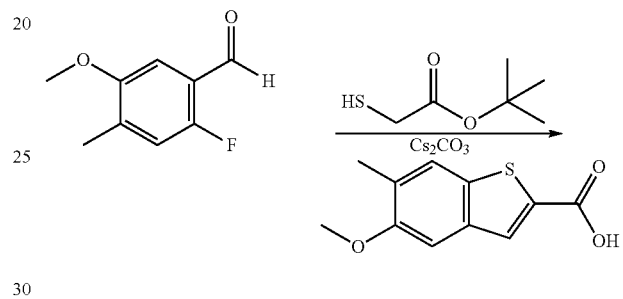

To a stirred solution of 2-fluoro-5-methoxy-4-methylbenzaldehyde (Biogene Organics, 336 mg, 2.00 mmol), tert-butyl 2-mercaptoacetate (356 mg, 2.40 mmol) and toluene (5 ml) was added $Cs_2CO_3$ (1.30 g, 4.00 mmol), and the reaction was heated at reflux for 2 h. The reaction mixture was filtered, and the filtrate was washed with toluene (5 mL). TFA (10 mL) was then added to the filtrate, and the mixture was stirred for 1 h. The reaction mixture was filtered, washed with toluene and Hex, and dried under reduced pressure to afford 5-methoxy-6-methylbenzo[b]thiophene-2-carboxylic acid. LCMS ($C_{11}H_9O_3S$) (ES, m/z): 221 [M−H]⁻.

Step 2: (S)-4-(5-methoxy-6-methylbenzo[b]thiophen-2-yl)-2-methyl-4-oxobutanoic acid

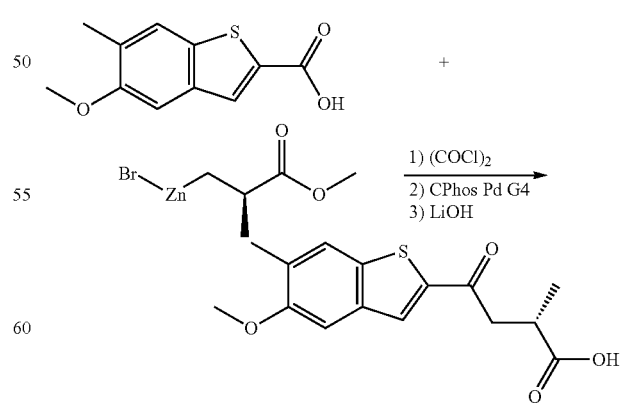

To a mixture of 5-methoxy-6-methylbenzo[b]thiophene-2-carboxylic acid (0.044 g, 0.20 mmol) and DCM (2 ml) was added DMF (4 uL, 0.055 mmol). $(COCl)_2$ (0.175 mL, 2.00 mmol) was then added, and the reaction was stirred at rt for 1 h. The solvent was removed under reduced pressure. The residue was redissolved in THF (2.0 ml), CPhos Pd G4 (0.033 g, 0.040 mmol) was added, and the mixture was stirred while (R)-(3-methoxy-2-methyl-3-oxopropyl)zinc (II) bromide (0.40 ml, 0.5M in THF, 0.20 mmol) was added all at once. The reaction was stirred for 2 h, and then LiOH (48 mg, 2.0 mmol), $H_2O$ (1 mL), and MeOH (1 mL) were added. The reaction mixture was stirred for another 2 h, and then the solvent was removed under reduced pressure. The residue was then purified via prep-HPLC (ACN/$H_2O$ with 0.1% TFA) to afford (S)-4-(5-methoxy-6-methylbenzo[b]thiophen-2-yl)-2-methyl-4-oxobutanoic acid. LCMS ($C_{15}H_{17}O_4S$) (ES, m/z): 293 [M+H]$^+$. $^1$H NMR (600 MHz, DMSO-$d_6$): δ 8.21 (s, 1H), 7.75 (s, 1H), 7.42 (s, 1H), 3.83 (s, 3H), 3.38 (dd, J=17.4, 8.5 Hz, 1H), 3.06 (dd, J=17.4, 5.2 Hz, 1H), 2.88-2.83 (m, 1H), 2.24 (s, 3H), 1.15 (d, J=7.2 Hz, 3H).

Example 23: 4-(6-Chloro-5-methoxybenzo[b]thiophen-2-yl)-4-oxobutanoic acid

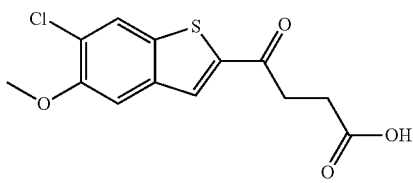

Step 1: 6-Chloro-5-methoxybenzo[b]thiophene-2-carboxylic acid

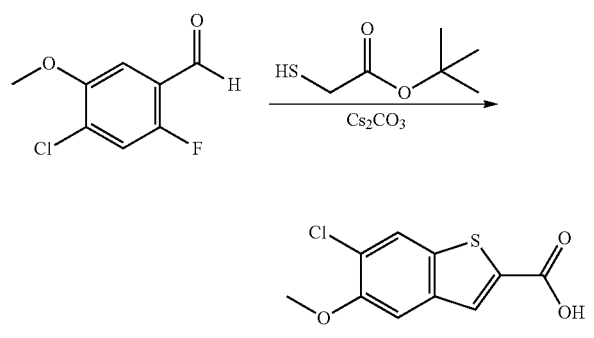

To a stirred solution of 4-chloro-2-fluoro-5-methoxybenzaldehyde (38 mg, 0.20 mmol), tert-butyl 2-mercaptoacetate (54 mg, 0.30 mmol) and 1,4-dioxane (2 ml) was added $Cs_2CO_3$ (326 mg, 1.00 mmol), and the reaction was heated at reflux for 4 h. The reaction mixture was then filtered, washed with 1,4-dioxane (2 mL), and concentrated under reduced pressure. The concentrate was slurried in DCM (1 mL), and TFA (1 mL) was added. Then, the reaction was stirred at rt for 2 h. The solvent was removed under reduced pressure to afford 6-chloro-5-methoxybenzo[b]thiophene-2-carboxylic acid. LCMS ($C_{10}H_6ClO_3S$) (ES, m/z): 241 [M−H]$^−$.

Step 2: 4-(6-Chloro-5-methoxybenzo[b]thiophen-2-yl)-4-oxobutanoic acid

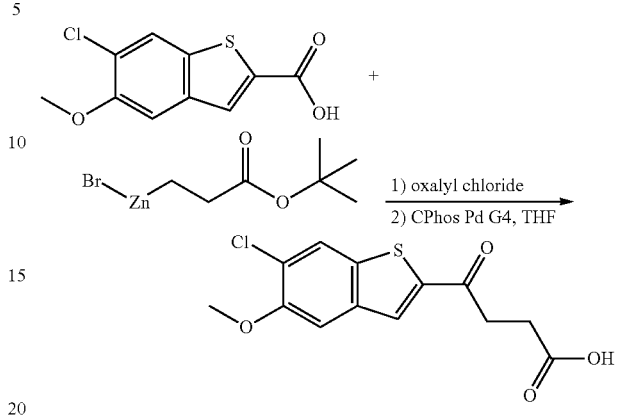

To a mixture of 6-chloro-5-methoxybenzo[b]thiophene-2-carboxylic acid (0.045 g, 0.20 mmol) and DCM (2 ml) was added DMF (4 uL, 0.055 mmol). (COCl)$_2$ (0.175 mL, 2.00 mmol) was then added. The reaction was stirred at rt for 1 h, and the solvent was removed under reduced pressure. The residue was redissolved in THF (2.0 ml), CPhos Pd G4 from Preparation 1 (0.033 g, 0.040 mmol) was added, and the mixture was stirred while 3-tert-butoxy-3-oxopropylzinc bromide (0.40 ml, 0.5M in THF, 0.20 mmol) was added all at once. The reaction was stirred for 2 h, and then the solvent was removed under reduced pressure. Then, DCM (1 mL) and TFA (1 mL) were added. The reaction mixture was stirred for another 2 h, and then the solvent was removed under reduced pressure. The residue was then purified via prep-HPLC (ACN/$H_2O$ with 0.1% TFA) to afford 4-(6-chloro-5-methoxybenzo[b]thiophen-2-yl)-4-oxobutanoic acid. LCMS ($C_{13}H_{12}ClO_4S$) (ES, m/z): 299 [M+H]$^+$. $^1$H NMR (600 MHz, DMSO-$d_6$): δ 8.23 (s, 1H), 8.18 (s, 1H), 7.65 (s, 1H), 3.89 (s, 3H), 3.23 (t, J=6.6 Hz, 2H), 2.52 (t, J=6.4 Hz, 2H).

Example 24: (S)-4-(5-Bromo-6-methoxybenzo[b]thiophen-2-yl)-2-methyl-4-oxobutanoic acid

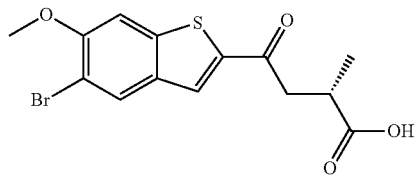 [SMILES: COc1cc2sc(C(=O)C[C@H](C)C(=O)O)cc2cc1Br]

Step 1: Methyl (S)-4-(5-bromo-6-methoxybenzo[b]thiophen-2-yl)-2-methyl-4-oxobutanoate

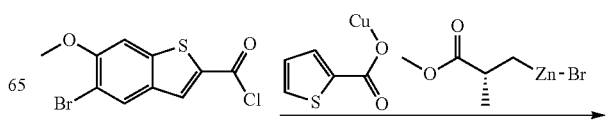

-continued

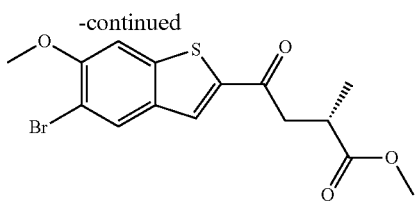

A solution of (R)-(3-methoxy-2-methyl-3-oxopropyl)zinc (II) bromide (57.7 mL, 0.50M) in THF (28.9 mmol) was added to an oven-dried flask containing ((thiophene-2-carbonyl)oxy)copper (5.50 g, 28.9 mmol) under Ar atmosphere at 0° C. The reaction mixture was stirred for 20 min at 0° C. under Ar atmosphere. An Ar-degassed solution of 5-bromo-6-methoxybenzo[b]thiophene-2-carbonyl chloride from Example 18, step 4 (6.39 g, 20.9 mmol) in THF (100 mL) was then added via cannula to the reaction mixture at 0° C. The resulting suspension was allowed to warm to rt and was stirred for an additional 3 h. The reaction mixture was cooled to 0° C. and added via cannula to a stirring mixture of sat aq NH$_4$Cl (300 mL) and EtOAc (500 mL). The mixture was allowed to warm to rt and stirred for an additional 16 h. The mixture was filtered, and the filtrate was diluted with EtOAc (1000 mL) and brine (100 mL). The organic layer was separated, washed with additional brine (50 mL), dried over MgSO$_4$, filtered, and concentrated under reduced pressure. The residue was purified by silica gel column chromatography (EtOAc in DCM) to afford methyl (S)-4-(5-bromo-6-methoxybenzo[b]thiophen-2-yl)-2-methyl-4-oxobutanoate. LCMS (C$_{15}$H$_{16}$BrO$_4$S) (ES, m/z): 371, 373 [M+H]$^+$. $^1$H NMR (500 MHz, DMSO-d$_6$): δ 8.27-8.24 (m, 2H), 7.80 (s, 1H), 3.94 (s, 3H), 3.59 (s, 3H), 3.46-3.39 (m, 1H), 3.23-3.16 (m, 1H), 3.01-2.93 (m, 1H), 1.19 (d, J=7.0 Hz, 3H).

Step 2: (S)-4-(5-Bromo-6-methoxybenzo[b]thiophen-2-yl)-2-methyl-4-oxobutanoic acid

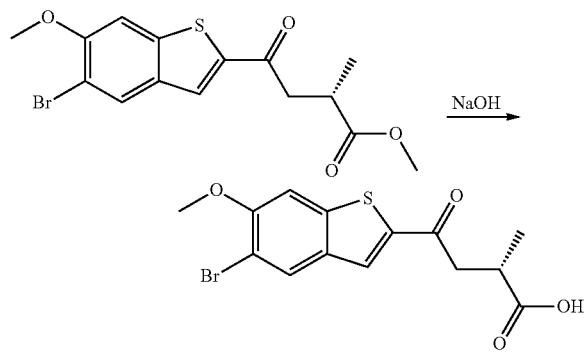

An aq NaOH solution (0.61 mL, 1.0M, 0.61 mmol) was added to a solution of methyl (S)-4-(5-bromo-6-methoxybenzo[b]thiophen-2-yl)-2-methyl-4-oxobutanoate (50 mg, 0.14 mmol) in THF (4.0 mL). The reaction mixture was stirred at rt for 18 h. The reaction mixture was quenched with aq HCl solution (0.61 mL, 1.0M, 0.61 mmol). The mixture was then concentrated under reduced pressure to afford the crude product residue, which was purified by prep-HPLC (ACN/H$_2$O with 0.1% TFA) to afford (S)-4-(5-bromo-6-methoxybenzo[b]thiophen-2-yl)-2-methyl-4-oxobutanoic acid. LCMS (C$_{14}$H$_{14}$BrO$_4$S) (ES, m/z): 357, 359 [M+H]$^+$. $^1$H NMR (500 MHz, DMSO-d$_6$): δ 12.22 (s, 1H), 8.27-8.24 (m, 2H), 7.81 (s, 1H), 3.93 (s, 3H), 3.44-3.35 (m, 1H), 3.14-3.06 (m, 1H), 2.94-2.85 (m, 1H), 1.18 (d, J=7.5 Hz, 3H).

Example 25: 4-(4-Fluoro-5,6-dimethoxybenzoibithiophen-2-yl)-4-oxobutanoic acid

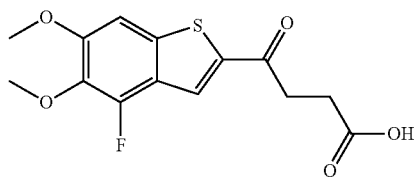 [SMILES: COc1cc2sc(C(=O)CCC(=O)O)cc2c(F)c1OC]

Step 1: Methyl 4-fluoro-5,6-dimethoxybenzo[b]thiophene-2-carboxylate

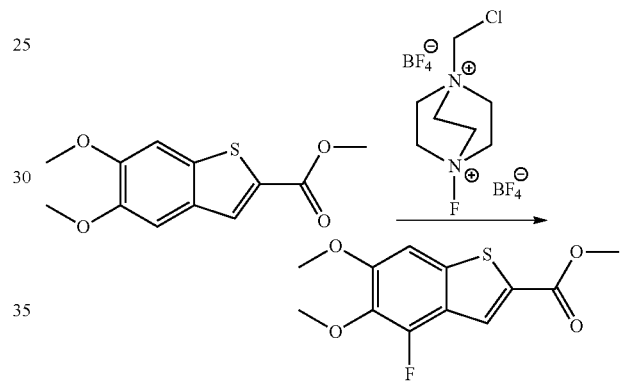

1-Chloromethyl-4-fluoro-1,4-diazoniabicyclo[2.2.2]octane bis(tetrafluoroborate) (SELECTFLUOR™, 77 mg, 0.22 mmol) was added to a mixture of methyl 5,6-dimethoxybenzo[b]thiophene-2-carboxylate from Preparation 2 (50 mg, 0.20 mmol) in ACN (1 ml) at rt. The resulting mixture was stirred at 45° C. for 15 h. The mixture was cooled to rt, diluted with sat aq NaHCO$_3$ (10 mL), and extracted with EtOAc (3×10 mL). The combined organic layers were washed with brine (10 mL), dried over anhydrous Na$_2$SO$_4$, filtered, and concentrated under reduced pressure. The residue was purified by prep-TLC (SiO$_2$, EtOAc in PE) to give methyl 4-fluoro-5,6-dimethoxybenzo[b]thiophene-2-carboxylate. LCMS (C$_{12}$H$_{12}$FO$_4$S) (ES, m/z): 293 [M+H]$^+$. $^1$H NMR (400 MHz, CDCl$_3$): δ 8.05 (s, 1H), 7.08 (s, 1H), 3.99 (s, 3H), 3.97 (s, 3H), 3.94 (s, 3H).

Step 2: 4-Fluoro-5,6-dimethoxybenzo[b]thiophene-2-carboxylic acid

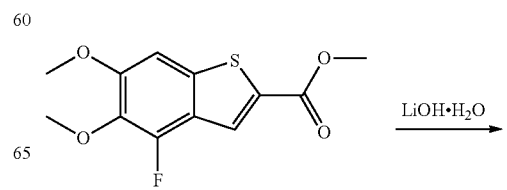

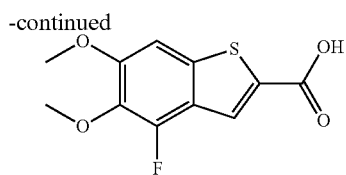

LiOH.H$_2$O (71.4 mg, 1.70 mmol) was added portionwise to a mixture of methyl 4-fluoro-5,6-dimethoxybenzo[b]thiophene-2-carboxylate (46 mg, 0.170 mmol) in THF (3 ml), MeOH (1 ml), and H$_2$O (1 ml) at rt. Then, the mixture was stirred for 15 h. The mixture was adjusted to pH=5 with 1N HCl and extracted with EtOAc (3×10 ml). The combined organic layers were washed with brine (10 mL), dried over anhydrous Na$_2$SO$_4$, filtered, and concentrated under reduced pressure. The residue was purified by prep-HPLC (ACN/H$_2$O with 0.1% TFA) to give 4-fluoro-5,6-dimethoxybenzo[b]thiophene-2-carboxylic acid. LCMS (C$_{11}$H$_9$FO$_4$S) (ES, m/z): 257 [M+H]$^+$. $^1$H NMR (400 MHz, CDCl$_3$): δ 8.12 (s, 1H), 7.09 (s, 1H), 3.99 (s, 3H), 3.97 (s, 3H).

Step 3: 4-Fluoro-5,6-dimethoxybenzo[b]thiophene-2-carbonyl chloride

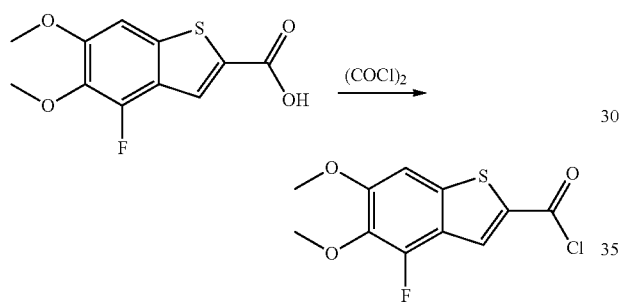

To a stirred solution of 4-fluoro-5,6-dimethoxybenzo[b]thiophene-2-carboxylic acid (153 mg, 0.60 minol) in anhydrous THF (5 mL) was added (COCl)$_2$ (0.21 mL, 2.40 minol) dropwise at 0° C. The mixture was stirred at 0° C. for 1 h and then at rt for 1 h. The solvent was removed under reduced pressure to give 4-fluoro-5,6-dimethoxybenzo[b]thiophene-2-carbonyl chloride, which was used without further purification.

Step 4: Ethyl 4-(4-fluoro-5,6-dimethoxybenzo[b]thiophen-2-yl)-4-oxobutanoate

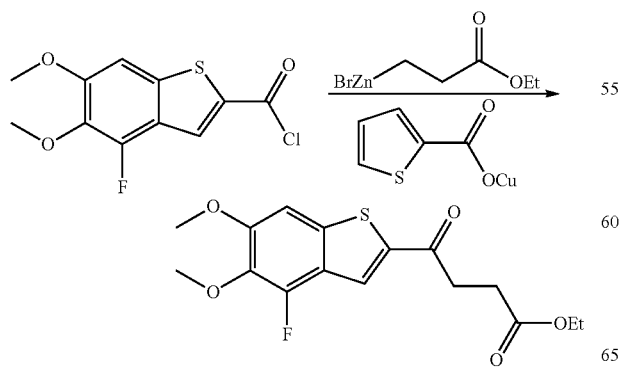

A suspension of copper(I) thiophene-2-carboxylate (125 mg, 0.65 mmol) was sparged with N$_2$ for 5 min and then cooled to 0° C. A solution of (3-ethoxy-3-oxopropyl)zinc(II) bromide (17.7 mL, 0.5M in THF, 8.83 mmol) was added under N$_2$ atmosphere at 0° C., and the reaction mixture was stirred for 20 min at 0° C. A N$_2$-sparged solution of 4-fluoro-5,6-dimethoxybenzo[b]thiophene-2-carbonyl chloride (130 mg, 0.47 mmol) in THF (3 mL) was then added to the reaction mixture at 0° C. The resulting suspension was allowed to warm to rt and was stirred for an additional 8 h. The reaction mixture was poured into sat aq NH$_4$Cl (20 mL) with stirring. The mixture was extracted with EtOAc (2×20 mL). The combined organic layers were washed with H$_2$O and brine, dried over MgSO$_4$, filtered, and concentrated under reduced pressure. The residue was purified by silica gel column chromatography (EtOAc in Hex) to give ethyl 4-(4-fluoro-5,6-dimethoxybenzo[b]thiophen-2-yl)-4-oxobutanoate. LCMS (C$_{16}$H$_{18}$FO$_5$S) (ES, m/z): 341 [M+H]$^+$. $^1$H NMR (500 MHz, CDCl$_3$) δ 8.02 (d, J=0.7 Hz, 1H), 7.10 (t, J=1.0 Hz, 1H), 4.19 (q, J=7.2 Hz, 2H), 4.05-3.97 (m, 6H), 3.36 (t, J=6.7 Hz, 2H), 2.81 (t, J=6.7 Hz, 2H), 1.29 (t, J=7.2 Hz, 3H).

Step 5: 4-(4-Fluoro-5,6-dimethoxybenzo[b]thiophen-2-yl)-4-oxobutanoic acid

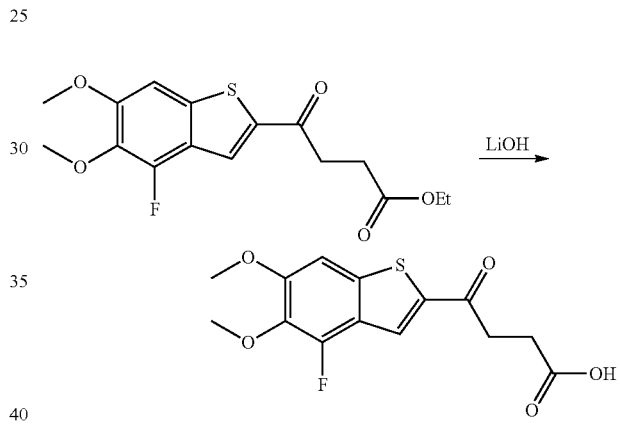

To a solution of ethyl 4-(4-fluoro-5,6-dimethoxybenzo[b]thiophen-2-yl)-4-oxobutanoate (124 mg, 0.36 mmol) in MeOH (1.5 mL) and THF (1.5 mL) was added 1N aq LiOH (1.5 mL, 1.5 mmol). The reaction mixture was stirred at rt for 1 h, and then aq 1N HCl (1.5 mL, 1.5 mmol) was added. The resulting precipitate was collected by suction filtration and purified by prep-HPLC (ACN/H$_2$O with 0.1% TFA) to afford 4-(4-fluoro-5,6-dimethoxybenzo[b] thiophen-2-yl)-4-oxobutanoic acid. LCMS (C$_{14}$H$_{14}$FO$_5$S) (ES, m/z): 313 [M+H]$^+$. $^1$H NMR (500 MHz, DMSO-d$_6$) δ 12.19 (s, 1H), 8.33 (d, J=0.7 Hz, 1H), 7.59 (d, J=1.2 Hz, 1H), 3.93 (s, 3H), 3.87 (s, 3H), 3.35-3.28 (m, 2H), 2.64-2.57 (m, 2H).

Example 26: (S)-4-(4-fluoro-5,6-dimethoxybenzo[b]thiophen-2-yl)-2-methyl-4-oxobutanoic acid

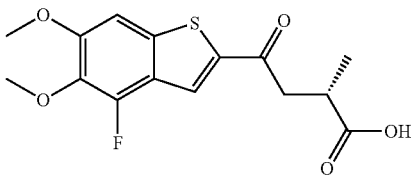 [SMILES: COc1cc2sc(C(=O)C[C@H](C)C(=O)O)cc2c(F)c1OC]

Step 1: Methyl (S)-4-(4-fluoro-5,6-dimethoxybenzo[b]thiophen-2-yl)-2-methyl-4-oxobutanoate

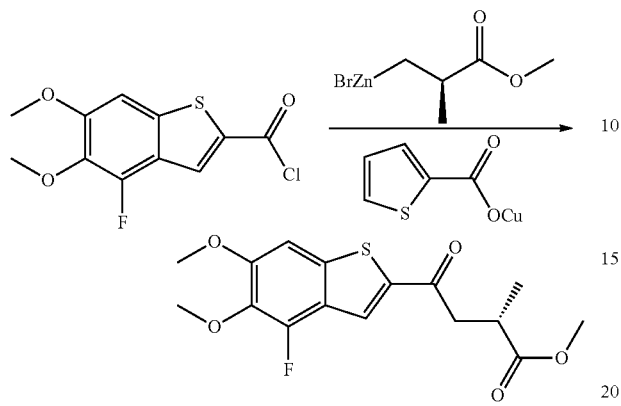

A suspension of copper(I) thiophene-2-carboxylate (125 mg, 0.65 mmol) was sparged with N₂ for 5 min and then cooled to 0° C. A solution of (R)-(3-methoxy-2-methyl-3-oxopropyl)zinc(II) bromide (1.21 mL, 0.5M in THF, 0.606 mmol) was added under an N₂-atmosphere, and the reaction mixture was stirred for 20 min at 0° C. A N₂-sparged solution of 4-fluoro-5,6-dimethoxybenzo[b]thiophene-2-carbonyl chloride from Example 25, step 3 (130 mg, 0.47 mmol) in THF (3 mL) was then added, and the resulting suspension was allowed to warm to rt and was stirred for an additional 8 h. The reaction mixture was poured into sat aq NH₄Cl (20 mL) with stirring and then extracted with EtOAc (2×20 mL). The combined organic layers were washed with H₂O and brine, dried over Na₂SO₄, filtered, and concentrated under reduced pressure. The residue was purified by silica gel column chromatography (EtOAc in Hex) to give methyl (S)-4-(4-fluoro-5,6-dimethoxybenzo[b]thiophen-2-yl)-2-methyl-4-oxobutanoate. LCMS (C₁₆H₁₈FO₅S) (ES, m/z): 341 [M+H]⁺. ¹H NMR (500 MHz, CDCl₃) δ 7.98 (d, J=0.7 Hz, 1H), 7.09 (t, J=1.0 Hz, 1H), 4.04-3.95 (m, 6H), 3.72 (s, 3H), 3.50 (dd, J=17.0, 7.9 Hz, 1H), 3.23-3.12 (m, 1H), 3.06 (dd, J=17.0, 5.7 Hz, 1H), 1.32 (d, J=7.2 Hz, 3H).

Step 2: (S)-4-(4-fluoro-5,6-dimethoxybenzo[b]thiophen-2-yl)-2-methyl-4-oxobutanoic acid

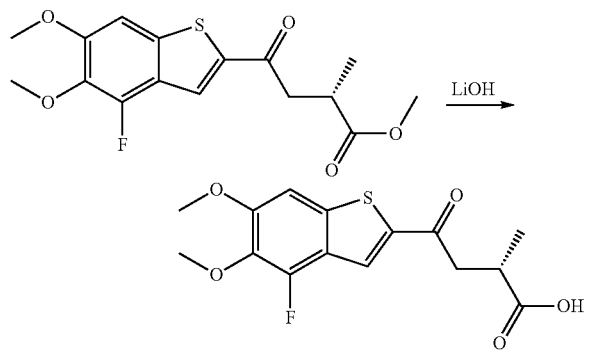

To a solution of methyl (S)-4-(4-fluoro-5,6-dimethoxybenzo[b]thiophen-2-yl)-2-methyl-4-oxobutanoate (90 mg, 0.26 mmol) in MeOH (1.5 mL), and THF (1.5 mL) was added 1N aq LiOH (1.5 mL, 1.5 mmol). The reaction mixture was stirred at rt for 1 h, and then aq 1N HCl (1.5 mL, 1.5 mmol) was added. The resulting precipitate was collected by suction filtration and purified by prep-HPLC (ACN/H₂O with 0.1% TFA) to afford (S)-4-(4-fluoro-5,6-dimethoxybenzo[b]thiophen-2-yl)-2-methyl-4-oxobutanoic acid. LCMS (C₁₅H₁₆FO₅S) (ES, m/z): 327 [M+H]⁺. ¹H NMR (500 MHz, DMSO-d₆) δ 12.21 (s, 1H), 8.33 (d, J=0.7 Hz, 1H), 7.59 (d, J=1.1 Hz, 1H), 3.93 (s, 3H), 3.87 (s, 3H), 3.48 (dd, J=17.6, 8.7 Hz, 1H), 3.14 (dd, J=17.6, 5.0 Hz, 1H), 2.95-2.84 (m, 1H), 1.19 (d, J=7.3 Hz, 3H).

Example 27: 4-(3-chloro-5,6-dimethoxybenzo[b]thiophen-2-yl)-4-oxobutanoic acid

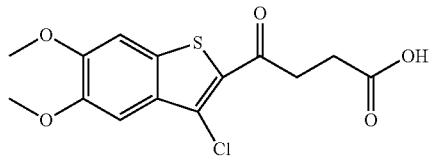 [SMILES: COc1cc2sc(C(=O)CCC(=O)O)c(Cl)c2cc1OC]

Step 1: 3-chloro-5,6-dimethoxybenzo[b]thiophene-2-carbonyl chloride

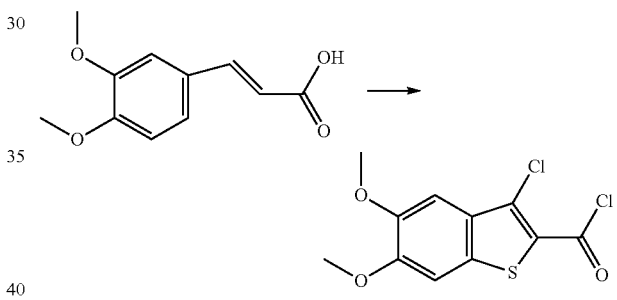

To a reaction mixture of (E)-3-(3,4-dimethoxyphenyl) acrylic acid (5.7 g, 27 mmol) in chlorobenzene (40 mL) was added SOCl₂ (9.0 mL, 120 mmol) slowly. After 30 min at rt, py (0.58 mL, 7.1 mmol) was added slowly. The mixture was then heated to reflux for 24 h. Upon cooling to rt, the mixture was concentrated under reduced pressure to afford 3-chloro-5,6-dimethoxybenzo[b]thiophene-2-carbonylchloride that was taken on to the next step without further purification.

Step 2: ethyl 4-(3-chloro-5,6-dimethoxybenzo[b]thiophen-2-yl)-4-oxobutanoate

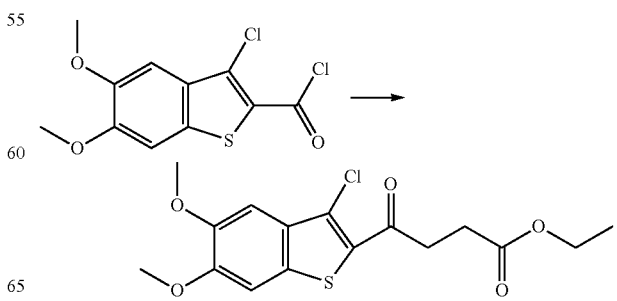

To an oven-dried round bottom flask was added Cu—Cl (510 mg, 5.2 mmol). The reaction flask was purged with Ar. (3-ethoxy-3-oxopropyl)zinc(II) bromide (0.5M in THF, 12 mL, 6.2 mmol) was added at rt. After 30 min at rt, a mixture of 3-chloro-5,6-dimethoxybenzo [b]thiophene-2-carbonyl chloride (1.5 g, 5.2 mmol) in THF (10 mL) was added. After 30 min, the mixture was quenched with sat NH$_4$Cl (6.0 mL) and diluted with EtOAc. The organic layer was separated and then concentrated under reduced pressure to provide a residue that was purified by silica gel column chromatography (EtOAc in Hex) to give ethyl 4-(3-chloro-5,6-dimethoxybenzo [b]thiophen-2-yl)-4-oxobutanoate. LCMS (C$_{16}$H$_{18}$ClO$_5$S) (ES, m/z): 357 [M+H]$^+$. $^1$H NMR (500 MHz, Acetone-d$_6$) δ 7.56 (s, 1H), 7.36 (s, 1H), 4.13 (q, J=7.1 Hz, 2H), 3.98 (s, 3H), 3.97 (s, 3H), 3.47 (t, J=6.3 Hz, 2H), 2.75 (t, J=6.3 Hz, 2H), 1.24 (t, J=7.1 Hz, 3H).

Step 3: 4-(3-chloro-5,6-dimethoxybenzo[b]thiophen-2-yl)-4-oxobutanoic acid

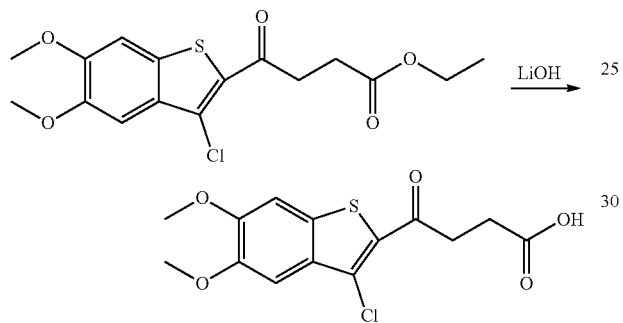

A mixture of ethyl 4-(3-chloro-5,6-dimethoxybenzo[b]thiophen-2-yl)-4-oxobutanoate (58 mg, 0.16 mmol) and LiOH (23 mg, 0.98 mmol) in THF (1.5 mL), H$_2$O (0.40 mL) and MeOH (1.0 mL) was allowed to stir at rt for 1.5 h. The reaction mixture was adjusted to a pH between 3 and 4 with HCl (1.0N in H$_2$O) and then diluted with DCM. The organic layer was separated, and then the H$_2$O layer was re-extracted with DCM (2×20 mL). The combined organic layers were concentrated under reduced pressure to afford the crude product. The crude product was purified by prep HPLC (ACN/H2O in 0.1% TFA). The liquid fractions containing pure product were combined and then freeze-dried with a lyophilzer to yield 4-(3-chloro-5,6-dimethoxybenzo[b]thiophen-2-yl)-4-oxobutanoic acid. LCMS (C$_{14}$H$_{14}$ClO$_5$S) (ES, m/z): 329 [M+H]$^+$. $^1$H NMR (500 MHz, DMSO-d$_6$) δ 12.22 (s, 1H), 7.67 (s, 1H), 7.29 (s, 1H), 3.90 (s, 3H), 3.88 (s, 3H), 3.34 (t, J=5.0 Hz, 2H), 2.62 (t, J=6.2 Hz, 2H).

Example 28: (S)-4-(5-chloro-6-methoxybenzo[b]thiophen-2-yl)-2-methyl-4-oxobutanoic acid

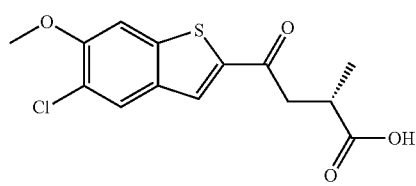 [SMILES: COc1cc2sc(C(=O)C[C@H](C)C(=O)O)cc2cc1Cl]

Step 1: tert-butyl 5-chloro-6-methoxybenzo[b]thiophene-2-carboxylate

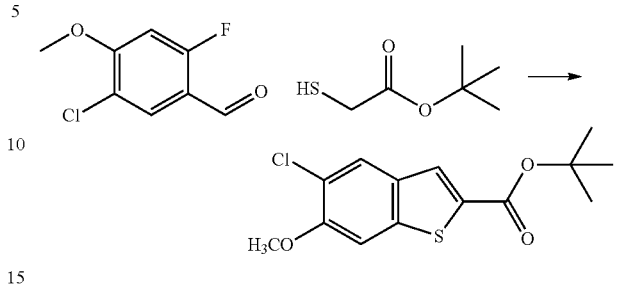

To a mixture of 5-chloro-2-fluoro-4-methoxybenzaldehyde (0.055 g, 0.3 mmol), Cs$_2$CO$_3$ (0.49 g, 1.5 mmol), and dioxane (1.5 mL) was added tert-butyl 2-mercaptoacetate (0.053 g, 0.36 mmol). The reaction was heated at reflux for 6 h. After 6 h, the mixture was allowed to cool to rt and then diluted with dioxane (2.0 mL). Macroporous polystyrene-bound isocyanate (1.59 mmol/g-0.50 g) was added, and the reaction was shaken at rt for 1 h. After 1 h, the mixture was filtered, washed with dioxane and concentrated under reduced pressure to afford a crude mixture containing tert-butyl 5-chloro-6-methoxybenzo[b]thiophene-2-carboxylate that was taken on to the next step without further purification or characterization.

Step 2: 5-chloro-6-methoxybenzo[b]thiophene-2-carboxylic acid

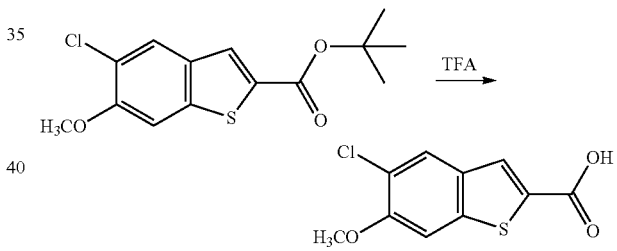

To the crude residue containing tert-butyl 5-chloro-6-methoxybenzo[b]thiophene-2-carboxylate was added DCM (1.0 mL) and TFA (1.0 mL). After 1 h, the mixture was diluted with Hex (2.0 mL) and then concentrated under reduced pressure to provide 5-chloro-6-methoxybenzo[b]thiophene-2-carboxylic acid that was taken on to the next step without further purification or characterization.

Step 3: 5-chloro-6-methoxybenzo[b]thiophene-2-carbonyl chloride

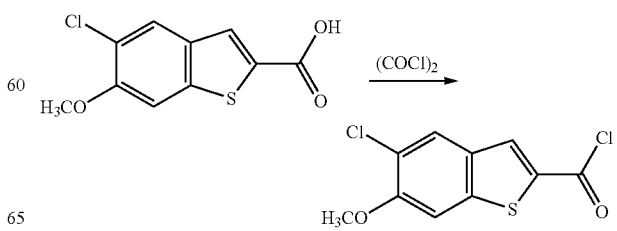

To the crude residue containing 5-chloro-6-methoxy-benzo[b]thiophene-2-carboxylic acid was added a mixture of DMF in DCM (0.05M DMF in DCM, 1.5 mL). (COCl)$_2$ (0.13 mL, 1.5 mmol) was added slowly to the reaction mixture, and the mixture was allowed to stir for 1 h. After 1 h, the mixture was diluted with Hex and then concentrated under reduced pressure to provide 5-chloro-6-methoxy-benzo[b]thiophene-2-carbonyl chloride that was taken on to the next step without further purification or characterization.

Step 4: methyl (S)-4-(5-chloro-6-methoxybenzo[b]thiophen-2-yl)-2-methyl-4-oxobutanoate

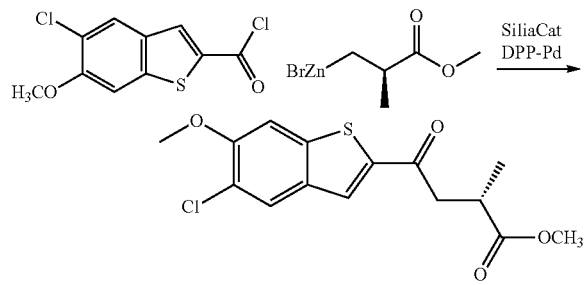

To the crude residue containing 5-chloro-6-methoxybenzo[b]thiophene-2-carbonyl chloride and (R)-(3-methoxy-2-methyl-3-oxopropyl)zinc(II) bromide (0.5M in THF, 1.2 mL, 0.60 mmol) was added a diphenylphosphine-Pd(II) catalyst bound to an organosilica matrix (([O$_3$Si]$_n$(CH$_2$)$_y$DPP-Pd), commercially available as SILIACAT® DPP-Pd R390-100, from Silicycle, 0.25 mmol/g, 0.23 g, 0.060 mmol), and the reaction was stirred at rt for 18 h. The mixture was then diluted with THF (4 mL) and N,N-diethanolaminomethyl polystyrene (1.6 mmol/g, 0.50 g) was added. The mixture was allowed to stir for 1 h. After 1 h, the mixture was filtered, the solids were washed with THF (3.5 mL), and the filtrate was concentrated under reduced pressure to afford methyl (S)-4-(5-chloro-6-methoxybenzo[b]thiophen-2-yl)-2-methyl-4-oxobutanoate that was taken on to the next step without further purification or characterization.

Step 5: (S)-4-(5-chloro-6-methoxybenzo[b]thiophen-2-yl)-2-methyl-4-oxobutanoic acid

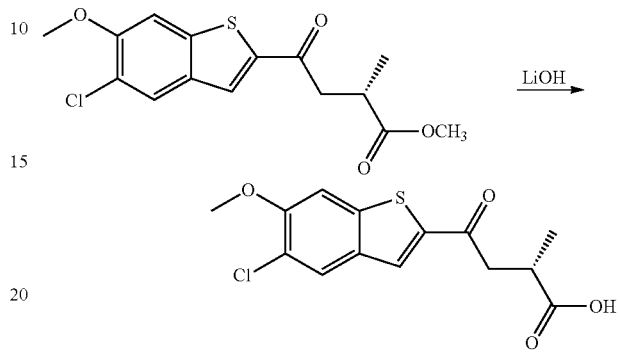

To the crude reaction mixture containing methyl (S)-4-(5-chloro-6-methoxybenzo[b]thiophen-2-yl)-2-methyl-4-oxobutanoate was added THF (1.0 mL), MeOH (0.30 mL) and aq LiOH (1.0M in H$_2$O, 1.0 mL, 1.0 mmol). After 3 h at rt, the mixture was quenched with AcOH (0.20 mL), and the mixture was concentrated under reduced pressure. The residue was taken up in DMSO (1.5 mL), and the mixture was purified by reverse phase HPLC (ACN/H$_2$O 0.1% TFA) to provide (S)-4-(5-chloro-6-methoxybenzo[b]thiophen-2-yl)-2-methyl-4-oxobutanoic acid. LCMS (C$_{14}$H$_{13}$ClO$_4$S) (ES, m/z): 313 [M+H]$^+$. $^1$H NMR (500 MHz, DMSO-d$_6$) δ 8.26 (s, 1H), 8.11 (s, 1H), 7.84 (s, 1H), 3.95 (s, 3H), 3.41 (dd, J=17.2, 8.4 Hz, 1H), 3.09 (dd, J=17.4, 5.0 Hz, 1H), 2.94-2.85 (m, 1H), 1.19 (d, J=7.2 Hz, 3H).

Examples 29 through 34, as shown in Table 3 below, were or may be prepared according to procedures analogous to those outlined in Example 28 above using the appropriate starting materials, decribed as Preparations or as obtained from commercial sources.

TABLE 3

| Ex. | Structure | Name | Mass [M + H]$^+$ |
| --- | --- | --- | --- |
| 29 | 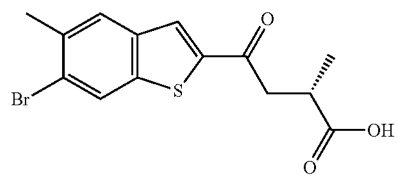 [SMILES: Cc1cc2cc(C(=O)C[C@H](C)C(=O)O)sc2cc1Br] | (S)-4-(6-bromo-5-methylbenzo[b]thiophen-2-yl)-2-methyl-4-oxobutanoic acid | 341, 343 |
| 30 | 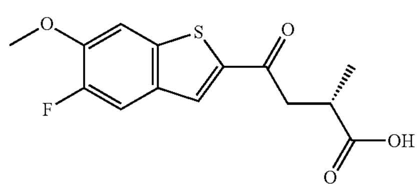 | (S)-4-(5-fluoro-6-methoxybenzo[b]thiophen-2-yl)-2-methyl-4-oxobutanoic acid | 297 |

TABLE 3-continued

| Ex. | Structure | Name | Mass [M + H]+ |
|---|---|---|---|
| 31 | 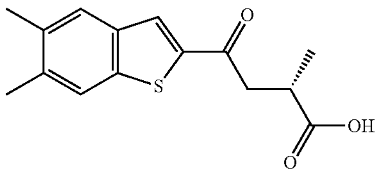 [SMILES: Cc1cc2cc(C(=O)C[C@H](C)C(=O)O)sc2cc1C] | (S)-4-(5,6-dimethylbenzo[b]thiophen-2-yl)-2-methyl-4-oxobutanoic acid | 337 |
| 32 | 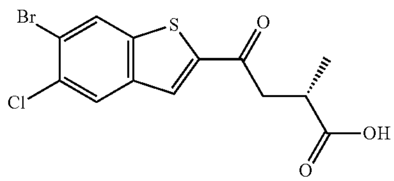 [SMILES: C[C@@H](CC(=O)c1cc2cc(Cl)c(Br)cc2s1)C(=O)O] | (S)-4-(6-bromo-5-chlorobenzo[b]thiophen-2-yl)-2-methyl-4-oxobutanoic acid | 361, 363 |
| 33 | 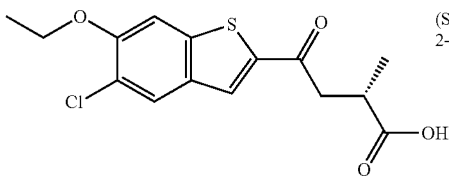 [SMILES: CCOc1cc2sc(C(=O)C[C@H](C)C(=O)O)cc2cc1Cl] | (S)-4-(5-chloro-6-ethoxybenzo[b]thiophen-2-yl)-2-methyl-4-oxobutanoic acid | 327 |
| 34 | 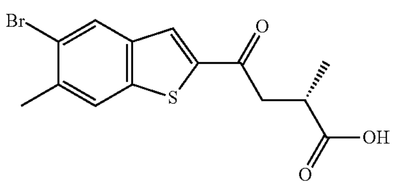 [SMILES: Cc1cc2sc(C(=O)C[C@H](C)C(=O)O)cc2cc1Br] | (S)-4-(5-bromo-6-methylbenzo[b]thiophen-2-yl)-2-methyl-4-oxobutanoic acid | 341, 343 |

Example 35: 4-(5,6-dimethoxybenzo[b]thiophen-2-yl)-2-methyl-4-oxobutanoic acid

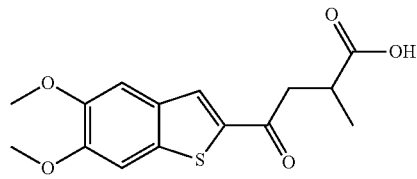 [SMILES: COc1cc2cc(C(=O)CC(C)C(=O)O)sc2cc1OC]

Step 1: tert-butyl 3-(5,6-dimethoxybenzo[b]thiophen-2-yl)-3-oxopropanoate

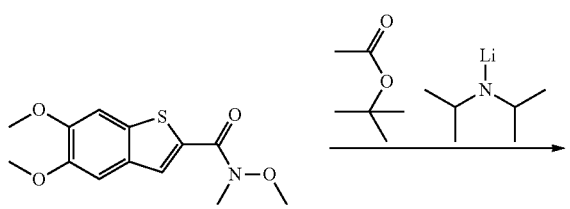

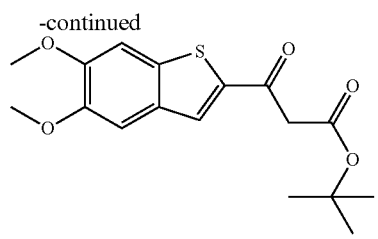

To a flask containing THF (10 mL) at −78° C. was added LDA (2.0M in THF/heptane/benzene, 4.2 mL, 8.4 mmol). Tert-butyl acetate (1.1 mL, 8.3 mmol) was added dropwise. After the addition was complete, the mixture was allowed to stir at −78° C. for 15 min. A mixture of N,5,6-trimethoxy-N-methylbenzo[b]thiophene-2-carboxamide (1.9 g, 6.9 mmol) in THF (15 mL) was added dropwise. After complete addition, the mixture was allowed to stir at −78° C. for 1 h. The mixture was then allowed to warm to rt. After warming to rt, the mixture was cooled to 5° C. and then quenched with aq HCl (1N) until pH=2. The mixture was extracted with isopropyl acetate (2×20 mL). The combined organics were washed with sat aq $NaHCO_3$ and brine, dried over $MgSO_4$, filtered and concentrated under reduced pressure. The crude residue was purified by silica gel chromatography (EtOAc in Hex) to afford tert-butyl dimethoxybenzo[b]thiophen-2-yl)-3-oxopropanoate. LCMS ($C_{17}H_{21}O_5S$—$C_4H_8$) (ES, m/z): 281 [M+H]+. 1H NMR (600 MHz, DMSO-$d_6$) δ 8.12 (s, 1H), 7.57 (s, 1H), 7.44 (s, 1H), 4.00 (s, 2H), 3.82 (s, 3H), 3.79 (s, 3H), 1.36 (s, 9H).

Step 2: 4-(5,6-dimethoxybenzo[b]thiophen-2-yl)-2-methyl-4-oxobutanoic acid

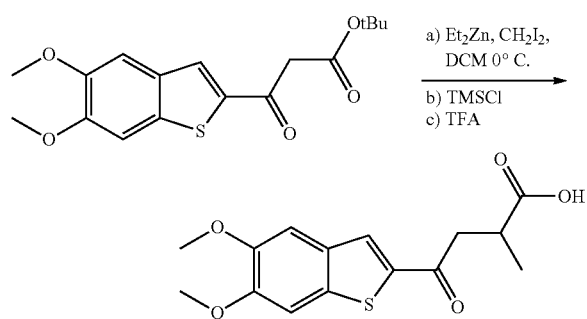

Et$_2$Zn (1.0M in Hex, 6.0 mL, 6.0 mmol) was added to DCM (20 mL) at 0° C. under N$_2$ atmosphere. CH$_2$I$_2$ (0.50 mL, 6.0 mmol) was then added dropwise. After the mixture was allowed to stir at 0° C. for 10 min, tert-butyl 3-(5,6-dimethoxybenzo[b]thiophen-2-yl)-3-oxopropanoate (0.50 g, 1.5 mmol) was added followed by TMSCl (20 µL, 0.15 mmol). The mixture was allowed to warm to rt and then stirred for 18 h. The reaction mixture was then quenched with sat aq NH$_4$Cl and extracted with DCM (3×20 mL). The combined organics were concentrated under reduced pressure. The residue was reconstituted in DCM (30 mL), and TFA (0.50 mL, 6.0 mmol) was added. After the reaction mixture was stirred for 20 min, the reaction mixture was concentrated under reduced pressure. The product was purified by reverse phase Prep-HPLC (ACN/H$_2$O with 0.1% TFA) to afford 4-(5,6-dimethoxybenzo[b]thiophen-2-yl)-2-methyl-4-oxobutanoic acid. LCMS (C$_{15}$H$_{16}$O$_5$S) (ES, m/z): 309 [M+H]$^+$. $^1$H NMR (CD$_3$OD, 600 MHz): δ 8.06 (s, 1H), 7.43-7.40 (m, 2H), 3.90 (s, 3H), 3.88 (s, 3H), 3.46 (dd, J=17, 8 Hz, 1H), 3.08 (dd, J=17, 5 Hz, 1H), 3.02 (sextet, J=7.0 Hz, 1H), 1.26 (d, J=7 Hz, 3H)

Example 36: 4-(5-Ethynyl-6-methoxybenzo[b]thiophen-2-yl)-4-oxobutanoic acid

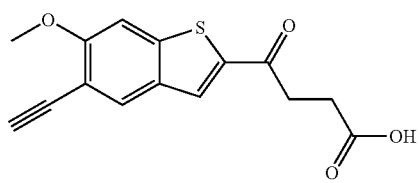 [SMILES: C#Cc1cc2cc(C(=O)CCC(=O)O)sc2cc1OC]

Step 1: Ethyl 4-(6-methoxy-5-((trimethylsilyl)ethynyl)benzo[b]thiophen-2-yl)-4-oxobutanoate

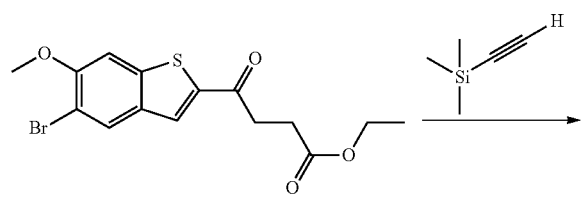

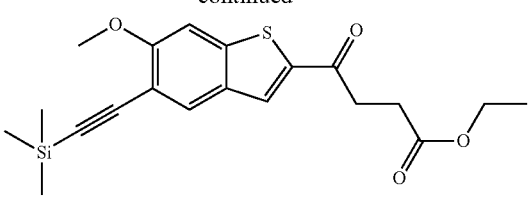

To an Ar-degassed mixture of ethyl 4-(5-bromo-6-methoxybenzo[b]thiophen-2-yl)-4-oxobutanoate (100 mg, 0.269 mmol), Pd(Ph$_3$P)$_4$ (78 mg, 0.067 mmol), and Cu—I (51 mg, 0.27 mmol) was added DMF (1.0 mL) followed by triethylamine (0.188 mL, 1.35 mmol) and ethynyltrimethylsilane (0.192 L, 1.35 mmol) at rt while degassing with Ar. The mixture was stirred for 5 mins while degassing with Ar (subsurface sparge), after which time the mixture was stirred under Ar at 20° C. for 18 h. The reaction mixture was diluted with EtOAc (50 mL) and filtered through CELITE. The filtrate was concentrated under reduced pressure to afford the crude product residue. The crude product residue was purified by silica gel chromatography (EtOAc in Hex) to afford ethyl 4-(6-methoxy-5-((trimethylsilyl)ethynyl)benzo[b]thiophen-2-yl)-4-oxobutanoate. LCMS (C$_{20}$H$_{25}$O$_4$SSi) (ES, m/z): 389 [M+H]$^+$. $^1$H NMR (500 MHz, DMSO-d$_6$): δ 8.25 (s, 1H), 8.06 (s, 1H), 7.72 (s, 1H), 4.06 (q, J=7.0 Hz, 2H), 3.90 (s, 3H), 3.34-3.30 (m, 2H), 2.68-2.64 (m, 2H), 1.17 (t, J=7.0 Hz, 3H), 0.24 (s, 9H).

Step 2: 4-(5-Ethynyl-6-methoxybenzo[b]thiophen-2-yl)-4-oxobutanoic acid

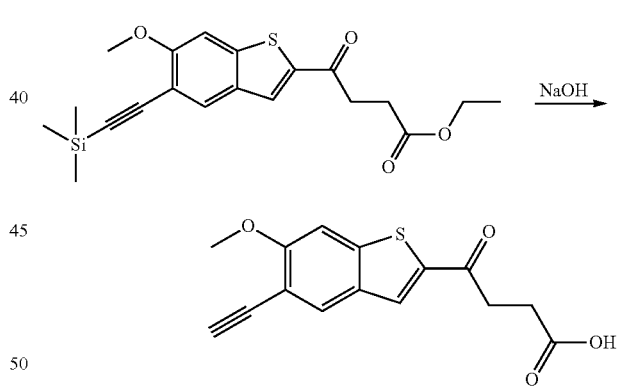

NaOH (1.0M in H$_2$O, 1.0 mL, 1.0 mmol) was added to a suspension of ethyl 4-(6-methoxy-5-((trimethylsilyl)ethynyl)benzo[b]thiophen-2-yl)-4-oxobutanoate (61 mg, 0.16 mmol) in MeOH (5.0 mL). The resulting suspension was stirred at 20° C. for 2.5 h. The reaction mixture was quenched with HCl (37% in H$_2$O, 0.083 mL, 1.0 mmol). The mixture was then concentrated under reduced pressure to afford the crude product residue. The crude product residue was by prep-HPLC (ACN/H$_2$O with 0.1% TFA) to afford 4-(5-ethynyl-6-methoxybenzo[b]thiophen-2-yl)-4-oxobutanoic acid. LCMS (C$_{15}$H$_{13}$O$_4$S) (ES, m/z): 289 [M+H]$^+$. $^1$H NMR (500 MHz, DMSO-d$_6$): δ 12.22 (s, 1H), 8.27 (s, 1H), 8.08 (s, 1H), 7.73 (s, 1H), 4.33 (s, 1H), 3.91 (s, 3H), 3.30-3.24 (m, 2H), 2.63-2.57 (m, 2H).

Example 37: (S)-4-(5-methoxy-6-(methylamino)benzo[b]thiophen-2-yl)-2-methyl-4-oxobutanoic acid

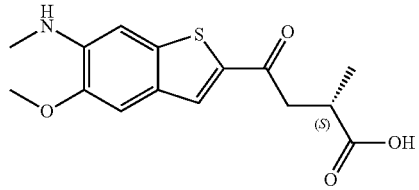

Step 1: (S)-methyl 4-(6-(((tert-butoxycarbonyl)(methyl)amino)-5-methoxybenzo[b]thiophen-2-yl)-2-methyl-4-oxobutanoate

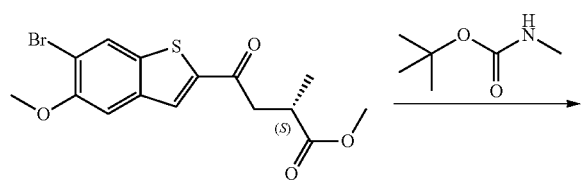

To an Ar-degassed mixture of (S)-methyl 4-(6-bromo-5-methoxybenzo[b] thiophen-2-yl)-2-methyl-4-oxobutanoate (40 mg, 0.11 mmol), tert-butyl methylcarbamate (21 mg, 0.16 mmol), Pd$_2$(dba)$_3$ (5 mg, 5 μmol), 4,5-bis(diphenylphosphino)-9,9-dimethylxanthene (XANTPHOS, 9 mg, 0.02 mmol), and Cs$_2$CO$_3$ (70 mg, 0.22 mmol) was added dioxane (0.50 mL) at rt while degassing with Ar. The mixture was stirred for 5 min while degassing with Ar (subsurface sparge), after which time the mixture was heated to 95° C. under Ar atmosphere for 12 h. The reaction mixture was cooled to rt and diluted with EtOAc (20 mL). The resulting suspension was filtered through a frit containing CELITE. The filtrate was concentrated under reduced pressure to afford the crude product residue. The crude product residue was purified by silica gel chromatography (EtOAc in Hex) to afford (S)-methyl 4-(6-((tert-butoxycarbonyl)(methyl)amino)-5-methoxybenzo[b]thiophen-2-yl)-2-methyl-4-oxobutanoate. LCMS (C$_{21}$H$_{28}$NO$_6$S) (ES, m/z): 422 [M+H]$^+$.

Step 2: (S)-methyl 4-(5-methoxy-6-(methylamino)benzo[b]thiophen-2-yl)-2-methyl-4-oxobutanoate

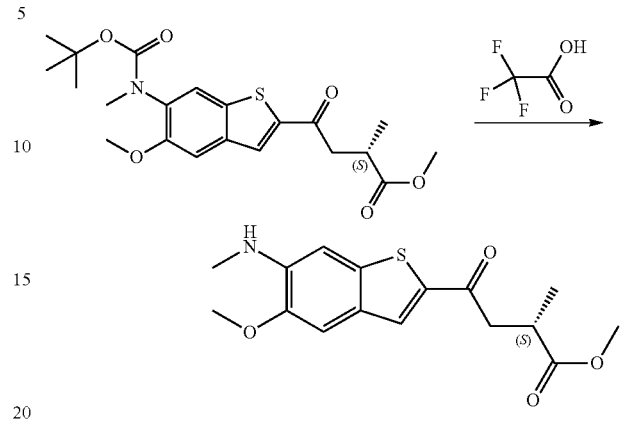

TFA (0.34 mL, 4.4 mmol) was added to a mixture of (S)-methyl 4-(6-((tert-butoxycarbonyl)(methyl)amino)-5-methoxybenzo[b]thiophen-2-yl)-2-methyl-4-oxobutanoate (37 mg, 0.088 mmol) in DCM (2.0 mL) at 20° C. The reaction mixture was stirred at 20° C. for 2 h. The reaction mixture was concentrated under reduced pressure to afford (S)-methyl 4-(5-methoxy-6-(methylamino)benzo[b]thiophen-2-yl)-2-methyl-4-oxobutanoate as the crude product residue. The crude product residue was used without workup or purification in the subsequent step. LCMS (C$_{16}$H$_{20}$NO$_4$S) (ES, m/z): 322 [M+H]$^+$.

Step 3: (S)-4-(5-methoxy-6-(methylamino)benzo[b]thiophen-2-yl)-2-methyl-4-oxobutanoic acid

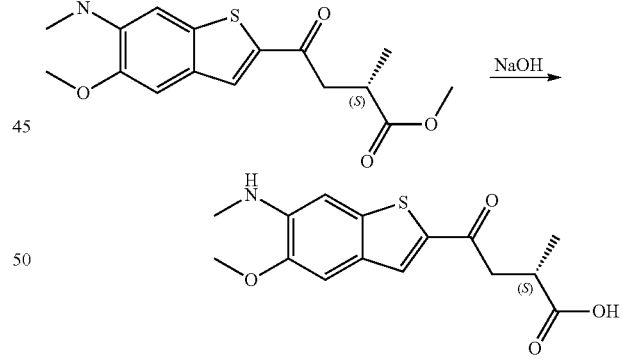

NaOH (2.0M in H$_2$O, 0.35 mL, 0.70 mmol) was added to a mixture of (S)-methyl 4-(5-methoxy-6-(methylamino)benzo[b]thiophen-2-yl)-2-methyl-4-oxobutanoate (28 mg, 0.087 mmol) in DMSO (0.50 mL) and MeOH (2.0 mL) at 20° C. The reaction mixture was stirred at 20° C. for 18 h. The reaction mixture was quenched with HCl (0.057 mL, 37% in H$_2$O, 0.70 mmol) and then diluted with additional DMSO (1.0 mL). The crude product residue was by reverse phase prep-HPLC (ACN/H$_2$O with 0.1% TFA) to afford (S)-4-(5-methoxy-6-(methylamino)benzo[b]thiophen-2-yl)-2-methyl-4-oxobutanoic acid. LCMS (C$_{15}$H$_{18}$NO$_4$S) (ES, m/z): 308 [M+H]$^+$. $^1$H NMR (500 MHz, DMSO-d$_6$): δ 8.07

(s, 1H), 7.27 (s, 1H), 6.89 (s, 1H), 3.86 (s, 3H), 3.34-3.29 (m, 1H), 3.04-2.96 (m, 1H), 2.90-2.82 (m, 1H), 2.79 (s, 3H), 1.16 (d, J=7.0 Hz, 3H).

Example 38: (S)-4-(5-methoxy-6-(methylthio)benzo[b]thiophen-2-yl)-2-methyl-4-oxobutanoic acid

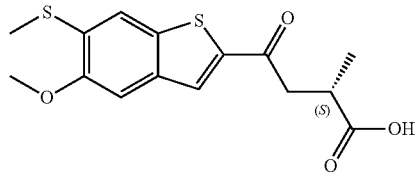

Step 1: (S)-methyl 4-(5-methoxy-6-(methylthio)benzo[b]thiophen-2-yl)-2-methyl-4-oxobutanoate

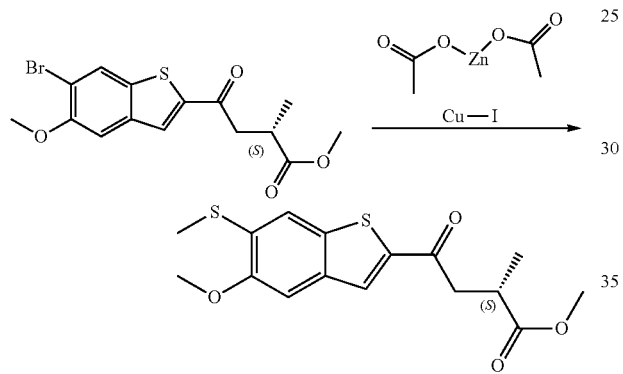

DMSO (1.00 mL) was added to a mixture of (S)-methyl 4-(6-bromo-5-methoxybenzo[b]thiophen-2-yl)-2-methyl-4-oxobutanoate (95 mg, 0.26 mmol), Cu—I (12 mg, 0.064 mmol), and zinc acetate (94 mg, 0.51 mmol). The resulting mixture was heated to 120° C. for 20 h under $N_2$. The reaction mixture was cooled to rt and diluted with EtOAc (50 mL) and then filtered through CELITE. The filtrate was concentrated under reduced pressure to afford the crude product residue. The crude product residue was purified by prep-HPLC (ACN/$H_2O$ with 0.1% TFA) to afford (S)-methyl 4-(5-methoxy-6-(methylthio)benzo[b]thiophen-2-yl)-2-methyl-4-oxobutanoate. LCMS ($C_{16}H_{19}O_4S_2$) (ES, m/z): 339 [M+H]$^+$.

Step 2: (S)-4-(5-methoxy-6-(methylthio)benzo[b]thiophen-2-yl)-2-methyl-4-oxobutanoic acid

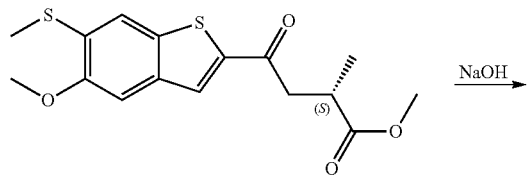

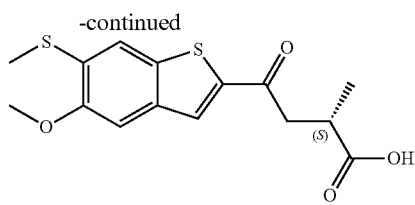

NaOH (2.0M in $H_2O$, 0.19 mL, 0.38 mmol) was added to a solution of (S)-methyl 4-(5-methoxy-6-(methylthio)benzo[b]thiophen-2-yl)-2-methyl-4-oxobutanoate (32 mg, 0.095 mmol) in DMSO (1.00 mL) at 20° C. The resulting mixture was stirred at 20° C. for 15 min under $N_2$. The reaction mixture was then quenched with HCl (0.035 mL, 37% in $H_2O$, 0.43 mmol). The reaction mixture was filtered and purified by prep-HPLC (ACN/$H_2O$ with 0.1% TFA) to afford (S)-4-(5-methoxy-6-(methylthio)benzo[b]thiophen-2-yl)-2-methyl-4-oxobutanoic acid. LCMS ($C_{15}H_{17}O_4S_2$) (ES, m/z): 325 [M+H]$^+$. $^1$H NMR (500 MHz, DMSO-$d_6$): δ 8.23 (s, 1H), 7.75 (s, 1H), 7.47 (s, 1H), 3.89 (s, 3H), 3.45-3.37 (m, 1H), 3.13-3.07 (m, 1H), 2.91-2.88 (m, 1H), 2.47 (s, 3H), 1.18 (d, J=7.0 Hz, 3H).

Example 39: (1S,2R)-2-(6-methoxy-5-vinylbenzo[b]thiophene-2-carbonyl)cyclopropane-1-carboxylic acid

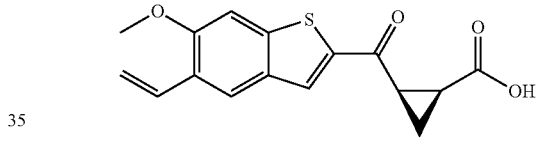

Step 1: (1S,2R)-methyl 2-(5-bromo-6-methoxybenzo[b]thiophene-2-carbonyl)cyclopropanecarboxylate

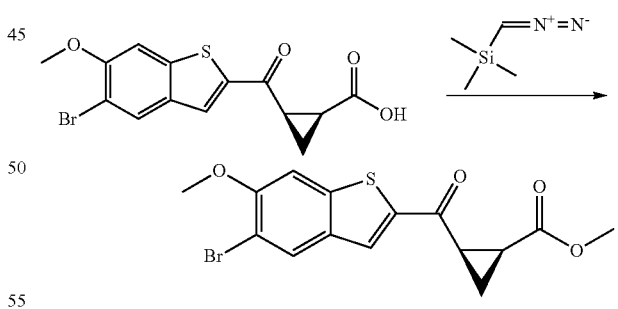

TMS-diazomethane (2.0M in Hex, 1.4 mL, 2.8 mmol) was added to a mixture of (1S,2R)-2-(5-bromo-6-methoxybenzo[b]thiophene-2-carbonyl)cyclopropanecarboxylic acid (891 mg, 2.51 mmol) in DCM (20 mL) and MeOH (20 mL) at 0° C. The reaction mixture was stirred at 0° C. for 1 h. The reaction mixture was concentrated under reduced pressure to afford the crude product residue. The crude product residue was purified by silica gel chromatography (EtOAc in Hex) to afford (1S,2R)-methyl 2-(5-bromo-6-methoxybenzo[b]thiophene-2-carbonyl) cyclopropanecarboxylate. LCMS ($C_{15}H_{14}BrO_4S$) (ES, m/z): 369, 371 [M+H]$^+$. $^1$H NMR (500

MHz, DMSO-$d_6$): δ 8.30 (s, 1H), 8.28 (s, 1H), 7.81 (s, 1H), 3.94 (s, 3H), 3.47 (s, 3H), 3.18-3.12 (m, 1H), 2.44-2.39 (m, 1H), 1.60-1.57 (m, 1H), 1.42-1.39 (m, 1H).

Step 2: (1S,2R)-methyl 2-(6-methoxy-5-vinylbenzo[b]thiophene-2-carbonyl)cyclopropanecarboxylate

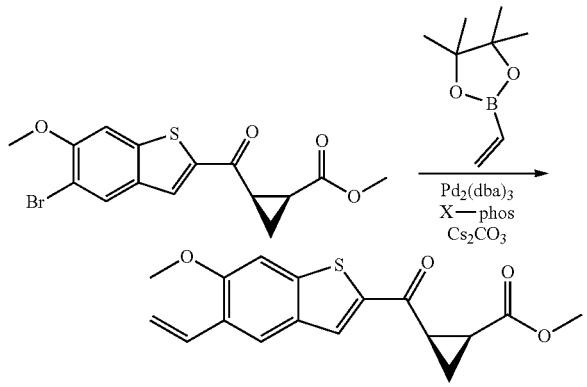

To an Ar-degassed mixture of (1S,2R)-methyl 2-(5-bromo-6-methoxybenzo[b] thiophene-2-carbonyl)cyclopropanecarboxylate (100 mg, 0.271 mmol), 4,4,5,5-tetramethyl-2-vinyl-1,3,2-dioxaborolane (50 mg, 0.33 mmol), $Pd_2(dba)_3$ (12 mg, 0.014 mmol), X-Phos (12 mg, 0.027 mmol), and $Cs_2CO_3$ (176 mg, 0.542 mmol) was added dioxane (1.50 ml) and $H_2O$ (0.2 ml) at rt while degassing with Ar. The mixture was stirred for 5 min while degassing with Ar (subsurface sparge), after which time the mixture was heated to 90° C. under Ar atmosphere for 16 h. The reaction mixture was cooled to rt and diluted with EtOAc (20 mL). The resulting suspension was filtered through a frit containing $MgSO_4$. The filtrate was concentrated under reduced pressure to afford the crude product residue. The crude product residue was purified by silica gel chromatography (EtOAc in Hex) to afford (1S,2R)-methyl 2-(6-methoxy-5-vinylbenzo[b]thiophene-2-carbonyl)cyclopropanecarboxylate. LCMS ($C_{17}H_{17}O_4S$) (ES, m/z): 317 [M+H]$^+$. $^1$H NMR (500 MHz, DMSO-$d_6$): δ 8.31 (s, 1H), 8.14 (s, 1H), 7.66 (s, 1H), 7.05-6.97 (m, 1H), 5.88 (d, J=17.5 Hz, 1H), 5.34 (d, J=11.5 Hz, 1H), 3.91 (s, 3H), 3.47 (s, 3H), 3.20-3.13 (m, 1H), 2.46-2.38 (m, 1H), 1.62-1.56 (m, 1H), 1.44-1.36 (m, 1H).

Step 3: (1S,2R)-2-(6-methoxy-5-vinylbenzo[b]thiophene-2-carbonyl)cyclopropane-1-carboxylic acid

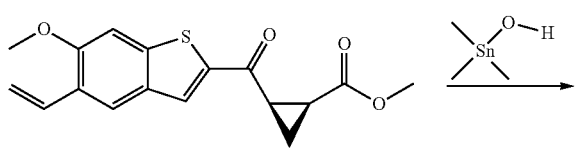

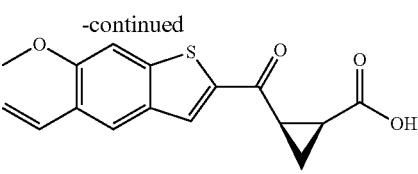

Trimethyltin hydroxide (34 mg, 0.19 mmol) was added to a mixture of (1S,2R)-methyl 2-(6-methoxy-5-vinylbenzo[b]thiophene-2-carbonyl)cyclopropanecarboxylate (30 mg, 0.095 mmol) in 1,2-dichloroethane (2.0 mL) at 20° C. The reaction mixture was stirred and heated to 85° C. for 2 days. The reaction mixture was cooled to rt and quenched with $NaHSO_4$ (2.0M in $H_2O$, 0.19 mL, 0.378 mmol) and then diluted with EtOAc (100 mL) and $H_2O$ (25 mL). The organic layer was separated, washed with brine (10 mL), dried over $MgSO_4$, filtered, and concentrated under reduced pressure to afford the crude product residue. The crude product residue was purified by prep-HPLC (ACN/$H_2O$ with 0.1% TFA) to afford (1S,2R)-2-(6-methoxy-5-vinylbenzo[b]thiophene-2-carbonyl)cyclopropane-1-carboxylic acid. LCMS ($C_{16}H_{15}O_4S$) (ES, m/z): 303 [M+H]$^+$. $^1$H NMR (500 MHz, DMSO-$d_6$): δ 12.22 (s, 1H), 8.28 (s, 1H), 8.15 (s, 1H), 7.65 (s, 1H), 7.05-6.96 (m, 1H), 5.88 (d, J=17.5 Hz, 1H), 5.33 (d, J=11.5 Hz, 1H), 3.90 (s, 3H), 3.10-3.02 (m, 1H), 2.30-2.25 (m, 1H), 1.56-1.50 (m, 1H), 1.34-1.30 (m, 1H).

Example 40, as shown in Table 4 below, was or may be prepared according to procedures analogous to those outlined in Example 39 above using the appropriate starting materials, decribed as Preparations or as obtained from commercial sources.

TABLE 4

| Ex. | Structure | Name | Mass [M + H]$^+$ |
|---|---|---|---|
| 40 | 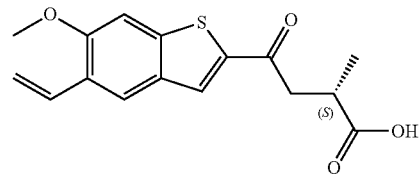 | 2-(6-methoxy-5-(methylthio)benzo[b]thiophene-2-carbonyl)cyclopropane-1-carboxylic acid | 323 |

Example 41: (S)-4-(6-methoxy-5-vinylbenzo[b]thiophen-2-yl)-2-methyl-4-oxobutanoic acid

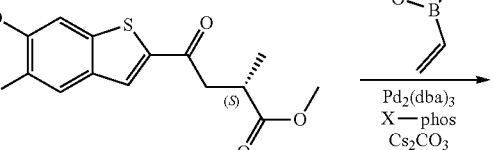

Step 1: (S)-methyl 4-(6-methoxy-5-vinylbenzo[b]thiophen-2-yl)-2-methyl-4-oxobutanoate -continued

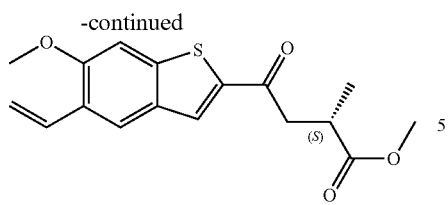

To an Ar-degassed mixture of (S)-methyl 4-(5-bromo-6-methoxybenzo[b] thiophen-2-yl)-2-methyl-4-oxobutanoate (122 mg, 0.329 mmol), 4,4,5,5-tetramethyl-2-vinyl-1,3,2-dioxaborolane (61 mg, 0.39 mmol), $Pd_2(dba)_3$ (15 mg, 0.016 mmol), X-Phos (15 mg, 0.033 mmol), and $Cs_2CO_3$ (321 mg, 0.986 mmol) was added dioxane (3.0 mL) and $H_2O$ (0.30 mL) at rt while degassing with Ar. The mixture was stirred for 5 min while degassing with Ar (subsurface sparge), after which time the mixture was heated to 90° C. under Ar atmosphere for 2 h. The reaction mixture was cooled to rt and diluted with EtOAc (20 mL). The resulting suspension was filtered through a frit containing $MgSO_4$. The filtrate was concentrated under reduced pressure to afford the crude product residue. The crude product residue was purified by silica gel chromatography (EtOAc in Hex) to afford (S)-methyl 4-(6-methoxy-5-vinylbenzo[b] thiophen-2-yl)-2-methyl-4-oxobutanoate. LCMS ($C_{17}H_{19}O_4S$) (ES, m/z): 319 [M+H]$^+$. $^1$H NMR (500 MHz, DMSO-$d_6$): δ 8.28 (s, 1H), 8.10 (s, 1H), 7.66 (s, 1H), 7.05-6.96 (m, 1H), 5.86 (d, J=17.5 Hz, 1H), 5.34 (d, J=11.5 Hz, 1H), 3.91 (s, 3H), 3.59 (s, 3H), 3.47-3.40 (m, 1H), 3.24-3.16 (m, 1H), 3.00-2.93 (m, 1H), 1.19 (d, J=6.5 Hz, 3H).

Step 2: (S)-4-(6-methoxy-5-vinylbenzo[b]thiophen-2-yl)-2-methyl-4-oxobutanoic acid

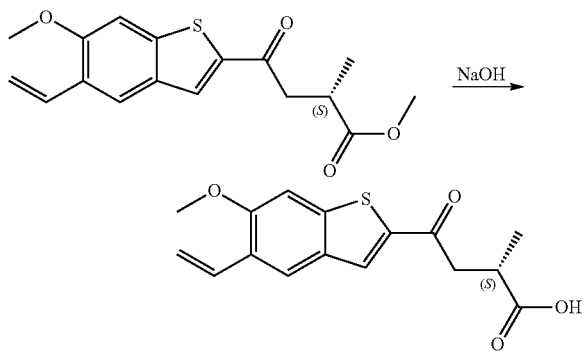

NaOH (1.0M in $H_2O$, 0.41 mL, 0.41 mmol) was added to a solution of (S)-methyl 4-(6-methoxy-5-vinylbenzo[b]thiophen-2-yl)-2-methyl-4-oxobutanoate (26 mg, 0.082 mmol) in THF (3.0 mL). The resulting suspension was stirred at 20° C. for 18 h. The reaction mixture was quenched with HCl (1.0M in $H_2O$, 0.41 mL, 0.41 mmol). The reaction mixture was then concentrated under reduced pressure to afford the crude product residue. The crude product residue was purified by prep-HPLC (ACN/$H_2O$ with 0.1% TFA) to afford (S)-4-(6-methoxy-5-vinylbenzo[b]thiophen-2-yl)-2-methyl-4-oxobutanoic acid. LCMS ($C_{16}H_{17}O_4S$) (ES, m/z): 305 [M+H]$^+$. $^1$H NMR (500 MHz, DMSO-$d_6$): δ 12.21 (s, 1H), 8.27 (s, 1H), 8.10 (s, 1H), 7.65 (s, 1H), 7.06-6.96 (m, 1H), 5.92-5.81 (m, 1H), 5.38-5.30 (m, 1H), 3.90 (s, 3H), 3.44-3.36 (m, 1H), 3.14-3.05 (m, 1H), 2.93-2.85 (m, 1H), 1.18 (bs, 3H).

Example 42: (S)-(4R,5R)-5-hydroxy-1,2-dithian-4-yl 4(5,6-dimethoxybenzo[b]thiophen-2-yl)-2-methyl-4-oxobutanoate

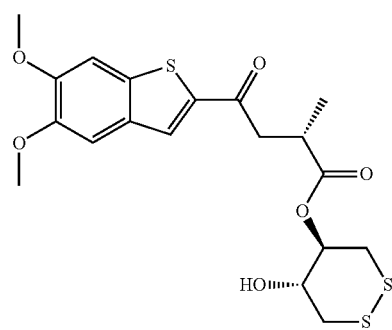 [SMILES: COc1cc2cc(C(=O)C[C@H](C)C(=O)O[C@H]3CSSC[C@@H]3O)sc2cc1OC]

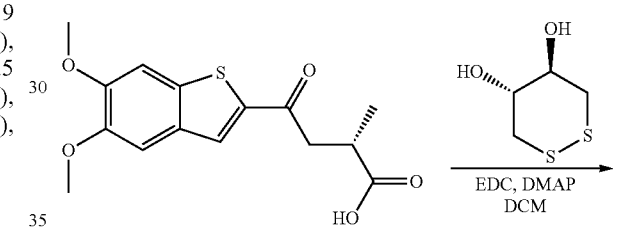

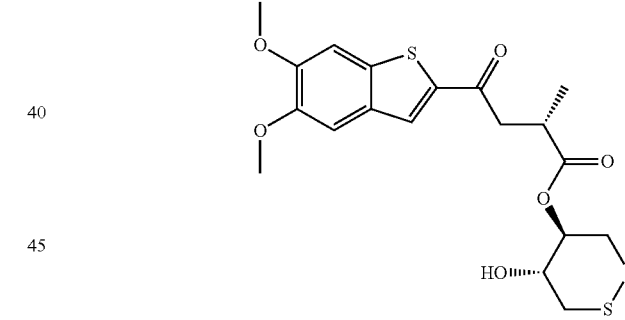

To a stirred solution of (S)-4-(5,6-dimethoxybenzo[b]thiophen-2-yl)-2-methyl-4-oxobutanoic acid (81 mg, 0.26 mmol) and EDC (50 mg, 0.26 mmol) in DCM (2.0 mL) were added (4R,5R)-1,2-dithiane-4,5-diol (30 mg, 0.20 mmol) and DMAP (1.6 mg, 0.013 mmol). The solution was left to stir for 3 days and purified by silica gel column chromatography (EtOAc in Hex). The desired fractions were combined, concentrated, and re-purified by prep-HPLC (ACN/$H_2O$ with 0.1% TFA) to afford (S)-(4R,5R)-5-hydroxy-1,2-dithian-4-yl 4-(5,6-dimethoxybenzo[b] thiophen-2-yl)-2-methyl-4-oxobutanoate. LCMS ($C_{19}H_{23}O_6S_3$) (ES, m/z): 443 [M+H]$^+$. $^1$H NMR (600 MHz, DMSO-$d_6$) δ 8.22 (s, 1H), 7.60 (s, 1H), 7.46 (s, 1H), 5.49 (d, J=5.6 Hz, 1H), 4.66 (m, 1H), 3.86 (s, 3H), 3.83 (s, 3H), 3.60 (m, 1H), 3.40 (dd, J=17.3, 8.3 Hz, 1H), 3.22 (dd, J=17.3, 5.1 Hz, 1H), 3.15-3.09 (m, 2H), 2.98 (m, 1H), 2.89-2.83 (m, 2H), 1.21 (d, J=7.1 Hz, 3H).

Example 43: (S)-4-(6-hydroxy-5-methoxybenzo[b]thiophen-2-yl)-2-methyl-4-oxobutanoic acid

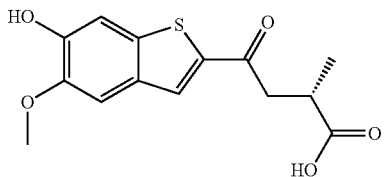 [SMILES: COc1cc2cc(C(=O)C[C@H](C)C(=O)O)sc2cc1O]

Step 1: (S)-4-(6-hydroxy-5-methoxybenzo[b]thiophen-2-yl)-2-methyl-4-oxobutanoic acid

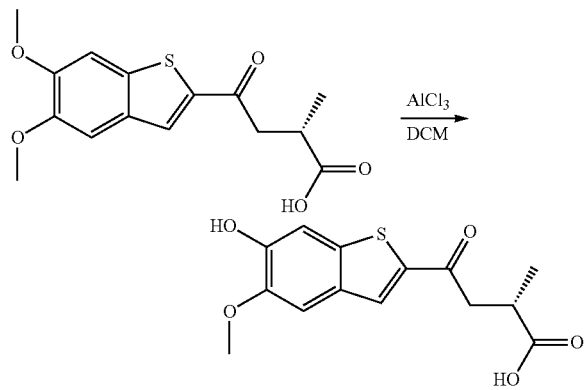

To a stirred solution of (S)-4-(5,6-dimethoxybenzo[b]thiophen-2-yl)-2-methyl-4-oxobutanoic acid (47 mg, 0.15 mmol) in DCM (2.0 mL) was added $AlCl_3$ (140 mg, 1.10 mmol). The reaction mixture was left to stir for 2 h, concentrated, and purified by prep-HPLC (ACN/$H_2O$ with 0.1% TFA). The mixture of (S)-4-(6-hydroxy-5-methoxybenzo[b]thiophen-2-yl)-2-methyl-4-oxobutanoic acid and (S)-4-(5-hydroxy-6-methoxybenzo[b]thiophen-2-yl)-2-methyl-4-oxobutanoic acid was re-purified by chiral-SFC (Column AD-H (21×250 mm), 40% MeOH with 0.25% DMEA in $CO_2$) to afford the product (retention time 6.2 min) as the DMEA salt. The salt was dissolved in $H_2O$ and acidified with 1N HCl to pH of 2. The precipitate was filtered, washed with $H_2O$, and dried under high vacuum to afford the product. LCMS ($C_{14}H_{15}O_5S$) (ES, m/z): 295 [M+H]$^+$. $^1$H NMR (600 MHz, DMSO-$d_6$) δ 12.19 (s, 1H), 9.88 (s, 1H), 8.16 (s, 1H), 7.44 (s, 1H), 7.30 (s, 1H), 3.85 (s, 3H), 3.37 (m, 1H), 3.05 (dd, J=17.1, 5.1 Hz, 1H), 2.88 (m, 1H), 1.17 (d, J=7.1 Hz, 3H).

Example 44: (2S)-4-(5-methoxy-6-propyl-1-benzothiophen-2-yl)-2-methyl-4-oxobutanoic acid

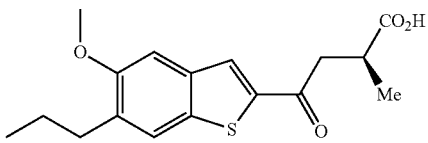 [SMILES: CCCc1cc2sc(C(=O)C[C@H](C)C(=O)O)cc2cc1OC]

Step 1: methyl(2S)-4-(5-methoxy-6-propyl-1-benzothiophen-2-yl)-2-methyl-4-oxobutanoate

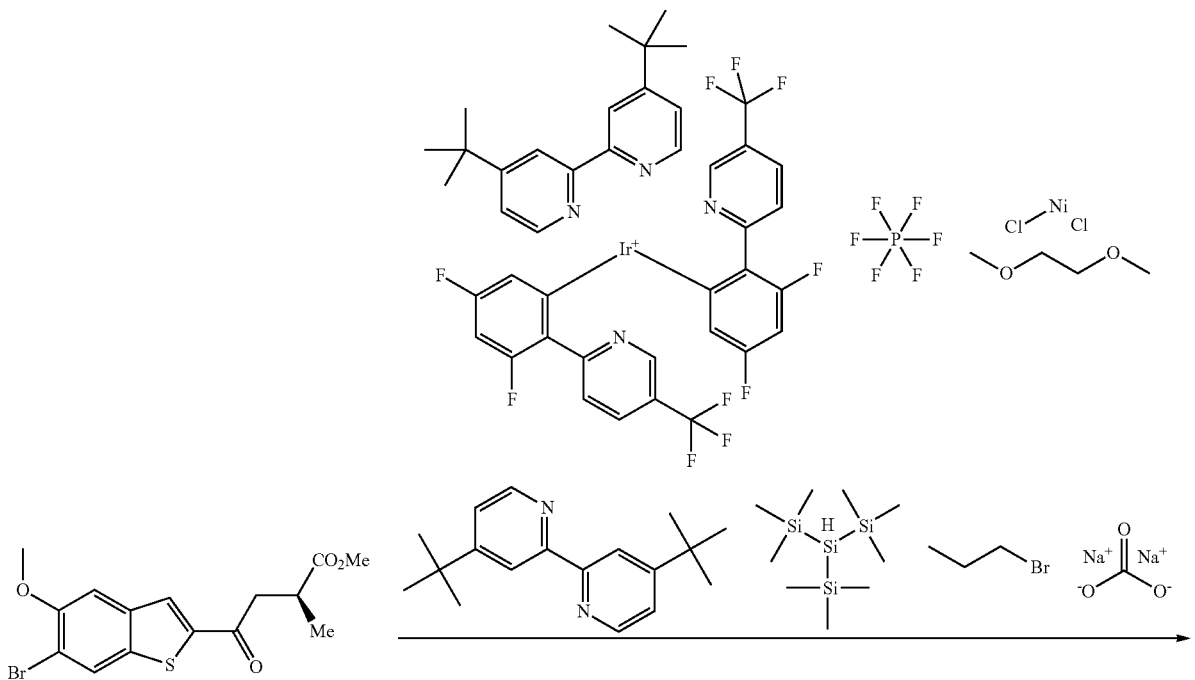

Anhydrous Na₂CO₃ (16 mg, 0.15 mmol) was heated to 125° C. under high vacuum in a capped microwave vial for 1 h before use. This vial was moved inside of a glove box. Inside the glove box, degassed dimethoxyethane (7.0 mL) was added to a 2-drain vial containing Nickel(II) chloride ethylene glycol dimethyl ether complex (5.8 mg) and 4,4'-di-tert-butyl-2,2'-bipyridine (8.0 mg). The resulting mixture was stirred for 25 min. at rt to prepare Solution A.

To a second vial degassed dimethoxyethane (2.4 mL) was added to Ir(2-(2,4-difluorophenyl)-5-(trifluoromethyl)pyridine)₂(4,4'-di-tert-butyl-2,2'-bipyridine)PF₆ (7.2 mg). The resulting mixture was stirred for 10 min at rt to prepare Solution B.

To a third vial, degassed dimethoxyethane (0.38 mL) was added to a mixture of methyl (2S)-4-(6-bromo-5-methoxy-1-benzothiophen-2-yl)-2-methyl-4-oxobutanoate (0.075 mmol), and tris(trimethylsilyl)silane (23 μL, 0.075 mmol). To this vial was added Solution A (101 μL), Solution B (280 μL), 1-bromopropane (28 mg, 0.23 mmol), and Na₂CO₃ (16 mg, 0.15 mmol). The vial was capped and sealed with paraffin film (PARAFILM). The reaction mixture was taken outside of the glovebox, stirred and irridiated with two 34 W blue LED lamps for 4 h. Note that the lamps were situated at an appropriate distance from the reaction vessel to provide irradiation without heating the reaction mixture significantly above rt. The crude reaction mixture containing methyl (2S)-4-(5-methoxy-6-propyl-1-benzothiophen-2-yl)-2-methyl-4-oxobutanoate was used in the next step without further purification or characterization.

Step 2: (2S)-4-(5-methoxy-6-propyl-1-benzothiophen-2-yl)-2-methyl-4-oxobutanoic acid

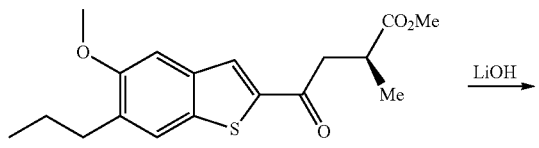

To the crude mixture of methyl (2S)-4-(5-methoxy-6-propyl-1-benzothiophen-2-yl)-2-methyl-4-oxobutanoate in dimethoxyethane (0.76 mL), was added MeOH (0.76 mL), H₂O (0.19 mL), and LiOH (22 mg, 0.91 mmol) at rt. The resulting mixture was stirred for 1.5 h at rt, and was then adjusted to pH=5 with aq HCl (2.0N) and filtered. The filtrate was purified by reverse phase prep-HPLC (ACN/H₂O with 0.1% TFA) to afford (2S)-4-(5-methoxy-6-propyl-1-benzothiophen-2-yl)-2-methyl-4-oxobutanoic acid. LCMS ($C_{17}H_{21}O_4S$) (ES, m/z): 321 [M+H]⁺. ¹H NMR (500 MHz, DMSO-d₆): δ 8.25 (s, 1H), 7.77 (s, 1H), 7.47 (s, 1H), 3.86 (s, 3H), 3.45-3.39 (m, 1H), 3.12-3.07 (m, 1H), 2.92-2.87 (m, 1H), 2.65 (t, J=7.5 Hz, 2H), 1.60 (sextet, J=7.4 Hz, 2H), 1.18 (d, J=7.5 Hz, 3H), 0.91 (t, J=7.3 Hz, 3H).

Examples 45 through 47, as shown in Table 5 below, were or may be prepared according to procedures analogous to those outlined in Example 44 above using the appropriate starting materials, decribed as Preparations or as obtained from commercial sources.

TABLE 5

| Ex. | Structure | Name | Mass [M + H]⁺ |
|---|---|---|---|
| 45 | 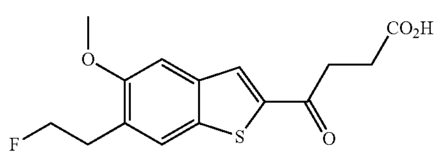 [SMILES: COc1cc2cc(C(=O)CCC(=O)O)sc2cc1CCF] | 4-[6-(2-fluoroethyl)-5-methoxy-1-benzothiophen-2-yl]-4-oxobutanoic acid | 311 |
| 46 | 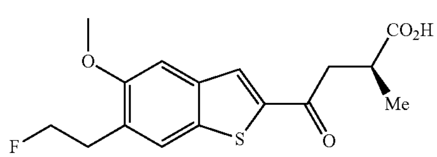 [SMILES: COc1cc2cc(C(=O)C[C@H](C)C(=O)O)sc2cc1CCF] | (2S)-4-[6-(2-fluoroethyl)-5-methoxy-1-benzothiophen-2-yl]-2-methyl-4-oxobutanoic acid | 325 |

| Ex. | Structure | Name | Mass [M + H]+ |
|---|---|---|---|
| 47 | 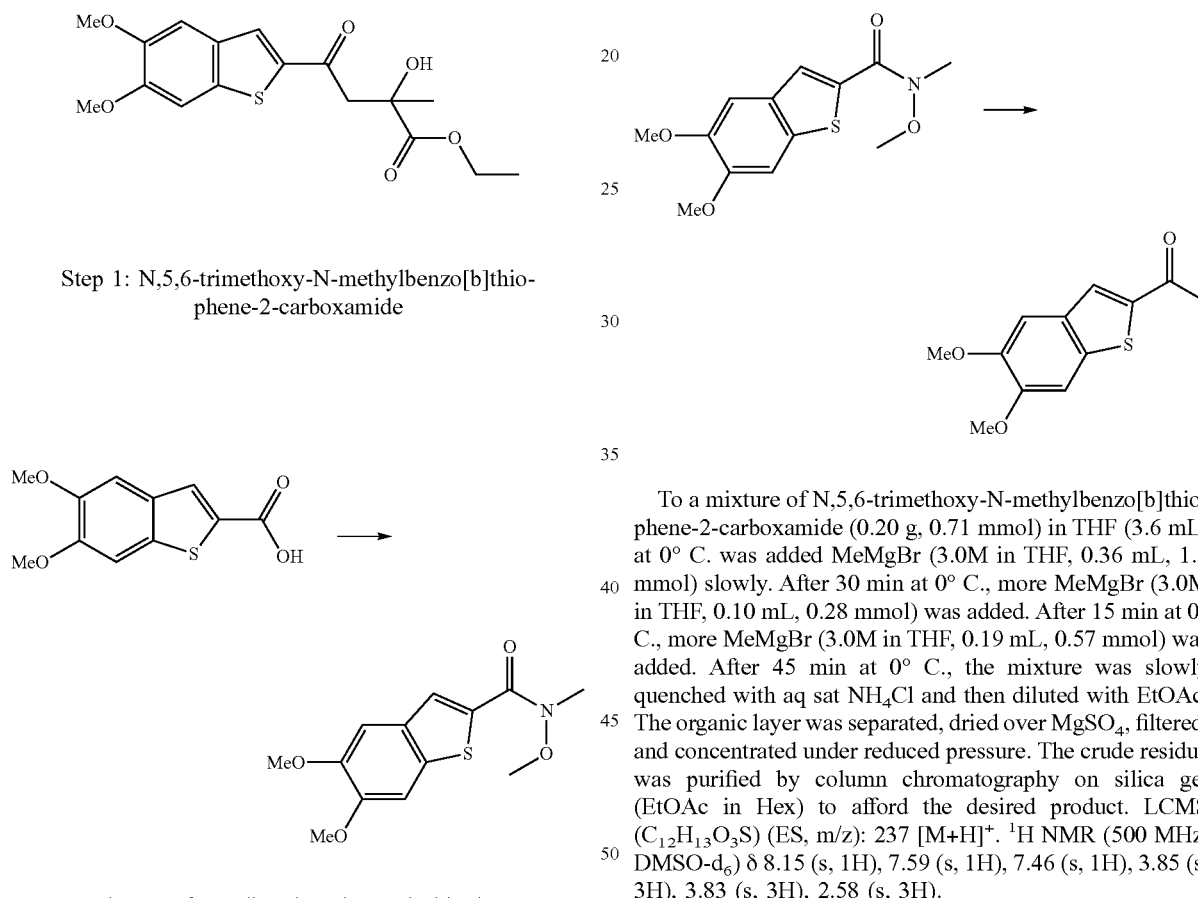 | (2S)-4-(6-methoxy-5-propyl-1-benzothiophen-2-yl)-2-methyl-4-oxobutanoic acid | 321 |

Example 48: Ethyl 4-(5,6-dimethoxybenzo[b]thiophen-2-yl)-2-hydroxy-2-methyl-4-oxobutanoate Step 1: N,5,6-trimethoxy-N-methylbenzo[b]thiophene-2-carboxamide To a mixture of 5,6-dimethoxybenzo[b]thiophene-2-carboxylic acid (2.0 g, 8.4 mmol) in THF (17 mL) at 0° C. was added N,O-dimethylhydroxylamine hydrochloride (1.6 g, 17 mmol), EDC (3.2 g, 17 mmol) and then Hunig's Base (5.9 mL, 34 mmol). The mixture was allowed to warm to rt and was stirred for 18 h. The mixture was then diluted with EtOAc and H$_2$O. The organic layer was separated, dried over MgSO$_4$, filtered and concentrated under reduced pressure. The crude residue was purified by column chromatography on silica gel (EtOAc in Hex) to afford the desired product. LCMS (C$_{13}$H$_{16}$NO$_4$S) (ES, m/z): 282 [M+H]+. $^1$H NMR (500 MHz, DMSO-d$_6$) δ 8.05 (s, 1H), 7.55 (s, 1H), 7.49 (s, 1H), 3.84 (s, 3H), 3.81 (s, 3H), 3.80 (s, 3H), 3.30 (s, 3H).

Step 2: 1-(5,6-dimethoxybenzo[b]thiophen-2-yl)ethan-1-one

To a mixture of N,5,6-trimethoxy-N-methylbenzo[b]thiophene-2-carboxamide (0.20 g, 0.71 mmol) in THF (3.6 mL) at 0° C. was added MeMgBr (3.0M in THF, 0.36 mL, 1.1 mmol) slowly. After 30 min at 0° C., more MeMgBr (3.0M in THF, 0.10 mL, 0.28 mmol) was added. After 15 min at 0° C., more MeMgBr (3.0M in THF, 0.19 mL, 0.57 mmol) was added. After 45 min at 0° C., the mixture was slowly quenched with aq sat NH$_4$Cl and then diluted with EtOAc. The organic layer was separated, dried over MgSO$_4$, filtered, and concentrated under reduced pressure. The crude residue was purified by column chromatography on silica gel (EtOAc in Hex) to afford the desired product. LCMS (C$_{12}$H$_{13}$O$_3$S) (ES, m/z): 237 [M+H]+. $^1$H NMR (500 MHz, DMSO-d$_6$) δ 8.15 (s, 1H), 7.59 (s, 1H), 7.46 (s, 1H), 3.85 (s, 3H), 3.83 (s, 3H), 2.58 (s, 3H).

Step 3: ethyl 4-(5,6-dimethoxybenzo[b]thiophen-2-yl)-2-hydroxy-2-methyl-4-oxobutanoate

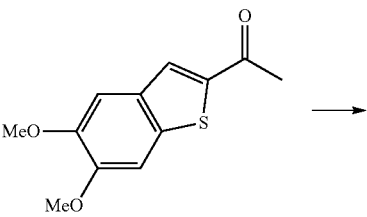

-continued

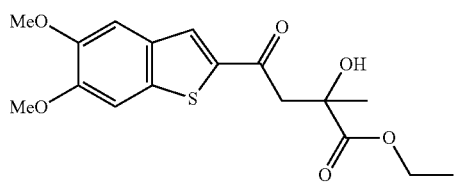 [SMILES: CCOC(=O)C(C)(O)CC(=O)c1cc2cc(OC)c(OC)cc2s1]

To a mixture of 1-(5,6-dimethoxybenzo[b]thiophen-2-yl)ethanone (50 mg, 0.21 mmol) in THF (4.2 mL) at −78° C. was added LDA (2.0M in THF/heptane/benzene, 0.50 mL, 1.0 mmol). After 45 min at −78° C., ethyl pyruvate (78 μl, 0.70 mmol) was added, and the mixture was stirred for 30 min at −78° C. After 30 min, the mixture was quenched with sat aq NH$_4$Cl and allowed to warm to rt. EtOAc was added, and the organic layer was separated, dried over MgSO$_4$, filtered and concentrated under reduced pressure. The residue was purified by column chromatography on silica gel (EtOAc in Hex) to afford the desired product as a racemic mixture. The purified racemic mixture was then purified by chiral-SFC (ES Industries, ChromegaChiral CCC, 21×250 mm column, 40% MeOH (+0.25% DMEA) in CO$_2$), affording two compounds with retention times of 3.9 min and 6.3 min. Concentration of the first eluting peak afforded the product. LCMS (C$_{17}$H$_{21}$O$_6$S) (ES, m/z): 353 [M+H]$^+$. $^1$H NMR (500 MHz, DMSO-d$_6$) δ 8.16 (s, 1H), 7.59 (s, 1H), 7.46 (s, 1H), 5.39 (s, 1H), 4.08 (q, J=6.8 Hz, 2H), 3.85 (s, 3H), 3.83 (s, 3H), 3.47 (d, J=16.0 Hz, 1H), 3.35 (d, J=15.0 Hz, 1H), 1.40 (s, 3H), 1.16 (t, J=7.1 Hz, 3H).

Example 49: 2-(2-(5,6-dimethoxybenzo[b]thiophen-2-yl)-2-oxoethyl)pentanoic acid

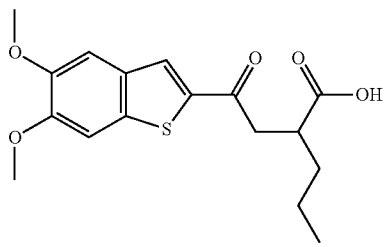 [SMILES: CCCC(CC(=O)c1cc2cc(OC)c(OC)cc2s1)C(=O)O]

Step 1: 1-(tert-butyl)4-methyl 2-(5,6-dimethoxy-benzo[b]thiophene-2-carbonyl)-3-propylsuccinate

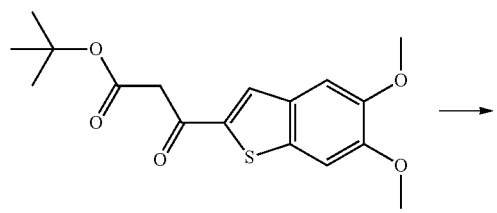

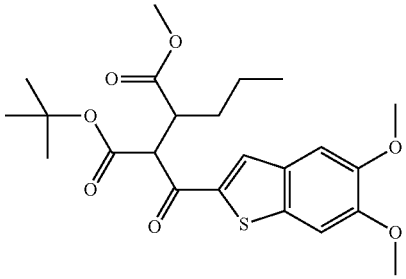

To a mixture of tert-butyl 3-(5,6-dimethoxybenzo[b]thiophen-2-yl)-3-oxopropanoate (0.15 g, 0.45 mmol) in DMF (4.5 mL) was added Cs$_2$CO$_3$ (0.29 g, 0.89 mmol), and the mixture was stirred for 20 min. After 20 min, methyl 2-bromopentanoate (0.17 g, 0.89 mmol) was added, and the mixture was stirred for 30 min. After 30 min, the mixture was diluted with EtOAc and brine. The organic layer was separated, dried over MgSO$_4$, filtered and concentrated under reduced pressure. The residue was purified by silica gel column chromatography to afford 1-(tert-butyl) 4-methyl 2-(5,6-dimethoxybenzo[b]thiophene-2-carbonyl)-3-propylsuccinate as a mixture of isomers. LCMS (C$_{23}$H$_{31}$O$_7$S) (ES, m/z): 451 [M+H]$^+$.

Step 2: methyl 2-(2-(5,6-dimethoxybenzo[b]thiophen-2-yl)-2-oxoethyl)pentanoate

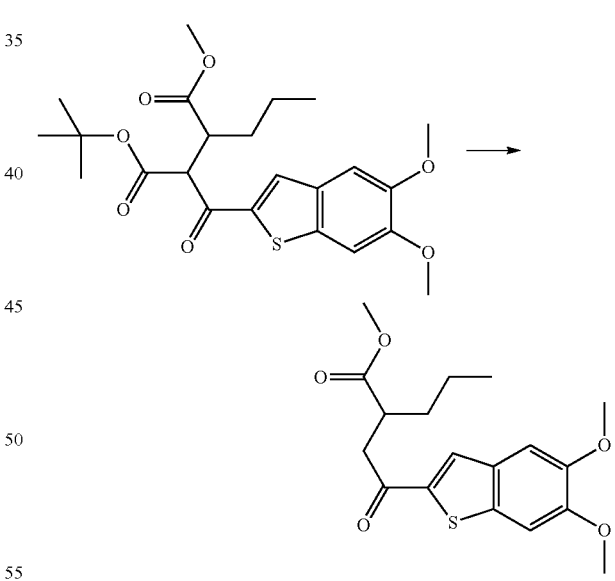

To 1-tert-butyl 4-methyl 2-(5,6-dimethoxybenzo[b]thiophene-2-carbonyl)-3-propylsuccinate (0.16 g, 0.35 mmol) in CH$_2$Cl$_2$ (0.94 mL) was added TFA (0.47 mL), and the mixture was stirred overnight at rt. The mixture was diluted with EtOAc and sat NaHCO$_3$. The organic layer was separated, dried over MgSO$_4$, filtered and concentrated under reduced pressure. The residue was purified by silica gel column chromatography to provide methyl 2-(2-(5,6-dimethoxybenzo[b]thiophen-2-yl)-2-oxoethyl)pentanoate. LCMS (C$_{18}$H$_{23}$O$_5$S) (ES, m/z): 351 [M+H]$^+$.

143

Step 3: 2-(2-(5,6-dimethoxybenzo[b]thiophen-2-yl)-2-oxoethyl)pentanoic acid

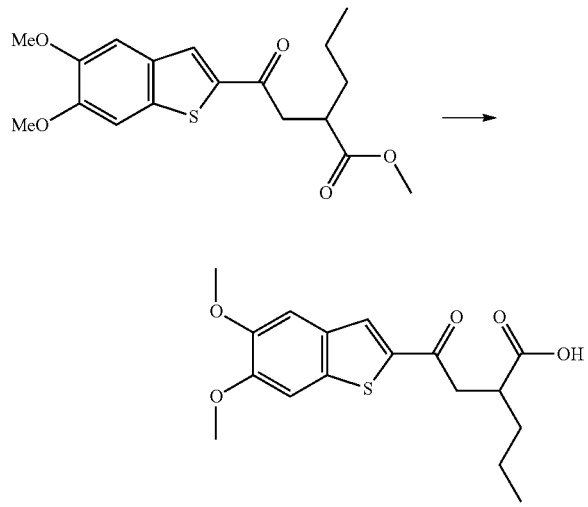

To a mixture of methyl 2-(2-(5,6-dimethoxybenzo[b]thiophen-2-yl)-2-oxoethyl) pentanoate (69 mg, 0.20 mmol) in THF (1.0 mL), MeOH (0.50 mL) and H₂O (0.50 mL) was added LiOH (24 mg, 0.99 mmol), and the mixture was stirred for 2 h at rt. After 2 h, the mixture was quenched with aq HCl (2.0N, 0.50 mL, 1.0 mmol) and then diluted with EtOAc and H₂O. The organic layer was separated, dried over MgSO₄, filtered and concentrated under reduced pressure. The residue was purified by chiral-SFC (CHIRALCEL, OJ-H, 21×250 mm, 20% MeOH (+0.25% DMEA) in CO₂) to provide the separated enantiomers with retention times of 4.2 min and 6.7 min. The fractions containing the first peak were combined and concentrated under reduced pressure. The residue was then taken up in H₂O and freeze-dried via lyophilization to afford 2-(2-(5,6-dimethoxybenzo[b]thiophen-2-yl)-2-oxoethyl)pentanoic acid. LCMS (C₁₇H₂₁O₅S) (ES, m/z): 337 [M+H]⁺. ¹H NMR (600 MHz, DMSO-d₆) δ 12.02 (s, 1H), 8.18 (s, 1H), 7.55 (s, 1H), 7.42 (s, 1H), 3.82 (s, 3H), 3.79 (s, 3H), 3.36-3.31 (m, 1H), 3.04 (dd, J=17.2, 4.3 Hz, 1H), 2.82-2.76 (m, 1H), 1.59-1.51 (m, 1H), 1.51-1.42 (m, 1H), 1.36-1.26 (m, 2H), 0.85 (t, J=7.2 Hz, 3H).

Example 50: 2-ethyl-4-(4-fluoro-5,6-dimethoxy-benzo[b]thiophen-2-yl)-4-oxobutanoic acid

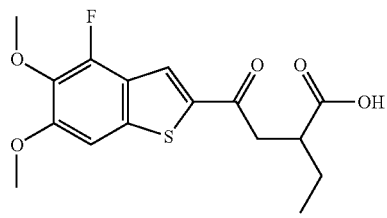 [SMILES: CCC(CC(=O)c1cc2c(F)c(OC)c(OC)cc2s1)C(=O)O]

144

Step 1: tert-butyl 3-(4-fluoro-5,6-dimethoxybenzo[b]thiophen-2-yl)-3-oxopropanoate

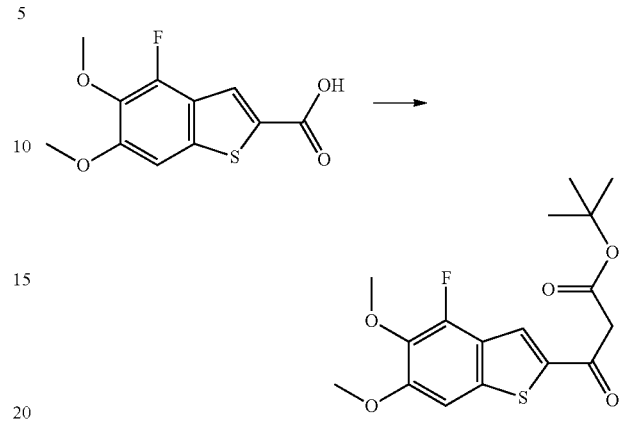

To a mixture of 4-fluoro-5,6-dimethoxybenzo[b]thiophene-2-carboxylic acid (290 mg, 1.1 mmol) in 7.5 mL of THF was added 1,1'-carbonyldiimidazole (220 mg, 1.4 mmol). After 2 h, magnesium 3-(tert-butoxy)-3-oxopropanoate (0.58 g, 1.7 mmol) was added, and the reaction mixture was allowed to stir for 18 h. The mixture was then diluted with EtOAc and H₂O. The organic layer was separated, dried over MgSO₄, filtered and concentrated under reduced pressure. The crude residue was purified by silica gel column chromatography (EtOAc in Hex) to afford tert-butyl 3-(4-fluoro-5,6-dimethoxybenzo[b]thiophen-2-yl)-3-oxopropanoate. LCMS (C₁₇H₂₀FO₅S—C₄H₈) (ES, m/z): 299 [M+H]⁺. ¹H NMR (500 MHz, DMSO-d₆) δ 8.32 (s, 1H), 7.60 (s, 1H), 4.13 (s, 2H), 3.92 (s, 3H), 3.85 (s, 3H), 1.40 (s, 9H).

Step 2: methyl 2-ethyl-4-(4-fluoro-5,6-dimethoxy-benzo[b]thiophen-2-yl)-4-oxobutanoate

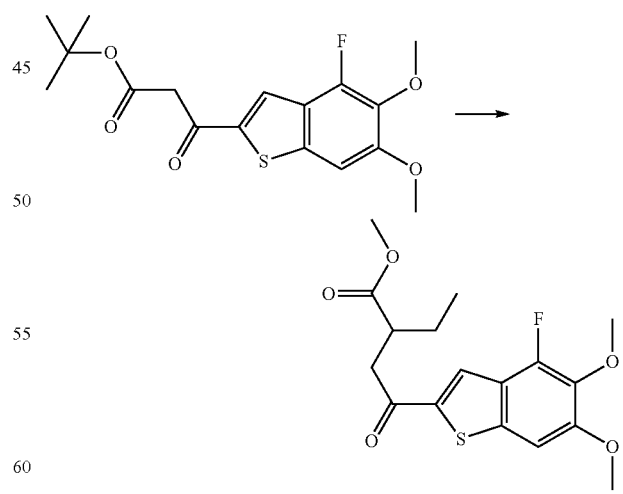

To a mixture of tert-butyl 3-(4-fluoro-5,6-dimethoxybenzo[b]thiophen-2-yl)-3-oxopropanoate (0.12 g, 0.34 mmol) in DMF (1.0 mL) was added Cs₂CO₃ (0.22 g, 0.68 mmol), and the mixture was stirred for 20 min. Methyl 2-bromobutyrate (78 μl, 0.68 mmol) was then added, and the mixture was allowed to stir for 3 h at rt. After 3 h, the mixture was diluted with EtOAc and H₂O. The organic layer was separated, dried over MgSO₄, filtered and concentrated under reduced pressure. To the crude residue was added CH₂Cl₂ (1.7 mL) and TFA (0.85 mL), and the mixture was heated to 50° C. for 4 h. Upon cooling to rt, the mixture was diluted with EtOAc and sat aq NaHCO₃. The organic layer was separated, dried over MgSO₄, filtered and concentrated under reduced pressure. The crude residue was purified by silica gel column chromatography (EtOAc in Hex) to afford methyl 2-ethyl-4-(4-fluoro-5,6-dimethoxybenzo[b]thiophen-2-yl)-4-oxobutanoate. LCMS (C₁₇H₂₀FO₅S) (ES, m/z): 355 [M+H]⁺.

Step 3: 2-ethyl-4-(4-fluoro-5,6-dimethoxybenzo[b]thiophen-2-yl)-4-oxobutanoic acid

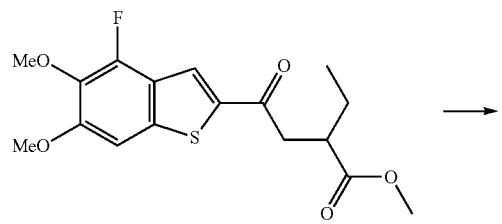

To a mixture of methyl 2-ethyl-4-(4-fluoro-5,6-dimethoxybenzo[b]thiophen-2-yl)-4-oxobutanoate (57 mg, 0.16 mmol) in THF (1.0 mL), MeOH (0.50 mL), and H₂O (0.50 mL) was added LiOH (19 mg, 0.80 mmol), and the mixture was stirred for 2 h at 40° C. After 2 h, the mixture was cooled to rt and then quenched with aq HCl (2.0M, 0.40 mL, 0.80 mmol) and then diluted with EtOAc and H₂O. The organic layer was separated, dried over MgSO₄, filtered and concentrated under reduced pressure. The residue was purified by chiral-SFC (Lux-4, 21×250 mm, 45% MeOH (+0.25% DMEA) in CO₂) to provide the separated enantiomers with retention times of 2.8 min and 5.3 min. The fractions containing the second peak were combined and concentrated. The residue was then taken up in H₂O and freeze-dried via lyophilization to afford 2-ethyl-4-(4-fluoro-5,6-dimethoxybenzo[b]thiophen-2-yl)-4-oxobutanoic acid. LCMS (C₁₆H₁₈FO₅S) (ES, m/z): 341 [M+H]⁺. ¹H NMR (500 MHz, DMSO-d₆) δ 11.97 (s, 1H), 8.35 (s, 1H), 7.57 (s, 1H), 3.91 (s, 3H), 3.85 (s, 3H), 3.52-3.42 (m, 1H), 3.15-3.07 (m, 1H), 2.81-2.71 (m, 1H), 1.68-1.55 (m, 2H), 0.92 (t, J=7.3 Hz, 3H).

Example 51 and 52

(1R,2S)-2-(4-fluoro-5,6-dimethoxybenzo[b]thiophene-2-carbonyl)cyclopropane-1-carboxylic acid and (1S,2R)-2-(4-fluoro-5,6-dimethoxybenzo[b]thiophene-2-carbonyl)cyclopropane-1-carboxylic acid

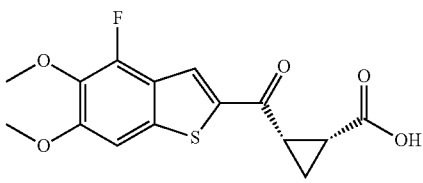

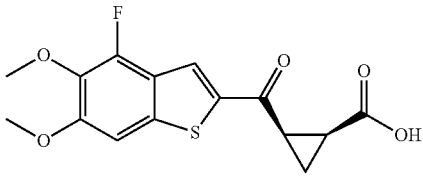

Step 1: 4-fluoro-5,6-dimethoxybenzo[b]thiophene

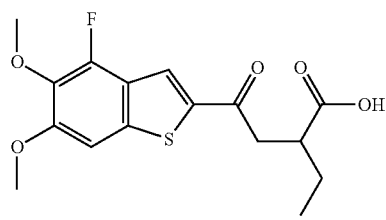

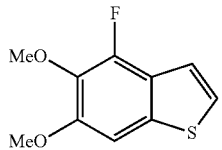

To a mixture of 4-fluoro-5,6-dimethoxybenzo[b]thiophene-2-carboxylic acid (0.090 g, 0.35 mmol) in quinoline (0.83 mL, 7.0 mmol) was added copper (0.038 g, 0.60 mmol), and the mixture was heated to 190° C. for 2 h. After 2 h, the mixture was allowed to cool to rt and was then diluted with EtOAc and 2N HCl. The mixture was filtered, and then the organic layer was separated. The organic layer was then washed successively with H₂O, sat aq NaHCO₃ and brine. The organic layer was dried over MgSO₄, filtered and concentrated under reduced pressure. The mixture was purified by column chromatography on silica gel (EtOAc in Hex) to provide 4-fluoro-5,6-dimethoxybenzo[b]thiophene. LCMS (C₁₀H₁₀FO₂S) (ES, m/z): 213 [M+H]⁺. ¹H NMR (500 MHz, Chloroform-d) δ 7.33 (d, J=5.4 Hz, 1H), 7.27 (d, J=5.2 Hz, 1H), 7.14 (s, 1H), 3.99 (s, 3H), 3.95 (s, 3H).

Step 2: 2-(4 fluoro-5,6-dimethoxybenzo[b]thiophene-2-carbonyl)cyclopropane-1-carboxylic acid

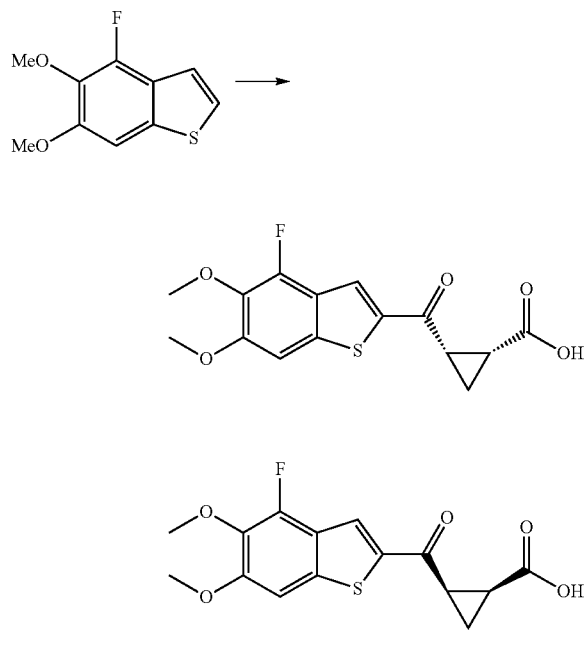

To a mixture of 4-fluoro-5,6-dimethoxybenzo[b]thiophene (45 mg, 0.21 mmol) in $CH_2Cl_2$ (2.0 mL) at 0° C. was added $AlCl_3$ (37 mg, 0.28 mmol) and then 3-oxabicyclo [3.1.0] hexane-2,4-dione (48 mg, 0.42 mmol). The mixture was stirred for 1 h at 0° C. and then allowed to warm to rt and stirred for 18 h. After 18 h, the mixture was diluted with EtOAc and $H_2O$. The organic layer was separated, dried over $MgSO_4$, filtered and concentrated under reduced pressure. The resulting residue was purified by silica gel column chromatography (EtOAc in Hex) to afford a racemic mixture of the desired product. The enantiomers were then separated by chiral-SFC (Lux-4, 21×250 mm, 45% MeOH (+0.25% DMEA) in $CO_2$) to provide (1R,2S)-2-(4-fluoro-5,6-dimethoxybenzo[b]thiophene-2-carbonyl)cyclopropane-1-carboxylic acid and (1S,2R)-2-(4-fluoro-5,6-dimethoxybenzo[b]thiophene-2-carbonyl)cyclopropane-1-carboxylic acid with retention times of 4.0 min and 4.9 min. The fractions containing the first peak (retention time 4.0 min) were combined and concentrated. The residue was taken up in $H_2O$ and freeze-dried via lyophilization to afford one of the pure enantiomers. LCMS ($C_{15}H_{14}FO_5S$) (ES, m/z): 325 [M+H]$^+$. $^1$H NMR (500 MHz, DMSO-$d_6$) δ 8.31 (s, 1H), 7.58 (s, 1H), 3.92 (s, 3H), 3.85 (s, 3H), 3.15 (q, J=8.0 Hz, 1H), 2.33-2.28 (m, 1H), 1.58-1.48 (m, 1H), 1.34-1.27 (m, 1H). The fractions containing the second peak (retention time 4.9 min) were combined and concentrated. The residue was taken up in $H_2O$ and freeze-dried via lyophilization to afford one of the pure enantiomers. LCMS ($C_{15}H_{14}FO_5S$) (ES, m/z): 325 [M+H]$^+$. $^1$H NMR (500 MHz, DMSO-$d_6$) δ 12.18 (s, 1H), 8.31 (s, 1H), 7.58 (s, 1H), 3.91 (s, 3H), 3.85 (s, 3H), 3.14 (q, J=7.9 Hz, 1H), 2.29 (q, J=8.0 Hz, 1H), 1.57-1.49 (m, 1H), 1.34-1.27 (m, 1H).

Example 53: 4-(6-(difluoromethoxy)-5-methoxybenzo[b]thiophen-2-yl)-4-oxobutanoic acid

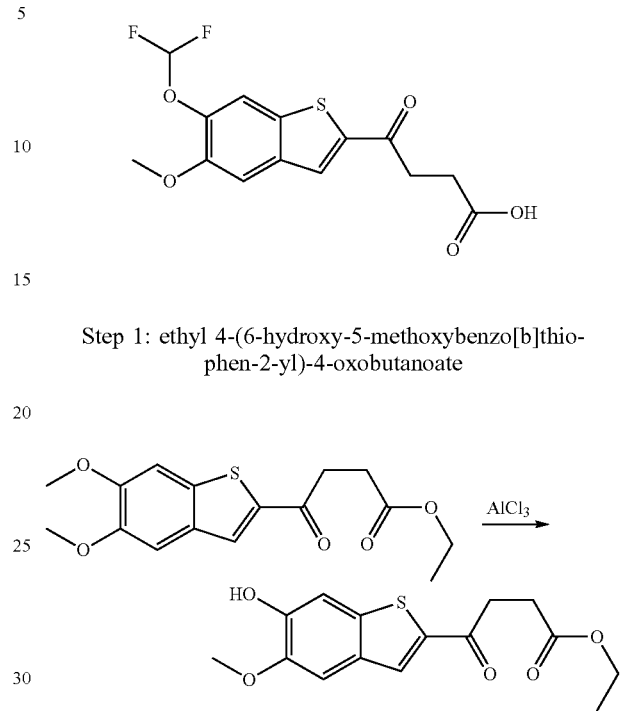

Step 1: ethyl 4-(6-hydroxy-5-methoxybenzo[b]thiophen-2-yl)-4-oxobutanoate

To a mixture of ethyl 4-(5,6-dimethoxybenzo[b]thiophen-2-yl)-4-oxobutanoate (0.45 g, 1.4 mmol) and DCM (12 mL) was added $AlCl_3$ (0.56 g, 4.2 mmol) at 25° C. The mixture was stirred at 25° C. for 15 h. After 15 h, more $AlCl_3$ (1.0 g, 7.5 mmol) was added to the mixture. The resulting mixture was stirred at 25° C. for 16 h. After 16 h, the mixture was quenched with aq HCl (1.0N, 20 mL, 20 mm) and extracted with DCM (3×30 mL). The combined organic phases were washed with brine (20 mL), dried over anhydrous $Na_2SO_4$, filtered and concentrated under reduced pressure. The resulting residue was purified by silica gel column chromatography (EtOAc in PE) to give crude ethyl 4-(6-hydroxy-5-methoxybenzo[b]thiophen-2-yl)-4-oxobutanoate. The crude product was then purified by chiral-SFC to provide ethyl 4-(6-hydroxy-5-methoxybenzo[b]thiophen-2-yl)-4-oxobutanoate. LCMS ($C_{15}H_{17}O_5S$) (ES, m/z): 309. $^1$H NMR (400 MHz, CDCl$_3$) δ=7.88 (s, 1H), 7.34 (s, 1H), 7.24 (s, 1H), 6.08 (s, 1H), 4.17 (q, J=7.3 Hz, 2H), 3.99 (s, 3H), 3.31 (t, J=6.7 Hz, 2H), 2.78 (t, J=6.8 Hz, 2H), 1.27 (t, J=7.0 Hz, 3H).

Step 2: ethyl 4-(6-(difluoromethoxy)-5-methoxybenzo[b]thiophen-2-yl)-4-oxobutanoate

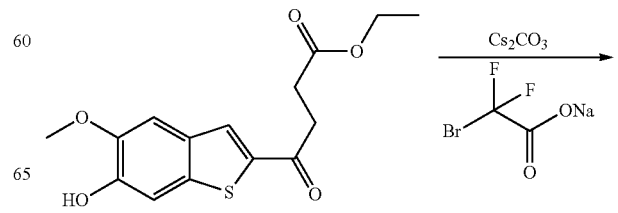

-continued

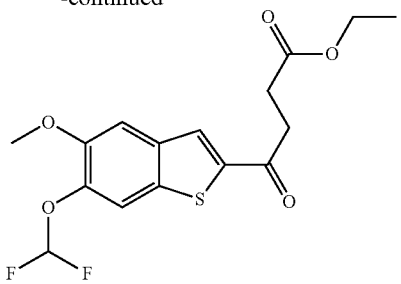

To a mixture of ethyl 4-(6-hydroxy-5-methoxybenzo[b]thiophen-2-yl)-4-oxobutanoate (25 mg, 0.081 mmol) in DMF (1.5 ml) was added sodium 2-bromo-2,2-difluoroacetate (48 mg, 0.24 mmol) and $Cs_2CO_3$ (79 mg, 0.24 mmol) at 30° C. The resulting mixture was heated to 100° C. for 3 h. Upon cooling to rt, the mixture was diluted with $H_2O$ (10 mL) and extracted with EtOAc (3×10 mL). The combined organic layers were washed with $H_2O$ (20 mL) and brine (20 mL), dried over anhydrous $Na_2SO_4$, filtered and concentrated under reduced pressure to give crude product. The crude was purified by reverse phase prep-HPLC (ACN/$H_2O$ with 0.1% TFA) to provide ethyl 4-(6-(difluoromethoxy)-5-methoxybenzo[b] thiophen-2-yl)-4-oxobutanoate. LCMS ($C_{16}H_{17}F_2O_5S$) (ES, m/z): 359 [M+H]$^+$. $^1$H NMR (400 MHz, $CDCl_3$) δ 7.90 (s, 1H), 7.61 (s, 1H), 7.34 (s, 1H), 6.60 (t, J=74 Hz, 1H), 4.15 (q, J=7.2 Hz, 2H), 3.93 (s, 3H), 3.31 (t, J=6.4 Hz, 2H), 2.77 (t, J=6.4 Hz, 2H), 1.25 (t, J=7.2 Hz, 3H).

Step 3: 4-(6-(difluoromethoxy)-5-methoxybenzo[b]thiophen-2-yl)-4-oxobutanoic acid

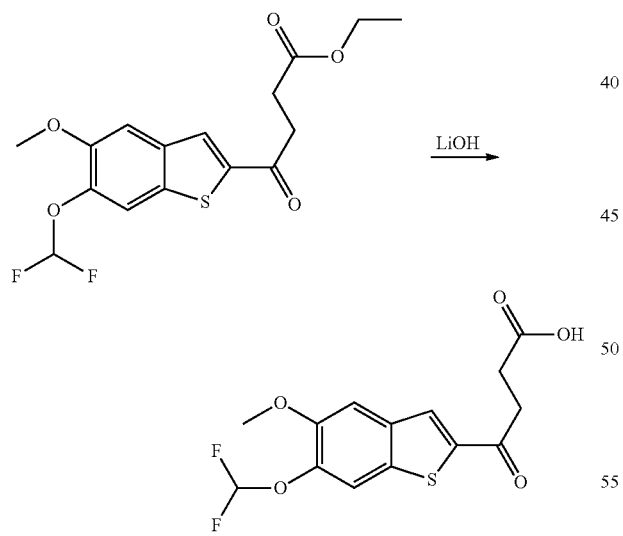

To a mixture of ethyl 4-(6-(difluoromethoxy)-5-methoxybenzo[b]thiophen-2-yl)-4-oxobutanoate (5.0 mg, 0.014 mmol) in MeOH (0.50 mL), THF (0.50 mL) and $H_2O$ (0.50 mL) was added LiOH (3.3 mg, 0.14 mmol). The mixture was heated to 50° C. for 2 h. After 2 h, the mixture was allowed to cool to rt and aq HCl (1.0M) was added until the mixture had a pH=6. The mixture was concentrated under reduced pressure. The resulting residue was dissolved in DMF (2 mL) and purified by reverse phase prep-HPLC (ACN/$H_2O$ with 0.1% TFA) to provide 4-(6-(difluoromethoxy)-5-methoxybenzo[b]thiophen-2-yl)-4-oxobutanoic acid. LCMS ($C_{14}H_{13}F_2O_5S$) (ES, m/z): 331 [M+H]$^+$. $^1$H NMR (400 MHz, $CDCl_3$) δ 8.15 (s, 1H), 7.69 (s, 1H), 7.61 (s, 1H), 6.83 (t, J=75 Hz, 1H), 3.96 (s, 3H), 3.36 (t, J=6.0 Hz, 2H), 2.73 (t, J=6.0 Hz, 2H).

Example 54: (S)-4-(4-methoxy-2-methylthieno[2',3': 5,6]benzo[1,2-d]oxazol-7-yl)-2-methyl-4-oxobutanoic acid

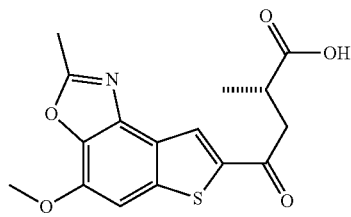 [SMILES: COc1cc2sc(C(=O)C[C@H](C)C(=O)O)cc2c2nc(C)oc12]

Step 1: 4-fluoro-2-methoxy-6-nitrophenol

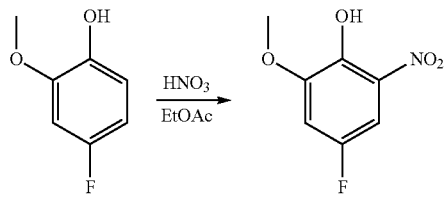

To a 50 mL round-bottom flask was added 4-fluoro-2-methoxyphenol (3.7 mL, 32 mmol) and EtOAc (90 mL). The mixture was cooled to 0° C. and stirred. To the stirring mixture was added nitric acid (2.1 mL, 33 mmol) drop wise over 5 min. The reaction was stirred at this temperature for 30 min. The mixture was diluted with EtOAc (30 mL), washed with $H_2O$ (100 mL), dried over anhydrous $Na_2SO_4$, filtered and evaporated under reduced pressure. The resulting residue was purified by column chromatography on silica gel (EtOAc in Hex) to give 4-fluoro-2-methoxy-6-nitrophenol. $^1$H NMR (500 MHz, $CDCl_3$): δ 10.60 (s, 1H), 7.41 (dd, J=8.4, 2.7 Hz, 1H), 6.94 (dd, J=9.2, 2.4 Hz, 1H), 3.97 (s, 3H).

Step 2: 2-amino-4-fluoro-6-methoxyphenol

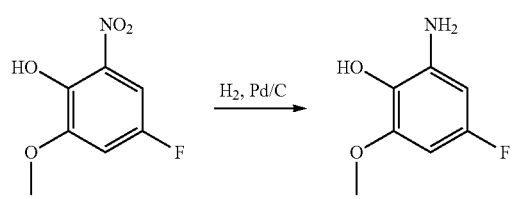

To a 100 mL round-bottom flask was added 4-fluoro-2-methoxy-6-nitrophenol (826 mg, 4.41 mmol), Pd/C (235 mg, 0.221 mmol), and EtOAc (30 mL). The mixture was stirred. The mixture was degassed with $N_2$ then placed under $H_2$. After stirring for 16 h, the reaction was filtered through CELITE, and the filter cake was washed with EtOAc. The combined filtrates were concentrated under reduced pressure to afford 2-amino-4-fluoro-6-methoxyphenol that was used in the next step without further purification. LCMS ($C_7H_9FNO_2$) (ES, m/z): 158 [M+H]$^+$. $^1$H NMR (500 MHz, CDCl$_3$): δ 6.23-6.01 (m, 2H), 3.85 (s, 3H).

Step 3: 5-fluoro-7-methoxy-2-methylbenzo[d]oxazole

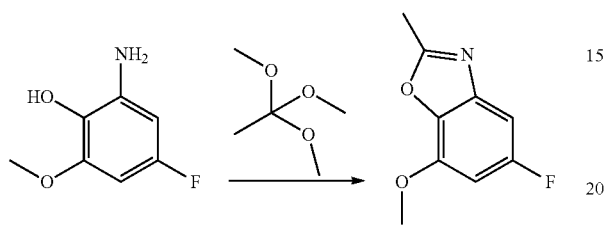

To a 20 mL vial was added 2-amino-4-fluoro-6-methoxyphenol (0.58 g, 3.7 mmol) and 1,1,1-trimethoxyethane (4.0 mL, 31 mmol). The mixture was stirred and heated to 70° C. After 10 min, the mixture was allowed to cool to rt, and the solvents were evaporated under reduced pressure to afford a crude residue that was purified by silica gel chromatography (EtOAc in Hex) to provide 5-fluoro-7-methoxy-2-methylbenzo[d]oxazole. LCMS ($C_9H_9FNO_2$) (ES, m/z): 182 [M+H]$^+$. $^1$H NMR (500 MHz, CDCl$_3$): δ 7.05-6.90 (m, 1H), 6.61 (d, J=11.1 Hz, 1H), 4.01 (s, 3H), 2.66 (s, 3H).

Step 4: 5-fluoro-7-methoxy-2-methylbenzo[d]oxazole-4-carbaldehyde

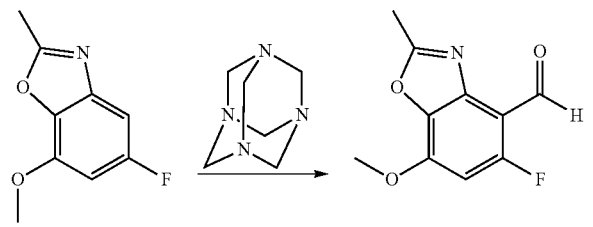

To a 20 mL vial was added 5-fluoro-7-methoxy-2-methylbenzo[d]oxazole (423 mg, 2.33 mmol), 1,3,5,7-tetraazaadamantane (556 mg, 3.97 mmol), and TFA (0.50 mL). The mixture was stirred and heated to 90° C. for 3 h. The reaction was allowed to cool to rt, diluted with EtOAc (40 mL) and partitioned with sat aq NaHCO$_3$ (100 mL). The organic layer was dried over anhydrous Na$_2$SO$_4$, filtered, and concentrated under reduced pressure to afford a crude residue that was purified by silica gel chromatography (EtOAc in Hex) to provide 5-fluoro-7-methoxy-2-methylbenzo[d]oxazole-4-carbaldehyde. LCMS ($C_{10}H_9FNO_3$) (ES, m/z): 210 [M+H]$^+$. $^1$H NMR (500 MHz, CDCl$_3$): δ 10.42 (s, 1H), 6.60 (d, J=12.7 Hz, 1H), 4.05 (s, 3H), 2.68 (s, 3H).

Step 5: 4-methoxy-2-methylthieno[2',3':5,6]benzo[1,2-d]oxazole-7-carboxylic acid

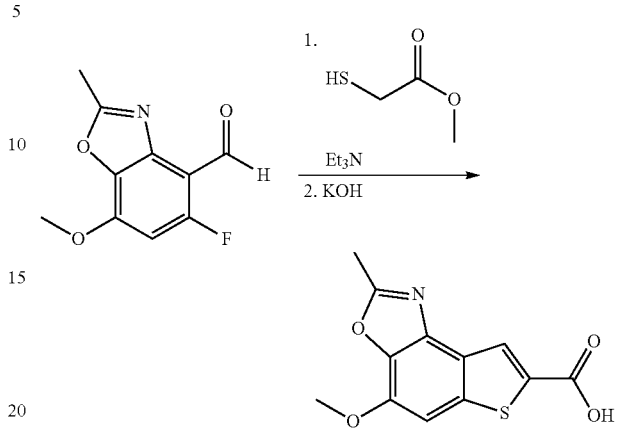

To a 4 mL vial was added 5-fluoro-7-methoxy-2-methylbenzo[d]oxazole-4-carbaldehyde (185 mg, 0.884 mmol) and DMSO (4.0 mL). The mixture was stirred. To the mixture was added Et$_3$N (1.2 mL, 8.8 mmol) and methyl 2-mercaptoacetate (0.79 mL, 8.8 mmol). The mixture was heated to 100° C. for 15 min. The mixture was allowed to cool to rt. Aq KOH (10M, 1.8 mL, 18 mmol) was added, and the mixture stirred for 10 min. The reaction was acidified to pH 3 with aq HCl (6M). The precipitate was collected by filtration, washed with H$_2$O (2×20 mL) and then MeOH (2×2 mL), yielding 4-methoxy-2-methylthieno[2',3':5,6]benzo[1,2-d]oxazole-7-carboxylic acid. LCMS ($C_{12}H_{10}NO_4S$) (ES, m/z): 264 [M+H]$^+$. $^1$H NMR (500 MHz, CDCl$_3$): δ 8.05 (s, 1H), 7.05 (s, 1H), 3.82 (s, 3H), 2.47 (s, 3H).

Step 6: 4-methoxy-2-methylthieno[2',3':5,6]benzo[1,2-d]oxazole-7-carbonyl chloride

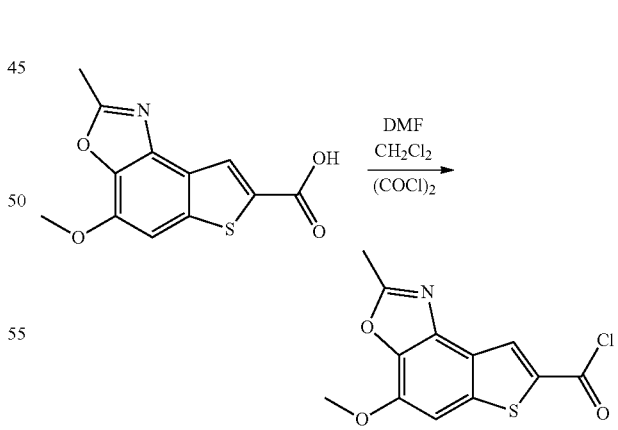

To a 20 ml vial was added 4-methoxy-2-methylthieno[2',3':5,6]benzo[1,2-d]oxazole-7-carboxylic acid (106 mg, 0.404 mmol), CH$_2$Cl$_2$ (1.0 mL), and DMF (6.34, 0.081 mmol). The mixture was stirred and cooled to 0° C. (COCl)$_2$ (0.074 mL, 0.85 mmol) was added. After 5 min, the reaction was warmed to rt and stirred for 35 min. The reaction was concentrated under reduced pressure to provide crude 4-methoxy-2-methylthieno[2',3':5,6] benzo[1,2-d]oxazole-7-carbonyl chloride was used in the next step without further purification.

Step 7: methyl (S)-4-(4-methoxy-2-methylthieno[2',3':5,6]benzo[1,2-d]oxazol-7-yl)-2-methyl-4-oxobutanoate

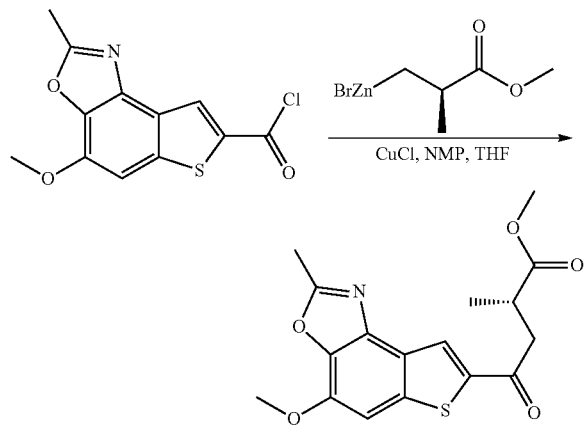

To a 20 mL vial was added Cu—Cl (14 mg, 0.15 mmol). The vial was evacuated then refilled with $N_2$ 3 times. To the vial was added THF (0.25 mL). The mixture was cooled to 0° C. To the stirring mixture was added (R)-(3-methoxy-2-methyl-3-oxopropyl)zinc (II) bromide (0.5M in THF, 1.5 mL, 0.73 mmol) drop wise over 2 min. The mixture was then stirred for 10 min. To the mixture was added 4-methoxy-2-methylthieno[2',3':5,6]benzo[1,2-d]oxazole-7-carbonyl chloride (41 mg, 0.15 mmol) as a solution in NMP (2.0 mL) drop wise over 2 min. The mixture was stirred for 20 min. The reaction was diluted with EtOAc (15 mL) and washed with aq $NH_4OH$ (3M, 30 mL, 90 mmol). The organic layer was dried over anhydrous $Na_2SO_4$, filtered, and concentrated under reduced pressure. The resulting residue was purified by silica gel chromatography (EtOAc in Hex) to provide methyl (S)-4-(4-methoxy-2-methylthieno[2',3':5,6] benzo [1,2-d]oxazol-7-yl)-2-methyl-4-oxobutanoate. LCMS ($C_{17}H_{18}NO_5S$) (ES, m/z): 348 [M+H]$^+$. $^1$H NMR (500 MHz, CDCl$_3$): δ 8.36 (s, 1H), 7.24 (s, 1H), 4.11 (s, 3H), 3.73 (s, 3H), 3.54 (dd, J=16.6, 7.5 Hz, 1H), 3.20-3.09 (m, 2H), 2.78 (s, 3H), 1.32 (d, J=7.0 Hz, 3H).

Step 8: (S)-4-(4-methoxy-2-methylthieno[2',3':5,6] benzo[1,2-d]oxazol-7-yl)-2-methyl-4-oxobutanoic acid

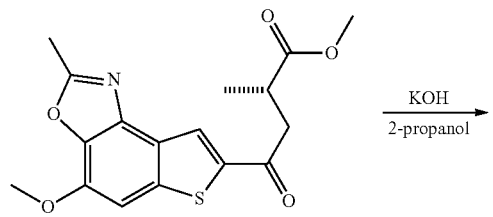

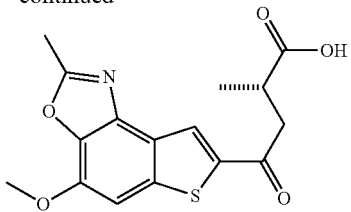

To a 4 mL vial was added (S)-methyl 4-(4-methoxy-2-methylthieno[2',3':5,6] benzo[1,2-d]oxazol-7-yl)-2-methyl-4-oxobutanoate (48 mg, 0.14 mmol), aq KOH (0.5M, 0.55 mL, 0.28 mmol), and 2-propanol (1.4 mL) at rt. After 30 min, the mixture was acidified to pH 3 with aq HCl. The precipitate was collected by filtration and washed with $H_2O$ (2×5 mL) and MeOH (2 mL). The precipitate was further purified by silica gel chromatography (MeOH in DCM) providing (S)-4-(4-methoxy-2-methylthieno[2',3':5,6]benzo [1,2-d]oxazol-7-yl)-2-methyl-4-oxobutanoic acid. LCMS ($C_{16}H_{16}NO_5S$) (ES, m/z): 334 [M+H]$^+$. $^1$H NMR (500 MHz, DMSO-d$_6$): δ 12.20 (s, 1H), 8.51 (s, 1H), 7.70 (s, 1H), 4.04 (s, 3H), 3.51 (dd, J=17.4, 8.6 Hz, 1H), 3.18 (dd, J=17.5, 4.9 Hz, 1H), 2.95-2.85 (m, 1H), 2.71 (s, 3H), 1.20 (d, J=7.2 Hz, 3H).

Biological Evaluation

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and (ii) demonstrating interferon production with a 6% or greater induction of IFN-β secretion at 30 uM in the THP1 cell assay (where induction caused by cGAMP at 30 uM was set at 100%).

[$^3$H]-cGAMP Synthesis 2.3 mL of buffer solution containing 80 mM TrisCl, 200 mM MgCl$_2$, and 20 mM NaCl followed by 0.32 mL of a 10 mM aq solution of GTP was added to a plastic 50 mL AMICON tube. A solution of [$^3$H]ATP (21 Ci/mmol, 45 mCi) in 0.5 mL $H_2O$ was then added followed by 1 mL of a 1 mg/mL solution of DNA (Herring testes activator DNA, Sigma, # D6898) and 53 uL of a 47 mM solution of cGAS enzyme. Additional $H_2O$ was added to bring the total volume to 10 mL.

The reaction was stirred for 2 h at 37° C. and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5 mCi of [$^3$H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in ROSETTA™ 2(DE3) Single Competent Cells (Novagen). Affinity purification was carried out using HIS-Select HF Nickel Affinity Gel (Sigma) followed by size exclusion chromatography using a Hi-Load 26/60 SUPERDEX200 prep grade column (GE Healthcare). Fractions were pooled, concentrated, flash-frozen in liquid nitrogen and stored at −80° C. until needed.

Example 55: $^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length HAQ STING and tritiated cGAMP ligand.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 1) was prepared by diluting concentrated membrane into assay buffer (1×PBS; Invitrogen # SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control was added to the appropriate wells using a BIOMEK FX. Compound and membrane then preincubated for 60 min at RT to allow compound binding to equilibrate. Following equilibration, 8 nM of [$^3$H] c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TOMTEC MACH III Cell Harvester equipped with 20 mM HEPES buffer (Fisher Scientific, # BP299500). The filter plates were then dried at 55° C. for 30 min using a pressurized oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
| --- | --- | --- |
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.0010 μM with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 10 μL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 2) at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900II SFM media containing 5 μg/mL gentamicin (Invitrogen #15710072). The infected cells were then incubated at 27° C. for 3 days while shaking at 110 rpm (ATR Biotech Multitron Infors HT # AJ118). On day 3, P1 cultures were counted using a ViCell XR (Beckman Coulter Life Sciences #383556) to confirm infection had occurred (cell size≥3 μm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma # D2650), and 5 μg/ml gentamicin was prepared and sterilized through 0.22 μM filter immediately prior to use. P1 cell pellets were resuspended to a density of 2e7 cells/ml and aliquoted into cryovials (1 mL per vial). Cryovials were placed in MR. FROSTY™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10$^5$ cells/mL to allow for one overnight doubling) in Sf-900II SFM media containing 5 μg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (HAQ) Expression

To generate STING membranes, P1/P2 BIICs were amplified overnight by adding thawed BIICs to Sf21 cells seeded at a density of 1.0×10$^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size≥3 μm larger than uninfected cells and viability approximately 80-90%). The volume of infected Sf21 cells from the overnight amplification used to infect the large-scale expression of Trichoplusia ni (T. ni; Expression Systems, cat #94-002F, www.expressionsystems.com) seeded at a density of $1.0 \times 10^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. T. ni cells were counted on a ViCell XR to confirm infection had occurred (cell size≥3 μm larger than uninfected cells and viability approximately 80-90%) prior to harvest.

Full-Length STING (HAQ) Membrane Generation

Buffer Stock Reagents:
1) 1M HEPES pH 7.5, Teknova, Cat # H1035
2) 5M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (HAQ) prepared above at 5 mL Lysis buffer per g of cell pellet. The pellet was resuspended and dounced twenty times using a Wheaton Dounce Homogenizer to disrupt the cell membrane. Homogenized lysate was then passed through the EMULSIFLEX-C5 microfluidizer at a pressure close to 5000 PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH7.5, 1 mM $MgCl_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

```
Full-Length HAQ STING
[STING(1-379)R71H,G230A,H232R,R293Q-GG-AviTag-GS-HRV3C-
HIS8]Amino Acid Sequence:
                                                (SEQ. ID. No. 1)
MPHSSLHPSIPCPRGHGAQKAALVLLSACLVTLWGLGEPPEHTLRYLVLHLASLQLGLL

LNGVCSLAEELHHIHSRYRGSYWRTVRACLGCPLRRGALLLLSIYFYYSLPNAVGPPFT

WMLALLGLSQALNILLGLKGLAPAEISAVCEKGNFNVAHGLAWSYYIGYLRLILPELQA

RIRTYNQHYNNLLRGAVSQRLYILLPLDCGVPDNLSMADPNIRFLDKLPQQTADRAGIK

DRVYSNSIYELLENGQRAGTCVLEYATPLQTLFAMSQYSQAGFSREDRLEQAKLFCQTL

EDILADAPESQNNCRLIAYQEPADDSSFSLSQEVLRHLRQEEKEEVTVGSLKTSAVPSTST

MSQEPELLISGMEKPLPLRTDFSGGGLNDIFEAQKIEWHEGSLEVLFQGPHHHHHHHH

Full-length HAQ
[STING(1-379)R71H,G230A,H232R,R293Q-GG-AviTag-GS-HRV3C-
HI58/pBAC1] Plasmid DNA Sequence:
                                                (SEQ. ID. No. 2)
GGAACGGCTCCGCCCACTATTAATGAAATTAAAAATTCCAATTTTAAAAAACGCAG

CAAGAGAAACATTTGTATGAAAGAATGCGTAGAAGGAAAGAAAAATGTCGTCGAC

ATGCTGAACAACAAGATTAATATGCCTCCGTGTATAAAAAAAATATTGAACGATTTG

AAAGAAAACAATGTACCGCGCGGCGGTATGTACAGGAAGAGGTTTATACTAAACTG

TTACATTGCAAACGTGGTTTCGTGTGCCAAGTGTGAAAACCGATGTTTAATCAAGGC

TCTGACGCATTTCTACAACCACGACTCCAAGTGTGTGGGTGAAGTCATGCATCTTTT

AATCAAATCCCAAGATGTGTATAAACCACCAAACTGCCAAAAAATGAAAACTGTCG

ACAAGCTCTGTCCGTTTGCTGGCAACTGCAAGGGTCTCAATCCTATTTGTAATTATTG

AATAATAAAACAATTATAAATGCTAAATTTGTTTTTTATTAACGATACAAACCAAAC

GCAACAAGAACATTTGTAGTATTATCTATAATTGAAAACGCGTAGTTATAATCGCTG

AGGTAATATTTAAAATCATTTTCAAATGATTCACAGTTAATTTGCGACAATATAATT

TTATTTTCACATAAACTAGACGCCTTGTCGTCTTCTTCTTCGTATTCCTTCTCTTTTTC

ATTTTTCTCTTCATAAAAATTAACATAGTTATTATCGTATCCATATATGTATCTATCG
```

-continued

```
TATAGAGTAAATTTTTTGTTGTCATAAATATATATGTCTTTTTTAATGGGGTGTATAG

TACCGCTGCGCATAGTTTTTCTGTAATTTACAACAGTGCTATTTTCTGGTAGTTCTTC

GGAGTGTGTTGCTTTAATTATTAAATTTATATAATCAATGAATTTGGGATCGTCGGTT

TTGTACAATATGTTGCCGGCATAGTACGCAGCTTCTTCTAGTTCAATTACACCATTTT

TTAGCAGCACCGGATTAACATAACTTTCCAAAATGTTGTACGAACCGTTAAACAAAA

ACAGTTCACCTCCCTTTTCTATACTATTGTCTGCGAGCAGTTGTTTGTTGTTAAAAAT

AACAGCCATTGTAATGAGACGCACAAACTAATATCACAAACTGGAAATGTCTATCA

ATATATAGTTGCTGATCAGATCTGATCATGGAGATAATTAAAATGATAACCATCTCG

CAAATAAATAAGTATTTTACTGTTTTCGTAACAGTTTTGTAATAAAAAAACCTATAA

ATATAGGATCCATGCCCCACTCCAGCCTGCATCCATCCCGTGTCCCAGGGGTC

ACGGGGCCCAGAAGGCAGCCTTGGTTCTGCTGAGTGCCTGCCTGGTGACCCTTTGGG

GGCTAGGAGAGCCACCAGAGCACACTCTCCGGTACCTGGTGCTCCACCTAGCCTCCC

TGCAGCTGGGACTGCTGTTAAACGGGGTCTGCAGCCTGGCTGAGGAGCTGCACCAC

ATCCACTCCAGGTACCGGGGCAGCTACTGGAGGACTGTGCGGGCCTGCCTGGGCTG

CCCCCTCCGCCGTGGGGCCCTGTTGCTGCTGTCCATCTATTTCTACTACTCCCTCCCA

AATGCGGTCGGCCCGCCCTTCACTTGGATGCTTGCCCTCCTGGGCCTCTCGCAGGCA

CTGAACATCCTCCTGGGCCTCAAGGGCCTGGCCCCAGCTGAGATCTCTGCAGTGTGT

GAAAAGGGAATTTCAACGTGGCCCATGGGCTGGCATGGTCATATTACATCGGATA

TCTGCGGCTGATCCTGCCAGAGCTCCAGGCCCGGATTCGAACTTACAATCAGCATTA

CAACAACCTGCTACGGGGTGCAGTGAGCCAGCGGCTGTATATTCTCCTCCCATTGGA

CTGTGGGGTGCCTGATAACCTGAGTATGGCTGACCCCAACATTCGCTTCCTGGATAA

ACTGCCCCAGCAGACCGCTGACCGTGCTGGCATCAAGGATCGGGTTTACAGCAACA

GCATCTATGAGCTTCTGGAGAACGGGCAGCGGGCGGGCACCTGTGTCCTGGAGTAC

GCCACCCCCTTGCAGACTTTGTTTGCCATGTCACAATACAGTCAAGCTGGCTTTAGC

CGGGAGGATAGGCTTGAGCAGGCCAAACTCTTCTGCCAGACACTTGAGGACATCCT

GGCAGATGCCCCTGAGTCTCAGAACAACTGCCGCCTCATTGCCTACCAGGAACCTGC

AGATGACAGCAGCTTCTCGCTGTCCCAGGAGGTTCTCCGGCACCTGCGGCAGGAGG

AAAAGGAAGAGGTTACTGTGGGCAGCTTGAAGACCTCAGCGGTGCCCAGTACCTCC

ACGATGTCCCAAGAGCCTGAGCTCCTCATCAGTGGAATGGAAAAGCCCCTCCCTCTC

CGCACGGATTTCTCTGGCGGTGGCCTGAACGACATCTTCGAAGCCCAGAAAATCGA

ATGGCATGAAGGCAGCCTGGAAGTGCTGTTCCAGGGCCCACACCACCATCATCACC

ATCACCATTAATGAGCGGCCGCACTCGAGCACCACCACCACCACCACTAACCTAGG

TAGCTGAGCGCATGCAAGCTGATCCGGGTTATTAGTACATTTATTAAGCGCTAGATT

CTGTGCGTTGTTGATTTACAGACAATTGTTGTACGTATTTTAATAATTCATTAAATTT

ATAATCTTTAGGGTGGTATGTTAGAGCGAAAATCAAATGATTTTCAGCGTCTTTATA

TCTGAATTTAAATATTAAATCCTCAATAGATTTGTAAAATAGGTTTCGATTAGTTTCA

AACAAGGGTTGTTTTTCCGAACCGATGGCTGGACTATCTAATGGATTTTCGCTCAAC

GCCACAAAACTTGCCAAATCTTGTAGCAGCAATCTAGCTTTGTCGATATTCGTTTGT

GTTTTGTTTTGTAATAAAGGTTCGACGTCGTTCAAAATATTATGCGCTTTTGTATTTC

TTTCATCACTGTCGTTAGTGTACAATTGACTCGACGTAAACACGTTAAATAGAGCTT

GGACATATTTAACATCGGGCGTGTTAGCTTTATTAGGCCGATTATCGTCGTCGTCCC
```

```
AACCCTCGTCGTTAGAAGTTGCTTCCGAAGACGATTTTGCCATAGCCACACGACGCC

TATTAATTGTGTCGGCTAACACGTCCGCGATCAAATTTGTAGTTGAGCTTTTTGGAAT

TATTTCTGATTGCGGGCGTTTTTGGGCGGGTTTCAATCTAACTGTGCCCGATTTTAAT

TCAGACAACACGTTAGAAAGCGATGGTGCAGGCGGTGGTAACATTTCAGACGGCAA

ATCTACTAATGGCGGCGGTGGTGGAGCTGATGATAAATCTACCATCGGTGGAGGCG

CAGGCGGGGCTGGCGGCGGAGGCGGAGGCGGAGGTGGTGGCGGTGATGCAGACGG

CGGTTTAGGCTCAAATGTCTCTTTAGGCAACACAGTCGGCACCTCAACTATTGTACT

GGTTTCGGGCGCCGTTTTTGGTTTGACCGGTCTGAGACGAGTGCGATTTTTTTCGTTT

CTAATAGCTTCCAACAATTGTTGTCTGTCGTCTAAAGGTGCAGCGGGTTGAGGTTCC

GTCGGCATTGGTGGAGCGGGCGGCAATTCAGACATCGATGGTGGTGGTGGTGGTGG

AGGCGCTGGAATGTTAGGCACGGGAGAAGGTGGTGGCGGCGGTGCCGCCGGTATAA

TTTGTTCTGGTTTAGTTTGTTCGCGCACGATTGTGGGCACCGGCGCAGGCGCCGCTG

GCTGCACAACGGAAGGTCGTCTGCTTCGAGGCAGCGCTTGGGGTGGTGGCAATTCA

ATATTATAATTGGAATACAAATCGTAAAAATCTGCTATAAGCATTGTAATTTCGCTA

TCGTTTACCGTGCCGATATTTAACAACCGCTCAATGTAAGCAATTGTATTGTAAAGA

GATTGTCTCAAGCTCGGATCGATCCCGCACGCCGATAACAAGCCTTTTCATTTTTACT

ACAGCATTGTAGTGGCGAGACACTTCGCTGTCGTCGAGGTTTAAACGCTTCCTCGCT

CACTGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCG

TGCGCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACT

GGCAGCAGCCACTGGTAACAGGATTAGCAGAGCGAGGTATGTAGGCGGTGCTACAG

AGTTCTTGAAGTGGTGGCCTAACTACGGCTACACTAGAAGGACAGTATTTGGTATCT

GCGCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCGCA

GAAAAAAGGATCTCAAGAAGATCCTTTGATCTTTTCTACGGGGTCTGACGCTCAGT

GGAACGAAAACTCACGTTAAGGGATTTTGGTCATGAGATTATCAAAAGGATCTTC

ACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATC

TGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGCAT

CGTGGTGTCACGCTCGTCGTTTGGTATGGCTTCATTCAGCTCCGGTTCCCAACGATCA
```

-continued

```
AGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGT

TTCTGGGTGAGCAAAAACAGGAAGGCAAATGCCGCAAAAAAGGGAATAAGGGCG

ACACGGAAATGTTGAATACTCATACTCTTCCTTTTTCAATATTATTGAAGCATTTATC

AGGGTTATTGTCTCATGAGCGGATACATATTTGAATGTATTTAGAAAAATAAACAAA

TAGGGGTTCCGCGCACATTTCCCCGAAAAGTGCCACCTGACGCGCCCTGTAGCGGCG

CATTAAGCGCGGCGGGTGTGGTGGTTACGCGCAGCGTGACCGCTACACTTGCCAGC

GCCCTAGCGCCCGCTCCTTTCGCTTTCTTCCCTTCCTTTCTCGCCACGTTCGCCGGCTT

TCCCCGTCAAGCTCTAAATCGGGGGCTCCCTTTAGGGTTCCGATTTAGTGCTTTACG

GCACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGACTC

TTGTTCCAAACTGGAACAACACTCAACCCTATCTCGGTCTATTCTTTTGATTTATAAG

GGATTTTGCCGATTTCGGCCTATTGGTTAAAAAATGAGCTGATTTAACAAAAATTTA

ACGCGAATTTTAACAAAATATTAACGTTTACAATTTCCCATTCGCCATTCAGGCTGC

GCAACTGTTGGGAAGGGCGATCGGTGCGGGCCTCTTCGCTATTACGCCA
```

Certain compounds of the disclosure were evaluated in HAQ STING in vitro binding assay as described above. The following table tabulates the biological data for these compounds as $EC_{50}$ values.

TABLE 6

$^3$H-cGAMP filtration binding assay for HAQ STING

| Compound | $EC_{50}$ (nM) |
|---|---|
| Example 1 | 3405 |
| Example 2 | 9587 |
| Example 3 | 10640 |
| Example 4 | 1903 |
| Example 5 | 1143 |
| Example 6 | 703 |
| Example 7 | 9335 |
| Example 8 | 6773 |
| Example 9 | 2575 |
| Example 10 | 13980 |
| Example 11 | 2735 |
| Example 12 | 5990 |
| Example 13 | 1375 |
| Example 14 | 4073 |
| Example 15 | 894 |
| Example 16 | 1720 |
| Example 17 | 5865 |
| Example 18 | 12500 |
| Example 19 | 9705 |
| Example 20 | 10720 |
| Example 21 | 6341 |
| Example 22 | 8808 |
| Example 23 | 6054 |
| Example 24 | 2636 |
| Example 25 | 4073 |
| Example 26 | 1375 |
| Example 27 | 13170 |

TABLE 6-continued $^3$H-cGAMP filtration binding assay for HAQ STING

| Compound | $EC_{50}$ (nM) |
|---|---|
| Example 28 | 1952 |
| Example 29 | 13760 |
| Example 30 | 5050 |
| Example 31 | 5943 |
| Example 32 | 3627 |
| Example 33 | 6461 |
| Example 34 | 10420 |
| Example 35 | 5547 |
| Example 36 | 14430 |
| Example 37 | 5612 |
| Example 38 | 1926 |
| Example 39 | 1146 |
| Example 40 | 3938 |
| Example 41 | 5700 |
| Example 42 | 759 |
| Example 43 | 1197 |
| Example 44 | 15740 |
| Example 45 | 14670 |
| Example 46 | 7454 |
| Example 47 | 5056 |
| Example 48 | 19250 |
| Example 49 | 2718 |
| Example 50 | 890 |
| Example 51 | 17840 |
| Example 52 | 599 |
| Example 53 | 13670 |
| Example 54 | 531 |

Example 56: ³H-cGAMP Filtration Binding Assay (WT STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length WT STING and tritiated cGAMP ligand.

The basic WT STING filtration assay protocol is as follows:

16 nM of [³H] c-GAMP ligand was prepared by diluting into assay buffer, and 50 uL of this working stock was manually added to each well of the assay plate. After ligand addition, 2 uL of either titrated test compound, DMSO control (Sigma #276855), or cold cGAMP control was added to the appropriate wells using a BIOMEK FX. The serially titrated compound was prepared on a Hamilton STARPlus CORE in a 96-well plate (Greiner, #651201) using a 1:3 ten-point dose response format. Following compound addition, a 2.2 ug/ml working concentration of STING membrane (SEQ. ID. No. 3) was prepared by diluting concentrated membrane into assay buffer (1×PBS; Invitrogen # SH30028.02) and douncing 7× using a manual tissue homogenizer (Wheaton, #357546). 148 uL of this prepared membrane was then manually added to each well of a 96-well deep-well polypropylene plate (Fisher Scientific, #12-566-121). Compound, ligand, and membrane then incubated for 60 min at RT before the contents of each assay plate were filtered through a 96-well GF/B filter plate (PerkinElmer, #6005250) using a TOMTEC MACH III Cell Harvester equipped with 20 mM HEPES buffer (Fisher Scientific, # BP299500). The filter plates were then dried at 55° C. for 30 min using a pressurized VWR oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
|---|---|---|
| STING membrane | 148 | 1.5 ug/ml |
| ³H-cGAMP | 50 | 4.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 µM with 1.0% residual DMSO.

Full-Length STING (WT) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of WT STING[STING(1-379)H232R-gg-AviTag-gs-HRV3C-HIS8/pBAC1] (Genewiz custom synthesis) with 1 mL Sf-900II SFM media containing 10 µL CELLFECTIN® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA [(SEQ. ID. No. 4) and linearized viral backbone BestBac 2.0] at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10⁵ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT # AJ118). On day 3, P1 cultures were counted using a ViCell XR (Beckman Coulter Life Sciences #383556) to confirm infection had occurred (cell size≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma # D2650), and 5 µg/ml gentamicin was prepared and sterilized through 0.2204 filter immediately prior to use. P1 cell pellets were resuspended to a density of 2e7 cells/ml and aliquoted into cryovials (1 mL per vial). Cryovials were placed in MR. FROSTY™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10⁵ cells/mL to allow for one overnight doubling) in Sf-900II SFM media containing 5 µg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (WT) Expression

To generate STING membranes, P1/P2 BIICs were amplified overnight by adding thawed BIICs to Sf21 cells seeded at a density of 1.0×10⁶ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size≥3 µm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of 1.0×10⁶ in cell media (ESF921 SFM containing 5 µg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size≥3 µm larger than uninfected cells and viability approximately 80-90%) prior to harvest.

Full-Length STING (WT) Membrane Generation

Buffer Stock Reagents:

1) 1 M HEPES pH 7.5, Teknova, Cat # H1035
2) 5 M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM MgCl$_2$, 20 mM KCl, (Benzonase 1:5000, Complete Protease Inhibitor tab/50 mL)] was added to the pellet of cells expressing full-length STING (WT) prepared above at 5 mL Lysis buffer per g of cell pellet. The pellet was resuspended and dounced twenty times using a Wheaton Dounce Homogenizer to disrupt the cell membrane. Homogenized lysate was then passed through the emulsiflex-C5 microfluidizer at a pressure close to 5000 PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH 7.5, 1 mM MgCl$_2$, 20 mM KCl, 1M NaCl (Complete Protease Inhibitor tab/50 mL)] at a volume of 50 mL/pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (ltablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

```
Full-Length STING WT [STING(1-379)H232R-gg-AviTag-gs-HRV3C-HIS8]
Amino Acid Sequence:
                                                   (SEQ. ID. No. 3)
MPHSSLHPSIPCPRGHGAQKAALVLLSACLVTLWGLGEPPEHTLRYLVLHLASLQLGLL

LNGVCSLAEELRHIHSRYRGSYWRTVRACLGCPLRRGALLLLSIYFYYSLPNAVGPPFT

WMLALLGLSQALNILLGLKGLAPAEISAVCEKGNFNVAHGLAWSYYIGYLRLILPELQA

RIRTYNQHYNNLLRGAVSQRLYILLPLDCGVPDNLSMADPNIRFLDKLPQQTADRAGIK

DRVYSNSIYELLENGQRAGTCVLEYATPLQTLFAMSQYSQAGFSREDRLEQAKLFCRTL

EDILADAPESQNNCRLIAYQEPADDSSFSLSQEVLRHLRQEEKEEVTVGSLKTSAVPSTST

MSQEPELLISGMEKPLPLRTDFSGGGLNDIFEAQKIEWHEGSLEVLFQGPHHHHHHHH

Full-length WT STING [STING(1-379)H232R-gg-AviTag-gs-HRV3C-HIS8/pBAC1]
plasmid sequence:
                                                   (SEQ. ID. No. 4)
GGAACGGCTCCGCCCACTATTAATGAAATTAAAAATTCCAATTTTAAAAAACGCAG

CAAGAGAAACATTTGTATGAAAGAATGCGTAGAAGGAAAGAAAAATGTCGTCGAC

ATGCTGAACAACAAGATTAATATGCCTCCGTGTATAAAAAAAATATTGAACGATTTG

AAAGAAAACAATGTACCGCGCGGCGGTATGTACAGGAAGAGGTTTATACTAAACTG

TTACATTGCAAACGTGGTTTCGTGTGCCAAGTGTGAAAACCGATGTTTAATCAAGGC

TCTGACGCATTTCTACAACCACGACTCCAAGTGTGTGGGTGAAGTCATGCATCTTTT

AATCAAATCCCAAGATGTGTATAAACCACCAAACTGCCAAAAAATGAAAACTGTCG

ACAAGCTCTGTCCGTTTGCTGGCAACTGCAAGGGTCTCAATCCTATTTGTAATTATTG

AATAATAAAACAATTATAAATGTCAAATTTGTTTTTTATTAACGATACAAACCAAAC

GCAACAAGAACATTTGTAGTATTATCTATAATTGAAAACGCGTAGTTATAATCGCTG

AGGTAATATTTAAAATCATTTTCAAATGATTCACAGTTAATTTGCGACAATATAATT

TTATTTTCACATAAACTAGACGCCTTGTCGTCTTCTTCTTCGTATTCCTTCTCTTTTTC

ATTTTTCTCTTCATAAAAATTAACATAGTTATTATCGTATCCATATATGTATCTATCG

TATAGAGTAAATTTTTTGTTGTCATAAATATATATGTCTTTTTTAATGGGGTGTATAG

TACCGCTGCGCATAGTTTTTCTGTAATTTACAACAGTGCTATTTTCTGGTAGTTCTTC

GGAGTGTGTTGCTTTAATTATTAAATTTATATAATCAATGAATTTGGGATCGTCGGTT

TTGTACAATATGTTGCCGGCATAGTACGCAGCTTCTTCTAGTTCAATTACACCATTTT

TTAGCAGCACCGGATTAACATAACTTTCCAAAATGTTGTACGAACCGTTAAACAAAA
```

```
ACAGTTCACCTCCCTTTTCTATACTATTGTCTGCGAGCAGTTGTTTGTTGTTAAAAAT
AACAGCCATTGTAATGAGACGCACAAACTAATATCACAAACTGGAAATGTCTATCA
ATATATAGTTGCTGATCAGATCTGATCATGGAGATAATTAAAATGATAACCATCTCG
CAAATAAATAAGTATTTTACTGTTTTCGTAACAGTTTTGTAATAAAAAAACCTATAA
ATATAGGATCCATGCCCCACTCCAGCCTGCATCCATCCATCCCGTGTCCCAGGGGTC
ACGGGGCCCAGAAGGCAGCCTTGGTTCTGCTGAGTGCCTGCCTGGTGACCCTTTGGG
GGCTAGGAGAGCCACCAGAGCACACTCTCCGGTACCTGGTGCTCCACCTAGCCTCCC
TGCAGCTGGGACTGCTGTTAAACGGGGTCTGCAGCCTGGCTGAGGAGCTGCGCCAC
ATCCACTCCAGGTACCGGGGCAGCTACTGGAGGACTGTGCGGGCCTGCCTGGGCTG
CCCCCTCCGCCGTGGGGCCCTGTTGCTGCTGTCCATCTATTTCTACTACTCCCTCCCA
AATGCGGTCGGCCCGCCCTTCACTTGGATGCTTGCCCTCCTGGGCCTCTCGCAGGCA
CTGAACATCCTCCTGGGCCTCAAGGGCCTGGCCCCAGCTGAGATCTCTGCAGTGTGT
GAAAAAGGGAATTTCAACGTGGCCCATGGGCTGGCATGGTCATATTACATCGGATA
TCTGCGGCTGATCCTGCCAGAGCTCCAGGCCCGGATTCGAACTTACAATCAGCATTA
CAACAACCTGCTACGGGGTGCAGTGAGCCAGCGGCTGTATATTCTCCTCCCATTGGA
CTGTGGGGTGCCTGATAACCTGAGTATGGCTGACCCCAACATTCGCTTCCTGGATAA
ACTGCCCCAGCAGACCGGTGACCGTGCTGGCATCAAGGATCGGGTTTACAGCAACA
GCATCTATGAGCTTCTGGAGAACGGGCAGCGGGCGGGCACCTGTGTCCTGGAGTAC
GCCACCCCCTTGCAGACTTTGTTTGCCATGTCACAATACAGTCAAGCTGGCTTTAGC
CGGGAGGATAGGCTTGAGCAGGCCAAACTCTTCTGCCGGACACTTGAGGACATCCT
GGCAGATGCCCCTGAGTCTCAGAACAACTGCCGCCTCATTGCCTACCAGGAACCTGC
AGATGACAGCAGCTTCTCGCTGTCCCAGGAGGTTCTCCGGCACCTGCGGCAGGAGG
AAAAGGAAGAGGTTACTGTGGGCAGCTTGAAGACCTCAGCGGTGCCCAGTACCTCC
ACGATGTCCCAAGAGCCTGAGCTCCTCATCAGTGGAATGGAAAAGCCCCTCCCTCTC
CGCACGGATTTCTCTGGCGGTGGCCTGAACGACATCTTCGAAGCCCAGAAAATCGA
ATGGCATGAAGGCAGCCTGGAAGTGCTGTTCCAGGGCCCACACCACCATCATCACC
ATCACCATTAATGAGCGGCCGCACTCGAGCACCACCACCACCACCACTAACCTAGG
TAGCTGAGCGCATGCAAGCTGATCCGGGTTATTAGTACATTTATTAAGCGCTAGATT
CTGTGCGTTGTTGATTTACAGACAATTGTTGTACGTATTTTAATAATTCATTAAATTT
ATAATCTTTAGGGTGGTATGTTAGAGCGAAAATCAAATGATTTTCAGCGTCTTTATA
TCTGAATTTAAATATTAAATCCTCAATAGATTTGTAAAATAGGTTTCGATTAGTTTCA
AACAAGGGTTGTTTTTCCGAACCGATGGCTGGACTATCTAATGGATTTTCGCTCAAC
GCCACAAAACTTGCCAAATCTTGTAGCAGCAATCTAGCTTTGTCGATATTCGTTTGT
GTTTTGTTTTGTAATAAAGGTTCGACGTCGTTCAAAATATTATGCGCTTTTGTATTTC
TTTCATCACTGTCGTTAGTGTACAATTGACTCGACGTAAACACGTTAAATAGAGCTT
GGACATATTTAACATCGGGCGTGTTAGCTTTATTAGGCCGATTATCGTCGTCGTCCC
AACCCTCGTCGTTAGAAGTTGCTTCCGAAGACGATTTTGCCATAGCCACACGACGCC
TATTAATTGTGTCGGCTAACACGTCCGCGATCAAATTTGTAGTTGAGCTTTTTGGAAT
TATTTCTGATTGCGGGCGTTTTTGGGCGGGTTTCAATCTAACTGTGCCCGATTTTAAT
TCAGACAACACGTTAGAAAGCGATGGTGCAGGCGGTGGTAACATTTCAGACGGCAA
```

-continued

```
ATCTACTAATGGCGGCGGTGGTGGAGCTGATGATAAATCTACCATCGGTGGAGGCG

CAGGCGGGGCTGGCGGCGGAGGCGGAGGCGGAGGTGGTGGCGGTGATGCAGACGG

CGGTTTAGGCTCAAATGTCTCTTTAGGCAACACAGTCGGCACCTCAACTATTGTACT

GGTTTCGGGCGCCGTTTTTGGTTTGACCGGTCTGAGACGAGTGCGATTTTTTTCGTTT

CTAATAGCTTCCAACAATTGTTGTCTGTCGTCTAAAGGTGCAGCGGGTTGAGGTTCC

GTCGGCATTGGTGGAGCGGGCGGCAATTCAGACATCGATGGTGGTGGTGGTGGTGG

AGGCGCTGGAATGTTAGGCACGGGAGAAGGTGGTGGCGGCGGTGCCGCCGGTATAA

TTTGTTCTGGTTTAGTTTGTTCGCGCACGATTGTGGGCACCGGCGCAGGCGCCGCTG

GCTGCACAACGGAAGGTCGTCTGCTTCGAGGCAGCGCTTGGGGTGGTGGCAATTCA

ATATTATAATTGGAATACAAATCGTAAAAATCTGCTATAAGCATTGTAATTTCGCTA

TCGTTTACCGTGCCGATATTTAACAACCGCTCAATGTAAGCAATTGTATTGTAAAGA

GATTGTCTCAAGCTCGGATCGATCCCGCACGCCGATAACAAGCCTTTTCATTTTTACT

ACAGCATTGTAGTGGCGAGACACTTCGCTGTCGTCGAGGTTTAAACGCTTCCTCGCT

CACTGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCG

TGCGCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACT

GGCAGCAGCCACTGGTAACAGGATTAGCAGAGCGAGGTATGTAGGCGGTGCTACAG

AGTTCTTGAAGTGGTGGCCTAACTACGGCTACACTAGAAGGACAGTATTTGGTATCT

GCGCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCGCA

GAAAAAAAGGATCTCAAGAAGATCCTTTGATCTTTTCTACGGGGTCTGACGCTCAGT

GGAACGAAAACTCACGTTAAGGGATTTTGGTCATGAGATTATCAAAAGGATCTTC

ACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATC

TGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGCAT

CGTGGTGTCACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCATTG
```

```
GAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGT

TTCTGGGTGAGCAAAAACAGGAAGGCAAAATGCCGCAAAAAAGGGAATAAGGGCG

ACACGGAAATGTTGAATACTCATACTCTTCCTTTTTCAATATTATTGAAGCATTTATC

AGGGTTATTGTCTCATGAGCGGATACATATTTGAATGTATTTAGAAAAATAAACAAA

TAGGGGTTCCGCGCACATTTCCCCGAAAAGTGCCACCTGACGCGCCCTGTAGCGGCG

CATTAAGCGCGGCGGGTGTGGTGGTTACGCGCAGCGTGACCGCTACACTTGCCAGC

GCCCTAGCGCCCGCTCCTTTCGCTTTCTTCCCTTCCTTTCTCGCCACGTTCGCCGGCTT

TCCCCGTCAAGCTCTAAATCGGGGCTCCCTTTAGGGTTCCGATTTAGTGCTTTACG

GCACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGACTC

TTGTTCCAAACTGGAACAACACTCAACCCTATCTCGGTCTATTCTTTTGATTTATAAG

GGATTTTGCCGATTTCGGCCTATTGGTTAAAAAATGAGCTGATTTAACAAAAATTTA

ACGCGAATTTTAACAAAATATTAACGTTTACAATTTCCCATTCGCCATTCAGGCTGC

GCAACTGTTGGGAAGGGCGATCGGTGCGGGCCTCTTCGCTATTACGCCA
```

Certain compounds of the disclosure were evaluated in WT STING in vitro binding assay as described above. The following table tabulates the biological data for these compounds as $EC_{50}$ values.

TABLE 7

$^3$H-cGAMP filtration binding assay for WT STING

| Compound | $EC_{50}$ (nM) |
| --- | --- |
| Example 1 | 5172 |
| Example 2 | 11210 |
| Example 3 | 41% Inh @ 20 uM |
| Example 4 | 1145 |
| Example 7 | 20% Inh @ 20 uM |
| Example 8 | 15520 |
| Example 9 | 10890 |
| Example 10 | 31% Inh @ 20 uM |
| Example 11 | 3873 |
| Example 13 | 2081 |
| Example 14 | 8644 |
| Example 15 | 894 |
| Example 16 | 2480 |
| Example 17 | 14750 |
| Example 18 | 21% Inh @ 20 uM |
| Example 19 | 30% Inh @ 20 uM |
| Example 20 | 33% Inh @ 20 uM |
| Example 21 | 14290 |
| Example 22 | 17100 |
| Example 23 | 37% Inh @ 20 uM |
| Example 24 | 8540 |
| Example 25 | 8644 |
| Example 26 | 2081 |
| Example 27 | 19% Inh @ 20 μM |
| Example 28 | 9259 |
| Example 29 | 16% Inh @ 20 μM |
| Example 30 | 18670 |

TABLE 7-continued $^3$H-cGAMP filtration binding assay for WT STING

| Compound | $EC_{50}$ (nM) |
| --- | --- |
| Example 31 | 10% Inh @ 20 μM |
| Example 32 | 17030 |
| Example 33 | 30% Inh @ 20 μM |
| Example 34 | 18% Inh @ 20 μM |
| Example 35 | 7671 |
| Example 36 | 9% Inh @ 20 μM |
| Example 41 | 14690 |
| Example 43 | 4108 |
| Example 46 | 24% Inh @ 20 μM |
| Example 48 | 23% Inh @ 20 μM |
| Example 50 | 2144 |
| Example 51 | 3% Inh @ 20 μM |
| Example 52 | 101% Inh @ 20 μM |
| Example 53 | 7% Inh @ 20 μM |

Example 57: IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; 1× non-essential amino acids; Life Technologies, Cat. No. 11140-050). The cell viability and count was ascertained using a Beckman Coulter V-Cell XR cell counter. The cells suspension was centrifuged at 200×g for 5 min at RT. Cells were resuspended to a density of $0.8 \times 10^6$/mL in 37° C. assay medium. Subsequent liquid transfers were performed using either a Matrix electronic multichannel pipette or an Agilent Bravo Automated Liquid Handling Platform.

The assay was started by dispensing 40 µL of the previously prepared cell suspension into the wells of the plate containing compounds. After 5 h incubation at 37° C., 5% $CO_2$ in a humidified atmosphere, the plate of cells and compounds was centrifuged at 200×g for 5 min at RT. From each well, 5 µL of supernatant was transferred into corresponding wells of a white 384-well plate (Perkin Elmer, Cat. No. 6005620). To these supernatant-containing wells was added 10 µL of 5× Anti-Analyte Acceptor beads (50 µg/mL of AlphaLISA HiBlock Buffer) and incubated for 30 min at RT while shaking on an orbital plate shaker. To each well was added 10 µL of 5× Biotinylated Antibody Anti-analyte (5 nM in AlphaLISA HiBlock Buffer) and incubated on an orbital plate shaker for 60 min at RT or overnight at 4° C. To each well was added 25 µL of 2× SA-Donor beads (80 µg/mL in AlphaLISA HiBlock Buffer) and incubated for 30-45 min at RT in the dark while shaking on an orbital plate shaker. The plate was then read on a Perkin Elmer Envision ($\lambda_{ex}$=680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate $EC_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 µM concentration.

TABLE 8

IFN-β secretion in THP1 cell culture (5 h)

| Compound | % Effect at 30 µM relative to 2'3'-cGAMP |
|---|---|
| Example 1 | 144 |
| Example 2 | 149 |
| Example 3 | 59 |
| Example 4 | 34 |
| Example 5 | 77 |
| Example 6 | 130 |
| Example 7 | 290 |
| Example 8 | 260 |
| Example 9 | 298 |
| Example 10 | 182 |
| Example 11 | 132 |
| Example 12 | 16 |
| Example 13 | 228 |
| Example 14 | 394 |
| Example 15 | 115 |
| Example 16 | 129 |
| Example 17 | 21 |
| Example 18 | 273 |
| Example 19 | 153 |
| Example 20 | 47 |
| Example 21 | 162 |
| Example 22 | 43 |
| Example 23 | 191 |
| Example 24 | 214 |
| Example 25 | 394 |
| Example 26 | 228 |
| Example 27 | 14 |
| Example 28 | 86 |
| Example 29 | 9 |
| Example 30 | 15 |
| Example 31 | 24 |
| Example 32 | 24 |
| Example 33 | 25 |
| Example 34 | 34 |
| Example 35 | 57 |
| Example 36 | 11 |
| Example 37 | 42 |
| Example 38 | 154 |
| Example 39 | 193 |
| Example 40 | 93 |
| Example 41 | 312 |
| Example 42 | 6 |
| Example 43 | 56 |
| Example 44 | 20 |
| Example 45 | 104 |
| Example 46 | 205 |
| Example 47 | 90 |
| Example 48 | 71 |
| Example 49 | 111 |
| Example 50 | 115 |
| Example 51 | 31 |
| Example 52 | 142 |
| Example 53 | 182 |
| Example 54 | 66 |

It will be appreciated that various of the above-discussed and other features and functions, or alternatives thereof, may be desirably combined into many other different systems or applications. It also will be appreciated that various presently unforeseen or unanticipated alternatives, modifications, variations or improvements therein may be subsequently made by those skilled in the art and are also intended to be encompassed by the following claims.

What is claimed is:

1. A method of inducing an immune response in a subject, said method comprising administering a therapeutically effective amount of a compound according to formula (I') to the subject, wherein the compound of formula (I') is

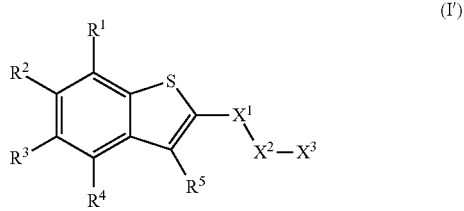

or a pharmaceutically acceptable salt thereof, wherein $R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

$R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

optionally $R^3$ and $R^4$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl;

$R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), $O(C_1$-$C_3$ haloalkyl);

$X^1$ is $C(O)$;

$X^2$ is $(C(R^8)_2)_{(1-3)}$;

each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

optionally 2 $R^8$ on different carbon atoms may be taken together, along with the atoms to which they are attached, to form a 3- to 6-membered fused ring;

optionally 2 $R^8$ on a single carbon atom may be taken together, along with the atoms to which they are attached, to form a 3- to 6-membered spirocycle;

$X^3$ is selected from the group consisting of $COOR^6$,

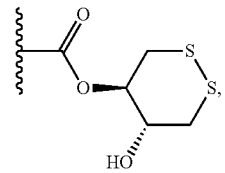

$C(O)SR^6$, $C(S)OR^6$, $SO_2R^6$, and $C(O)N(R^9)_2$; and each $R^9$ is independently selected from the group consisting of H, $COOR^6$, and $SO_2R^6$.

2. A method of inducing an immune response in a subject, said method comprising:

(a) administering a therapeutically effective amount of a pharmaceutical composition to the subject, said pharmaceutical composition comprising a compound according to formula (I') to the subject, wherein the compound of formula (I') is

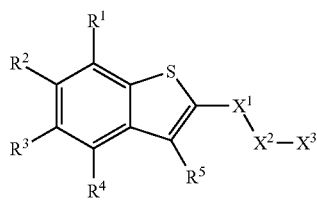
(I')

or a pharmaceutically acceptable salt thereof, wherein
$R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

$R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

optionally $R^3$ and $R^4$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl;

$R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, $O(C_1$-$C_3$ alkyl), $O(C_1$-$C_3$ haloalkyl);

$X^1$ is C(O);

$X^2$ is $(C(R^8)_2)_{(1-3)}$;

each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

optionally 2 $R^8$ on different carbon atoms may be taken together, along with the atoms to which they are attached, to form a 3- to 6-membered fused ring;

optionally 2 $R^8$ on a single carbon atom may be taken together, along with the atoms to which they are attached, to form a 3- to 6-membered spirocycle;

$X^3$ is selected from the group consisting of $COOR^6$,

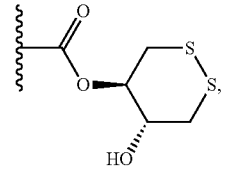 [SMILES: *C(=O)O[C@H]1CSSC[C@@H]1O]

$C(O)SR^6$, $C(S)OR^6$, $SO_2R^6$, and $C(O)N(R^9)_2$; and each $R^9$ is independently selected from the group consisting of H, $COOR^6$, and $SO_2R^6$.

3. A method of inducing STING-dependent type I interferon production in a subject, said method comprising administering a therapeutically effective amount of a compound according to formula (I') to the subject, wherein the compound of formula (I') is

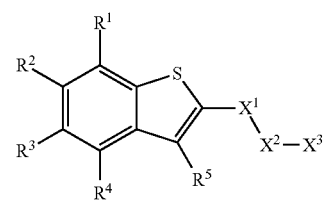
(I')

or a pharmaceutically acceptable salt thereof, wherein
$R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

$R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

optionally $R^3$ and $R^4$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl;

$R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

each $R^6$ is independently selected from the group consisting of H, $C_1$-$C_6$ alkyl, and $C_1$-$C_6$ haloalkyl, wherein said $C_1$-$C_6$ alkyl and $C_1$-$C_6$ haloalkyl are optionally substituted with OH, $O(C_1$-$C_3$ alkyl), $O(C_1$-$C_3$ haloalkyl);

$X^1$ is C(O);
$X^2$ is $(C(R^8)_2)_{(1-3)}$;
each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

optionally 2 $R^8$ on different carbon atoms may be taken together, along with the atoms to which they are attached, to form a 3- to 6-membered fused ring;

optionally 2 $R^8$ on a single carbon atom may be taken together, along with the atoms to which they are attached, to form a 3- to 6-membered spirocycle;

$X^3$ is selected from the group consisting of $COOR^6$,

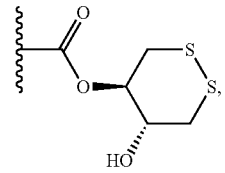 [SMILES: *C(=O)O[C@H]1CSSC[C@@H]1O]

$C(O)SR^6$, $C(S)OR^6$, $SO_2R^6$, and $C(O)N(R^9)_2$; and
each $R^9$ is independently selected from the group consisting of H, $COOR^6$, and $SO_2R^6$.

4. A method of inducing STING-dependent type I interferon production in a subject, said method comprising administering a therapeutically effective amount of a pharmaceutical composition to the subject, said pharmaceutical composition comprising a compound according to formula (I') to the subject, wherein the compound of formula (I') is

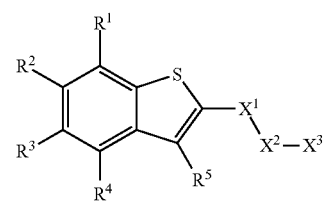

(I')

or a pharmaceutically acceptable salt thereof, wherein
$R^1$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

$R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and N($R^6$), wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and N($R^6$), wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^4$ is selected from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

optionally $R^3$ and $R^4$ may be taken together with the atoms to which they are attached form a 5- or 6-membered heterocyclic ring including 1 to 2 ring members selected from the group consisting of O, S, N, and N($R^6$) wherein said heterocyclic ring is optionally substituted with or more members of the group consisting of $C_1$-$C_3$ alkyl and $C_1$-$C_3$ haloalkyl;

$R^5$ is selected from H, halogen, $OR^6$, $N(R^6)_2$, CN, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, O($C_1$-$C_3$ alkyl), O($C_1$-$C_3$ haloalkyl);

$X^1$ is C(O);

$X^2$ is $(C(R^8)_2)_{(1-3)}$;

each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and N($R^6$), wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

optionally 2 $R^8$ on different carbon atoms may be taken together, along with the atoms to which they are attached, to form a 3- to 6-membered fused ring;

optionally 2 $R^8$ on a single carbon atom may be taken together, along with the atoms to which they are attached, to form a 3- to 6-membered spirocycle;

$X^3$ is selected from the group consisting of $COOR^6$,

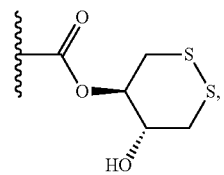 [SMILES: *C(=O)O[C@H]1CSSC[C@@H]1O]

$C(O)SR^6$, $C(S)OR^6$, $SO_2R^6$, and $C(O)N(R^9)_2$; and each $R^9$ is independently selected from the group consisting of H, $COOR^6$, and $SO_2R^6$.

5. A method of claim 1, wherein the compound selected from the group consisting of:

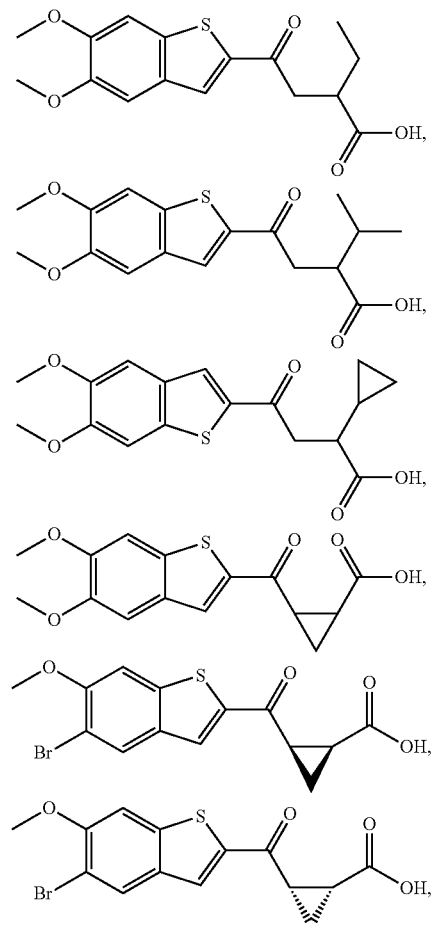

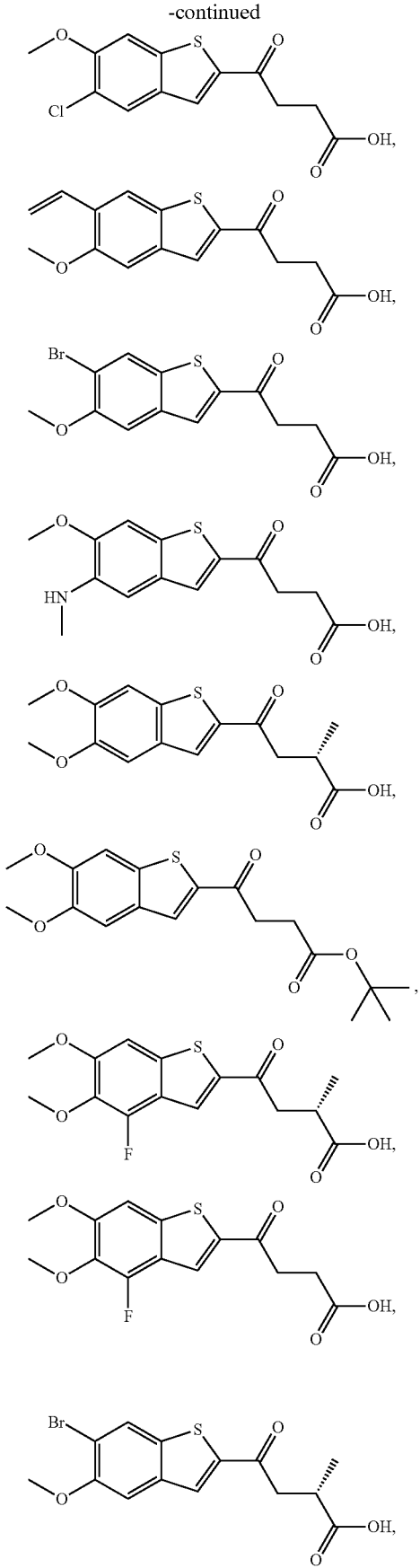
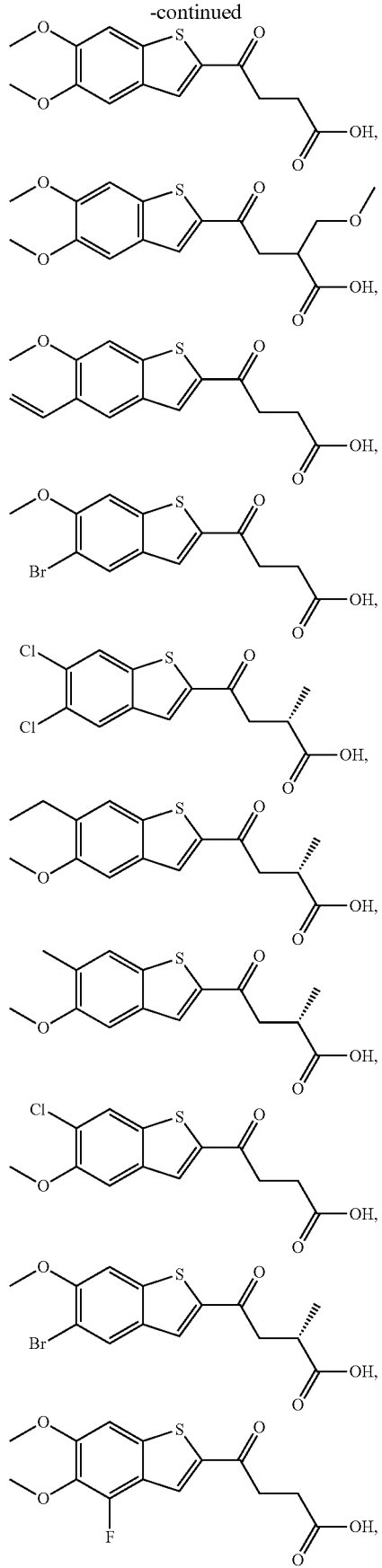

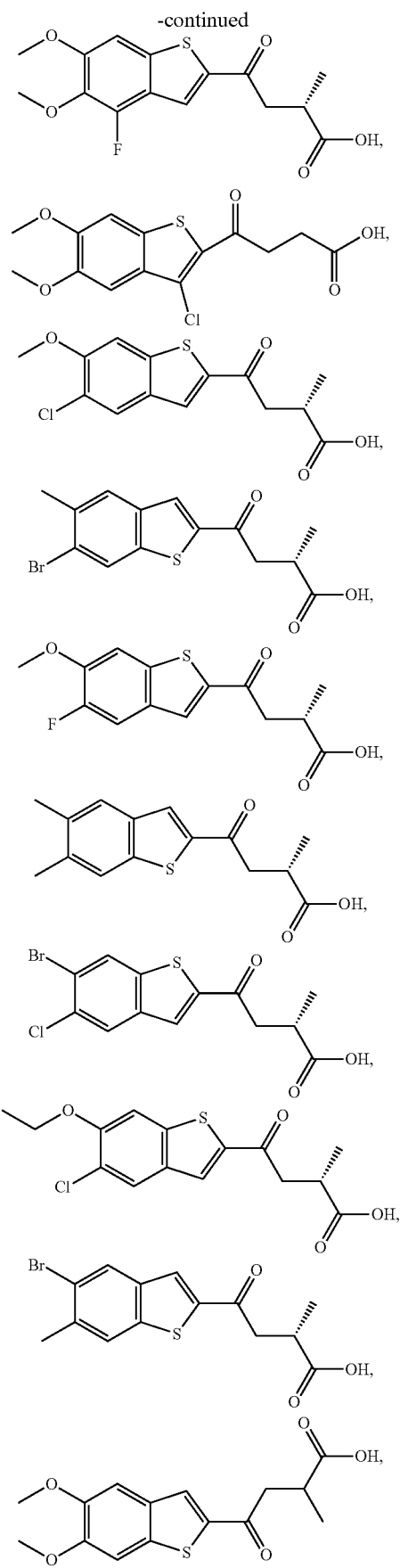
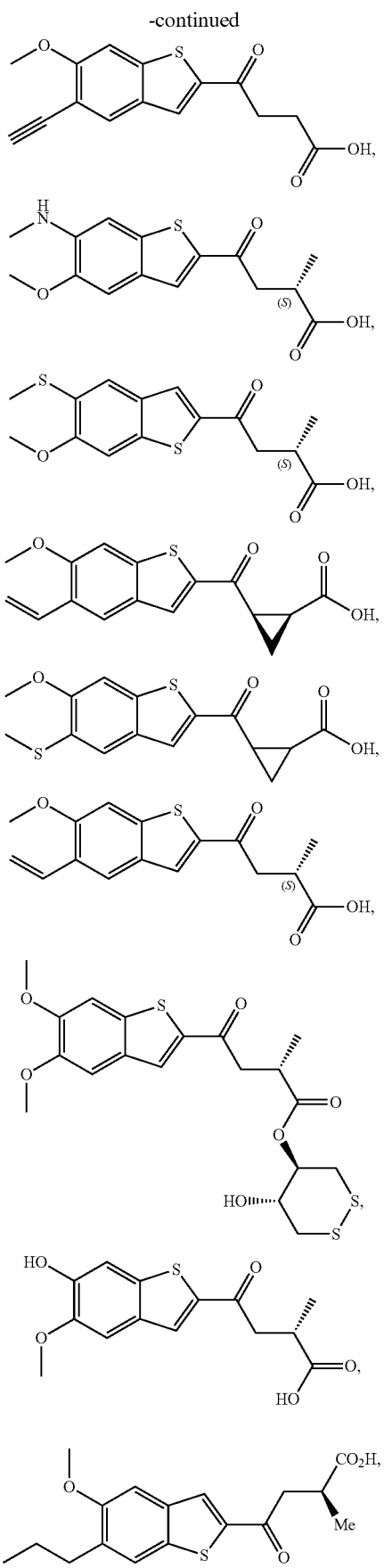

205
-continued
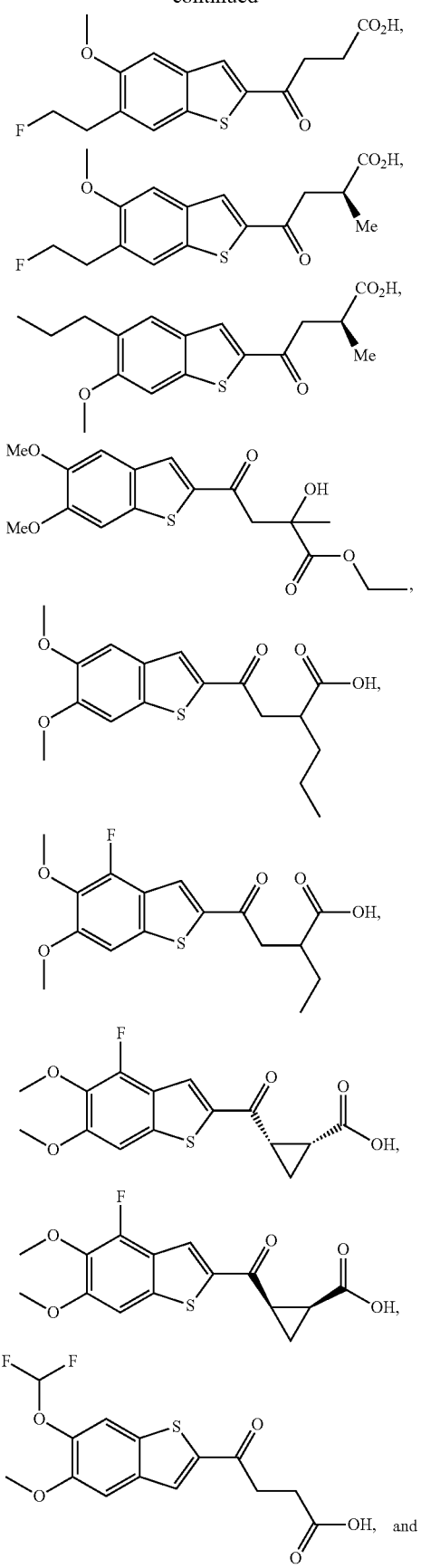
206
-continued
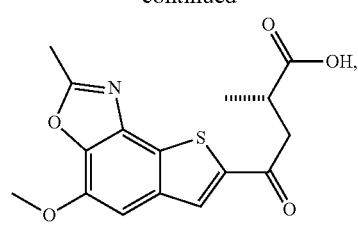
or a pharmaceutically acceptable salt thereof.
6. A method of claim 3, wherein the compound selected from the group consisting of:
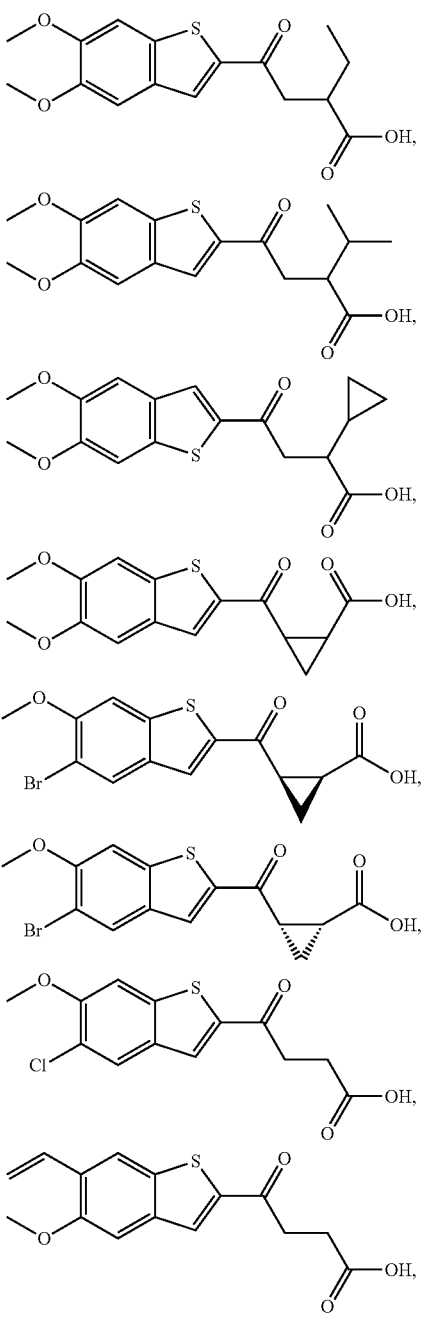

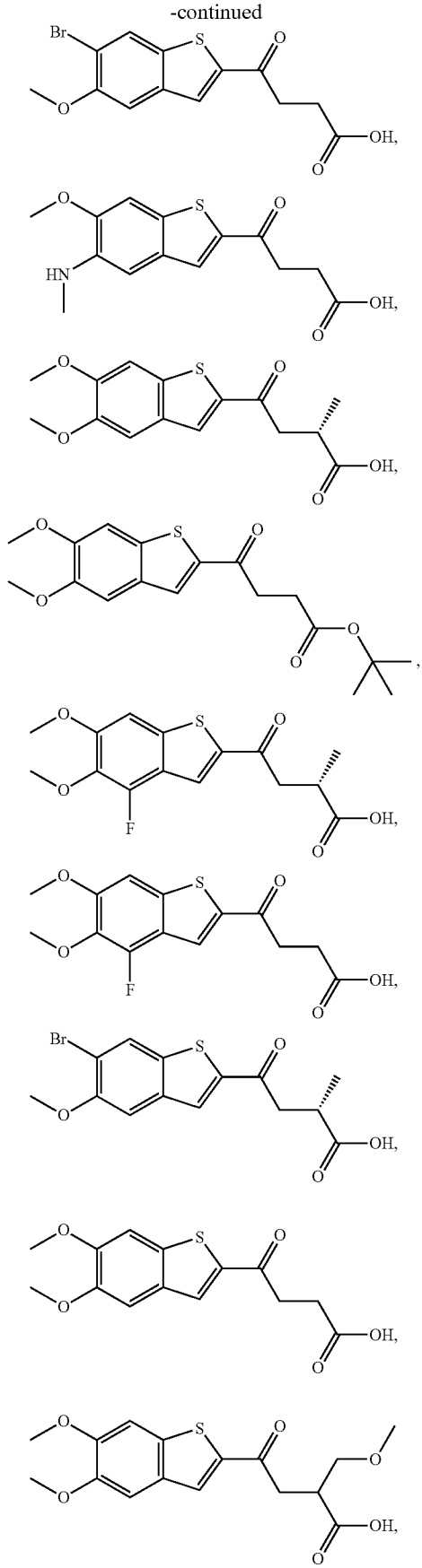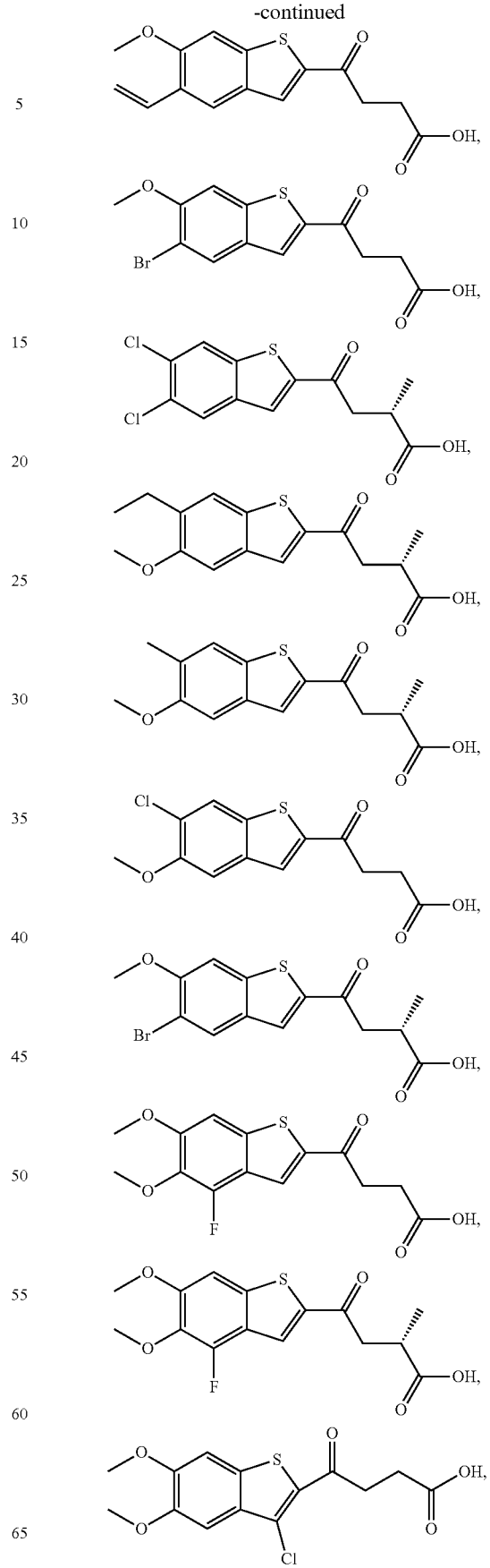

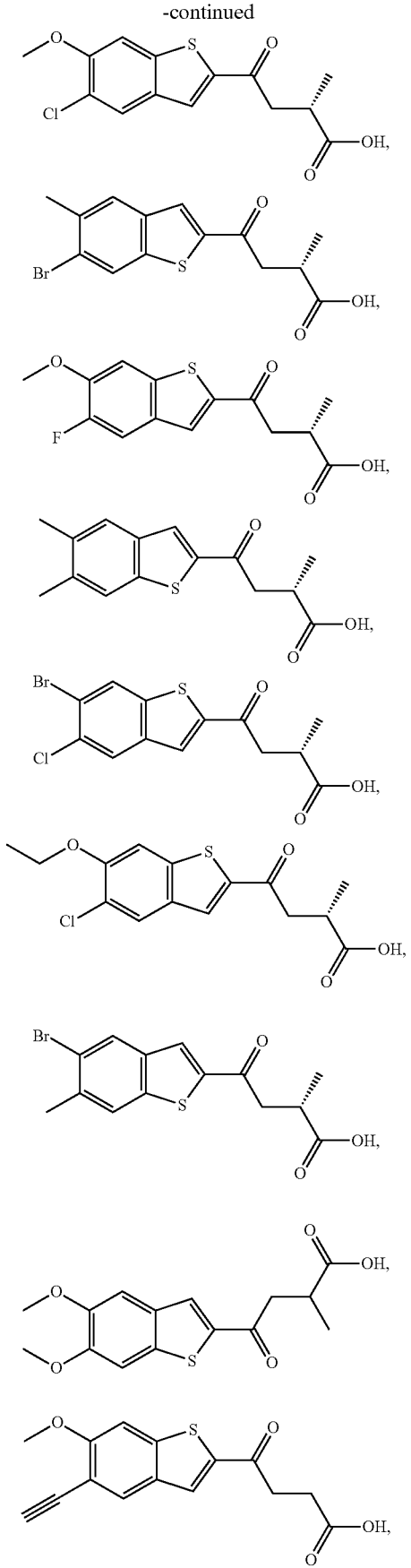
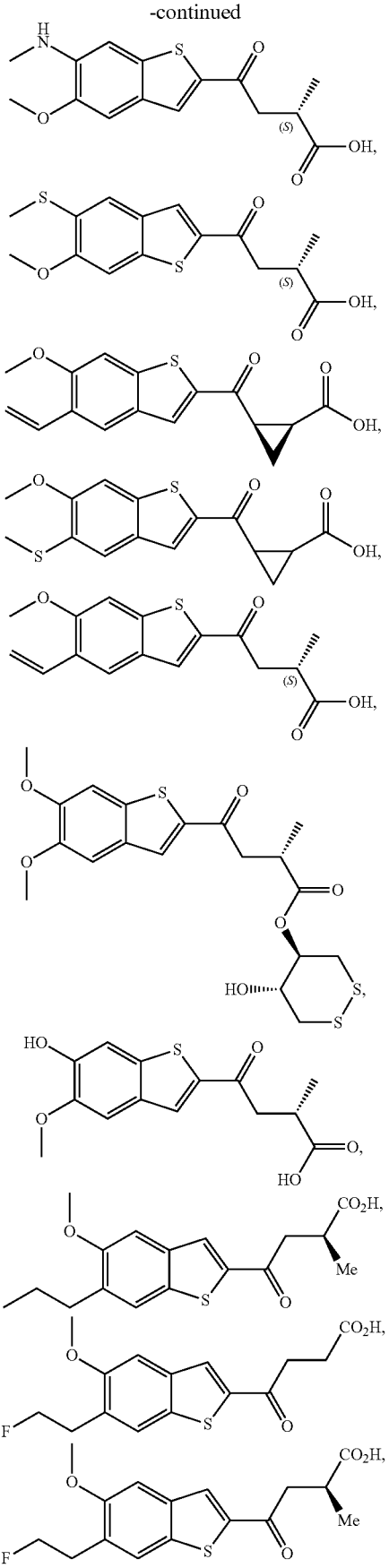

211
-continued
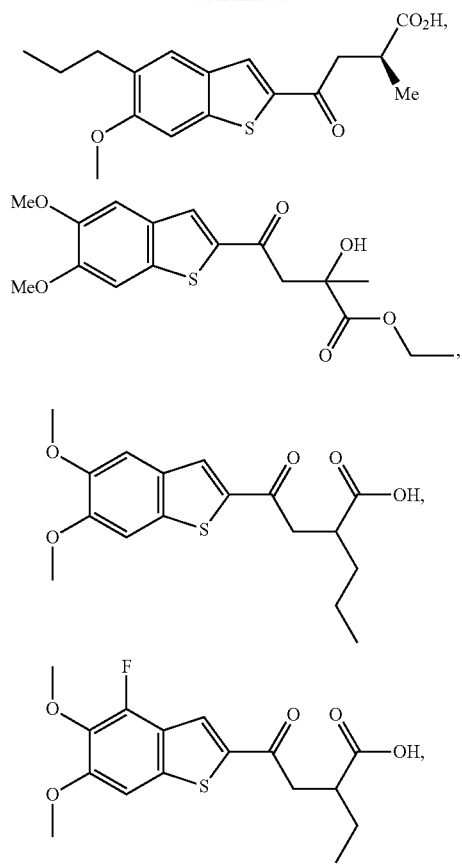
212
-continued
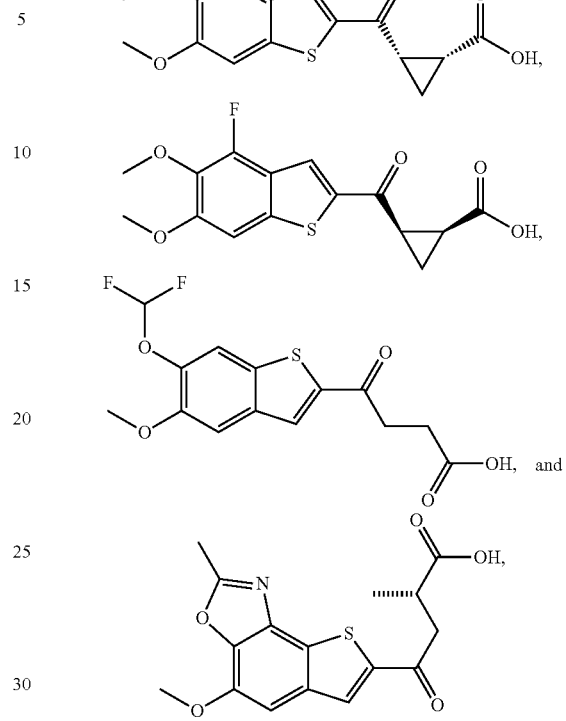
or a pharmaceutically acceptable salt thereof.
* * * * *

SEQUENCE LISTING

<160> NUMBER OF SEQ ID NOS: 4

<210> SEQ ID NO 1
<211> LENGTH: 414

-continued

```
<212> TYPE: PRT
<213> ORGANISM: Homo sapiens

<400> SEQUENCE: 1

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
    35                  40                  45

Leu His Leu Ala Ser Leu Gln Leu Gly Leu Leu Leu Asn Gly Val Cys
50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Leu Asn
    370                 375                 380

Asp Ile Phe Glu Ala Gln Lys Ile Glu Trp His Glu Gly Ser Leu Glu
385                 390                 395                 400
```

Val Leu Phe Gln Gly Pro His His His His His His His
            405                 410

<210> SEQ ID NO 2
<211> LENGTH: 6482
<212> TYPE: DNA
<213> ORGANISM: Homo sapiens

<400> SEQUENCE: 2

| | | | | | |
|---|---|---|---|---|---|
| ggaacggctc | cgcccactat | taatgaaatt | aaaaattcca | attttaaaaa | acgcagcaag | 60 |
| agaaacattt | gtatgaaaga | atgcgtagaa | ggaaagaaaa | atgtcgtcga | catgctgaac | 120 |
| aacaagatta | atatgcctcc | gtgtataaaa | aaaatattga | acgatttgaa | agaaaacaat | 180 |
| gtaccgcgcg | gcggtatgta | caggaagagg | tttatactaa | actgttacat | tgcaaacgtg | 240 |
| gtttcgtgtg | ccaagtgtga | aaaccgatgt | ttaatcaagg | ctctgacgca | tttctacaac | 300 |
| cacgactcca | agtgtgtggg | tgaagtcatg | catcttttaa | tcaaatccca | agatgtgtat | 360 |
| aaaccaccaa | actgccaaaa | aatgaaaact | gtcgacaagc | tctgtccgtt | tgctggcaac | 420 |
| tgcaagggtc | tcaatcctat | ttgtaattat | tgaataataa | aacaattata | aatgctaaat | 480 |
| ttgttttta | ttaacgatac | aaaccaaacg | caacaagaac | atttgtagta | ttatctataa | 540 |
| ttgaaaacgc | gtagttataa | tcgctgaggt | aatatttaaa | atcattttca | aatgattcac | 600 |
| agttaatttg | cgacaatata | attttatttt | cacataaact | agacgccttg | tcgtcttctt | 660 |
| cttcgtattc | cttctctttt | tcattttct | cttcataaaa | attaacatag | ttattatcgt | 720 |
| atccatatat | gtatctatcg | tatagagtaa | attttttgtt | gtcataaata | tatatgtctt | 780 |
| ttttaatggg | gtgtatagta | ccgctgcgca | tagttttttct | gtaatttaca | acagtgctat | 840 |
| tttctggtag | ttcttcggag | tgtgttgctt | taattattaa | atttatataa | tcaatgaatt | 900 |
| tgggatcgtc | ggttttgtac | aatatgttgc | cggcatagta | cgcagcttct | tctagttcaa | 960 |
| ttacaccatt | ttttagcagc | accggattaa | cataactttc | caaatgttg | tacgaaccgt | 1020 |
| taaacaaaaa | cagttcacct | ccctttttcta | tactattgtc | tgcgagcagt | tgtttgttgt | 1080 |
| taaaaataac | agccattgta | atgagacgca | caaactaata | tcacaaactg | gaaatgtcta | 1140 |
| tcaatatata | gttgctgatc | agatctgatc | atggagataa | ttaaaatgat | aaccatctcg | 1200 |
| caaataaata | agtattttac | tgtttttcgta | acagttttgt | aataaaaaaa | cctataaata | 1260 |
| taggatccat | gccccactcc | agcctgcatc | catccatccc | gtgtcccagg | ggtcacgggg | 1320 |
| cccagaaggc | agccttggtt | ctgctgagtg | cctgcctggt | gaccctttgg | gggctaggag | 1380 |
| agccaccaga | gcacactctc | cggtacctgg | tgctccacct | agcctccctg | cagctgggac | 1440 |
| tgctgttaaa | cggggtctgc | agcctggctg | aggagctgca | ccacatccac | tccaggtacc | 1500 |
| ggggcagcta | ctggaggact | gtgcgggcct | gcctggctg | cccctccgc | cgtggggccc | 1560 |
| tgttgctgct | gtccatctat | ttctactact | ccctcccaaa | tgcggtcggc | ccgcccttca | 1620 |
| cttggatgct | tgccctcctg | ggcctctcgc | aggcactgaa | catcctcctg | ggcctcaagg | 1680 |
| gcctggcccc | agctgagatc | tctgcagtgt | gtgaaaaagg | gaatttcaac | gtggcccatg | 1740 |
| ggctggcatg | gtcatattac | atcggatatc | tgcggctgat | cctgccagag | ctccaggccc | 1800 |
| ggattcgaac | ttacaatcag | cattacaaca | acctgctacg | gggtgcagtg | agccagcggc | 1860 |
| tgtatattct | cctcccattg | gactgtgggg | tgcctgataa | cctgagtatg | gctgacccca | 1920 |
| acattcgctt | cctggataaa | ctgccccagc | agacgctga | ccgtgctggc | atcaaggatc | 1980 |
| gggtttacag | caacagcatc | tatgagcttc | tggagaacgg | gcagcgggcg | ggcacctgtg | 2040 |

```
tcctggagta cgccaccccc ttgcagactt tgtttgccat gtcacaatac agtcaagctg   2100
gctttagccg ggaggatagg cttgagcagg ccaaactctt ctgccagaca cttgaggaca   2160
tcctggcaga tgcccctgag tctcagaaca actgccgcct cattgcctac caggaacctg   2220
cagatgacag cagcttctcg ctgtcccagg aggttctccg gcacctgcgg caggaggaaa   2280
aggaagaggt tactgtgggc agcttgaaga cctcagcggt gcccagtacc tccacgatgt   2340
cccaagagcc tgagctcctc atcagtggaa tggaaaagcc cctccctctc cgcacggatt   2400
tctctggcgg tggcctgaac gacatcttcg aagcccagaa aatcgaatgg catgaaggca   2460
gcctggaagt gctgttccag ggcccacacc accatcatca ccatcaccat taatgagcgg   2520
ccgcactcga gcaccaccac caccaccact aacctaggta gctgagcgca tgcaagctga   2580
tccgggttat tagtacattt attaagcgct agattctgtg cgttgttgat ttacagacaa   2640
ttgttgtacg tattttaata attcattaaa tttataatct ttagggtggt atgttagagc   2700
gaaaatcaaa tgattttcag cgtctttata tctgaattta atattaaat cctcaataga   2760 tttgtaaaat aggtttcgat tagtttcaaa caagggttgt ttttccgaac cgatggctgg   2820
actatctaat ggattttcgc tcaacgccac aaaacttgcc aaatcttgta gcagcaatct   2880
agctttgtcg atattcgttt gtgttttgtt ttgtaataaa ggttcgacgt cgttcaaaat   2940
attatgcgct tttgtatttc tttcatcact gtcgttagtg tacaattgac tcgacgtaaa   3000
cacgttaaat agagcttgga catatttaac atcgggcgtg ttagctttat taggccgatt   3060
atcgtcgtcg tcccaaccct cgtcgttaga agttgcttcc gaagacgatt ttgccatagc   3120
cacacgacgc ctattaattg tgtcggctaa cacgtccgcg atcaaatttg tagttgagct   3180
ttttggaatt atttctgatt gcgggcgttt ttgggcgggt ttcaatctaa ctgtgcccga   3240
ttttaattca gacaacacgt tagaaagcga tggtgcaggg ggtggtaaca tttcagacgg   3300
caaatctact aatggcggcg gtggtggagc tgatgataaa tctaccatcg gtggaggcgc   3360
aggcggggct ggcggcggag gcggaggcgg aggtggtggc ggtgatgcag acggcggttt   3420
aggctcaaat gtctctttag gcaacacagt cggcacctca actattgtac tggtttcggg   3480
cgccgttttt ggtttgaccg gtctgagacg agtgcgattt ttttcgtttc taatagcttc   3540
caacaattgt tgtctgtcgt ctaaaggtgc agcgggttga ggttccgtcg gcattggtgg   3600
agcgggcggc aattcagaca tcgatggtgg tggtggtggt ggaggcgctg gaatgttagg   3660
cacgggagaa ggtggtggcg gcggtgccgc cggtataatt tgttctggtt tagtttgttc   3720
gcgcacgatt gtgggcaccg cgcaggcgc cgctggctgc acaacggaag gtcgtctgct   3780
tcgaggcagc gcttggggtg gtggcaattc aatattataa ttggaataca atcgtaaaa   3840 atctgctata agcattgtaa tttcgctatc gtttaccgtg ccgatattta caaccgctc   3900 aatgtaagca attgtattgt aaagagattg tctcaagctc ggatcgatcc cgcacgccga   3960
taacaagcct tttcattttt actacagcat tgtagtggcg agacacttcg ctgtcgtcga   4020
ggtttaaacg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200 gcgttttttcc ataggctccg cccccctgac gagcatcaca aaaatcgacg ctcaagtcag   4260
aggtggcgaa acccgacagg actataaaga taccaggcgt ttccccctgg aagctccctc   4320
gtgcgctctc ctgttccgac cctgccgctt accggatacc tgtccgcctt tctcccttcg   4380
```

```
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca aacaaaccac cgctggtagc    4740
ggtggttttt ttgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640 tcttcgggc gaaaactctc aaggatctta ccgctgttga gatccagttc gatgtaaccc    5700
actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt cccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggttttc gccctttgac gttggagtcc    6240
acgttcttta atagtggact cttgttccaa actggaacaa cactcaaccc tatctcggtc    6300 tattctttg atttataagg gattttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                   6482
```

<210> SEQ ID NO 3
<211> LENGTH: 414
<212> TYPE: PRT
<213> ORGANISM: Homo sapiens

<400> SEQUENCE: 3

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
        130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
                180                 185                 190

Ala Val Ser Gln Arg Leu Tyr Ile Leu Leu Pro Leu Asp Cys Gly Val
            195                 200                 205

Pro Asp Asn Leu Ser Met Ala Asp Pro Asn Ile Arg Phe Leu Asp Lys
        210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Leu Asn
370                 375                 380

Asp Ile Phe Glu Ala Gln Lys Ile Glu Trp His Glu Gly Ser Leu Glu
385                 390                 395                 400

Val Leu Phe Gln Gly Pro His His His His His His
            405                 410
```

<210> SEQ ID NO 4
<211> LENGTH: 6482
<212> TYPE: DNA
<213> ORGANISM: Homo sapiens

<400> SEQUENCE: 4

```
ggaacggctc cgcccactat taatgaaatt aaaaattcca attttaaaaa acgcagcaag      60
agaaacattt gtatgaaaga atgcgtagaa ggaaagaaaa atgtcgtcga catgctgaac     120
aacaagatta atatgcctcc gtgtataaaa aaatattga acgatttgaa agaaaacaat      180
gtaccgcgcg gcggtatgta caggaagagg tttatactaa actgttacat tgcaaacgtg     240
gtttcgtgtg ccaagtgtga aaaccgatgt ttaatcaagg ctctgacgca tttctacaac     300
cacgactcca agtgtgtggg tgaagtcatg catcttttaa tcaaatccca agatgtgtat     360
aaaccaccaa actgccaaaa aatgaaaact gtcgacaagc tctgtccgtt tgctggcaac     420
tgcaagggtc tcaatcctat ttgtaattat tgaataataa acaattata aatgtcaaat      480
ttgtttttta ttaacgatac aaaccaaacg caacaagaac atttgtagta ttatctataa     540
ttgaaaacgc gtagttataa tcgctgaggt aatatttaaa atcattttca aatgattcac     600
agttaatttg cgacaatata attttatttt cacataaact agacgccttg tcgtcttctt     660
cttcgtattc cttctctttt tcattttct cttcataaaa attaacatag ttattatcgt      720
atccatatat gtatctatcg tatagagtaa atttttttgtt gtcataaata tatatgtctt     780
ttttaatggg gtgtatagta ccgctgcgca tagttttct gtaatttaca acagtgctat     840
tttctggtag ttcttcggag tgtgttgctt taattattaa atttatataa tcaatgaatt     900
tgggatcgtc ggttttgtac aatatgttgc cggcatagta cgcagcttct tctagttcaa     960
ttacaccatt ttttagcagc accggattaa cataactttc caaatgttg tacgaaccgt     1020
taaacaaaaa cagttcacct ccctttctta tactattgtc tgcgagcagt tgtttgttgt    1080
taaaaataac agccattgta atgagacgca caaactaata tcacaaactg gaaatgtcta    1140
tcaatatata gttgctgatc agatctgatc atggagataa ttaaaatgat aaccatctcg    1200
caaataaata agtatttac tgtttttcgta acagttttgt aataaaaaaa cctataaata    1260
taggatccat gccccactcc agcctgcatc catccatcc gtgtcccagg ggtcacgggg     1320
cccagaaggc agccttggtt ctgctgagtg cctgcctggt gacccttgg gggctaggag     1380
agccaccaga gcacactctc cggtacctgg tgctccacct agcctccctg cagctgggac    1440
tgctgttaaa cggggtctgc agcctggctg aggagctgcg ccacatccac tccaggtacc    1500
ggggcagcta ctggaggact gtgcgggcct gcctggctg ccccctccgc cgtggggccc     1560
tgttgctgct gtccatctat ttctactact ccctcccaaa tgcggtcggc cgcccttca     1620
cttggatgct tgccctcctg ggcctctcgc aggcactgaa catcctcctg ggcctcaagg    1680
gcctggcccc agctgagatc tctgcagtgt gtgaaaaagg gaatttcaac gtggcccatg    1740
ggctggcatg gtcatattac atcggatatc tgcggctgat cctgccagag ctccaggccc    1800
ggattcgaac ttacaatcag cattacaaca acctgctacg gggtgcagtg agccagcggc    1860
tgtatattct cctcccattg gactgtgggg tgcctgataa cctgagtatg ctgaccccca    1920
acattcgctt cctggataaa ctgccccagc agaccggtga ccgtgctggc atcaaggatc    1980
gggtttacag caacagcatc tatgagcttc tggagaacgg gcagcgggcg ggcacctgtg    2040
tcctggagta cgccaccccc ttgcagactt tgtttgccat gtcacaatac agtcaagctg    2100
gctttagccg ggaggatagg cttgagcagg ccaaactctt ctgccggaca cttgaggaca    2160
```

-continued

```
tcctggcaga tgcccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
gcctggaagt gctgttccag ggcccacacc accatcatca ccatcaccat taatgagcgg    2520
ccgcactcga gcaccaccac caccaccact aacctaggta gctgagcgca tgcaagctga    2580
tccgggttat tagtacattt attaagcgct agattctgtg cgttgttgat ttacagacaa    2640
ttgttgtacg tattttaata attcattaaa tttataatct ttagggtggt atgttagagc    2700
gaaaatcaaa tgattttcag cgtctttata tctgaattta aatattaaat cctcaataga    2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaacccct cgtcgttaga agttgcttcc gaagacgatt ttgccatagc    3120
cacacgacgc ctattaattg tgtcggctaa cacgtccgcg atcaaatttg tagttgagct    3180
ttttggaatt atttctgatt gcgggcgttt ttgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
tcgaggcagc gcttggggtg gtggcaattc aatattataa ttggaataca aatcgtaaaa    3840
atctgctata agcattgtaa tttcgctatc gtttaccgtg ccgatattta acaaccgctc    3900
aatgtaagca attgtattgt aaagagattg tctcaagctc ggatcgatcc cgcacgccga    3960
taacaagcct tttcattttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200 gcgttttttcc ataggctccg ccccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
```

```
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc aacccggta  agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca acaaaccac  cgctggtagc    4740 ggtggttttt ttgtttgcaa gcagcagatt acgcgcagaa aaaaggatc  tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata ataccgcgcc acatagcaga actttaaaag tgctcatcat tggaaaacgt    5640 tcttcgggc  gaaaactctc aaggatctta ccgctgttga tccagttc   gatgtaaccc    5700 actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggtttttc gccctttgac gttggagtcc    6240
acgttcttta atagtggact cttgttccaa actggaacaa cactcaaccc tatctcggtc    6300
tattcttttg atttataagg gattttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                   6482
```